US005961982A

United States Patent [19]
Cochran

[11] Patent Number: 5,961,982
[45] Date of Patent: Oct. 5, 1999

[54] RECOMBINANT HERPESVIRUS OF TURKEYS AND USES THEREOF

[75] Inventor: Mark D. Cochran, Carlsband, Calif.

[73] Assignee: Syntro Corporation, Lenexa, Kans.

[21] Appl. No.: 08/288,065

[22] Filed: Aug. 9, 1994

Related U.S. Application Data

[63] Continuation-in-part of application No. 08/023,610, Feb. 26, 1993, which is a continuation-in-part of application No. 07/898,087, Jun. 12, 1992, abandoned, application No. 07/225,032, Jul. 27, 1988, Pat. No. 5,223,424, application No. 07/649,380, Jan. 31, 1991, abandoned, and application No. 07/914,057, Jul. 13, 1992, abandoned, which is a continuation of application No. 07/696,262, Apr. 30, 1991, abandoned, which is a continuation of application No. 06/933,107, Nov. 20, 1986, abandoned, which is a continuation-in-part of application No. 06/773,430, Sep. 6, 1985, Pat. No. 4,877,737, application No. 06/823,102, Jan. 27, 1986, Pat. No. 5,068,192, said application No. 07/225,032, is a continuation-in-part of application No. 07/078,519, Jul. 27, 1987, abandoned, application No. 06/933,107, application No. 06/902,877, Sep. 2, 1986, abandoned, application No. 06/823,102, and application No. 06/773,430, said application No. 06/649,380, is a continuation of application No. 07/078,519, which is a continuation-in-part of application No. 06/933,107, application No. 06/902,877, application No. 06/887,140, Jul. 17, 1986, abandoned, and application No. 06/823,102.

[51] Int. Cl.[6] .................. A61K 39/12; A61K 39/245; C12N 15/00; C12N 7/00
[52] U.S. Cl. ..................... 424/199.1; 424/229.1; 435/235.1; 435/69.1; 435/69.3; 435/320.1
[58] Field of Search ................ 424/229.1, 199.1; 435/69.1, 69.3, 235.1

[56] References Cited

U.S. PATENT DOCUMENTS

| | | | |
|---|---|---|---|
| 4,877,737 | 10/1989 | Shih et al. | 424/205.1 |
| 5,047,237 | 9/1991 | Cochran | 424/205.1 |
| 5,171,677 | 12/1992 | Sakaguchi et al. | 435/172.3 |
| 5,187,087 | 2/1993 | Sondermeijer et al. | 435/172.1 |
| 5,223,424 | 6/1993 | Cochran et al. | 435/236 |
| 5,225,336 | 7/1993 | Paoletti | 435/69.1 |
| 5,240,703 | 8/1993 | Cochran | 424/205.1 |
| 5,252,717 | 10/1993 | Velicer et al. | 530/395 |
| 5,266,489 | 11/1993 | Rey-Senelonge et al. | 435/320.1 |

FOREIGN PATENT DOCUMENTS

| | | | |
|---|---|---|---|
| WO 9215672 | 9/1992 | WIPO | C12N 7/00 |
| WO 9410321 | 5/1994 | WIPO | C12N 15/86 |

OTHER PUBLICATIONS

Reilly, David J. and Silva, Robert F. (1993) "Cosmid library of the turkey herpesvirus genome constructed from nanogram quantities of viral DNA associated wiyj an excess of cellular DNA", J. Virological 41:323–332 (Ex. 4).

Sondermeijer, Paul J.A. et al. (1993) "Avian herpesvirus as a live viral vector for the expression of heterologous antigens", Vaccine, vol. 11, Issue 3 (Ex. 5).

Ross, L.J.N., et al., (1993) "Construction and properties of a turkey herpesvirus recombinant expressing the Marek's disease virus homologue of glycoprotein B of herpes simplex virus", 7 J. Virology 74, 371–377 (Ex. 6).

Scott, Simon D., et al. (1993) "Identification and sequence analysis of the homologues of the herpes simplex virus type 1 glycoprotein H in Marek's disease virus and the herpesvirus of turkeys", J. Virology 74, 1185–1190 (Ex. 7).

Marshall, D.R., et al. (1993) "Selection of Marek's Disease Virus Recombinants Expressing the *Escherichia coli* gpt Gene", Virology 195, 638–648 (Ex. 8).

Zelnik, V., et al. (1993) "The complete sequence and gene organization of the short unique region of herpesvirus of turkeys", J. Virology 74, 2151–2162 (Ex. 9).

Morgan, Robin W., et al. (1993) "Efficacy in chickens of a herpesvirus of Turkeys Recombinant Vaccine Containing the Fusion Gene of Newcastle Disease Virus: Onset of Protection and Effect of Maternal Antibodies", Avian Diseases 37:1032–1040 (Ex. 10).

Lindenmaier, W. and Bauer, H.J. (1994) "Cosmid cloning and restriction endonuclease mapping of the herpesvirus of turkeys (HVT) genome", Arch Virol 135:171–177 (Ex. 11).

Meignier, Bernard, (1991) "Genetically Engineered Attenuated Herpes Simplex Viruses", reviews of Infectious Diseases 13 (Suppl II): S895–S897 (Ex. 12).

Zuckermann, F.A. et al., (1989) "Role of Pseudorabies Virus Glycoproteins In Immune Response", Vaccinatio and Control of Aujeszky's Disease pp. 107–117 (Ex. 13).

Petrovskis, Erik A., et al. (1986) "Deletions in Vaccine Strains of Pseudorabies Virus and Their Effect on Synthesis of Glycoprotein gp63", J. Virology p. 1166–1169 vol. 60 No. 3 (Ex. 14).

Ben–Porat, T., et al. (1986) "Role of Glycoproteins of Pseudorabies Virus in Eliciting Neutralizing Antobodies", Virology 154, 325–334 (Ex. 15).

Price, Richard W., and Khan, Atia; (1981) "Resistance of Peripheral Autonomic Neurons to In Vivo Productive Infection by Herpes Simplex Virus Mutants Deficient in Thymidine Kinase Activity", Infection and Immunity, pp. 571–580. vol. 34, No. 2, (Ex. 16).

Tenser, Richard B., et al. (1983) "The Role of Pseudorabies Virus Thymidine Kinase Expression in Trigeminal Ganglion Infection", J. Gen. Virol. 64, 1369–1373 (Ex. 17).

Lomniczi, Bela, et al. (1984) "Deletions in the Genomes of Pseudorabies Virus Vaccine Strains and Existence of Flour Isomers of the Genomes", J. Virology p. 970–979; vol. 49 No. 3 (Ex. 18).

(List continued on next page.)

*Primary Examiner*—Mary E. Mosher
*Assistant Examiner*—Ali R. Salimi
*Attorney, Agent, or Firm*—John P. White

[57] ABSTRACT

The present invention provides a recombinant herpesvirus of turkeys designated S-HVT-050 (ATCC Accession No. VR 2400). A vaccine is provided which comprises an effective immunizing amount of S-HVT-050 and a suitable carrier. A method of immunizing a fowl against disease caused by Marek's disease virus and Newcastle disease virus is also provided which comprises administering to the fowl an effective immunizing dose of the vaccine of the present invention.

12 Claims, 23 Drawing Sheets

OTHER PUBLICATIONS

Thomsen, Darrell R., et al. (1987) "Pseudorabies virus as a live virus vector for expression of foreign genes", Gene 57, 261–265 (Ex. 19).

Honess, R.W., (1984) "Herpes Simplex and 'The Herpes Complex': Diverse Observations and A Unifying Hypothesis", J. Gen. Virol. 65,2077–2107 (Ex. 20).

Cook, Margery L. and Stevens, J.G., (1976) "Latent Herpetic Infections Following Experimental Viraemia", J.Gen. Virol. 31, 75–80 (Ex. 21).

Thompson, R.L., et al. (1983) "Physical Location of a Herpes Simplex Virus Type–1 Gene Function(s) Specifically Associated with a 10 Million–Fold Increase in HSV Neurovirulence", Virology 131, 180–192 (Ex. 22).

Fukuchi, K., et al. (1985) "The Structure of Marek disease virus DNA: The presence of unique expansion in nonpathogenic viral DNA", Proc.Natl.Acad.Sci.USA vol. 82, pp. 751–754 (Ex. 23).

Koomey, Michael J., et al. (1984) "Deletion of DNA Sequences in a Nonocogenic Variant of Herpesvirus saimiri", J.Virol. pp. 662–665, vol. 50 No. 2 (Ex. 24).

Spaete, Richard R. and Mocarski, Edward S., (1987) "Insertion and deletion mutagenesis of the human cytomegalovirus genome", Proc.Natl.Acad.Sci.USA vol. 84, pp. 7213–7217 (Ex. 25).

Shih, Meng–Fu et al. (1984) "Expressing of hepatitis B virus S gene by herpes simplex virus type 1 vectors carrying α–and β–regulated gene chimeras", Proc. Natl. Acad. Sci. USA vol. 81, pp. 5867–5870 (Ex. 26).

Edwards, Stirling J., (1988) "Plasmodium Falciparum Antigens In Recombinant HSV–1", Technological advances in Vaccine Development, p. 223–234 (Ex. 27).

Roizman, Bernard, et al. (1983) "Bioengineering of Herpes Simplex Virus Variants for potential Use as Live Vaccines", Cold Spring Harbor Ocnference on New Approaches to Virla Vaccines, pp. 275–281 (Ex. 28).

Moss, Bernard, (1991) "Vaccinia Virus: A Tool for Research and Vaccine Development" Science 252:1662–1667 (Ex. 29).

Weir, Jerry P., and Narayanan, P.R., (1988) "the use of β–galactosidase as a marker gene to define the regulatory sequences of the herpes simplex virus type 1 glycoprotein C gene in recombinant herpesviruses", Nucleic Acids Research 16:10267–10282 (Ex. 30).

FIGURE 2A
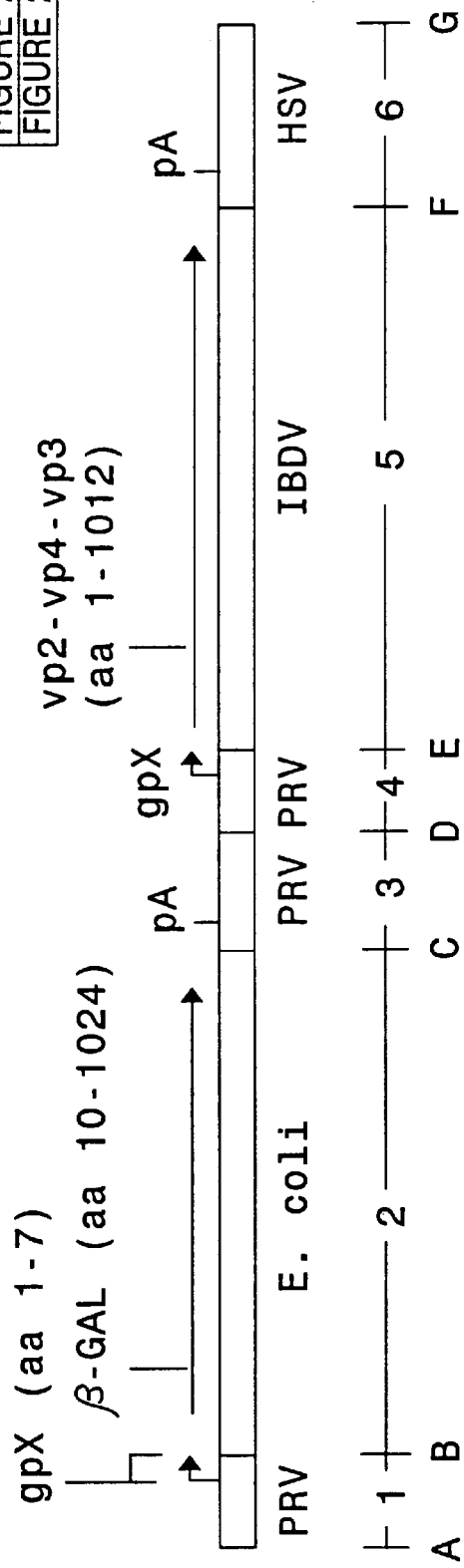
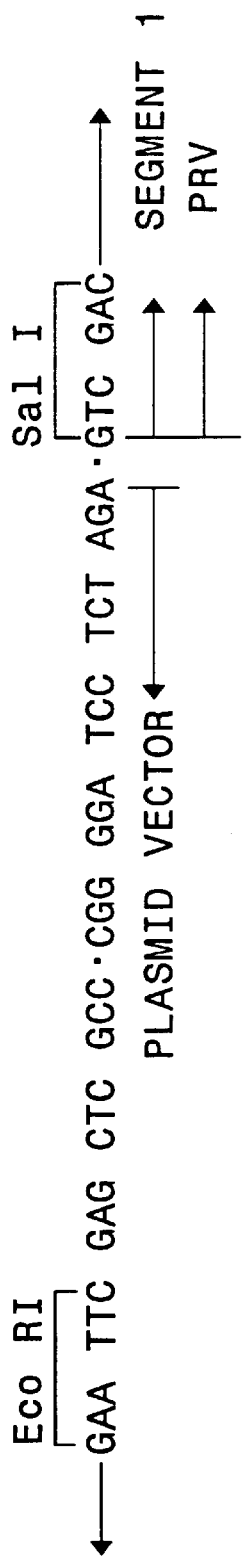

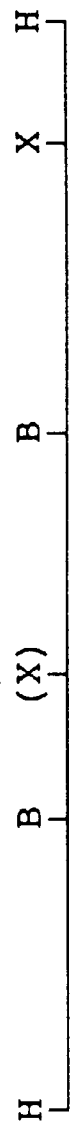
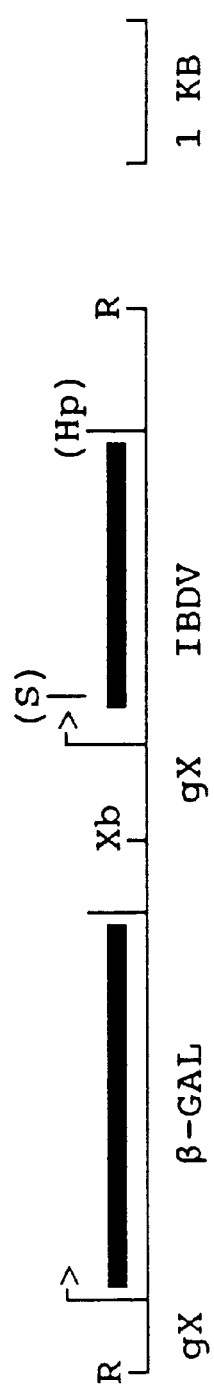
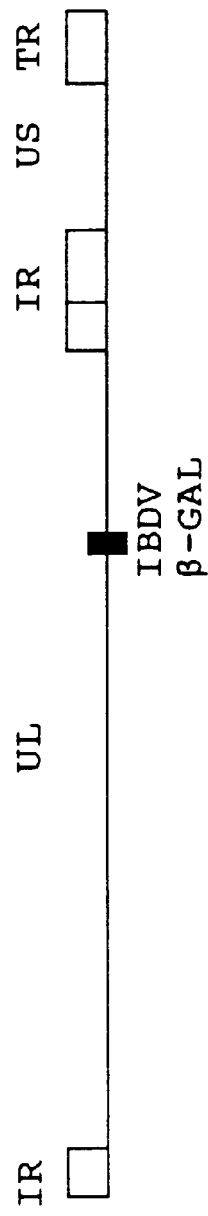
FIGURE 3A
FIGURE 3B
FIGURE 3C

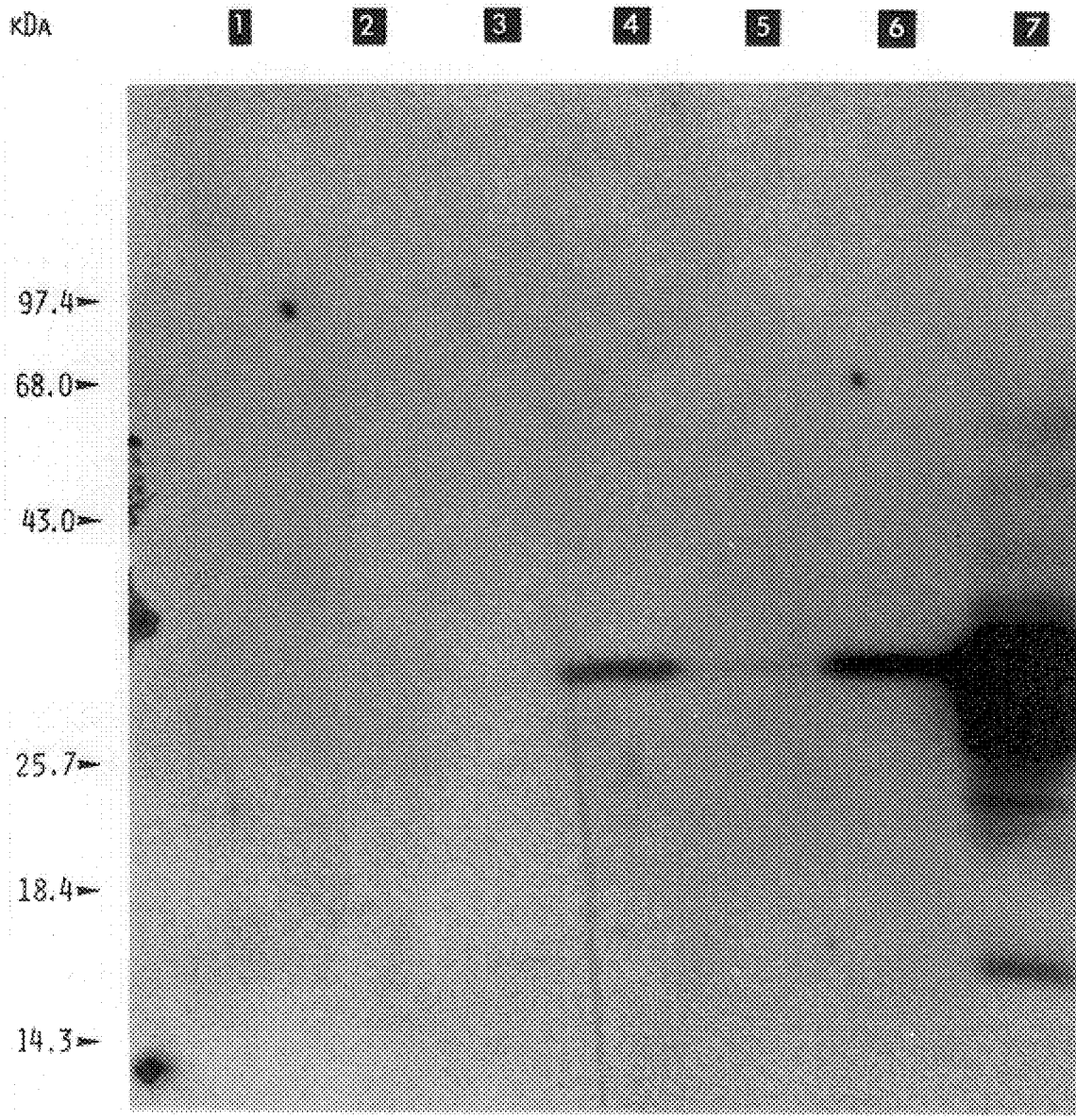

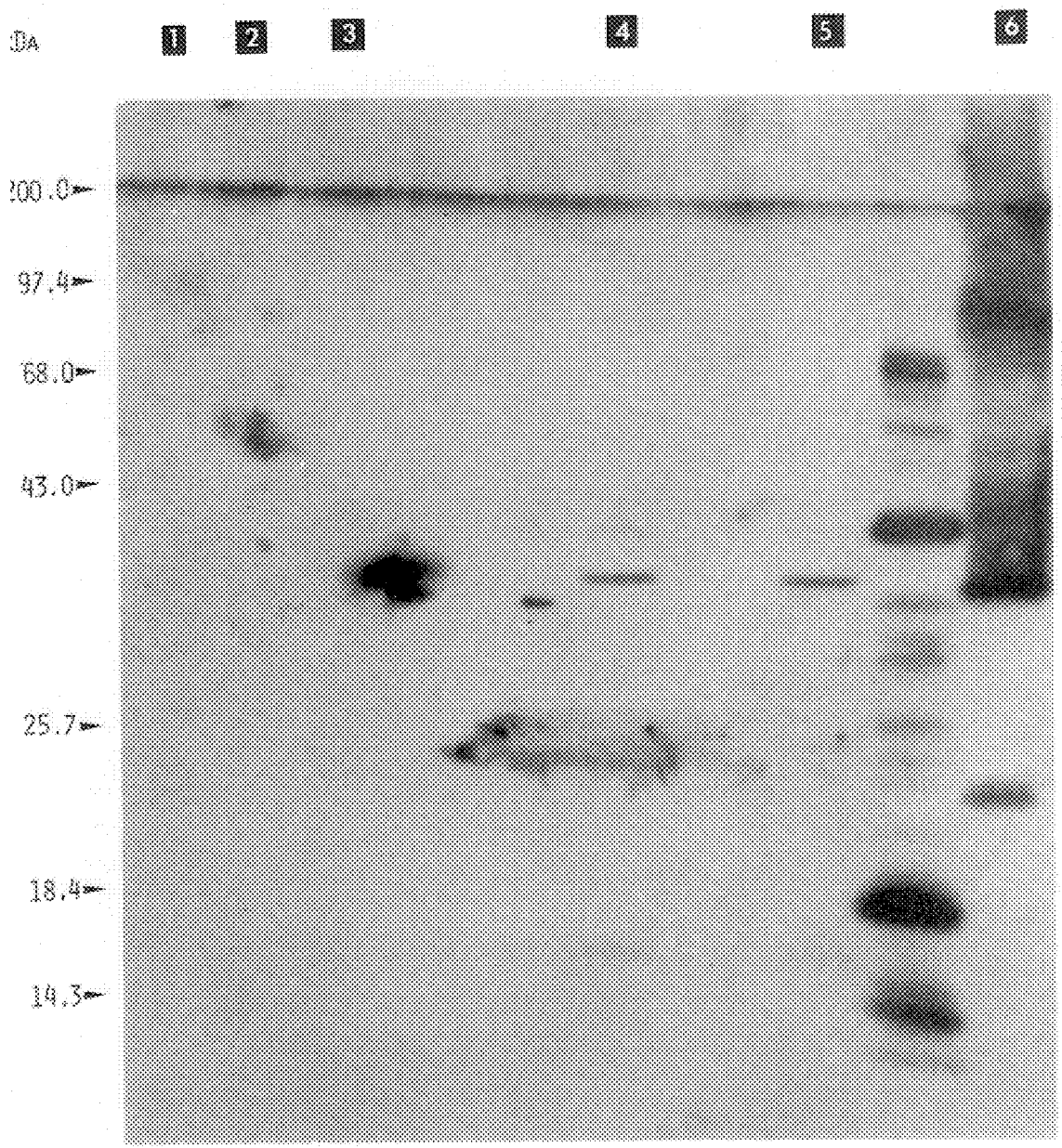

FIGURE 7A
| FIGURE 7A |
| --- |
| FIGURE 7B |
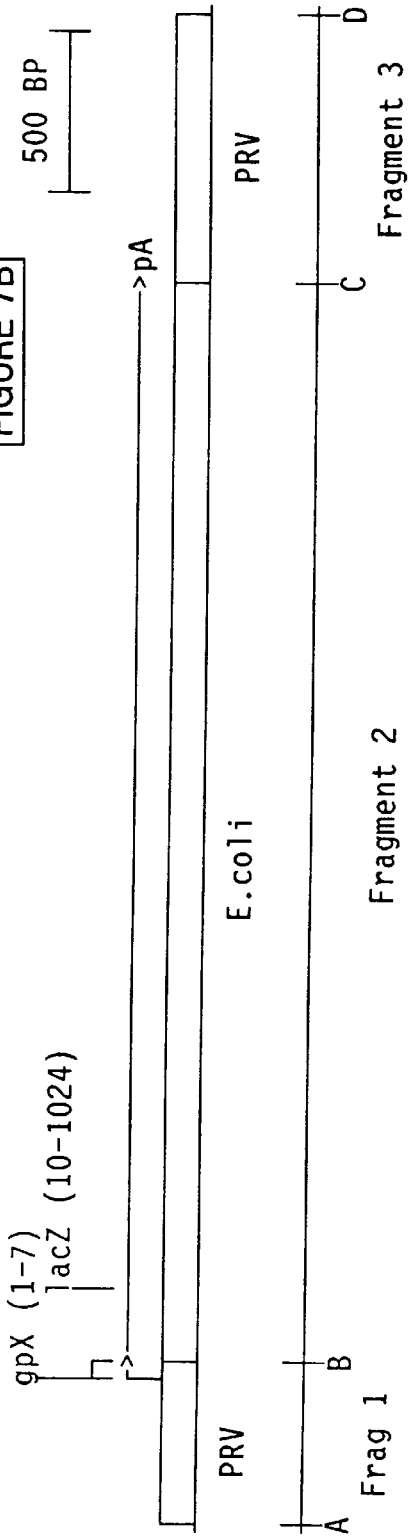
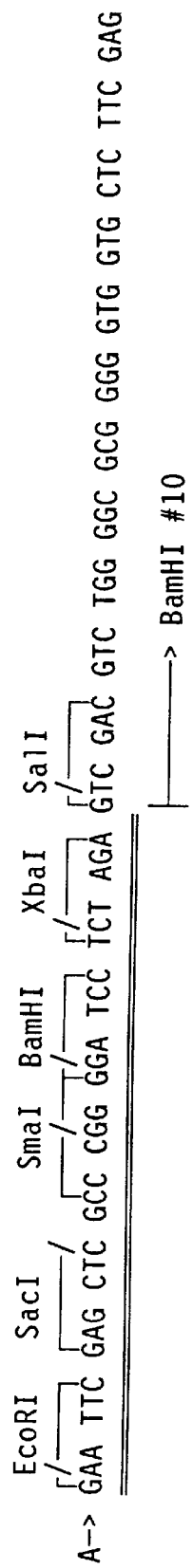
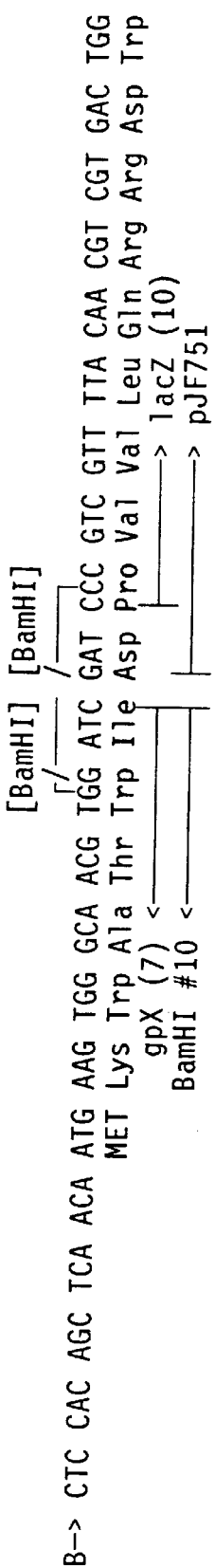

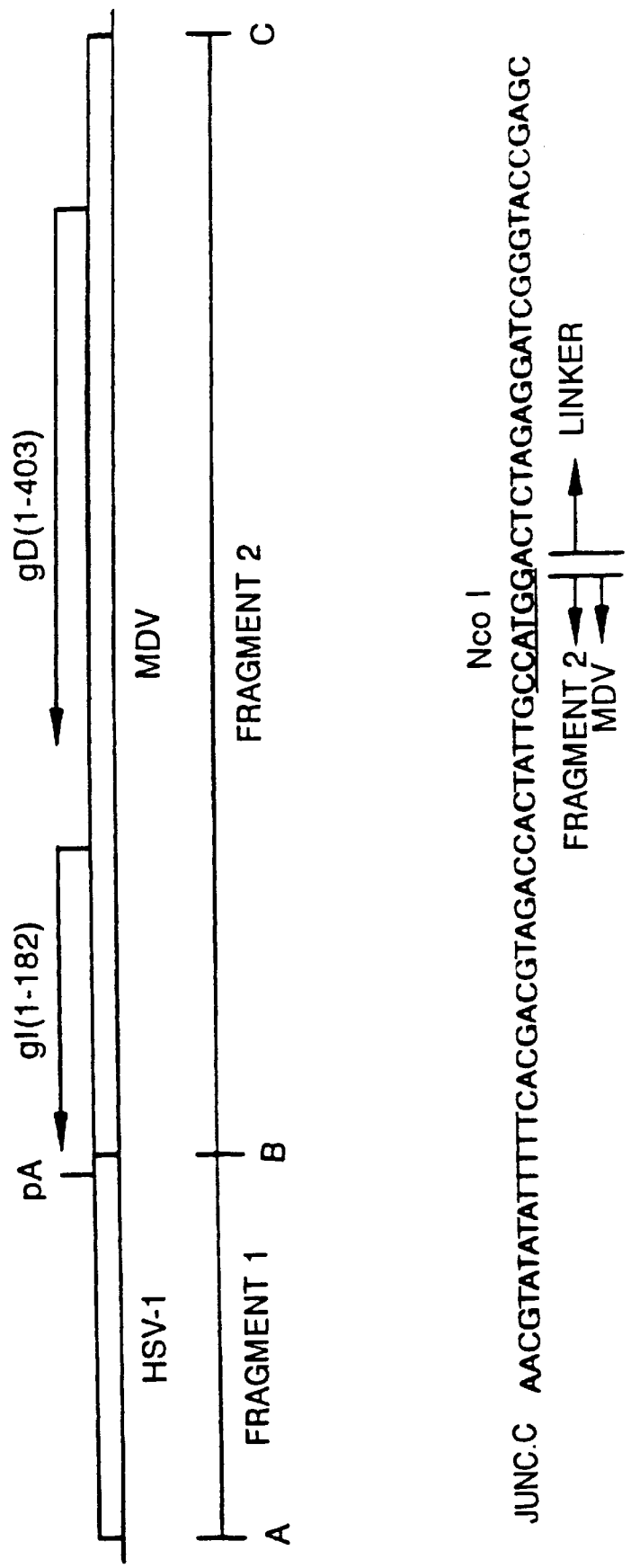

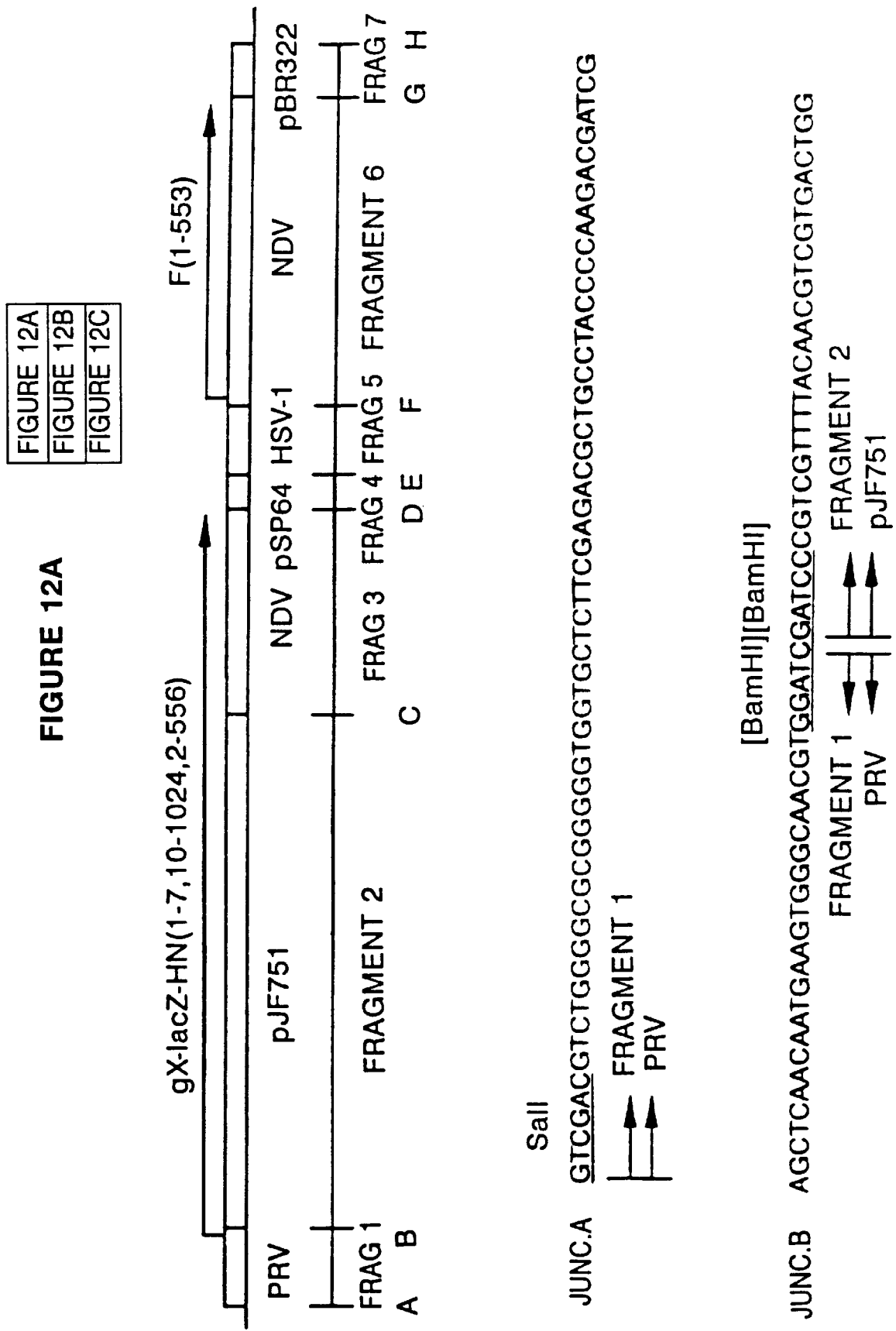

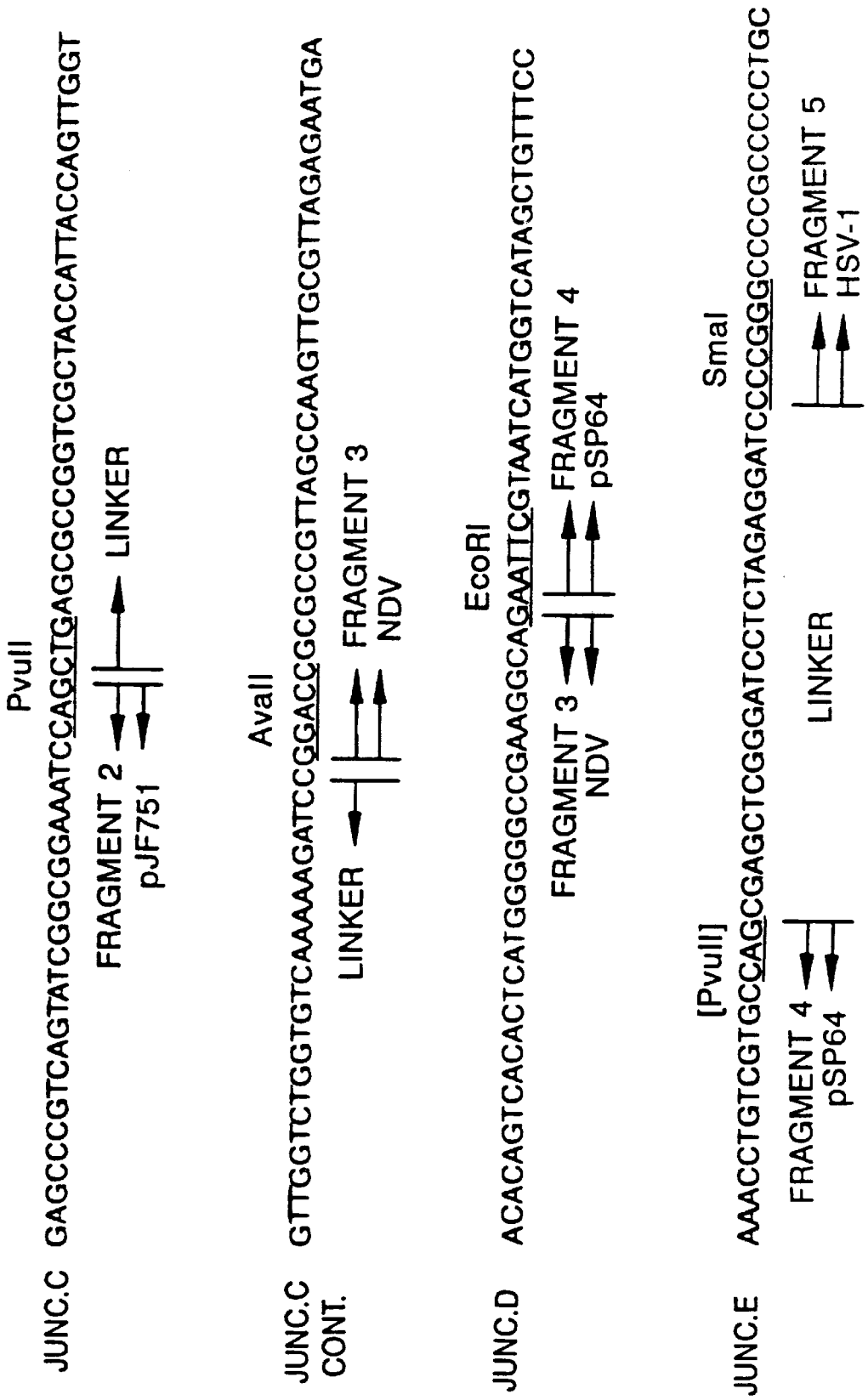

FIGURE 12C

JUNC.F  TCGTCCACACGGAGCGGGCTGCCGACACGGATCCCGGTTGGGCGCCCTCCAGGTGCAGGA
        ←———— FRAGMENT 5 ————→ BamHI ←———— FRAGMENT 6 ————→
            HSV-1                          NDV

JUNC.G  AACCCCCCCCCCCCCCCTGCAGGCATCGTGGTGTCACGCTCGTCGTTTG
        ←———— FRAGMENT 6

RECOMBINANT HERPESVIRUS OF TURKEYS AND USES THEREOF

This application is a continuation-in-part of U.S. Ser. No. 08/023,610 filed Feb. 26, 1993, which is a continuation-in-part of U.S. Ser. No. 07/898,087 filed Jun. 12, 1992, now abandoned; U.S. Ser. No. 07/225,032, filed Jul. 27, 1988, now U.S. Pat. No. 5,223,424, issued Jun. 29, 1993, which is a continuation-in-part of U.S. Ser. No. 07/078,519, filed Jul. 27, 1987, now abandoned, U.S. Ser. No. 06/933,107, filed Nov. 20, 1986, now abandoned, U.S. Ser. No. 06/902,887, filed Sep. 2, 1986, now abandoned, U.S. Ser. No. 06/823, 102, filed Jan. 27, 1986, now U.S. Pat. No. 5,068,192, issued Nov. 26, 1991, and U.S. Ser. No. 06/773,430, filed Sep. 6, 1985, now U.S. Pat. No. 4,877,737, issued Oct. 31, 1989; U.S. Ser. No. 07/649,380, filed Jan. 31, 1991, now abandoned, which is a continuation of U.S. Ser. No. 07/078, 519, filed Jul. 27, 1987, now abandoned, which is a continuation-in-part of U.S. Ser. No. 06/993,107, filed Nov. 20, 1986, now abandoned, U.S. Ser. No. 06/902,877, filed Sep. 2, 1986, now abandoned, U.S. Ser. No. 06/887,140, filed Jul. 17, 1986, now abandoned, U.S. Ser. No. 06/823, 102, filed Jan. 27, 1986, now U.S. Pat. No. 5,068,192, issued Nov. 26, 1991, and U.S. Ser. No. 07/914,057, filed Jul. 13, 1992, now abandoned, which is a continuation of U.S. Ser. No. 07/696,262, filed Apr. 30, 1991, now abandoned, which is a continuation of U.S. Ser. No. 06/933,107, filed Nov. 20, 1986, now abandoned, which is a continuation-in-part of U.S. Ser. No. 06/773,430, filed Sep. 6, 1985, now U.S. Pat. No. 4,877,737, issued Oct. 31, 1989, and U.S. Ser. No. 06/823,102 filed Jan. 27, 1986, now U.S. Pat. No. 5,068,192, issued Nov. 26, 1991.

BACKGROUND OF THE INVENTION

The ability to isolate DNA and clone such isolated DNA into bacterial plasmids has greatly expanded the approaches available to make viral vaccines. The methods used to make the present invention involve modifying cloned DNA sequences from various viral pathogens of animals, by insertions, deletions, single or multiple base changes, and subsequent insertions of these modified sequences into the genome of the virus. One utility of the addition of a foreign sequence is achieved when the foreign sequence encodes a foreign protein that is expressed during viral infection of the animal. The resulting live virus may then be used in a vaccine to elicit an immune response in a host animal and provide protection to the animal against disease. A virus with these characteristics is referred to as a viral vector, because it becomes a living vector that will carry and express the foreign protein in the host animal. In effect it becomes an elaborate delivery system for the foreign protein(s).

More specifically, the present invention relates to the use of herpesvirus of turkeys (HVT) as a viral vector for vaccination of birds against disease. The group of herpesviruses comprise various pathogenic agents that infect and cause disease in a number of target species: swine, cattle, chickens, horses, dogs, cats, etc. Each herpesvirus is specific for its host species, but they are all related in the structure of their genomes, their mode of replication, and to some extent in the pathology they cause in the host animal and in the mechanism of the host immune response to the virus infection.

The application of recombinant DNA techniques to animal viruses has a relatively recent history. The first viruses to be engineered have been those with the smallest genomes. In the case of the papovaviruses, because these viruses are so small and cannot accommodate much extra DNA, their use in genetic engineering has been as defective replicons. Foreign gene expression from these viruses requires a wild-type helper virus and is limited to cell culture systems. For adenoviruses, there is a small amount of nonessential DNA that can be replaced by foreign sequences. The only foreign DNA that seems to have been expressed in adenoviruses are the T-antigen genes from papovaviruses (Mansour, et al., *Proc. Natl. Acad. Sci. US*, 1985; Thummel, et al., *Cell*, 1983; Scolnick, et al., *Cell*, 1981; Thummel, et al., *Cell*, 1981), and the herpes simplex virus (HSV) thymidine kinase gene (Haj-Ahmed and Graham, *J. of Virology*, 1986). These publications do not identify the nonessential regions in HVT wherein foreign DNA may be inserted, nor do they teach how to achieve the expression of foreign genes in HVT, e.g., which promoter sequence and termination sequence to use.

Another group of viruses that have been engineered are the poxviruses. One member of this group, vaccinia, has been the subject of much research on foreign gene expression. Poxviruses are large DNA-containing viruses that replicate in the cytoplasm of the infected cell. They have a structure that is unique in that they do not contain any capsid that is based upon icosahedral symmetry or helical symmetry. The poxviruses are most likely to have evolved from bacterial-like microorganisms through the loss of function and degeneration. In part due to this uniqueness, the advances made in the genetic engineering of poxviruses cannot be directly extrapolated to other viral systems, including herpesviruses and HVT. Vaccinia recombinant virus constructs have been made in a number of laboratories that express the following inserted foreign genes: HSV thymidine kinase gene (Mackett, et al., *Proc. Natl. Acad. Sci. USA*, 1982; Panicali and Paoletti, *Proc. Natl. Acad. Sci. USA*, 1982, hepatitis B surface antigen (Paoletti, et al., *Proc. Natl. Acad. Sci. USA*, 1984; Smith et al., *Nature*, 1983), HSV glycoprotein D gene, infaluenzae hemagglutinin gene (Panicali, et al., *Proc. Natl. Acad. Sci. USA*, 1983; Smith, et al., *Proc. Natl. Acad. Sci. USA*, 1983), malaria antigen gene (Smith, et al., *Science*, 1984, and vesicular stomatitis glycoprotein G gent (Mackett, et al., *Science*, 1986). The general overall features of vaccinia recombinant DNA work are similar to the techniques used for all the viruses, especially as they relate to the techniques in reference (Maniatis, et al., *Molecular Cloning*, 1982). However in detail, the vaccinia techniques are not applicable to herpesviruses and HVT. The utility of vaccinia as a vaccine vector is in question because of its close relationship to human smallpox and its known pathogenicity to humans. Thus, the use of the host-specific herpesvirus HVT is a better solution to vaccination of poultry.

Among the primate herpesviruses, only HSV of humans and, to a limited extent, herpes saimiri of monkeys have been engineered to contain foreign DNA sequences. The first use of recombinant DNA to manipulate HSV involved cloning a piece of DNA from the L-S junction region into the unique long region of HSV DNA, specifically into the thymidine kinase gene (Moccarski, et al., *Cell*, 1980). This insert was not a foreign piece of DNA, rather it was a naturally occurring piece of herpesvirus DNA that was duplicated at another place in the genome. This piece of DNA was not engineered to specifically express a protein, and thus this work does not involve expression of protein in herpesviruses. The next manipulation of HSV involved the creation of deletions in the virus genome by a combination of recombinant DNA techniques and thymidine kinase selection. Using this approach, the HSV alpha-22 gene has been deleted (Post, et al., *Cell*, 1981), and a 15,000 basepair sequence of DNA has been deleted from the internal repeat of HSV (Poffenberger, et al., *Proc. Natl. Acad. Sci. USA*, 1981).

The following cases involve insertion of genes that encode protein into herpesviruses: the insertion of HSV glycoprotein C into a naturally occurring deletion mutant of this gene in HSV (Gibson and Spear, *J. of Virology*, 1983); the insertion of glycoprotein D of HSV type 2 into HSV type 1 (Lee, et al., *Proc. Natl. Acad. Sci. USA*, 1982), with no manipulation of promoter sequences since the gene is not 'foreign'; the insertion of hepatitis B surface antigen into HSV under the control of the HSV ICP4 promoter (Shih, et al., *Proc. Natl. Acad. Sci. USA*, 1984); and the insertion of bovine growth hormone into herpes saimiri virus with an SV40 promoter (the promoter did not work in this system and an endogenous upstream promoter served to transcribe the gene) (Desrosiers, et al., 1984). Two additional foreign genes (chicken ovalbumin gene and Epstein-Barr virus nuclear antigen) have been inserted into HSV (Arsenakis and Roizman, 1984), and glycoprotein X of pseudorabies virus has been inserted into HSV (Post, et al., 1985).

These cases of deletion or insertion of genes into herpesviruses demonstrate that it is possible to genetically engineer herpesvirus genomes by recombinant DNA techniques. The methods that have been used to insert genes involve homologous recombination between the viral DNA cloned in plasmids and purified viral DNA transfected into the same animal cell. However, the extent to which one can generalize the location of the deletion and the sites for insertion of foreign genes is not known from these previous studies.

One object of the present invention is a vaccine for Marek's disease. Marek's disease virus (MDV) is the causative agent of Marek's disease which encompasses fowl paralysis, a common lymphoproliferative disease of chickens. The disease occurs most commonly in young chickens between 2 and 5 months of age. The prominent clinical signs are progressive paralysis of one or more of the extremities, incoordination due to paralysis of legs, drooping of the limb due to wing involvement, and a lowered head position due to involvement of the neck muscles. In acute cases, severe depression may result. In the case of highly oncogenic strains, there is characteristic bursal and thymic atrophy. In addition, there are lymphoid tumors affecting the gonads, lungs, liver, spleen, kidney and thymus (Mohanty and Dutta, 1981).

Most chickens are vaccinated against MDV at one day of age to protect the bird against MDV for life. Prior to the present invention, the principal vaccination method for MDV involved using naturally occurring strains of turkey herpesvirus (HVT). It would be advantageous to incorporate other antigens into this vaccination at one day of age, but efforts to combine conventional vaccines have not proven satisfactory to date due to competition and immunosuppression between pathogens. The multivalent HVT-based vaccines engineered in this invention represent a novel way to simultaneously vaccinate against a number of different pathogens. For the first time, a recombinant HVT with a foreign gene inserted into a non-essential region of the HVT genome is disclosed.

The types of genetic engineering that have been performed on these herpesviruses consist of cloning parts of the virus DNA into plasmids in bacteria, reconstructuring the virus DNA while in the cloned state so that the DNA contains deletions of certain sequences, and furthermore adding foreign DNA sequences either in place of the deletions or at sites removed from the deletions.

A foreign gene of interest targeted for insertion into the genome of HVT may be obtained from any pathogenic organism of interest. Typically, the gene of interest will be derived from pathogens that in poultry cause diseases that have an economic impact on the poultry industry. The genes may be derived from organisms for which there are existing vaccines, and because of the novel advantages of the vectoring technology the HVT derived vaccines will be superior. Also, the gene of interest may be derived from pathogens for which there is currently no vaccine but where there is a requirement for control of the disease. Typically, the gene of interest encodes immunogenic polypeptides of the pathogen, and may represent surface proteins, secreted proteins and structural proteins.

A relevant avian pathogen that is a target for HVT vectoring is Infectious Laryngotracheitis virus (ILTV). ILTV is a member of the herpesviridae family, and this pathogen causes an acute disease of chickens which is characterized by respiratory depression, gasping and expectoration of bloody exudate. Viral replication is limited to cells of the respiratory tract, where in the trachea the infection gives rise to tissue erosion and hemorrhage. In chickens, no drug has been effective in reducing the degree of lesion formation or in decreasing clinical signs. Vaccination of birds with various modified forms of the ILT virus derived by cell passage and/or tedious regimes of administration have conferred acceptable protection in susceptible chickens. Because of the degree of attenuation of current ILT vaccines care must be taken to assure that the correct level of virus is maintained; enough to provide protection, but not enough to cause disease in the flock.

An additional target for the HVT vectoring approach is Newcastle disease, an infectious, highly contagious and debilitating disease that is caused by the Newcastle disease virus (NDV). NDV is a single-stranded RNA virus of the paramyxovirus family. The various pathotypes of NDV (velogenic, mesogenic, lentogenic) differ with regard to the severity of the disease, the specificity and symptoms, but most types seem to infect the respiratory system and the nervous system. NDV primarily infects chickens, turkeys and other avian species. Historically vaccination has been used to prevent disease, but because of maternal antibody interferences, life-span of the bird and route of administration, the producer needs to adapt immunization protocols to fit specific needs.

SUMMARY OF THE INVENTION

The present invention provides a recombinant herpesvirus of turkeys designated S-HVT-050 (ATCC Accession No. VR 2400). The present invention further provides a vaccine which comprises an effective immunizing amount of S-HVT-050 and a suitable carrier. A method of immunizing a fowl against disease caused by Marek's disease virus and Newcastle disease virus is also provided which comprises administering to the fowl an effective immunizing dose of the vaccine of the present invention.

BRIEF DESCRIPTION OF FIGURES

FIG. 1A shows BamHI restriction fragment map of the HVT genome. Fragments are numbered in order of decreasing size; letters refer to small fragments whose comparative size has not been determined.

FIG. 1B shows BamHI #16 fragment of the HVT genome showing location of β-galactosidase gene insertion in S-HVT-001.

FIG. 1C shows BamHI #19 fragment of the HVT genome showing location of β-galactosidase gene insertion.

Legend: B=BamHI; X=XhoI; H=HindIII; P=PstI; S=SalI; N=NdeI; R=EcoRI.

Figure 2B:
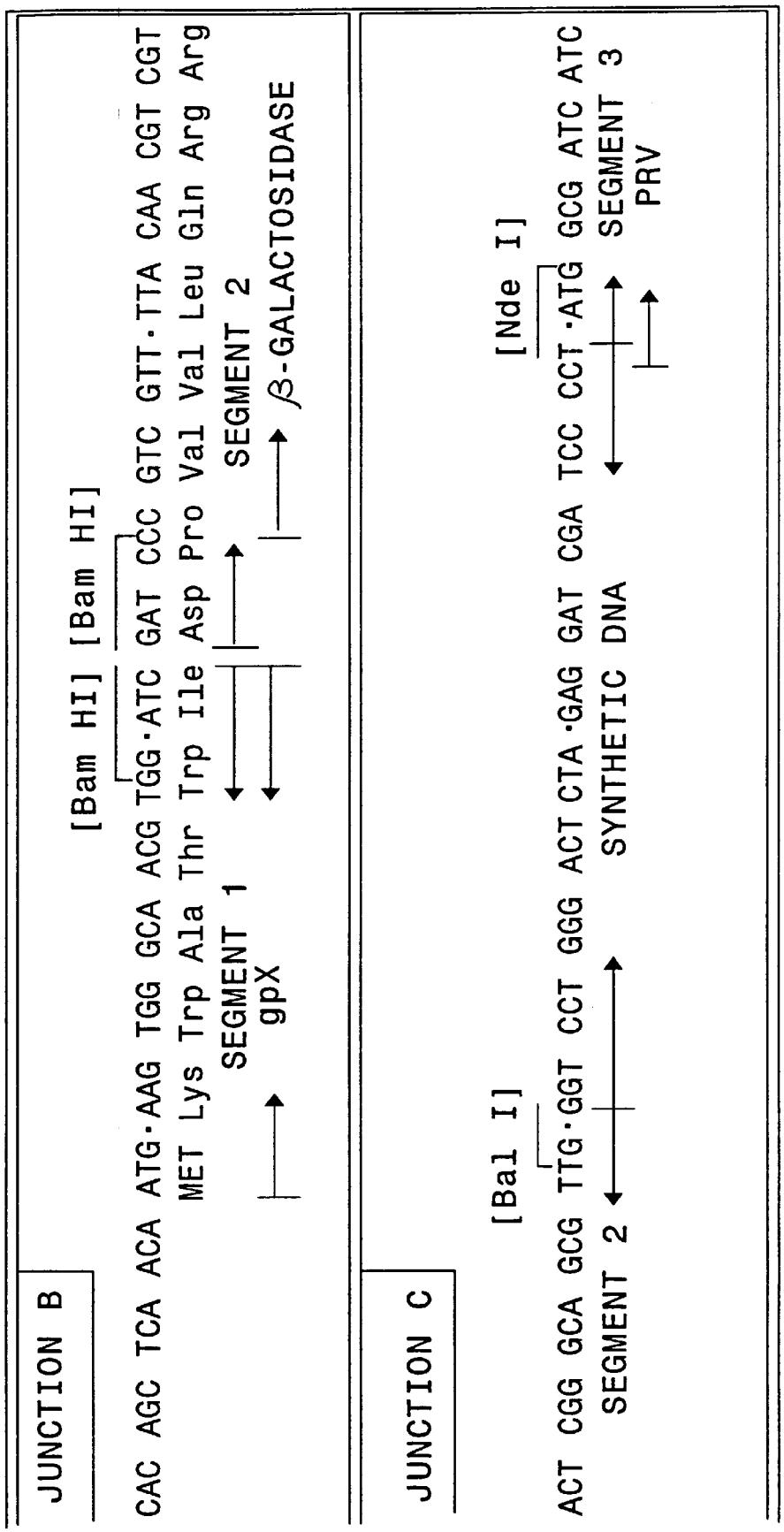
Figure 2C:
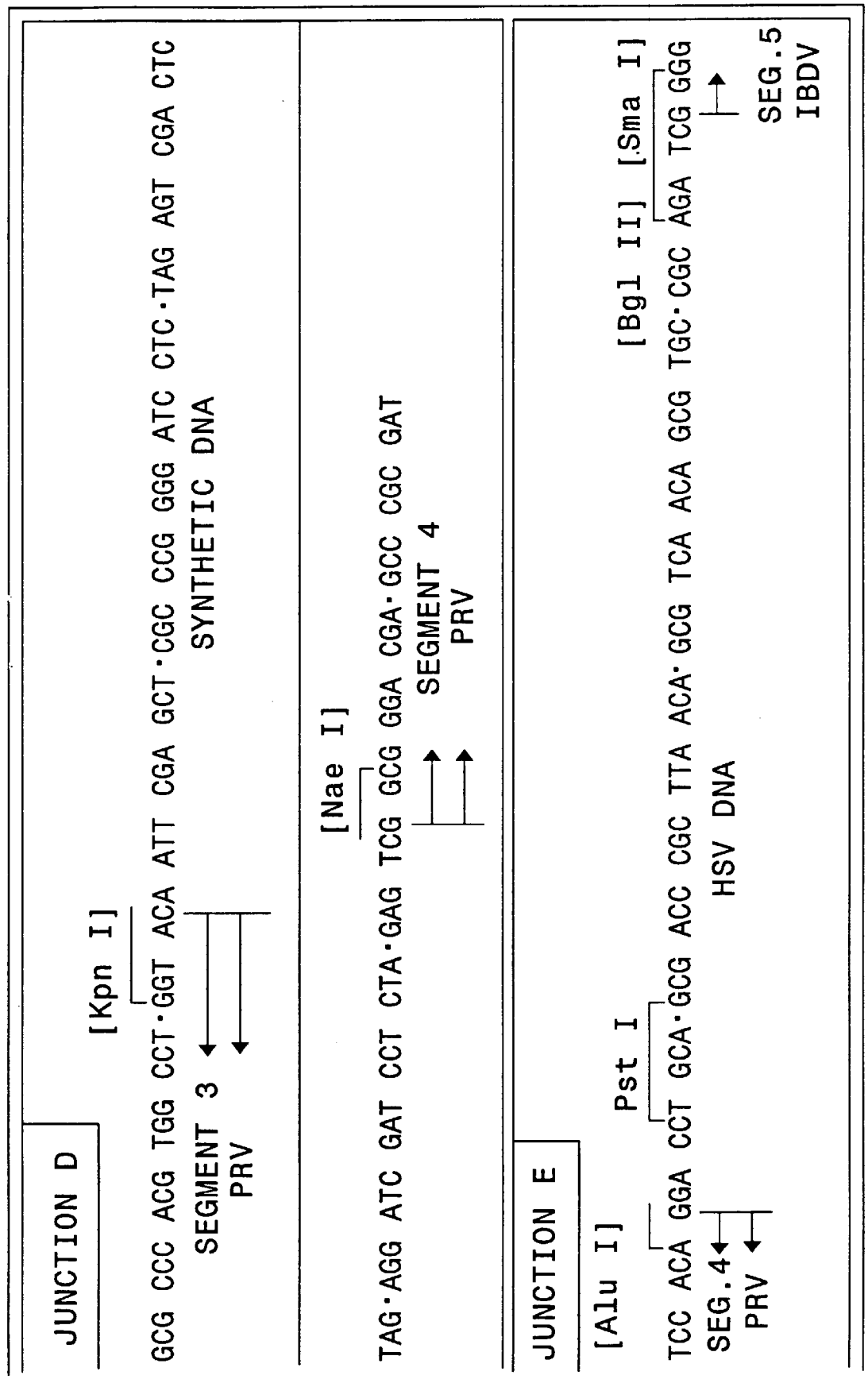
Figure 2D:
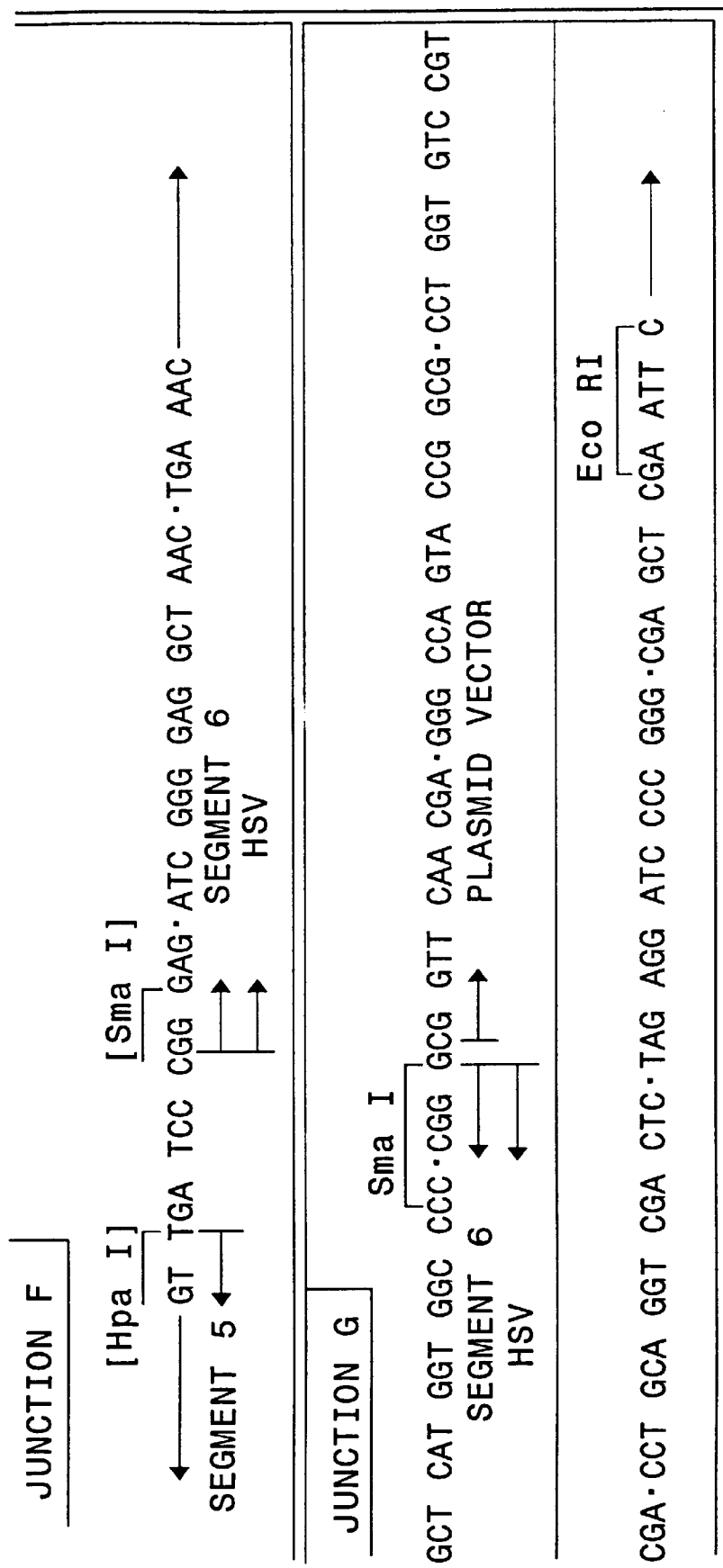

FIGS. 2A, 2B, 2C and 2D show insertion in Plasmid 191-47. FIG. 2A contains a diagram showing the orientation of DNA fragments assembled in plasmid 191-47. FIGS. 2A to 2D show the sequences located at each of the junctions between the DNA fragments in plasmid 191-47. (SEQ ID NOs: 20, 21, 22, 23, 24, 25, 26, and 27).

FIGS. 3A, 3B, and 3C show details of S-HVT-003 Construction.

FIG. 3A shows restriction map of HVT DNA in the region of the BamHI #16 fragment. This fragment is contained within large HindIII fragment. FIG. 3A also shows the XhoI site which was first changed to an EcoRI (R) site by use of a "linker" and standard cloning procedures. FIG. 3B also shows details of the construction of the beta-gal gene and IBVD gene inserted into the BamHI #16 fragment for use in homologous recombination. Both genes were under the control of the PRV gX gene promoter (gX).

FIG. 3C shows the S-HVT-003 genome, including the location of the two inserted foreign genes, β-gal and IBDV.

In FIG. 3: H=HindIII; B=BamHI; X=XhoI; R=EcoRI; Xb=XbaI; Hp=HpaI; S=SmaI; UL=unique long region; US=unique short region; IR=internal repeat region; TR=terminal repeat region.

FIG. 4 shows a Western blot indicating the differential expression of the IBDV 32 kD antigen in cellular lysates of S-HVT-003 infected cells (32 kD present) and S-HVT-001 infected cells (32 kD negative). IBDV specific polypeptides were identified by probing the blot with hyper-immune rat antiserum directed against denatured IBDV virions. This serum reacts primarily with the immunodominant 32 kD antigen (IBDV VP3). The lanes on the blot contain: 1) protein molecular weight standards, 2) uninfected CEF cells, 3) S-HVT-001 infected CEF's, 4) 5) & 6) S-HVT-003 and 7) IBDV virion polypeptides.

FIG. 5 shows a Western blot indicating the differential expression of the IBDV 42 kD (VP2) antigen in cellular lysates of S-HVT-003 infected cells (42 kD present) and S-HVT-001 infected cells (42 kD negative). IBDV specific polypeptides were identified using a VP2 specific rabbit anti-peptide antiserum. The lanes contain: 1) protein molecular weight standards, 2) wild-type HVT infected CEF's, 3) S-HVT-001 infected CEF's, 4) S-HVT-003 infected CEF's, 5) S-HVT-003 infected CEF's, and 6) IBDV virion polypeptides.

Figure 6A:
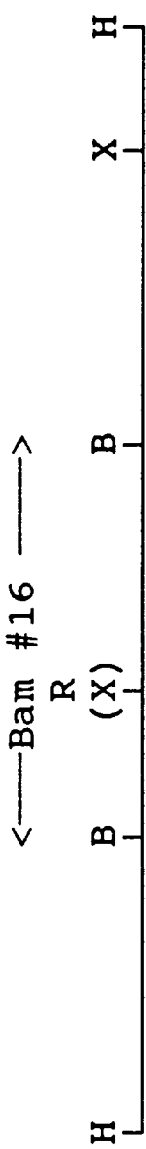
Figure 6B:
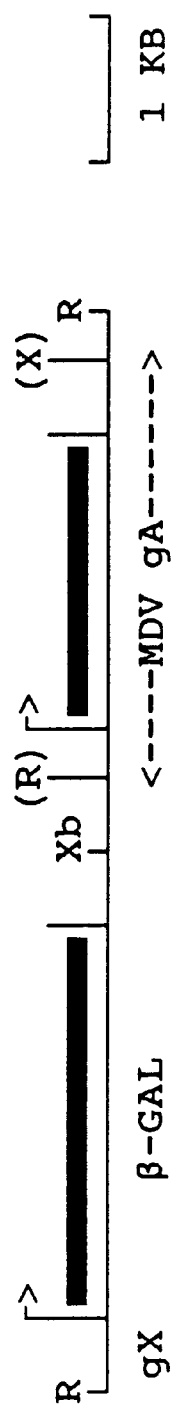
Figure 6C:
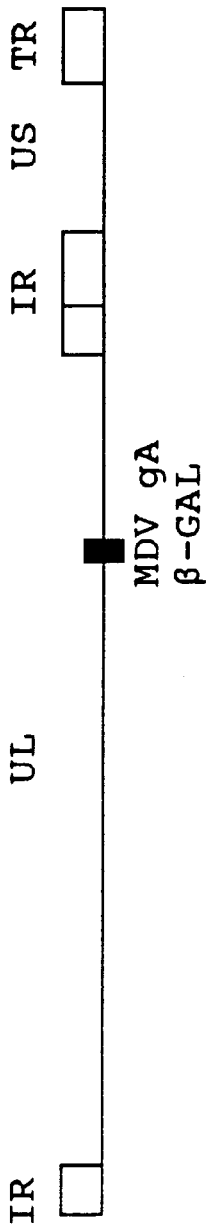

FIGS. 6A, 6B, and 6C provide details of S-HVT-004 Construction.

FIG. 6A is a restriction map of HVT DNA in the region of the BamHI #16 fragment. This fragment is contained within a large HindIII fragment. Shown also is the XhoI site (X) where applicants have made their insertion. Before the insertion, the XhoI was first changed to EcoRI (R) site by use of a "linker" and standard cloning procedures.

FIG. 6B provides details of the construction of the β-gal gene and MDV gA gene inserted into the BamHI #16 fragment for use in homologous recombination. Beta-gal was under the control of the PRV gX gene promoter (gX), while the MDV gA gene was under the control of its own promoter.

FIG. 6C is of S-HVT-004 genome showing the location of the two inserted foreign genes, β-gal and MDV gA.

In FIG. 6, H=HindIII; B=BamHI; X=XhoI; R=EcoRI; Xb=XbaI; UL=unique long region; US=unique short region; IR=internal repeat region; TR=terminal repeat region.

Figure 7B:
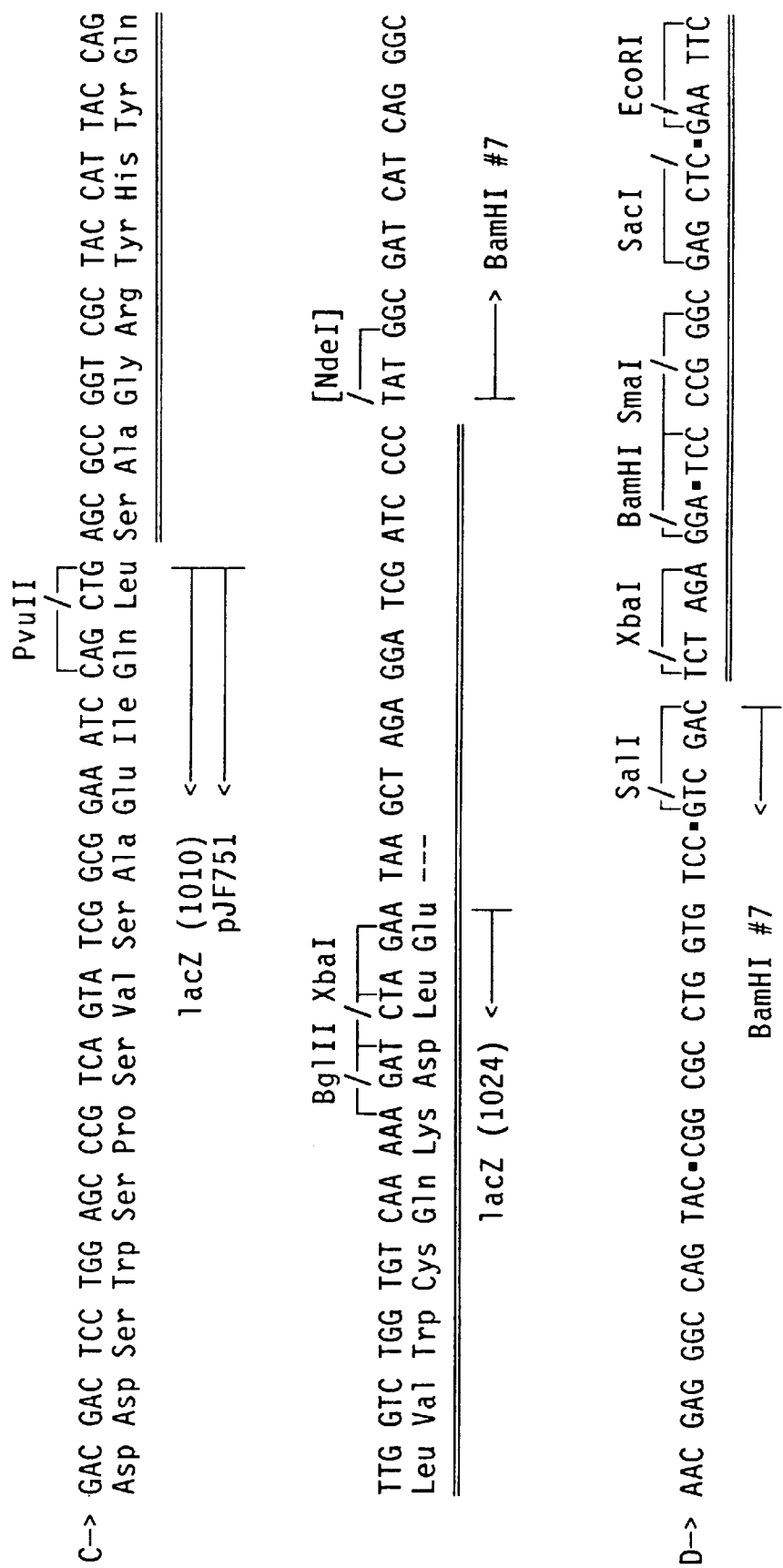

FIGS. 7A and 7B provide a detailed description of the β-galactosidase (lacZ) marker gene insertion in homology vector 467-22.A12. FIG. 7A shows a diagram indicating the orientation of DNA fragments assembled in the marker gene. The origin of each fragment is described in the Materials and Methods section. FIGS. 7A and 7B show the DNA sequences located at the junctions between DNA fragments and at the ends of the marker gene (SEQ ID NOs: 28, 29, 30, 31, 32, and 33). FIGS. 7A and 7B further show the restriction sites used to generate each DNA fragment at the appropriate junction and the location of the lacZ gene coding region. Numbers in parenthesis ( ) refer to amino acids, and restriction sites in brackets [ ] indicate the remnants of sites which were destroyed during construction. The following abbreviations are used, pseudorabies virus (PRV), lactose operon Z gene (lacZ), Escherichia coli (E. Coli), polyadenylation signal (pA), and glycoprotein X (gpX).

Figure 8:
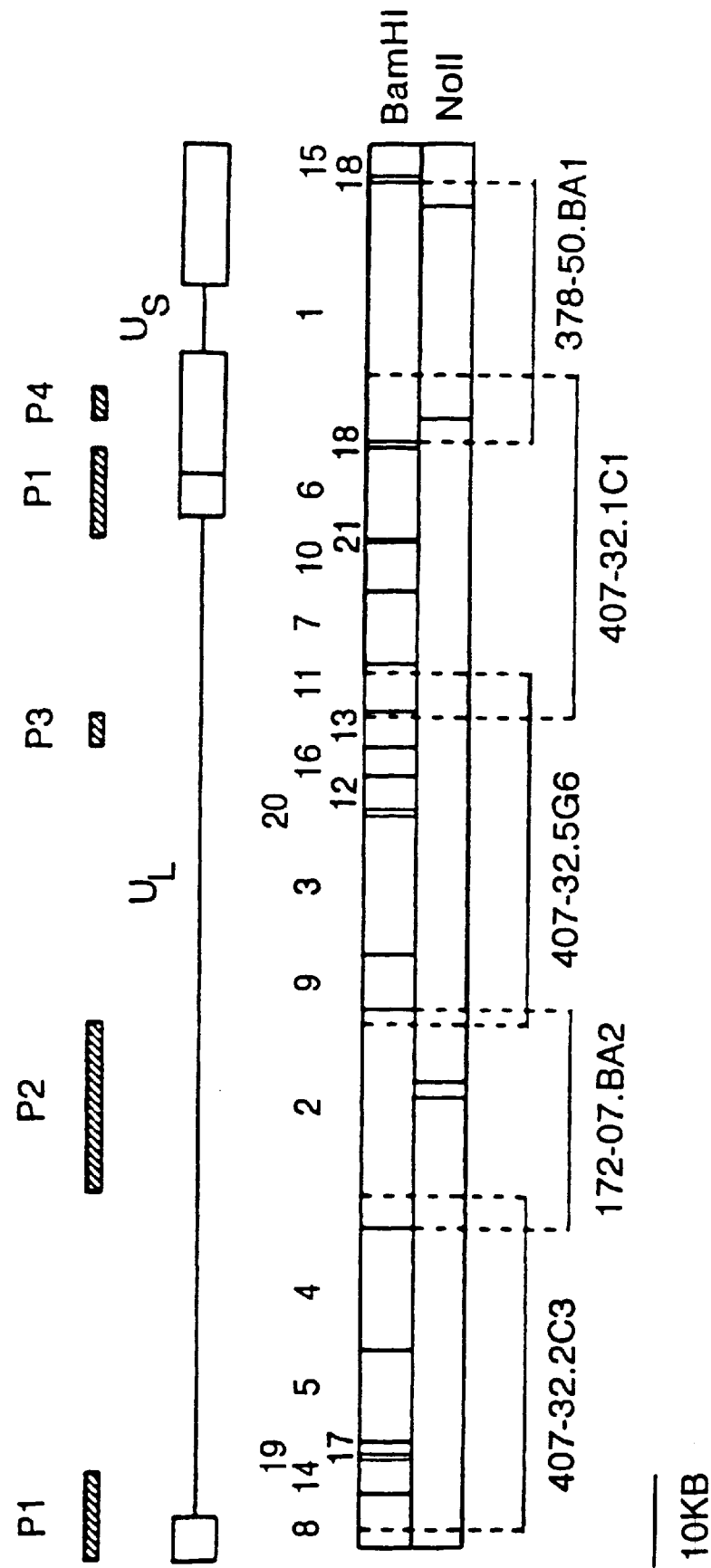

FIG. 8 is a BamHI, NotI restriction map of the HVT genome. The unique long (UL) and unique short (US) regions are shown. The long and short region repeats are indicated by boxes. The BamHI fragments are numbered in decreasing order of size. The location of probes P1–P4 are indicated. The origin of each probe is as follows:

P1-BamHI #6, P2-BamHI #2, P3-BamHI #13, and P4-4.0 kb BglII to StuI subfragment of HVT genomic XbaI fragment #5 (8.0 kb).

Figure 9:
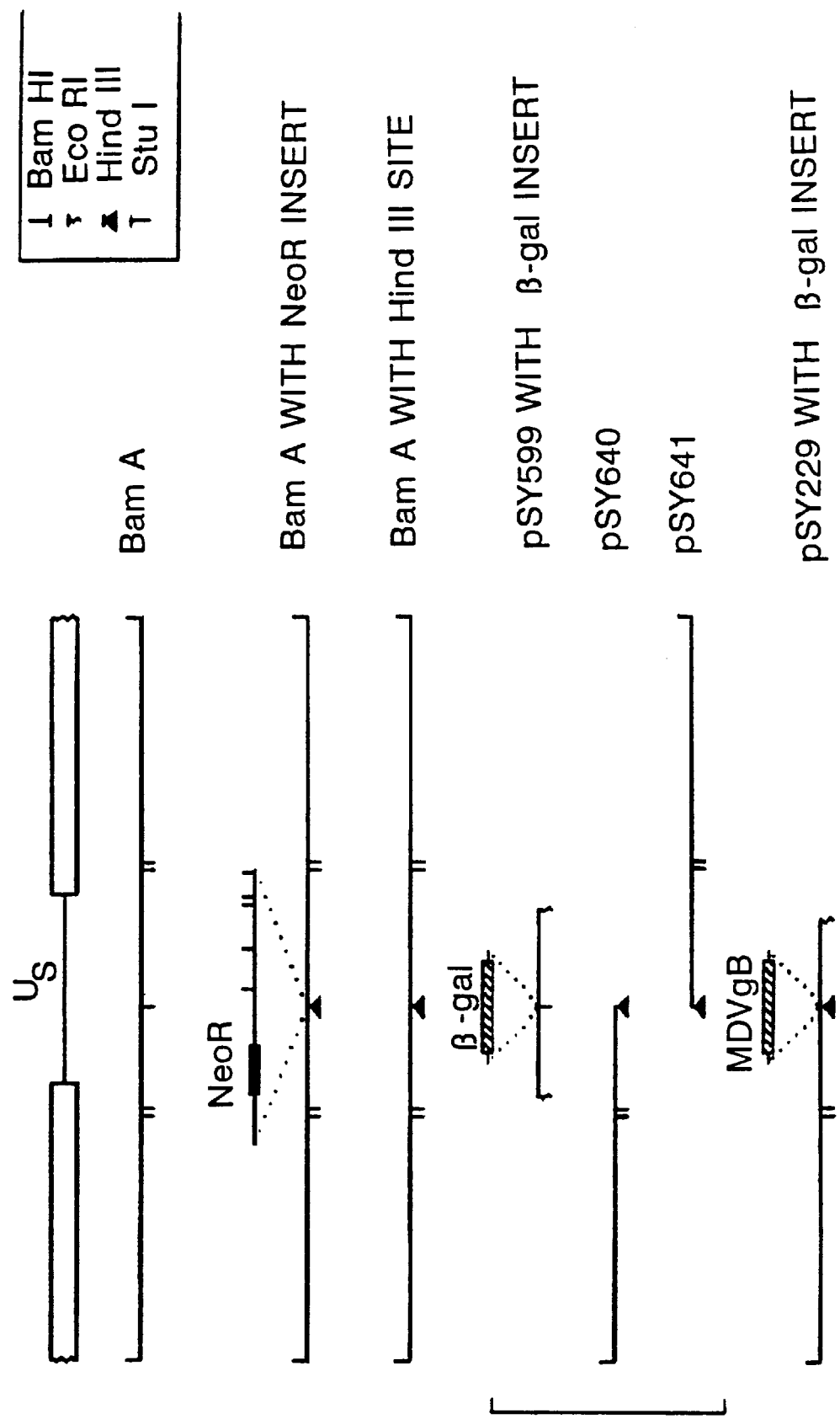

FIG. 9 outlines the procedure for construction of plasmid pSY229.

Figure 10A:
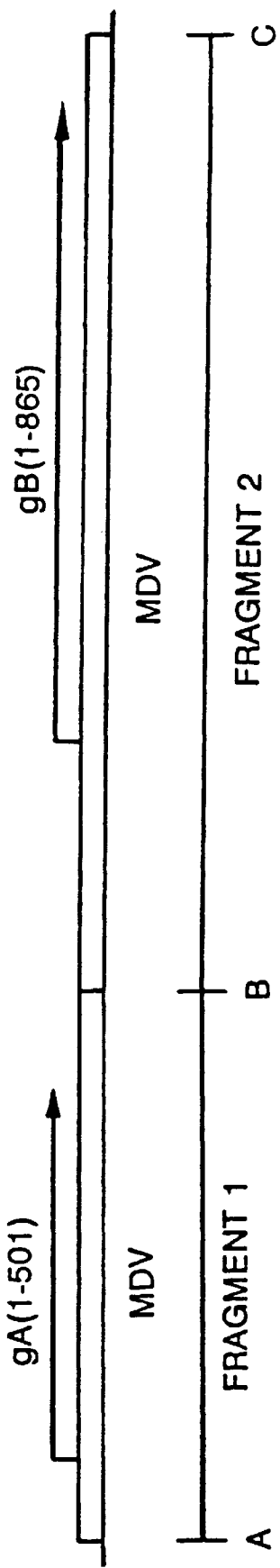
Figure 10B:
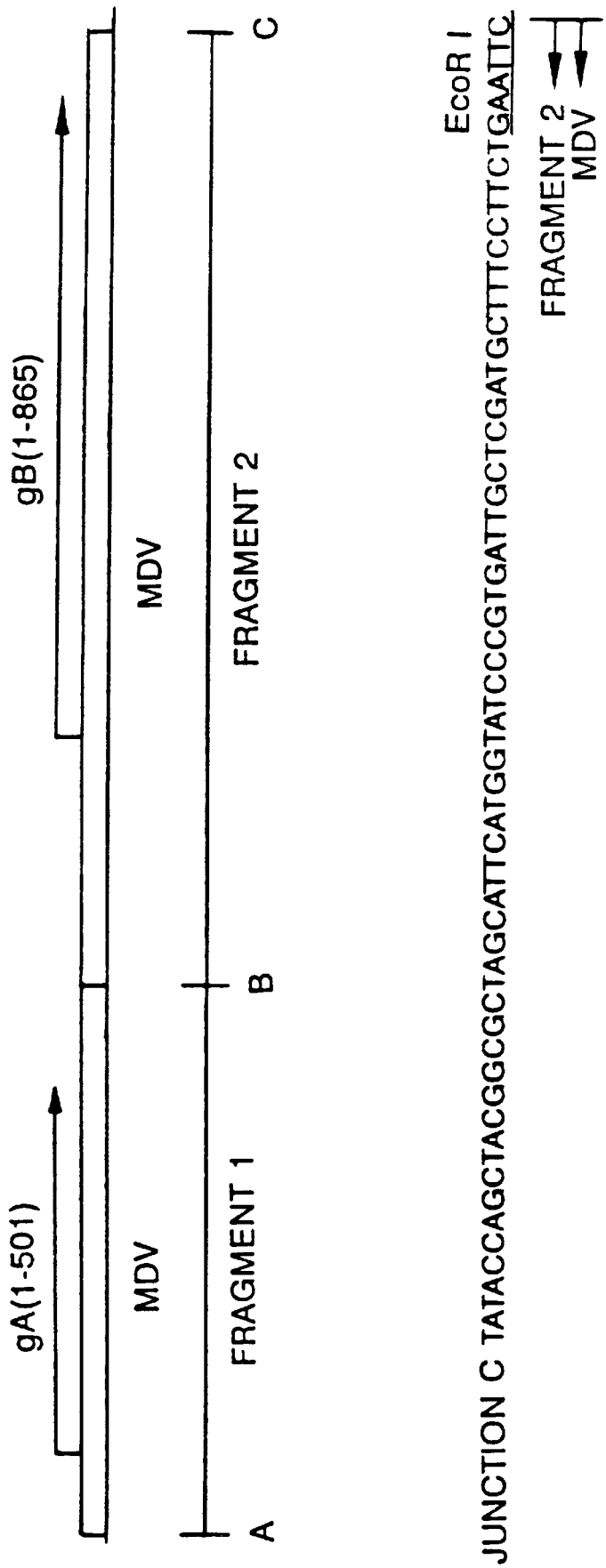

FIGS. 10A and 10B provide a detailed description of the MDV gene cassette insert in Homology Vectors 456-18.18 and 456-17.22. FIGS. 10A and 10B show a diagram indicating the orientation of DNA fragments assembled in the cassette and the location of the MDV gA and gB genes. The origin of each fragment is described in the Materials and Methods section. The sequences located at the junctions between each fragment and at the ends of the marker gene are shown in FIGS. 10A and 10B, including junction A (SEQ ID NO: 34), junction B (SEQ ID NO: 35), and junction C (SEQ ID NO: 36). The restriction sites used to generate each fragment are indicated at the appropriate junction. Numbers in parenthesis ( ) refer to amino acids, and restriction sites in brackets [ ] indicate the remnants of sites which were destroyed during construction.

Figure 11A:
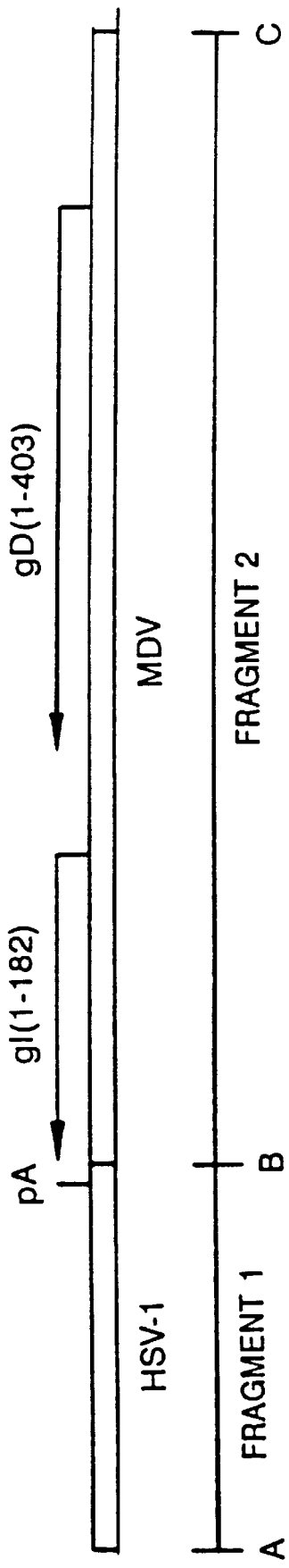

FIGS. 11A and 11B provide a detailed description of the HindIII fragment insert in Homology Vector 556-41.5. The diagram of FIGS. 11A and 11B show the orientation of DNA fragments assembled in the cassette. The origin of each fragment is described in the Materials and Methods section. FIGS. 11A and 11B further show the DNA sequences located at the junctions between each DNA fragment of the plasmid and at the ends of the marker gene, including junction A (SEQ ID NO: 37), junction B (SEQ ID NO: 38), and junction C (SEQ ID NO: 39). The restriction sites used to generate each fragment are indicated at the appropriate junction. The location of the MDV gD and a portion of the gI gene is also given. Numbers in parenthesis ( ) refer to amino acids, and restriction sites in brackets [ ] indicate the remnants of sites which were destroyed during construction.

FIGS. 12A, 12B, and 12C provide a detailed description of the SalI fragment insert in Homology Vector 255-18.B16. FIG. 12A shows a diagram indicating the orientation of DNA fragments assembled in the cassette. The origin of each fragment is described in the Materials and Methods section. FIGS. 12A to 12C further show the DNA sequences located at the junctions between each fragment and at the ends of the marker gene are shown, including junction A (SEQ ID NO: 40), junction B (SEQ ID NO: 41), junction C (SEQ ID NO: 42), junction D (SEQ ID NO: 43), junction E (SEQ ID NO: 44), junction F(SEQ ID NO: 45), junction G (SEQ ID NO: 46), and junction H (SEQ ID NO: 47). The restriction sites used to generate each fragment are indicated at the appropriate junction. The location of the NDV F and lacZ-NDV HN hybrid gene are shown. Numbers in parenthesis ( ) refer to amino acids, and restriction sites in brackets [ ] indicate the remnants of sites which were destroyed during construction.

Figure 13A:
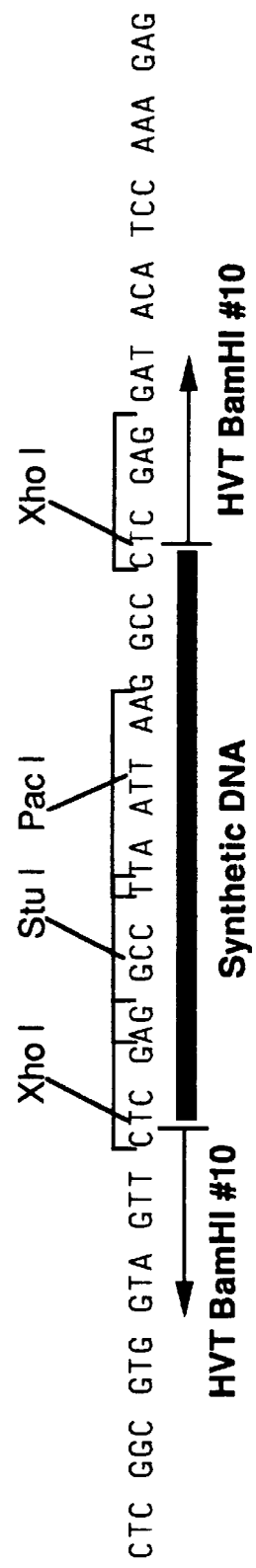
Figure 13B:
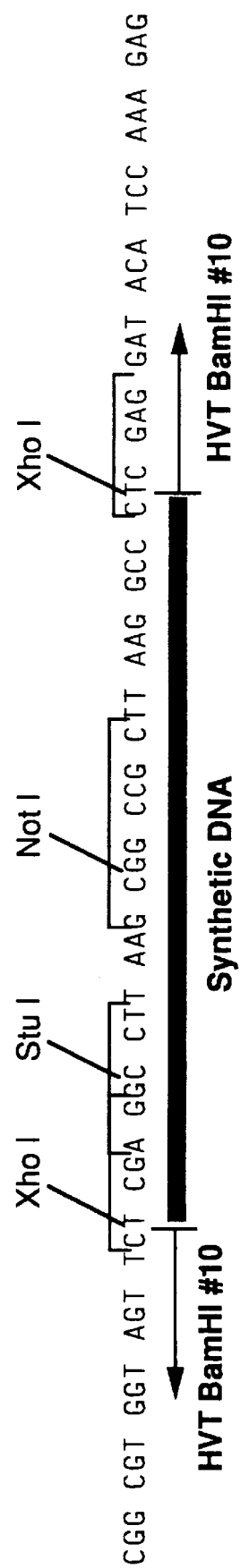

FIGS. 13A and 13B show how the unique XhoI site of the BamHI #10 fragment of the HVT genome was converted into a PacI site and a NotI site by insertion of the synthetic DNA sequence at the XhoI site (Nucleotides #1333-1338; SEQ ID NO. 48). FIG. 13A shows the XhoI site converted into a PacI site to generate Plasmid 654-45.1 (SEQ ID NO. 55) and FIG. 13B shows the XhoI site converted into a NotI site to generate Plasmid 686-63.A1 (SEQ ID NO. 56).

Figure 14:
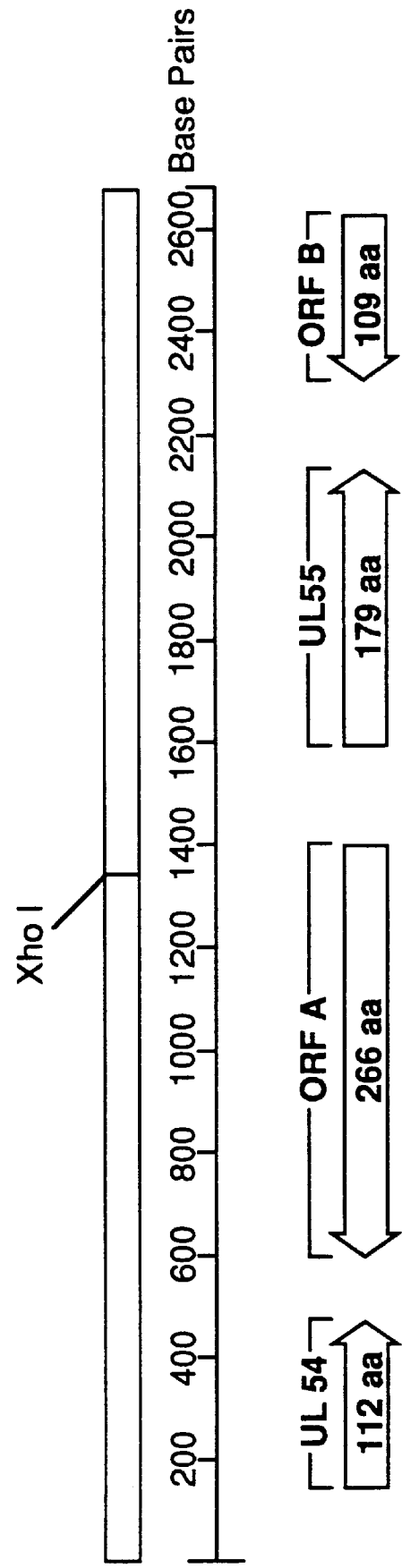

FIG. 14 shows a restriction map and open reading frames of the sequence surrounding the insertion site within the unique long of HVT (SEQ ID NO. 48). This map shows the XhoI restriction site (SEQ ID NO. 48; Nucl. 1333-1338) used for insertion of foreign genes. Also shown are four open reading frames within this sequence. ORF A is interrupted by insertion of DNA into the XhoI site. The ORF A amino acid sequence (SEQ ID NO. 50; Nucl. 1402 to 602; 267 amino acids) shows no significant sequence identity to any known amino acid sequence in the protein databases. UL 54 (SEQ ID NO. 49; Nucl. 146 to 481; 112 amino acids) and UL55 (SEQ ID NO. 51; Nucl. 1599 to 2135; 179 amino acids) show significant sequence identity to the herpes simplex virus type I UL54 and UL55 proteins, respectively. ORF B (SEQ ID NO. 52; Nucl. 2634 to 2308; 109 amino acids) shows no significant sequence identity to any known amino acid sequence in the protein databases. Searches were performed on NCBI databases using Blast software.

Figure 15:
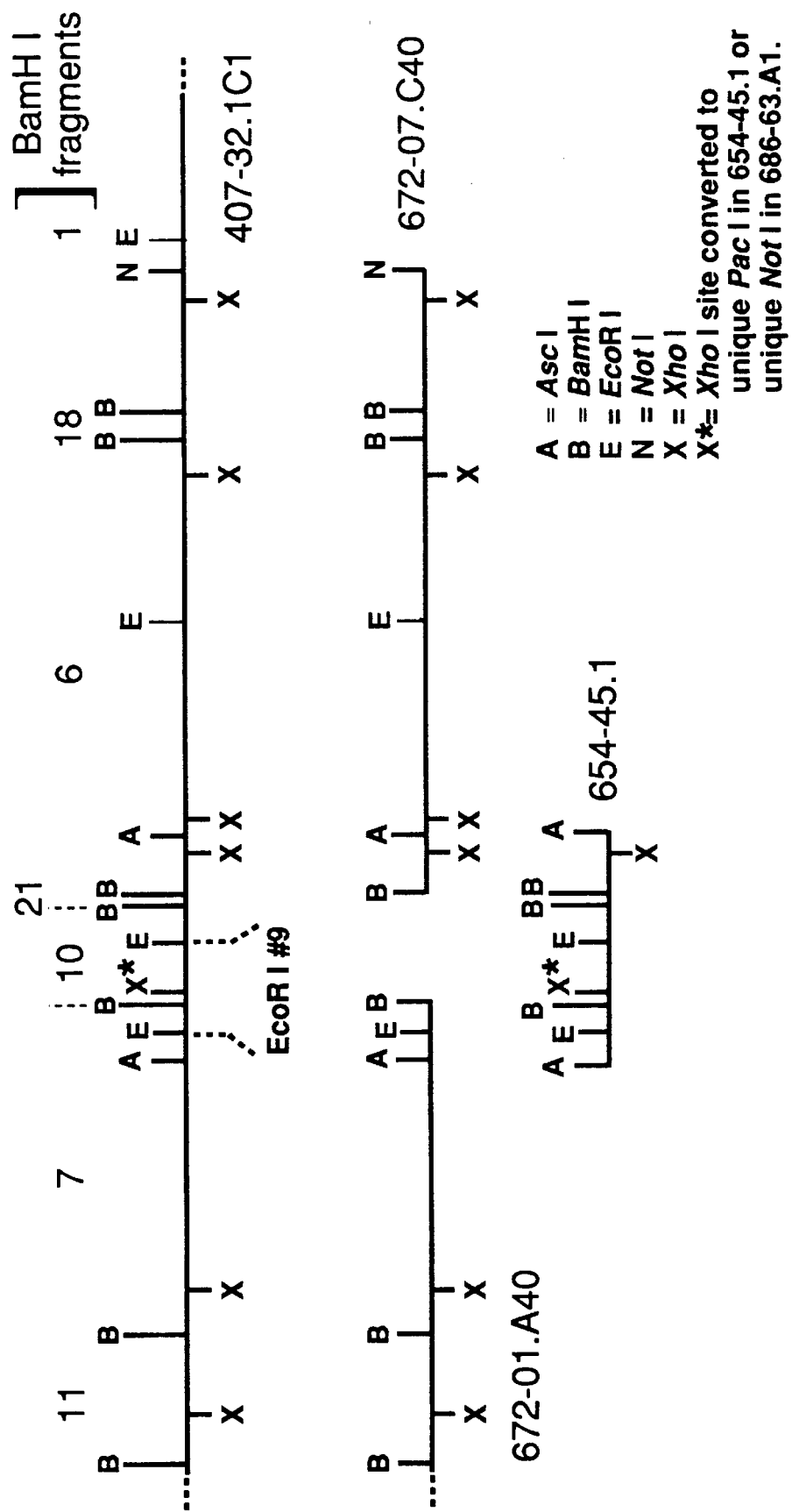

FIG. 15 shows a restriction map of cosmids 407-32.1C1, 672-01.A40, 672-07.C40, and 654-45.1. The overlap of HVT genomic DNA fragments EcoRI #9 and BamHI #10 is illustrated. A unique XhoI site within the EcoRI #9 and BamHI #10 fragments has been converted to a unique PacI site in Plasmid 654-45.1 or a unique NotI site in Plasmid 686-63.A1.

DETAILED DESCRIPTION OF THE INVENTION

The present invention provides a recombinant herpesvirus of turkeys (HVT) comprising a foreign DNA sequence inserted into a non-essential site in the HVT genome. The foreign DNA sequence is capable of being expressed in a host cell infected with the recombinant HVT and its expression is under control of a promoter located upstream of the foreign DNA sequence.

For purposes of this invention "a non-essential site in the HVT genome" means a region in the HVT genome which is not necessary for the viral infection or replication.

For purposes of this invention, "a foreign DNA sequence" means DNA which codes for a gene or part thereof that does not naturally in the HVT genome.

In one embodiment of the present invention, the foreign DNA sequence inserted into the HVT genome encodes a polypeptide. Preferably, the polypeptide is antigenic in the animal into which the recombinant HVT is introduced. Preferably, this antigenic polypeptide is a linear polymer of more than 10 amino acids linked by peptide bonds which stimulates the animal to produce antibodies.

Also provided are several appropriate insertion sites in the HVT genome useful for constructing the recombinant herpesvirus of the present invention. One such site is the BamHI #16 fragment of the HVT genome. A preferred insertion site within the BamHI #16 fragment lies within an open reading frame encoding HVT UL43 and a preferred insertion site within that open reading frame is a XhoI restriction endonuclease site.

Two other insertion sites are the EcoRI #9 fragment and the BamHI #10 fragment of the HVT genome, a preferred insertion site within both of those fragments being a XhoI restriction endonuclease site.

Yet another insertion site is the HVT US2 gene, with a preferred insertion site within it being a StuI restriction endonuclease site.

In one embodiment of the present invention, the recombinant herpesvirus of turkeys (HVT) contains a foreign DNA sequence encoding a detectable marker. Preferably, the detectable marker is E. coli B-galactosidase. Preferably, such recombinant HVT is designated S-HVT-001, S-HVT-014, or S-HVT-012.

S-HVT-012 has been deposited on Oct. 15, 1992 pursuant to the Budapest Treaty on the International Deposit of Microorganism for the Purposes of Patent Procedure with the Patent Culture Depository of the American Type Culture Collection, 12301 Parklawn Drive, Rockville, Md. 20852 U.S.A. under ATCC Accession No. VR 2382.

S-HVT-014 has been deposited on Dec. 7, 1993 pursuant to the Budapest Treaty on the International Deposit of Microorganisms for the Purpose of Patent Procedure with the Patent Culture Depository of the American Type Culture Collection, 12301 Parklawn Drive, Rockville, Md. 20852 U.S.A. under ATCC Accession No. VR 2440.

In one embodiment of the present invention, the recombinant herpesvirus (HVT) contains a foreign DNA sequence encoding an antigenic polypeptide from infectious bursal disease virus (IBDV), Marek's disease virus (MDV), Newcastle disease virus (NDV), infectious laryngotracheitis virus (ILTV), or infectious bronchitis virus (IBV).

When the foreign DNA sequence of the recombinant HVT of the present invention encodes an antigenic polypeptide from infectious bursal disease virus (IBDV), it is preferred that the antigenic polypeptide is IBDV VP2, VP3 or VP4 protein. Such recombinant HVT can be further engineered to contain a foreign DNA sequence encoding a detectable marker, such as E. coli B-galactosidase.

Recombinant HVT designated S-HVT-003 and S-HVT-096 are each an embodiment of a recombinant HVT comprising foreign DNA sequence encoding an antigenic polypeptide from IBDV and encoding a detectable marker. S-HVT-003 has been deposited on Jul. 21, 1987 pursuant to the Budapest Treaty on the International Deposit of Microorganism for the Purposes of Patent Procedure with the Patent Culture Depository of the American Type Culture Collection, 12301 Parklawn Drive, Rockville, Md. 20852 U.S.A. under ATCC Accession No. VR 2178).

The present invention also provides a recombinant HVT which contains one or more foreign DNA sequence encoding an antigenic polypeptide from IBDV as well as one or more foreign DNA sequence encoding an antigenic polypeptide from MDV. Preferably, the IBDV antigenic polypeptide is IBDV VP2, VP3, or VP4 and the MDV antigenic polypeptide is MDV glycoprotein B (gB), glycoprotein D (gD), or glycoprotein A (gA).

In one embodiment, a recombinant HVT contains foreign DNA sequence encoding IBDV VP2, MDV gA, MDV gD, and MDV gB. Preferably, such recombinant virus is designated S-HVT-137 or S-HVT-143.

The present invention provides a recombinant HVT which contains a foreign DNA sequence encoding an antigenic polypeptide from MDV. Preferably, the antigenic polypeptide is MDV gB, gA, or gD.

One embodiment of a recombinant HVT containing a foreign DNA sequence encoding MDV gA is a recombinant HVT designated S-HVT-004.

An embodiment of a recombinant HVT containing a foreign DNA sequence encoding MDV gB is also provided and this recombinant HVT is designated S-HVT-045. S-HVT-045 has been deposited on Oct. 15, 1992 pursuant to the Budapest Treaty on the International Deposit of Microorganism for the Purposes of Patent Procedure with the Patent Culture Depository of the American Type Culture Collection, 12301 Parklawn Drive, Rockville, Md. 20852 U.S.A. under ATCC Accession No. VR 2383.

The present also invention includes recombinant HVTs engineered to contain more than one foreign DNA sequence encoding an MDV antigen. For example, a foreign DNA sequence encoding MDV gA and gB can both be vectored into the HVT genome. Furthermore, a recombinant HVT can be constructed to include a foreign DNA sequence encoding MDV gA, gB and gD.

Recombinant HVT designated S-HVT-046 and S-HVT-047 provide embodiments of a recombinant HVT containing foreign DNA sequence encoding MDV gA and gB; recombinant HVT designated S-HVT-048 and S-HVT-062 provide embodiments of a recombinant HVT containing foreign DNA sequence encoding MDV gA, gB and gD. S-HVT-062 has been deposited on Feb. 23, 1993 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2401.

The present invention provides a recombinant HVT containing a foreign DNA sequence encoding an antigenic polypeptide from Newcastle disease virus (NDV). In such case, it is preferred that the antigenic polypeptide is NDV fusion (F) protein or NDV hemagglutinin-neuraminidase (HN) or a recombinant protein comprising E. coli B-galactosidase fused to NDV HN. One such virus is a recombinant HVT designated S-HVT-007.

The present invention also provides a recombinant HVT which contains one or more foreign DNA sequences encoding an antigenic polypeptide from MDV as well as one or more foreign DNA sequences encoding an antigenic polypeptide from NDV. Preferably, the MDV antigenic polypeptide is MDV gB, gD, or gA and the NDV antigenic polypeptide is NDV F or HN.

In one embodiment of the invention, the recombinant HVT contains foreign DNA sequence encoding MDV gB, MDV gA, and NDV F. Preferably, this recombinant HVT is designated S-HVT-048.

In one embodiment of the invention, the recombinant HVT contains foreign DNA sequence encoding MDV gB, MDV gA, and NDV HN. Preferably, this recombinant HVT is designated S-HVT-049.

In another embodiment of the invention, the recombinant HVT contains foreign DNA sequence encoding MDV gB, MDV gA, NDV F and NDV HN. Preferably, such recombinant HVT is designated S-HVT-050. S-HVT-050 has been deposited on Feb. 23, 1993 pursuant to the Budapest Treaty on the International Deposit of Microorganisms for the Purpose of Patent Procedure with the Patent Culture Depository of the American Type Culture Collection, 12301 Parklawn Drive, Rockville, Md. 20852 U.S.A. under ATCC Accession No. VR 2400.

In yet another embodiment of the invention, the recombinant HVT contains foreign DNA sequence encoding MDV gB, MDV gA, MDV gD, NDV F and NDV HN. Preferably, such recombinant HVT is designated S-HVT-106 or S-HVT-128.

The present invention further provides a recombinant HVT which contains a foreign DNA sequence encoding an antigenic polypeptide from infectious laryngotracheitis virus (ILTV). It is preferred that the antigenic polypeptide is ILTV glycoprotein B (gB), ILTV glycoprotein D (gD), or ILTV glycoprotein I (gI).

Also provided are recombinant HVTs which are engineered to contained more than one foreign DNA sequence encoding an ILTV antigen. For example, ILTV gB and gD can be vectored together into the HVT genome, so can ILTV gD and gI, and ILTV gB, gD and gI. Recombinant HVT designated S-HVT-051, S-HVT-052 and S-HVT-138 are embodiments of such recombinant virus.

The present invention also provides a recombinant HVT which contains one or more foreign DNA sequence encoding an antigenic polypeptide from MDV as well as one or more foreign DNA sequence encoding an antigenic polypeptide from ILTV. Preferably, the MDV antigenic polypeptide is MDV gB, gD, or gA and the ILTV antigenic polypeptide is ILTV gB, gD or gI.

In one embodiment of the invention, the recombinant HVT contains foreign DNA sequence encoding MDV gB, MDV gA, MDV gD, ILTV gD and ILTV gB. Preferably, this recombinant HVT is designated S-HVT-123.

In another embodiment of the invention, the recombinant HVT contains foreign DNA sequence encoding MDV gB, MDV gA, MDV gD, ILTV gI and ILTV gD. Preferably, this recombinant HVT is designated S-HVT-139 or S-HVT-140.

The present invention further provides a recombinant HVT which contains a foreign DNA sequence encoding an antigenic polypeptide from infectious bronchitis virus (IBV). Preferably, the antigenic polypeptide is IBV spike protein or IBV matrix protein.

The present invention also provides a recombinant HVT which contains one or more foreign DNA sequence encoding an antigenic polypeptide from IBV as well as one or more foreign DNA sequence encoding an antigenic polypeptide from MDV. Preferably, the IBV antigenic polypeptide is IBV spike protein or IBV matrix protein, and the MDV antigenic polypeptide is MDV gB, gD, or gA. One embodiment of such recombinant virus is designated S-HVT-066.

The expression of the inserted foreign DNA sequence is under control of a promoter located upstream of the foreign DNA sequence. Preferably, the promoter is a herpesvirus promoter. Preferably, the promoter is selected from a group consisting of PRV gX promoter, MDV gB promoter, MDV gA promoter, MDV gD promoter, ILTV gB promoter, ILTV gD promoter, HSV-1 alpha 4 promoter and HCMV immediate early promoter.

The present invention further provides for a homology vector for producing a recombinant herpesvirus of turkeys by inserting foreign DNA sequence into the HVT genome. The homology vector comprises a double-stranded DNA molecule consisting essentially of a double-stranded foreign DNA sequence, with at one end of the foreign DNA sequence, double-stranded DNA homologous to the genomic DNA located at one side of a non-essential site of the HVT genome, and at the other end of the foreign DNA sequence, double-stranded DNA homologous to the HVT genomic DNA sequence located at the other side of the same site. DNA sequence corresponding to a promoter is located upstream of the foreign DNA sequence and controls its expression.

In one embodiment of the invention, the foreign DNA sequence of the homology vector encodes a polypeptide. In one embodiment of the invention, the polypeptide is antigenic in the animal into which the recombinant herpesvirus of turkeys is introduced. Preferably, the antigenic polypeptide is from infectious bursal disease virus, Marek's disease virus, Newcastle disease virus, infectious laryngotracheitis virus, or infectious bronchitis virus. Preferably, the antigenic polypeptide is selected from a group consisting essentially of infectious bursal disease virus VP2 protein, infectious bursal disease virus VP3 protein, infectious bursal disease virus VP4 protein, Marek's disease virus glycoprotein gB, Marek's disease virus glycoprotein gA, Marek's disease virus glycoprotein gD, Newcastle disease virus fusion (F) protein, Newcastle disease virus hemagglutinin-neuraminidase (HN), infectious laryngotracheitis virus glycoprotein I, infectious laryngotracheitis virus glycoprotein D, infectious laryngotracheitis virus glycoprotein B, infectious bronchitis virus spike protein, or infectious bronchitis virus matrix protein.

In one embodiment of the invention, the polypeptide is a detectable marker. Preferably, the detectable marker is *E. coli* B-galactosidase.

In one embodiment of the invention, the double-stranded herpesvirus of turkeys DNA is homologous to DNA sequence present within the BamHI #16 fragment of the herpesvirus of turkeys genome. Preferably, the double-stranded herpesvirus of turkeys DNA is homologous to DNA sequences present within the open reading frame encoding UL 43 protein of the herpesvirus of turkeys genome. Preferably, this homology vector is designated 172-29.31.

For purposes of this invention, a "homology vector" is a plasmid constructed to insert foreign DNA sequence in a specific site on the genome of a herpesvirus of turkeys.

In one embodiment of the invention, the double-stranded herpesvirus of turkeys DNA is homologous to DNA sequences present within the EcoRI #9 fragment or BamHI #10 fragment of the herpesvirus of turkeys genome. Preferably, this homology vector is designated 172-63.1.

In one embodiment of the invention, the double-stranded herpesvirus of turkeys DNA is homologous to DNA sequence present within the US2 gene coding region of the herpesvirus of turkeys genome. Preferably, this homology vector is designated 435-47.1.

The invention further provides a vaccine which comprises an effective immunizing amount of a recombinant herpesvirus of turkeys of the present invention and a suitable carrier.

Suitable carriers for the herpesvirus of turkeys vaccine are well known in the art and include proteins, sugars, etc. One example of such suitable carrier is a physiologically balanced culture medium containing one or more stabilizing agents such as stabilized, hydrolyzed proteins, lactose, etc.

For purpose of this invention, an "neffective immunizing amount" of recombinant herpesvirus of the present invention is within the range of 102 to 109 PFU/dose.

The present invention further provides a method of immunizing a fowl. The present invention also provides a method of immunizing a fowl in ovo. For purposes of this invention, this includes immunizing a fowl against infectious bursal disease virus, Marek's disease virus, Newcastle disease virus, infectious laryngotracheitis virus, or infectious bronchitis virus. The method comprises administering to the fowl an effective immunizing dose of the vaccine of the present invention. The vaccine may be administered by any of the methods well known to those skilled in the art, for example, by intramuscular, subcutaneous, intraperitoneal or intravenous injection. Alternatively, the vaccine may be administered intranasally, orally or intraocularly.

The present invention also provides a host cell infected with a recombinant herpesvirus of turkeys of the present invention. Preferably, the host cell is an avian cell.

For purposes of this invention, a "host cell" is a cell used to propagate a vector and its insert. Infecting the cell was accomplished by methods well known to those skilled in the art, for example, as set forth in DNA TRANSFECTION FOR GENERATING RECOMBINANT HERPESVIRUS in Materials and Methods.

A recombinant herpesvirus of turkeys of the present invention provides a way for distinguishing an animal vaccinated with the vaccine of the present invention from an animal infected with a naturally-occurring, wild-type infectious bursal disease virus, Marek's disease virus, Newcastle disease virus, infectious laryngotracheitis virus, or infectious bronchitis virus. This is possible because recombinant herpesvirus of turkeys contain foreign DNA which encodes a limited number of antigens from the above mentioned viruses that are needed to confer protective immunity to the corresponding pathogens. Consequently, host animals vaccinated with those recombinant herpesviruses of turkeys can be distinguished from ones which have been infected with wild-type infectious bursal disease virus, Marek's disease virus, Newcastle disease virus, infectious laryngotracheitis virus, or infectious bronchitis virus by the absence of antigens that are normally present in the wild type viruses.

Methods for constructing, selecting and purifying recombinant herpesvirus of turkeys are detailed below in Materials and Methods.

Materials and Methods

PREPARATION OF HERPESVIRUS OF TURKEYS STOCK SAMPLES. Herpesvirus of turkeys stock samples were prepared by infecting tissue culture cells at a multiplicity of infection of 0.01 PFU/cell in Dulbecco's Modified Eagle Medium (DMEM) containing 2 mM glutamine, 100 units/ml penicillin, 100 units/ml streptomycin (these components are obtained from Irvine Scientific or an equivalent supplier, and hereafter are referred to as complete DME medium) plus 1% fetal bovine serum. After cytopathic effect was complete, the medium and cells were harvested and the cells were pelleted at 3000 rpm for 5 minutes in a clinical centrifuge. Infected cells were resuspended in complete medium containing 20% fetal bovine serum, 10% DMSO and stored frozen at −70° C.

PREPARATION OF HERPESVIRUS OF TURKEY DNA. All manipulations of herpesvirus of turkey (HVT) were made using strain FC-126 (ATCC #584-C). For the preparation of HVT viral DNA from the cytoplasm of infected cells, primary chicken embryo fibroblasts were infected at a MOI sufficient to cause extensive cytopathic effect before the cells overgrew. All incubations were carried out at 39° C. in a humidified incubator with 5% $CO_2$ in air. Best DNA yields were obtained by harvesting monolayers which were maximally infected, but showing incomplete cell lysis (typically 5–7 days). Infected cells were harvested by scraping the cells into the medium using a cell scraper (Costar brand). The cell suspension was centrifuged at 3000 rpm for 10 minutes at 5° C. in a GS-3 rotor (Sorvall Instruments). The resultant pellet was resuspended in cold PBS (20 ml/Roller Bottle) and subjected to another centrifugation for 10 minutes at 3000 rpm in the cold. After decanting the PBS, the cellular pellet was resuspended in 4 ml/roller bottle of RSB buffer (10 mM Tris pH 7.5, 1 mM EDTA, and 1.5 mM $MgCl_2$). NP40 (Nonidet P-40™;Sigma) was added to the sample to a final concentration of 0.5% minutes with occasional mixing. The sample was centrifuged for 10 minutes at 3000 rpm in the cold to pellet the nuclei and remove cellular debris. The supernatant fluid was carefully transferred to a 15 ml Corex centrifuge tube. Both EDTA (0.5M pH 8.0) and SDS (sodium dodecyl sulfate; stock 20%) were added to the sample to final concentrations of 5 mM and 1%, respectively. One hundred $\mu$l of proteinase-K (10 mg/ml; Boehringer Mannheim) was added per 4 ml of sample, mixed, and incubated at 45° C. for 1–2 hours. After this period, an equal volume of water-saturated phenol was added to the sample and gently mixed by hand. The sample was spun in a clinical centrifuge for 5 minutes at 3000 rpm to separate the phases. NaAc was added to the aqueous phase to a final concentration of 0.3M (stock solution 3M pH 5.2), and the nucleic acid precipitated at −70° C. for 30 minutes after the addition of 2.5 volumes of cold absolute ethanol. DNA in the sample was pelleted by spinning for 20 minutes to 8000 rpm in an HB-4 rotor at 5° C. The supernatant was carefully removed and the DNA pellet washed once with 25 ml of 80% ethanol. The DNA pellet was dried briefly by vacuum (2–3 minutes), and resuspended in 50 $\mu$l/roller bottle of infected cells of TE buffer (10 mM Tris pH 7.5, 1 mM EDTA). Typically, yields of viral DNA ranged between 5–10 $\mu$g/roller bottle of infected cells. All viral DNA was stored at approximately 10° C.

POLYMERASE FILL-IN REACTION. DNA was resuspended in buffer containing 50 mM Tris pH 7.4, 50 mM KC, 5 mM $MgCl_2$, and 400 micromolar each of the four deoxynucleotides. Ten units of Klenow DNA polymerase (BRL) were added and the reaction was allowed to proceed for 15 minutes at room temperature. The DNA was ther phenol extracted and ethanol precipitated as above.

DNA SEQUENCING. Sequencing was performed using the USB Sequenase Kit and $^{35}$S-dATP (NEN). Reactions using both the dGTP mixes and the dITP mixes were performed to clarify areas of compression. Alternatively, compressed areas were resolved on formamide gels. Templates were double-stranded plasmid subclones or single stranded M13 subclones, and primers were either made to the vector just outside the insert to be sequenced, or to previously obtained sequence. Sequence obtained was assembled and compared using Dnastar software. Manipulation and comparison of sequences obtained was performed with Superclone and Supersee programs from Coral Software.

MOLECULAR BIOLOGICAL TECHNIQUES. Techniques for the manipulation of bacteria and DNA, including such procedures as digestion with restriction endonucleases, gel electrophoresis, extraction of DNA from gels, ligation, phosphorylation with kinase, treatment with phosphatase, growth of bacterial cultures, transformation of bacteria with DNA, and other molecular biological methods are described by Maniatis et al (1982) and Sambrook et al (1989). The polymerase chain reaction (PCR) was used to introduce restriction sites convenient for the manipulation of various DNAs. The procedures used are described by Innis et al (1990). In general amplified fragments were less than 500 base pairs in size and critical regions of amplified fragments were confirmed by DNA sequencing. Except as noted, these techniques were used with minor variation.

SOUTHERN BLOTTING OF DNA. The general procedure for Southern blotting was taken from Maniatis et al. (1982). DNA was blotted to nitrocellulose filters (S&S BA85) in 20× SSC (1× ssc=0.15M NaCl, 0.015M sodium citrate, pH 7.0), and prehybridized in hybridization solution consisting of 30% formamide, 1× Denhardt's solution (0.02% polyvinylpyrrolidone (PVP), 0.02% bovine serum albumin (BSA), 0.02% Ficoll), 6× SSC, 50 mM $NaH_2PO_4$, pH 6.8, 200 $\mu$g/ml salmon sperm DNA for 4–24 hours at 55° C. Labeled probe DNA was added that had been labeled by nick translation using a kit from Bethesda Research Laboratories (BRL) and one $^{32}$P-labeled nucleotide. The probe DNA was separated from the unincorporated nucleotides by NACS column (BRL) or on a Sephadex G50 column (Pharmacia). After overnight hybridization at 55° C., the filter was washed once with 2× SSC at room temperature followed by two washes with 0.1× SSC, 0.1% sodium dodecyl sulfate (SDS) for 30 minutes at 55° C. The filter was dried and autoradiographed.

cDNA CLONING PROCEDURE. cDNA cloning refers to the methods used to convert RNA molecules into DNA molecules following state of the art procedures. Applicants' methods are described in (Gubler and Hoffman, 1983). Bethesda Research Laboratories (Gaithersburg, Md.) have designed a cDNA Cloning Kit that is very similar to the procedures used by applicants, and contains a set of reagents and protocols that may be used to duplicate our results.

For cloning virus mRNA species, a host cell line sensitive to infection by the virus was infected at 5–10 plaque forming units per cell. When cytopathic effect was evident, but before total destruction, the medium was removed and the cells were lysed in 10 mls lysis buffer (4 M guanidine thiocyanate, 0.1% antifoam A, 25 mM sodium citrate pH 7.0, 0.5% N-lauroyl sarcosine, 0.1 M beta-metcaptoethanol). The cell lysate was poured into a sterilized Dounce homogenizer and homogenized on ice 8–10 times until the solution was homogenous. For RNA purification, 8 mls of cell lysate were gently layered over 3.5 mls of CsCl solution (5.7 M CsCl, 25 mM sodium citrate pH 7.0) in Beckman SW41 centrifuge tube. The samples were centrifuged for 18 hrs at 20° C. at 36000 rpm in a Beckman SW41 rotor. The tubes were put on ice and the supernatants from the tubes were carefully removed by aspiration to leave the RNA pellet undisturbed. The pellet was resuspended in 400 $\mu$l glass distilled water, and 2.6 mls of guanidine solution (7.5 M guanidine-HCL, 25 mM sodium citrate pH 7.0, 5 mM dithiothreitol) were added. The 0.37 volumes of 1 M acetic acid were added, followed by 0.75 volumes of cold ethanol and the sample was put at −20° C. for 18 hrs to precipitate RNA. The precipitate was collected by centrifugation in a Sorvall centrifuge for 10 min a 40° C. at 10000 rpm in an SS34 rotor. The pellet was dissolved in 1.0 ml distilled water, recentrifuged at 13000 rpm, and the supernatant saved. RNA was re-extracted from the pellet 2 more times as above with 0.5 ml distilled water, and the supernatants were pooled. A 0.1 volume of 2 M potassium acetate solution was added to the sample followed by 2 volumes of cold ethanol and the sample was put at −20° C. for 18 hrs. The precipitated RNA was collected by centrifugation in the SS34 rotor at 40 ° C. for 10 min at 10000 rpm. The pellet was dissolved in 1 ml distilled water and the concentration taken by absorption at A260/280. The RNA was stored at −70° C.

mRNA containing polyadenylate tails (poly-A) was selected using oligo-dT cellulose (Pharmacia #27 5543-0). Three mg of total RNA was boiled and chilled and applied to the 100 mg oligo-dT cellulose column in binding buffer (0.1 M Tris pH 7.5, 0.5 M LiCl, 5mM EDTA pH 8.0, 0.1% lithium dodecyl sulfate). The retained poly-A RNA was eluted from the column with elution buffer (5 mM Tris pH 7.5, 1 mM EDTA pH 8.0, 0.1% sodium dodecyl sulfate). This mRNA was reapplied to an oligo-dT column in binding buffer and eluted again in elution buffer. The sample was precipitated with 200 mM sodium acetate and 2 volumes cold ethanol at −20° C. for 18 hrs. The RNA was resuspended in 50 μl distilled water. Ten μg poly-A RNA was denatured in 20 mM methyl mercury hydroxide for 6 min at 22° C. β-mercaptoethanol was added to 75 mM and the sample was incubated for 5 min at 22° C. The reaction mixture for first strand cDNA synthesis in 0.25 ml contained 1 μg oligo-dT primer (P-L Bio-chemicals) or 1 μg synthetic primer, 28 units placental ribonuclease inhibitor (Bethesda Research Labs #5518SA), 100 mM Tris pH 8.3, 140 mM KCl, 10 mM MgCl$_2$, 0.8 mM dATP, dCTP, dGTP, and dTTP (Pharmacia), 100 microcuries $^{32}$p-labeled dCTP (New England Nuclear #NEG-013H), and 180 units AMV reverse transcriptase (Molecular Genetics Resources #MG 101). The reaction was incubated at 42° C. for 90 min, and then was terminated with 20 mM EDTA pH 8.0. The sample was extracted with an equal volume of phenol/chloroform (1:1) and precipitated with 2 M ammonium acetate and 2 volumes of cold ethanol −20° C. for 3 hrs. After precipitation and centrifugation, the pellet was dissolved in 100 μl distilled water. The sample was loaded onto a 15 ml G-100 Sephadex column (Pharmacia) in buffer (100 mM Tris pH 7.5, 1 mM EDTA pH 8.0, 100 mM NaCl). The leading edge of the eluted DNA fractions was pooled, and DNA was concentrated by lyophilization until the volume was about 100 μl, then the DNA was precipitated with ammonium acetate plus ethanol as above.

The entire first strand sample was used for second strand reaction which followed the Gubler and Hoffman (1983) method except that 50 μg/ml dNTP's, 5.4 units DNA polymerase I (Boerhinger Mannheim #642-711), and 100 units/ml E. coli DNA ligase (New England Biolabs #205) in a total volume of 50 microliters were used. After second strand synthesis, the cDNA was phenol/chloroform extracted and precipitated. The DNA was resuspended in 10 μl distilled water, treated with 1 μg RNase A for 10 min at 22° C., and electrophoresed through a 1% agarose gel (Sigma Type II agarose) in 40 mM Tris-acetate pH 6.85. The gel was stained with ethidium bromide, and DNA in the expected size range was excised from the gel and electroeluted in 8 mM Tris-acetate pH 6.85. Electroeluted DNA was lyophilized to about 100 microliters, and precipitated with ammonium acetate and ethanol as above. The DNA was resuspended in 20 μl water.

Oligo-dC tails were added to the DNA to facilitate cloning. The reaction contained the DNA, 100 mM potassium cacodylate pH 7.2, 0.2 mM dithiothreitol, 2 mM CaCl$_2$, 80 moles dCTP, and 25 units terminal deoxynucleotidyl transferase (Molecular Genetic Resources #S1001) in 50 μl. After 30 min at 37° C., the reaction was terminated with 10 mM EDTA, and the sample was phenol/chloroform extracted and precipitated as above.

The dc-tailed DNA sample was annealed to 200 ng plasmid vector pBR322 that contained oligo-dG tails (Bethesda Research Labs #5355 SA/SB) in 200 μl of 0.01 M Tris pH 7.5, 0.1 M NaCl, 1 mM EDTA pH 8.0 at 65° C. for 2 min and then 57° C. for 2 hrs. Fresh competent E. coli DH-1 cells were prepared and transformed as described by Hanahan (1983) using half the annealed cDNA sample in twenty 200 μl aliquots of cells. Transformed cells were plated on L-broth agar plates plus 10 μg/ml tetracycline. Colonies were screened for the presence of inserts into the ampicillin gene using Ampscreen (Bethesda Research Labs #5537 UA), and the positive colonies were picked for analysis.

DNA TRANSFECTION FOR GENERATING RECOMBINANT HERPESVIRUS. The method is based upon the polybrene-DMSO procedure of Kawai and Nishizawa (1984) with the following modifications. Generation Qf recombinant HVT virus is dependent upon homologous recombination between HVT viral DNA and the plasmid homology vector containing the desired foreign DNA flanked by the appropriate herpesvirus cloned sequences. Transfections were carried out in 6 cm plates (Corning plastic) of 50% confluent primary chick embryo fibroblast (CEF) cells. The cells were plated out the day before in CEF growth media (1× F10/199, 5% fetal calf serum, 26% glutamine, 1% non-essential amino acids, and 2% penicillin/streptomycin) containing 4 μg/ml polybrene (stock 4 mg/ml in 1× HBSS). For cotransfections into CEF cells, 5 μg of intact HVT DNA, and suspended in 1 ml of CEF media containing 30 μg/ml polybrene (stock 4 mg/ml in 1× HBSS). The DNA-polybrene suspension (1 ml) was then added to a 6 cm plate of CEF cells from which the media had been aspirated, and incubated at 39° C. for 30 minutes. The plates were rocked periodically during this time to redistribute the inoculum. After this period, 4 ml of CEF growth media was added directly to wash plate, and incubated an additional 2.5 hours a 39° C. At this time, the media was removed from each plate, and the cells shocked with 2 ml of 30% DMSO (Dimethyl Sulfoxide, J.T. Baker Chemical Co.) in 1× HBSS for 4 minutes at room temperature. The 30% DMSO was carefully removed and the monolayers washed once with 1× HBSS at room temperature. The cells were then incubated at 39° C. after the addition of 5 mls of CEF growth media. The next day, the media was changed to remove any last traces of DMSO and to stimulate cell growth. Cytopathic effect from the virus becomes apparent within 6 days. Generation of a high titer stock (80%–90% CPE) can usually be made within 1 week from this date. HVT stock samples were prepared by resuspending the infected cells in CEF growth media containing 20% fetal calf serum, 10% DMSO and stored at −70° C.

PROCEDURE FOR GENERATING RECOMBINANT HERPESVIRUS FROM SUBGENOMIC DNA FRAGMENTS. The ability to generate herpesviruses by cotransfection of cloned overlapping subgenmoic fragments has been demonstrated for pseudorabies virus (Zijl et al., 1988). If deletions and/or insertions are engineered directly into the subgenomic fragments prior to the cotransfection, this procedure results in a high frequency of viruses containing the genomic alteration, greatly reducing the amount of screening required to purify the recombinant virus. We have used this procedure to construct recombinant HVT.

A library of subclones containing overlapping HVT subgenomic fragments was generated as follows. HVT DNA was obtained from the American Type Culture Collection (FC-126 ("Calnek")). It was sheared and then size selected on a glycerol gradient as described by van Zijl et al., (1988) with 40–50 kb fragments chosen as the insert population. The pooled fractions were diluted twofold with TE, one-tenth volume of 3M NaAc and 2.5 volumes of ethanol were added, and the DNA was precipitated at 30K rpm in a Beckman SW41 rotor for 1 hr. The sheared fragments were given blunt ends by initial treatment with T4 DNA polymerase, using low DNTP concentrations to promote 3' overhang removal, followed by treatment with Klenow polymerase to fill in recessed 3' ends. These insert fragments were then ligated to a pWE15 (Strategene) cosmid vector, which had been digested with BamHI, treated with calf intestinal phosphatase, and made blunt by treatment with Klenow polymerase. The ligated mixture was then packaged using Gigapack XL packaging extracts (Stratagene). Ligation and packaging was as recommended by the manufacturer.

Published restriction maps for the enzymes BamHI, HindIII, and XhoI permitted the use of subcloned fragments as specific probes to screen the cosmid library for subclones spanning the genome. Probes were generated from subcloned restriction fragments. The fragments were then labeled using a non-radioactive system (Genius, Boehringer Mannheim). Screening was facilitated by picking colonies to media followed by growth overnight. Sets of five filters and a master plate were stamped from microtiter dish and again grown overnight. Glycerol was added to the wells to 15% and the plates were frozen at −20° C. to provide stock cultures of each colony. Filters were BioRad Colony Lift Membranes and were treated and hybridized per manufacturer's instructions, and washed in 0.1× SSC, 0.1% SDS, 65° C. Clones which hybridized with the non-radioactive probe were detected according to the Genius kit directions.

Colonies were selected for further analysis on the basis of their hybridization to two or more of the specific probes. These were then digested with BamHI, and compared to published maps of HVT (Buckmaster et al., 1988). The three cosmids (407-32.2C3, 407-32.1G7, and 407-32.5G6) were obtained in this manner. A detailed description of each clone is given below. It was found that chloramphenicol amplification (Maniatis et al., 1982) was necessary to achieve reasonable yields of DNA from these clones. In addition, one cosmid clone (407-32.5G6) was unstable and had to be grown from the original frozen stock in order to obtain satisfactory DNA preparations.

The pWE15 vector allows the inserts to be excised with NotI. However, four NotI sites are present in the HVT genome, so that inserts spanning these sites cannot be excised with NotI. Two of the NotI sites are present in the BamHI #2 fragment of HVT, this fragment was cloned directly in pSP64. The other two sites are present in the unique short region within the BamHI #1 fragment. This fragment was cloned directly in the pWE15 vector. The three sheared cosmids and the two BamHI fragments cover all but a small portion of the ends of the HVT genome. Because these regions are repeated in the internal portions of the genome, all of the genetic information is available.

A StuI site within the HVT US2 gene was established as a useful site for foreign DNA insertion utilizing the HOMOLOGOUS RECOMBINATION PROCEDURE FOR GENERATING RECOMBINANT HERPESVIRUSES (see Example 6). The HVT US2 gene is located within the BamHI #1 fragment which contains five StuI sites. To facilitate the use of this site for insertion of foreign DNA by the StuI site within the US2 gene was converted to a unique HindIII site. This was accomplished by partially digesting the BamHI #1 subclone with StuI, and then inserting a 10 kb fragment conferring kanomycin resistance ($Neo^R$) into the site using HindIII linkers. The kanomycin resistance gene allowed positive selection of recombinant clones. The $Neo^R$ fragment was removed by digestion with HindIII followed by religation generating clone 430-84.215.

DNA was prepared for reconstruction experiments by restriction digestion with enzymes which cut the subclones outside or flanking the HVT insertions. In some instances, one cosmid in a reconstruction was used undigested. Digested DNAs were extracted once with phenol and precipitated with ethanol. DNA was resuspended at a concentration of 0.5 to 1 ug/ml. Viral reconstruction experiments were performed using Lipofectin (BRL) to mediate transfection. Two to three micrograms each of subclone were added to 0.5 ml of MEM media (Earle's salts) supplemented with 1% non-essential amino acids and 2% penicillin/Streptomysin (MEM+). Controls consisted of MEM+ with no DNA, with several ug of HVT DNA, or with 4 out of 5 of the subclones. Separately, 30 $\mu$l of the Lipofectin were added to another 0.5 ml. of MEM+. These two mixtures were then combined and incubated at RT for 15 minutes.

Chick embryo fibroblast (CEF) cells were prepared for transfection in the following manner. CEFs (Spafas) were grown in 6 well dishes at 39° C. in F10/M199 (1:1) media containing 1% non-essential amino acids, 2% penicillin/streptomycin, and 5% fetal calf serum (CEF+). Cells were transfected at a confluence of 90–95%. For transfection, wells were aspirated and rinsed 3 times with MEM+, and then incubated 4 hours at 39° C. with the 1 ml lipofectin/DNA mixture above. One ml more of CEF+was then added to the wells, and cells were incubated overnight and fed with CEF+. Plates were then examined daily for the appearance of plaques.

Lipofectin with control HVT DNA resulted in the appearance of plaques within 5 days. When only four of the five subclones were used, no plaques were obtained. When the five overlapping genomic fragments of HVT were used to reconstruct the virus, plaques appeared anywhere from 5 to 19 days after the initial lipofection. In the case of plaques appearing late, plaques were not initially seen on the infected monolayer, and it was only after passaging the monolayer and replating on a larger surface that plaques appeared. After passaging, plaques generally appeared within 3 days. Recombinant viruses were plaque purified approximately three and then analyzed for insertion of foreign DNAs.

BLUOGAL SCREEN FOR RECOMBINANT HERPESVIRUS. When the foreign gene encoded the enzyme β-galactosidase, the plaques that contained the gene were visualized more easily. The chemical Bluogal™ (Bethesda Research Labs) was incorporated at the level of 200–300 $\mu$g/ml into the agarose overlay during the plaque assay, and the plaques that expressed active β-galactosidase turned blue. The blue plaques were then picked and purified by further blue plaque isolations. Other foreign genes were inserted by homologous recombination such that they replaced the β-galactosidase gene; in this instance non-blue plaques were picked for purification of the recombinant virus.

SCREEN FOR FOREIGN GENE EXPRESSION IN RECOMBINANT HVT USING BLACK PLAQUE ASSAYS. To analyze expression of foreign antigens expressed by recombinant HVT viruses, monolayers of CEF cells are infected with recombinant HVT, overlaid with nutrient agarose media and incubated for 4–5 days at 39° C. Once plaques have developed, the agarose overlay is removed from the dish, the monolayer rinsed 1× with PBS, fixed with 100% methanol for 10 minutes at room temperature and the cells air dried. After re-hydrating the plate with PBS, the primary antibody is diluted to the appropriate dilution with PBS and incubated with the cell monolayer for 2 hours to overnight at room temperature. Unbound antibody is then removed from the cells by washing three times with PBS at room temperature. An alkaline phosphatase conjugated secondary antibody is diluted with PBS and incubated with the cells for 2 hours at room temperature. Unbound secondary antibody is then removed by washing the cells three times with PBS at room temperature. Next, the monolayer is rinsed in color development buffer (100 mM Tris pH 9.5/100 mM NaCl/5 mM MgCl2), and then incubated 10 minutes to overnight at room temperature with freshly prepared substrate solution (0.3 mg/ml Nitro Blue tetrazolium +0.15 mg/ml 5-Bromo-4-Chloro-3-Indolyl Phosphatase in color development buffer.) Finally, the reaction is stopped by replacing the substrate solution with TE (10 mM Tris, pH7.5/1 mM EDTA). Plaques expressing the correct antigen will stain black.

PLAQUE HYBRIDIZATION PROCEDURE FOR ASSESSING THE PURITY OF RECOMBINANT HVT STOCKS. When no suitable immunological reagent exists to detect the presence of a particular antigen in a recombinant HVT virus, plaque hybridization can be used to assess the purity of a stock. Initially, CEF cell monolayers are infected with various dilutions of the viral stocks to give ~50–100 plaques/10 cm.dish, overlaid with nutrient agarose media and incubated for 4–5 days at 39° C. Once plaque development occurs, the position of each plaque is marked on bottom of the dish. The agarose overlay is then removed, the plate washed with PBS, and the remaining CEF monolayer is transferred to a NC membrane or BioRad nylon membrane pre-wetted with PBS. (making note of the membrane position relative to the dish). Cells contained on the NC membranes are then lysed by placing the membranes in 1.5 mls of 1.5M NaCl and 0.5M NaOH for five minutes. The membranes are neutralized by placing them in 1.5 mls of 3M Sodium acetate (pH 5.2) for five minutes. DNA from the lysed cells is then bound to the NC membranes by baking at 80° C. for one hour. After this period the membranes are prehybridized in a solution containing 6× SSC, 3% skim milk, 0.5% SDS, (±) salmon sperm DNA (50 $\mu$g/ml) for one hour at 65° C. Radio-labeled probe DNA (alpha 32P-dCTP) is then added and the membranes incubated at 65° C. overnight (~12 hours). After hybridization the NC membranes are washed two times (30 minutes each) with 2× SSC at 65° C., followed by two additional washes at 65° C. with 0.5× SSC. The NC membranes are then dried and exposed to X-ray film (Kodak X-OMAT,AR) at −70° C. for 12 hours. Positive signals are then aligned with the position of the plaques on the dish and purity of the stock is recorded as the percentage of positive plaques over the total.

CONSTRUCTION OF HOMOLOGY VECTOR FOR INSERTION OF THE BETA-GALACTOSIDASE GENE INTO HVT US2 GENE. The beta-galactosidase (lacZ) gene was inserted into the HVT EcoRI #7 fragment at the unique StuI site. The marker gene is oriented in the same direction as the US2 gene. A detailed description of the marker gene is given in FIGS. 7A and 7B. It is constructed utilizing standard recombinant DNA techniques (Maniatis et al, 1982 and Sambrook et al, 1989), by joining restriction fragments from the following sources with the synthetic DNA sequences indicated in FIGS. 7A and 7B. Fragment 1 is an approximately 413 base pair SalI to BamHI restriction subfragment of the PRV BamHI restriction fragment 10 (Lomniczi et al., 1984). Fragment 2 is an approximately 3010 base pair BamHI to PvuII restriction fragment of plasmid pJF751 (Ferrari et al., 1985). Fragment 3 is an approximately 754 base pair NdeI to SalI restriction subfragment of the PRV BamHI restriction fragment #7 (Lomniczi et al., 1984).

SUBGENOMIC CLONE 172-07.BA2. Plasmid 172-07.BA2 was constructed for the purpose of generating recombinant HVT. It contains an approximately 25,000 base pair region of genomic HVT DNA. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This plasmid may be constructed utilizing standard recombinant DNA techniques (Maniatis et al, 1982 and Sambrook et al, 1989), by joining two restriction fragments from the following sources. The first fragment is an approximately 2999 base pair BamHI to BamHI restriction fragment of pSP64 (Promega). The second fragment is the approximately 25,000 base pair BamHI #2 fragment of HVT (Buckmaster et al., 1988). HOMOLOGY VECTOR 172-29.31. The plasmid 172-29.31 was constructed for the purpose of inserting foreign DNA into HVT. It contains a unique XhoI restriction enzyme site into which foreign DNA may be inserted. When a plasmid containing a foreign DNA insert at the XhoI site is used according to the DNA COTRANSFECTION FOR GENERATING RECOMBINANT HERPESVIRUSES or the PROCEDURE FOR GENERATING RECOMBINANT HERPESVIRUS FROM OVERLAPPING SUBGENOMIC FRAGMENTS a virus containing the foreign DNA will result. This plasmid may be constructed utilizing standard recombinant DNA techniques (Maniatis et al, 1982 and Sambrook et al, 1989), by joining two restriction fragments from the following sources. The first fragment is an approximately 2999 base pair BamHI to BamHI restriction fragment of pSP64 (Promega). The second fragment is the approximately 3300 base pair BamI #16 fragment of HVT (Buckmaster et al., 1988). The complete sequence of the BamHI #16 fragment is given in SEQ ID NO:3. Note that the fragment was cloned such that the UL43 ORF is in the opposite transcriptional orientation to the pSP64 β-lacatamase gene. HOMOLOGY VECTOR 172-63.1. The plasmid 172-63.1 was constructed for the purpose of inserting foreign DNA into HVT. It contains a unique XhoI restriction enzyme site into which foreign DNA may be inserted. When a plasmid containing a foreign DNA insert at the XhoI site is used according to the DNA COTRANSFECTION FOR GENERATING RECOMBINANT HERPESVIRUSES or the PROCEDURE FOR GENERATING RECOMBINANT HERPESVIRUS FROM OVERLAPPING SUBGENOMIC FRAGMENTS a virus containing the foreign DNA will result. This plasmid may be constructed utilizing standard recombinant DNA techniques (Maniatis et al, 1982 and Sambrook et al, 1989), by joining two restriction fragments from the following sources. The first fragment is an approximately 2999 base pair EcoRI to EcoRI restriction fragment of pSP64 (Promega). The second fragment is the approximately 5500 base pair EcoRI #9 fragment of HVT. Note that the EcoRI fragment was cloned such that the unique XhoI site is closest to the unique HindIII site in the pSP64 vector.

HOMOLOGY VECTORS 255-18.B16. The plasmid 255-18.B16 was constructed for the purpose of inserting the NDV HN and F genes into HVT. The NDV HN and F genes were inserted as a SalI fragment into the homology vector 172-29.31 at the XhoI site. The NDV HN and F genes were inserted in the same transcriptional orientation with the UL43 ORF in the parental homology vector. A detailed description of the SalI fragment is shown in FIGS. 12A, 12B and 12C. The inserted SalI fragment may be constructed utilizing standard recombinant DNA techniques (Maniatis et al, 1982 and Sambrook et al, 1989), by joining restriction fragments from the following sources with the synthetic DNA sequences indicated in FIGS. 12A, 12B and 12C. Fragment 1 is an approximately 416 base pair SalI to BamHI restriction subfragment of the PRV BamHI restriction fragment 10 (Lomniczi et al., 1984).

Fragment 2 is an approximately 3009 base pair BamHI to PvuII fragment of the plasmid pJF751 (Ferrari et al., 1985). Fragment 3 is an approximately 1200 base pair AvaII to EcoRI restriction fragment of full length NDV HN CDNA. Fragment 4 is an approximately 179 base pair EcORI to PvuII restriction fragment of the plasmid pSP64 (Promega). Fragment 5 is an approximately 357 base pair SmaI to BamHI restriction subfragment of the HSV-1 BamHI restriction fragment N. Fragment 6 is an approximately 1812 base pair BamHI to PstI restriction fragment of the full length NDV F CDNA. Fragment 7 is an approximately 235 base pair PstI to ScaI restriction fragment of the plasmid pBR322.

SUBGEMOMIC CLONE 378-50.BA1. Cosmid 378-50.BA1 was constructed for the purpose of generating recombinant HVT. It contains an approximately 29,500 base pair region of genomic HVT DNA. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This cosmid may be constructed by joining two restriction fragments from the following sources. The first fragment is an approximately 8164 base pair BamHI to BamHI restriction fragment of pWE15 (Stratagene). The second fragment is the approximately 29,500 base pair BamHI #1 fragment of HVT (Buckmaster et al., 1988).

SUBGEMOMIC CLONE 407-32.1C1. Cosmid 407-32.1C1 was constructed for the purpose of generating recombinant HVT. It contains an approximately 38,850 base pair region of genomic HVT DNA (see FIG. 8). This region includes BamHI fragments 11, 7, 8, 21, 6, 18, approximately 1250 base pairs of fragment 13, and approximately 6,700 base pairs of fragment 1. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This cosmid maybe constructed as described above in the PROCEDURE FOR GENERATING RECOMBINANT HERPESVIRUS FROM OVERLAPPING. SUBGENOMIC FRAGMENTS. It was isolated from the sheared DNA library by screening with the probes P1 and P4 (described in FIG. 8). A bacterial strain containing this cosmid has been deposited on Mar. 3, 1993 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. 75428.

SUBGEMOMIC CLONE 407-32.2C3. Cosmid 407-32.2C3 was constructed for the purpose of generating recombinant HVT. It contains an approximately 40,170 base pair region of genomic HVT DNA (see FIG. 8). This region includes BamHI fragments 10, 14, 19, 17, 5, and approximately 2,100 base pairs of fragment 2. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This cosmid may be constructed as described above in the PROCEDURE FOR GENERATING RECOMBINANT HERPESVIRUS FROM OVERLAPPING SUBGENOMIC FRAGMENTS. It was isolated from the sheared DNA library by screening with the probes P1 and P2 (described in FIG. 8). A bacterial strain containing this cosmid has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. 75430.

SUBGEMOMIC CLONE 407-32.5G6. Cosmid 407-32.5G6 was constructed for the purpose of generating recombinant HVT. It contains an approximately 40,000 base pair region of genomic HVT DNA (see FIG. 8). This region includes BamHI fragments 9, 3, 20, 12, 16, 13, approximately 1,650 base pairs of fragment 2, and approximately 4,000 base pairs of fragment 11. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This cosmid may be constructed as described above in the PROCEDURE FOR GENERATING RECOMBINANT HERPESVIRUS FROM OVERLAPPING SUBGENOMIC FRAGMENTS. It was isolated from the sheared DNA library by screening with the probes P2 and P3 (described in FIG. 8). A bacterial strain containing this cosmid has been deposited on Mar. 3, 1993 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. 75427.

HOMOLOGY VECTOR 435-47.1. The plasmid 435-47.1 was constructed for the purpose of inserting foreign DNA into HVT. It contains a unique HindIII restriction enzyme site into which foreign DNA may be inserted. When a plasmid containing a foreign DNA insert at the HindIII site is used according to the DNA COTRANSFECTION FOR GENERATING RECOMBINANT HERPESVIRUSES or the PROCEDURE FOR GENERATING RECOMBINANT HERPESVIRUS FROM OVERLAPPING SUBGENOMIC FRAGMENTS a virus containing the foreign DNA will result. This plasmid may be constructed utilizing standard recombinant DNA techniques (Maniatis et al, 1982 and Sambrook et al, 1989), by joining two restriction fragments from the following sources. The first fragment is an approximately 2999 base pair EcoRI to EcoRI restriction fragment of pSP64 (Promega). The second fragment is the approximately 7300 base pair EcoRI #7 fragment of HVT. Note that the HindIII site of the pSP64 vector was removed by digesting the subclone with HindIII followed by a Klenow fill in reaction and religation. A synthetic HindIII linker (CAAGCTTG) was then inserted into the unique StuI site of the EcoRI #7 fragment.

SUBGEMOMIC CLONE 437-26.24. Plasmid 437-26.24 was constructed for the purpose of generating recombinant HVT. It contains an approximately 13,600 base pair region of genomic HVT DNA. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This plasmid may be constructed utilizing standard recombinant DNA techniques (Maniatis et al, 1982 and Sambrook et al, 1989), by joining two restriction fragments from the following sources. The first fragment is an approximately 2970 base pair HindIII to BamHI restriction fragment of pSP64 (Promega). The second fragment is the approximately 13,600 base pair BamHI to StuI subfragment of the BamHI #2 fragment of HVT (Buckmaster et al., 1988). Note that the BamHI #2 fragment contains five StuI sites, the site utilized in this subcloning was converted to a HindIII site as described in the PROCEDURE FOR GENERATING RECOMBINANT HERPESVIRUS FROM OVERLAPPING SUBGENOMIC FRAGMENTS.

SUBGEMOMIC CLONE 437-26.26. Plasmid 437-26.26 was constructed for the purpose of generating recombinant HVT. It contains an approximately 15,300 base pair region of genomic HVT DNA. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This plasmid may be constructed utilizing standard recombinant DNA techniques (Maniatis et al, 1982 and Sambrook et al, 1989), by joining two restriction fragments from the following sources. The first fragment is an approximately 2970 base pair HindIII to BamHI restriction fragment of pSP64 (Promega). The second fragment is the approximately 15,300 base pair BamHI to StuI subfragment of the BamHI #2 fragment of HVT (Buckmaster et al., 1988). Note that the BamHI #2 fragment contains five StuI sites, the site utilized in this subcloning was converted to a HindIII site as described in the PROCEDURE FOR GENERATING RECOMBINANT HERPESVIRUS FROM OVERLAPPING SUBGENOMIC FRAGMENTS.

HOMOLOGY VECTORS 456-18.18 and 456-17.22. The plasmids 456-18.18 and 456-17.22 were constructed for the purpose of inserting the MDV gA and gB genes into HVT. The MDV genes were inserted as a cassette into the homology vector 435-47.1 at the unique HindIII site. The MDV genes were inserted at the blunt ended HindIII site as a blunt ended PstI to EcoRI fragment (see FIGS. 10A and 10B). The HindIII and EcoRI sites were blunted by the Klenow fill in reaction. The PstI site was blunted by the T4 DNA polymerase reaction. Note that the MDV cassette was inserted in both orientations. Plasmid 456-18.18 contains the MDV genes inserted in the opposite transcriptional orientation to the US2 gene in the parental homology vector. Plasmid 456-17.22 contains the MDV genes inserted in the same transcriptional orientation as the US2 gene in the parental homology vector. A detailed description of the MDV cassette is given in FIGS. 10A and 10B. It may be constructed utilizing standard recombinant DNA techniques (Maniatis et al, 1982 and Sambrook et al, 1989), by joining restriction fragments from the following sources with the synthetic DNA sequences indicated in FIG. 10A and 10B. Fragment 1 is an approximately 2178 base pair PvuII to EcoRV restriction subfragment of the MDV EcoRI 6.9 KB genomic restriction fragment (Ihara et al., 1989). Fragment 2 is an approximately 3898 base pair SalI to EcoRI genomic MDV fragment (Ross, et al., 1989).

HOMOLOGY VECTOR 528-03.37. The plasmid 528-03.37 was constructed for the purpose of inserting the infectious laryngotracheitis (ILT) virus gD gene into HVT. The gD gene followed by the PRV gX poly adenylation signal was inserted as a cassette into the homology vector 435-47.1 at the unique HindIII site. The cassette may be constructed utilizing standard recombinant DNA techniques (Maniatis et al, 1982 and Sambrook et al, 1989), by joining restriction fragments from the following sources. The first fragment is an approximately 2060 base pair EcoRI to BclI restriction subfragment of the ILT KpnI genomic restriction fragment #8 (10.6 KB). The second fragment is an approximately 754 base pair NdeI to SalI restriction subfragment of the PRV BamHI restriction fragment #7 (Lomniczi et al., 1984). Note that the fragments are oriented such that BclI and NdeI sites are contiguous.

HOMOLOGY VECTOR 528-11.43. The plasmid 528-11.43 was constructed for the purpose of inserting the infectious laryngotracheitis (ILT) virus gB gene (A. M. Grifin, 1991) into HVT. The gB gene was inserted as an EcoRI fragment into the homology vector 435-47.1 at the unique HindIII site. The gB gene was inserted at the blunt ended HindIII site as a blunt ended EcoRI fragment. The HindIII and EcoRI sites were blunted by the Klenow fill in reaction. The gB gene was inserted in the same transcriptional orientation as the US2 gene in the parental homology vector. The EcoRI fragment may be obtained as a 3.0 KB ILT virus genomic fragment.

HOMOLOGY VECTOR 518-46.B3. The plasmid 518-46.B3 was constructed for the purpose of inserting foreign DNA into HVT. It contains a unique HindIII restriction enzyme site into which foreign DNA may be inserted. When a plasmid containing a foreign DNA insert at the HindIII site is used according to the DNA COTRANSFECTION FOR GENERATING RECOMBINANT HERPESVIRUSES or the PROCEDURE FOR GENERATING RECOMBINANT HERPESVIRUS FROM OVERLAPPING SUBGENOMIC FRAGMENTS a virus containing the foreign DNA will result. This plasmid may be constructed utilizing standard recombinant DNA techniques (Maniatis et al, 1982 and Sambrook et al, 1989), by joining three restriction fragments from the following sources. The first fragment is an approximately 1649 base pair PvuI to SalI restriction fragment of pSP64 (Promega). The second fragment is an approximately 1368 base pair PvuI to SalI restriction fragment of pSP65 (Promega). The third fragment is the approximately 3400 base pair XhoI to XhoI fragment of plasmid 437-47.1.

HOMOLOGY VECTOR 535-70.3. The plasmid 535-70.3 was constructed for the purpose of inserting the MDV gB, and gA genes and the NDV F gene into HVT. The F gene was inserted as a cassette into homology vector 456-17.22 at the HindIII site located between the MDV gA and gB genes (see Junction B, FIG. 10A). The F gene is under the control of the HCMV immediate early promoter and followed by the HSV-1 TK poly adenylation signal. The F gene was inserted in the same transcriptional orientation as the US2 gene in the parental homology vector. The cassette may be constructed utilizing standard recombinant DNA techniques (Maniatis et al, 1982 and Sambrook et al, 1989), by joining restriction fragments from the following sources. The first fragment is an approximately 1191 base pair PstI to AvaII restriction subfragment of the HCMV genomic XbaI E fragment (D. R. Thomsen, et al., 1981). The second fragment is an approximately 1812 base pair BamHI to PstI restriction fragment of the full length NDV F cDNA clone (Bi strain). The last fragment is an approximately 784 base pair SmaI to SmaI restriction subfragment of the HSV-1 BamHI restriction fragment Q (McGeoch, et al., 1985).

HOMOLOGY VECTOR 549-24.15. The plasmid 549-24.15 was constructed for the purpose of inserting the MDV gB, and gA genes and the NDV HN and F genes into HVT. The HN and F genes were inserted as a cassette into homolgy vector 456-17.22 at the HindIII site located between the MDV gA and gB genes (see Junction B, FIG. 10A). The HN and F genes are under the control of the PRV gpX and HCMV immediate early promoters respectively. The HN and F genes are followed by the PRV gX poly and HSV-1 TK adenylation signals respectively. The cassette may be constructed utilizing standard recombinant DNA techniques (Maniatis et al, 1982 and Sambrook et al, 1989), by joining restriction fragments from the following sources. The first fragment is an approximately 413 base pair SalI to BamHI restriction subfragment of the PRV BamHI fragment

10 (Lomniczi, et al., 1984) The second fragment is an approximately 1811 base pair AvaII to NaeI restriction fragment of the full length NDV HN cDNA clone (B1 strain). The third fragment is an approximately 754 base pair NdeI to SalI restriction subfragment of the PRV BamHI restriction fragment #7 (Lomniczi, et al., 1984). The fourth fragment is an approximately 1191 base pair PstI to AvaII restriction subfragment of the HCMV genomic XbaI E fragment (D. R. Thomsen, et al., 1981). The fifth fragment is an approximately 1812 base pair BamHI to PstI restriction fragment of the full length NDV F cDNA clone (B1 strain). The last fragment is an approximately 784 base pair SmaI to SmaI restriction subfragment of the HSV-1 BamHI restriction fragment Q (McGeoch, et al., 1985).

HOMOLOGY VECTOR 549-62.10. The plasmid 549-62.10 was constructed for the purpose of inserting the MDV gB, and gA genes and the NDV HN gene into HVT. The HN gene was inserted as a cassette into homolgy vector 456-17.22 at the HindIII site located between the MDV gA and gB genes (see Junction B, FIG. 10A). The HN gene is under the control of the PRV gpX promoter and followed by the PRV gX poly adenylation signal. The HN gene was inserted in the same transcriptional orientation as the US2 gene in the parental homology vector. The cassette may be constructed utilizing standard recombinant DNA techniques (Maniatis et al, 1982 and Sambrook et al, 1989), by joining restriction fragments from the following sources. The first fragment is an approximately 413 base pair SalI to BamHI restriction subfragment of the PRV BamHI fragment #10 (Lomniczi, et al., 1984) The second fragment is an approximately 1811 base pair AvaII to NaeI restriction fragment of the full length NDV HN cDNA clone (B1 strain). The last fragment is an approximately 754 base pair NdeI to SalI restriction subfragment of the PRV BamHI restriction fragment #7 (Lomniczi, et al., 1984).

SUBGENOMIC CLONE 550-60.6 Plasmid 550-60.6 was constructed for the purpose of generating recombinant HVT. It contains an approximately 12,300 base pair region of genomic HVT DNA. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This plasmid may be constructed utilizing standard recombinant DNA techniques (Maniatis et al, 1982 and Sambrook et al, 1989), by joining two restriction fragments from the following sources. The first fragment is an approximately 4176 base pair EcoRV to BamHI restriction fragment of pBR322. The second fragment is the approximately 12,300 base pair subfragment fragment of the BainHI #2 fragment of HVT (Buckmaster et al., 1988). This fragment was generated in the following manner. Plasmid 437-26.26 was linearized with HindIII and then resected with the ExoIII Mung Bean Deletion Kit (Stratagene). Samples from the 3 and 4 minute reactions were combined and digested with BamHI resulting in a population of fragments containing the desired 12,300 base pair subfragment. This-population was cloned into the pBR322 fragment and the resulting clones were screened for the appropriate size and restriction map. Fortuitously the resected subfragment that generated clone 550-60.6 ended in the nucleotides GG which generated a second BamHI site when ligated to the EcoRV site (ATCC) of pBR322. A bacterial strain containing this plasmid has been deposited on Mar. 3, 1993 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. 75429.

HOMOLOGY VECTORS 566-41.5. The plasmid 566-41.5 was constructed for the purpose of inserting the MDV gA, gB and gD genes into HVT. The MDV gD gene was inserted as a HindIII fragment into the homology vector 456-17.22 at the HindIII site located between MDV gA and gB (see FIGS. 10A and 10B). The MDV gene was inserted in the same transcriptional orientation as gA and gB in the parental homology vector. A detailed description of the HindIII fragment containing the MDV gD gene is shown in FIGS. 11A and 11B. Note that a herpesvirus polyadenation signal was added to the gD gene cassette. The inserted HindIII fragment may be constructed utilizing standard recombinant DNA techniques (Maniatis et al, 1982 and Sambrook et al, 1989), by joining restriction fragments from the following sources with the synthetic DNA sequences indicated in FIGS. 11A and 11B. Fragment 1 is an approximately 784 base pair SmaI to SmaI restriction subfragment of the HSV-1 Ba HI restriction fragment Q (McGeoch et al., 1988). Note that this fragment is oriented such that the polyadenylation sequence (AATAAA) is located closest to junction B. Fragment 2 is an approximately 2177 base pair SalI to NcoI subfragment of the MDV BglII 4.2 KB genomic restriction fragment (Ross, et al., 1991).

HOMOLOGY VECTOR 567-72.1D. The plasmid 567-72.1D was constructed for the purpose of inserting the MDV gB, gA, and gD genes and the infectious bronchitis virus (IBV) matrix and spike genes into HVT. The IBV genes were inserted as a cassette into homolgy vector 566-41.5 at the unique NotI site located upstream of the MDV gD gene (see Junction C, FIG. 11B). The IBV spike and matrix genes are under the control of the HCMV immediate early and PRV gpX promoters respectively. The IBV spike and matrix genes are followed by the HSV-1 TK and PRV gX poly adenylation signals respectively. The IBV genes were inserted in the same transcriptional orientation as the US2 gene in the parental homology vector. The cassette may be constructed utilizing standard recombinant DNA techniques (Maniatis et al, 1982 and Sambrook et al, 1989), by joining restriction fragments from the following sources. The first fragment is an approximately 413 base pair SalI to BamHI restriction subfragment of the PRV BamHI fragment #10 (Lomniczi, et al., 1984) The second fragment contains amino acids 1 to 223 of the IBV matrix gene. The coding region was obtained from a cDNA clone of the Arkansas strain of IBV. The third fragment is an approximately 754 base pair NdeI to SalI restriction subfragment of the PRV BamHI restriction fragment #7 (Lomniczi, et al., 1984). The fourth fragment is an approximately 1191 base pair PstI to AvaII restriction subfragment of the HCMV genomic XbaI E fragment (D. R. Thomsen, et al., 1981). The fifth fragment contains amino acids 4 to 1162 of the IBV spike gene. The coding region was obtained from a cDNA clone of the Arkansas strain of IBV. The last fragment is an approximately 784 base pair SmaI to SmaI restriction subfragment of the HSV-1 BamHI restriction fragment Q (McGeoch, et al., 1985).

HOMOLOGY VECTOR 603-57.F1. The plasmid 603-57.F1 was constructed for the purpose of inserting the IBDV VP2 gene into HVT. The IBDV VP2 gene was inserted as a cassette into homolgy vector 435-47.1 at the unique HindIII site. The VP2 gene is under the control of the HCMV immediate early promoter and is followed by the HSV-1 TK poly adenylation signal. The VP2 gene was inserted in the same transcriptional orientation as the US2 in the parental homology vector. The cassette may be constructed utilizing standard recombinant DNA techniques (Maniatis et al, 1982 and Sambrook et al, 1989), by joining restriction fragments from the following sources. The first fragment is an approximately 1191 base pair PstI to AvaII restriction subfragment of the HCMV genomic XbaI E fragment (D. R. Thomsen, et al., 1981). The second fragment is an approximately 1081 base pair BclI to BamHI restriction subfragment of the full length IBDV cDNA clone (see SEQ ID NO:1). Note that the BclI site was introduced into the cDNA clone directly upstream of the VP2 initiator methionine by converting the sequence CGCAGC to TGATCA. The first and second fragments are oriented such that AvaII and BclI sites are contiguous. The third fragment is an approximately 784 base pair SmaI to SmaI restriction subfragment of the HSV-1 BamHI restriction fragment Q (McGeoch, et al., 1985).

HOMOLOGY VECTOR 633-13.27. The plasmid 633-13.27 was constructed for the purpose of inserting the MDV gB, gA and gD genes and the NDV HN and F genes into HVT. The HN and F genes are under the control of the PRV gpX and HCMV immediate early promoters respectively. The HN and F genes are followed by the PRV gX poly and HSV-1 TK adenylation signals respectively. All five genes were inserted in the same transcriptional orientation as the US2 gene in the parental homology vector. The genes were inserted in the following order MDV gA, NDV HN, NDV F,MDV gD, and MDV gB.

HOMOLOGY VECTOR 634-29.16. The plasmid 634-29.16 was constructed for the purpose of inserting the ILT virus gB and gD genes into HVT. The lacZ marker gene followed by the ILT gB and gD genes inserted as a cassette into the homology vector 172-29.31 at the unique XhoI site. The cassette may be constructed utilizing standard recombinant DNA techniques (Maniatis et al, 1982 and Sambrook et al, 1989), by joining restriction fragments from the following sources. The first fragment is an approximately 4229 base pair SalI to SalI restriction fragment derived from the lacZ marker gene described above and shown in FIGS. 7A and 7B. The second fragment is an approximately 2060 base pair EcoRI to BclI restriction subfragment of the ILT KpnI genomic restriction fragment #8 (10.6 KB). The third fragment is an approximately 754 base pair NdeI to SalI restriction subfragment of the PRV BamHI restriction fragment #7 (Lomniczi et al., 1984). Note that the second and third fragments are oriented such that BclI and NdeI sites are contiguous. The fourth fragment is the 3.0 KB ILT virus genomic EcoRI fragment containing the gB gene. All three genes are in the same transcriptional orientation as the UL43 gene.

SUBGENOMIC CLONE 415-09.BA1. Cosmid 415-09.BA1 was constructed for the purpose of generating recombinant HVT. It contains an approximately 29,500 base pair BamHI #1 fragment of genomic HVT DNA. It was used in conjuction with other subgenomic clones according to the PROCEDURE FOR GENERATING RECOMBINANT HERPESVIRUS FROM OVERLAPPING SUBGENOMIC FRAGMENTS for the construction of recombinant HVT. This cosmid was constructed by joining two restriction fragments (Sambrook, et al., 1989) from the following sources. The vector is an approximately 4430 base pair BamHI to BamHI restriction fragment of pSY1005 derived from pHC79 (Bethesda Research Labs, Inc.) and pWE15 (Stratagene, Inc.). The first fragment is the approximately 29,500 base pair BamHI #1 fragment of the HVT genome (Buckmaster et al., 1988).

SUBGENOMIC CLONE 672-01.A40. Cosmid 672-01.A40 was constructed for the purpose of generating recombinant HVT. It was isolated as a subclone of cosmid 407-32.1C1 (see FIGS. 8 and 15). Cosmid 672-01.A40 contains an approximately 14,000 base pair NotI to AscI subfragment and an approximately 1300 base pair AscI to BamHI subfragment of cosmid 407-32.1C1. The cosmid was constructed by joining restriction fragments (Sambrook, et al., 1989) from the following sources. The vector is an approximately 2700 base pair NotI to BamHI fragment constructed from pNEB193 (New England Biolabs, Inc.) which contains a NotI linker inserted into the SmaI site. Fragment 1 is an approximately 15,300 base pair region of genomic HVT DNA. This region includes BamHI fragments 11 and 7, and approximately 1250 base pairs of fragment 13. It was used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT.

SUBGENOMIC CLONE 654-45.1. Plasmid 654-45.1 was constructed for the purpose of generating recombinant HVT. It was isolated as an AscI subclone of cosmid 407-32.1C1 (see FIGS. 8 and 15). The cosmid was constructed by joining restriction fragments (Sambrook, et al., 1989) from the following sources. The vector is an approximately 2000 base pair AscI fragment constructed from a 2000 base pair AatII to PvuII fragment of PNEB 193 (New England Biolabs, Inc.) blunt ended with Klenow DNA polymerase and AscI linkers inserted. Fragment 1 is an approximately 8600 base pair ASCI to AscI fragment of genomic HVT DNA. This region includes BamHI fragments 10 and 21, and approximately 1100 base pairs of fragment 6 and approximately 1300 base pairs of fragment 7. The XhoI site (Nucleotide #1333-1338; SEQ ID NO. 48) has been converted to a unique PacI site using synthetic DNA linkers. The PacI site was used for the insertion and expression of foreign genes in HVT. (See FIG. 13A). It was used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT.

SUBGENOMIC CLONE 686-63.A1. Plasmid 686-63.A1 was constructed for the purpose of generating recombinant HVT. It was isolated as an AscI subclone of cosmid 407-32.1C1 (see FIGS. 8, 15). The cosmid was constructed by joining restriction fragments (Sambrook, et al., 1989) from the following sources. The vector is an approximately 2000 base pair AscI fragment constructed from a 2000 base pair AatII to PvuII fragment of pNEB193 (New England Biolabs, Inc.) blunt ended with Klenow DNA polymerase and AscI linkers inserted. Fragment 1 is an approximately 8600 base pair AscI to AscI fragment of genomic HVT DNA. This region includes BamHI fragments 10 and 21, and approximately 1100 base pairs of fragment 6 and approximately 1300 base pairs of fragment 7. The XhoI site (Nucleotide #1333-1338; SEQ ID NO. 48) has been converted to a unique NotI site using synthetic DNA linkers. The NotI site was used for the insertion and expression of foreign genes in HVT. (See FIG. 13B). It was used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT.

SUBGENOMIC CLONE 672-07.C40. Cosmid 672-07.C40 was constructed for the purpose of generating recombinant HVT. It was isolated as a subclone of cosmid 407-32.1C1 (see FIGS. 8 and 15). Cosmid 672-07.C40 contains an approximately 1100 base pair BamHI to AscI subfragment and an approximately 13,000 base pair AscI to NotI subfragment of cosmid 407-32.1C1. The cosmid was constructed by joining restriction fragments (Sambrook, et al., 1989) from the following sources. The vector is an approximately 2700 base pair NotI to BamHI fragment constructed from pNEB193 (New England Biolabs, Inc.) which contains a NotI linker inserted into the SmaI site. Fragment 1 is an approximately 14,100 base pair region of genomic HVT DNA. This region includes BamHI fragments 6 and 18, and an approximately 2600 base pair BamHI to NotI fragment within BamHI fragment #1. It was used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT.

SUBGENOMIC CLONE 706-57.A3. Plasmid 706-57.A3 was constructed for the purpose of generating recombinant HVT. Plasmid 706-57.A3 contains the IBDV VP2 gene inserted into the PacI site of plasmid 654-45.1. The IBDV VP2 gene uses the IBRV VP8 promoter and ILTV US3 polyadenylation signal. The cosmid was constructed utilizing standard recombinant DNA techniques (Sambrook, et al., 1989) by joining restriction fragments from the following sources. The vector is an approximately 2000 base pair AscI fragment constructed from a 2000 base pair AatII to PvuII fragment of PNEB193 (New England Biolabs, Inc.) blunt ended with Klenow DNA polymerase and AscI linkers inserted. The first fragment is a 208 base pair HindIII to BamHI fragment coding for the IBRV VP8 promoter (Carpenter et al., 1991). The second fragment is an approximately 1626 base pair fragment coding 4for the IBDV VP2 gene derived by reverse transcription and polymerase chain reaction (PCR) (Sambrook, et al., 1989) of IBDV standard challenge strain (USDA) genomic RNA (Kibenge et al., 1990). The antisense primer used for reverse transcription and PCR was 5'-CTCGCTCGCCCATGATCA TTAAGCAAGAATTCCGTCG-3' (SEQ ID NO. 53). The sense primer used for PCR was 5'-CTG GTTCGGCCCAT-GATCAGATGACAAACCTGCAAG ATC-3' (SEQ ID NO. 54). The DNA fragment generated by PCR was cloned into the PCR-Direct ™ vector (Clontech Laboratories, Inc., Palo Alto, Calif.). The IBDV VP2 fragment was subcloned next to the VP8 promoter using BclI sites generated by the PCR primers. The DNA sequence at this junction adds amino acids methionine, aspartate and glutamine before the native initiator methionine of VP2. The DNA fragment contains the coding sequence from amino acid 1 to amino acid 536 of the IBDV polyprotein (SEQ ID NO. 2) which includes the entire coding sequence of the VP2 protein. The third fragment is an approximately 494 base pair fragment coding for the ILTV US3 polyadenylation signal.

SUBGENOMIC CLONE 711-92.1A. Plasmid 711-92.1A was constructed for the purpose of generating recombinant HVT. Plasmid 711-92.1A contains the ILTV gD and gI genes inserted into the PacI site of plasmid 654-45.1. The ILTV gD and gI genes use their respective endogenous ILTV promoters and single shared endogenous polyadenylation signal. The plasmid was constructed utilizing standard recombinant DNA techniques (Sambrook, et al., 1989) by joining restriction fragments from the following sources. The vector is an approximately 2000 base pair AscI fragment constructed from a 2000 base pair AatII to PvuII fragment of pNEB193 (New England Biolabs, Inc.) blunt ended with Klenow DNA polymerase and AscI linkers inserted. The first fragment is an approximately 3556 base pair SalI to HindIII restriction subfragment of the ILTV Asp718I genomic fragment #8 (10.6 kb).

SUBGENOMIC CLONE 717-38.12. Plasmid 717-38.12 was constructed for the purpose of generating recombinant HVT. Plasmid 717-38.12 contains the NDV HN and F genes inserted into the PacI site of plasmid 654-45.1. The NDV HN gene uses the PRV gX promoter and the PRV gX polyadenylation signal. The NDV F gene uses the HCMV immediate early promoter and the HSV TK polyadenylation signal. The plasmid was constructed utilizing standard recombinant DNA techniques (Sambrook, et al., 1989) by joining restriction fragments from the following sources. The vector is an approximately 2000 base pair AscI fragment constructed from a 2000 base pair AatII to PvuII fragment of pNEB193 (New England Biolabs, Inc.) blunt ended with Klenow DNA polymerase and AscI linkers inserted. The first fragment is an approximately 413 base pair SalI to BamHI restriction subfragment of the PRV BamHI fragment #10 (Lomniczi, et al., 1984). The second fragment is an approximately 1811 base pair AvaII to NaeI restriction fragment of the full length NDV HN cDNA clone (B1 strain; SEQ ID NO. 10). The third fragment is an approximately 754 base pair NdeI to SalI restriction subfragment of the PRV Ba restriction fragment #7 (Lomniczi, et al., 1984). The fourth fragment is an approximately 1191 base pair PstI to AvaII restriction subfragment of the HCMV genomic XbaI E fragment (D. R. Thomsen, et al., 1981). The fifth fragment is an approximately 1812 base pair BamHI to PstI restriction fragment of the full length NDV F CDNA clone (B1 strain; SEQ ID NO. 12). The sixth fragment is an approximately 784 base pair SmaI to SmaI restriction subfragment of the HSV-1 BamHI restriction fragment Q (McGeoch, et al., 1985).

SUBGENOMIC CLONE 721-38.1J. Cosmid 721-38.1J was constructed for the purpose of inserting the MDV gA, gD, and gB genes into the unique short of HVT and for the purpose of generating recombinant HVr. Cosmid 721-38.1J contains the MDV gA, gD and gB genes inserted into a StuI site in the HVT US2 gene converted to a unique HindIII site within the BamHI #1 fragment of the unique short region of HVT. This region of the HVT BamHI #1 fragment containing the MDV genes was derived from S-HVT-062. Cosmid 721-38.1J was constructed by a partial restriction digest with BamHI of S-HVT-062 DNA and isolation of an approximately 39,300 base pair fragment. The cosmid was constructed utilizing standard recombinant DNA techniques (Sambrook, et al., 1989) by joining restriction fragments from the following sources. The vector is an approximately 8200 base pair BamHI fragment from cosmid vector pWE15. The first fragment is an approximately 900 base pair BamHI fragment from the repeat region of the HVT genome. The second fragment is an approximately 15,500 base pair BamHI to StuI subfragment of BamHI #1 of HVT. The third fragment is an approximately 8400 base pair cassette containing the MDV gA, gD, and gB genes (see FIGS. 10 and 11). The fourth fragment is an approximately 14,500 base pair HindIII to BamHI subfragment of the BamHI #1 of HVT.

SUBGENOMIC CLONE 722-60.E2. Cosmid 722-60.E2 was constructed for the purpose of inserting the MDV gA, gD, and gB genes and the NDV HN and F genes into the unique short of HVT and for the purpose of generating recombinant HVT. Cosmid 722-60.E2 contains the MDV gA, gD and gB genes and the NDV HN and F genes inserted into a StuI site in the HVT US2 gene converted to a unique HindIII site within the BamHI #1 fragment of the unique short region of HVT. All five genes were inserted in the same transcriptional orientation as the HVT US2 gene. This region of the HVT BamHI #1 fragment containing the MDV and NDV genes was derived from S-HVT-106. Cosmid 722-60.E2 was constructed by a partial restriction digest with BamHI of S-HVT-106 and isolation of an approximately 46,300 base pair fragment. The cosmid was constructed utilizing standard recombinant DNA techniques (Sambrook, et al., 1989) by joining restriction fragments from the following sources. The vector is an approximately 6100 base pair BamHI fragment from cosmid vector pSY1626 derived from pHC79 (Bethesda Research Labs, Inc.) and pWE15 (Strategene, Inc.). The first fragment is an approximately 900 base pair BamHI fragment from the repeat region of the HVT genome. The second fragment is an approximately 15,500 base pair BamHI to StuI subfragment of BamHI #1 of HVT. The third fragment is an approximately 15,400 base pair cassette containing the MDV gA gene, (FIGS. 10A and 10B, SEQ ID NO. 8), the PRV gX promoter (Lomniczi et al., 1984), the NDV HN gene (SEQ ID NO. 10), the PRV gX polyadenylation site (Lomniczi et al., 1984), the HCMV immediate early promoter (D. R. Thomsen, et al., 1981), the NDV F gene (SEQ ID NO. 12), the HSV TK polyadenylation site (McGeoch, et al., 1985), the MDV gD gene (FIGS. 11A and 11B), the approximately 450 base pair ILTV US3 polyadenylation site, and the MDV gB gene (FIGS. 10A and 10B). The fourth fragment is an approximately 14,500 base pair StuI to BamHI subfragment of the BamHI #1 of HVT.

SUBGENOMIC CLONE 729-37.1. Plasmid 729-37.1 was constructed for the purpose of generating recombinant HVT. Plasmid 729-37.1 contains the ILTV gD and gB genes inserted into the NotI site of plasmid 686-63.A1. The ILTV gD and gB genes use their respective endogenous ILTV promoters, and the ILTV gD and gB gene are each followed by PRV gX polyadenylation signals. The ILTV gD and gB gene cassette was constructed utilizing standard recombinant DNA techniques (Sambrook, et al., 1989) by joining restriction fragments from the following sources. The vector is an approximately 2000 base pair AscI fragment constructed from a 2000 base pair AatII to PvuII fragment of pNEB193 (New England Biolabs, Inc.) blunt ended with Klenow DNA polymerase and AscI linkers inserted. The first fragment is an approximately 2052 base pair SalI to XbaI restriction subfragment of the ILTV Asp78I genomic fragment #8 (10.6 kb). The second fragment is an approximately 572 base pair XbaI to Asp78I restriction subfragment of the PRV BamHI restriction fragment #7 (Lomniczi et al., 1984). The third fragment is an approximately 3059 base pair EcoRI to EcoRI restriction fragment of ILTV genomic DNA. The fourth fragment is an approximately 222 base pair EcoRI to SalI restriction subfragment of the PRV BamHI restriction fragment #7 (Lomniczi et al., 1984).

SUBGENOMIC CLONE 739-27.16. Cosmid 739-27.16 was constructed for the purpose of constructing a chimeric HVT/MDV virus containing the HVT genes of the unique long region and the MDV type 1 genes of the unique short region. Cosmid 739-27.16 contains the complete unique short region of MDV type 1. This region contains the entire SniaI B fragment and two SmaI K fragments. Cosmid 739-27.16 was constructed by a partial restriction digest with SmaI of MDV DNA and isolation of an approximately 29,000 to 33,000 base pair fragment. The cosmid was constructed utilizing standard recombinant DNA techniques (Sambrook, et al., 1989) by joining restriction fragments from the following sources. The vector is an approximately 8200 base pair BamHI fragment (made blunt-ended with Klenow DNA polymerase) from cosmid vector pWE15, The first fragment is an approximately 4050 base pair SmaI K fragment from the short internal repeat region of the MDV genome. The second fragment is an approximately 21,000 base pair fragment SmaI B of MDV. The third fragment is an approximately 3,650 base pair SmaI K fragment from the short terminal repeat region of the MDV genome (Fukuchi, et al., 1984, 1985).

EXAMPLES

Example 1

S-HVT-001

Figure 1A:
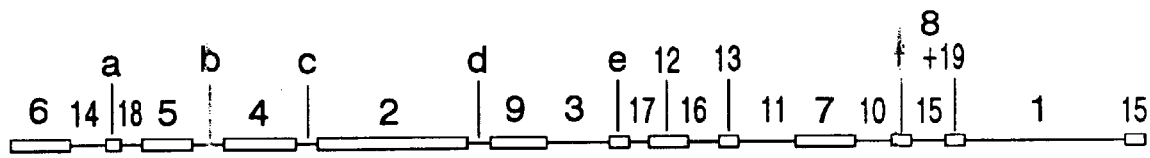
FIGS. 1A, 1B, and 1C show details of HVT Construction and Map Data.

S-HVT-001 is a herpesvirus of turkeys (HVT) that contains the E. coli β-galactosidase gene inserted into the unique long region of the HVT genome. The restriction enzyme map of HVT has been published (T. Igarashi, et al., 1985). This information was used as a starting point to engineer the insertion of foreign genes into HVT. The BamHI restriction map of HVT is shown in FIG. 1A. From this data, several different regions of HVT DNA into which insertions of foreign genes could be made were targeted. The foreign gene chosen for insertion was the E. coli β-galactosidase (lacZ) gene, which we have used in PRV. The promoter was the PRV gpX promoter. The lacZ gene was inserted into the unique long region of HVT, specifically into the XhoI site in the BamHI #16 (3329bp) fragment, and was shown to be expressed in an HVT recombinant by the formation of blue plaques using the substrate Bluogal™ (Bethesda Research Labs). Similarly, the lacZ gene has been inserted into the SalI site in the repeat region contained within the BamHI #19 (900 bp) fragment.

Figure 1B:
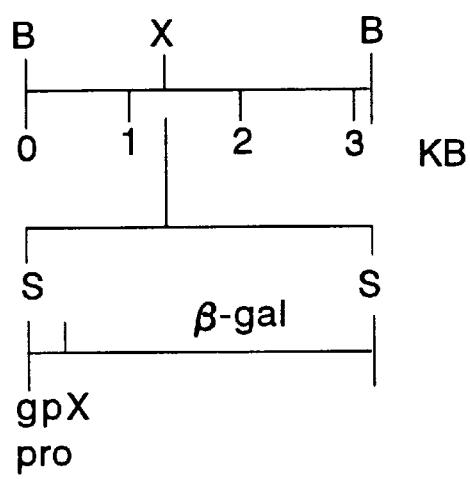
Figure 1C:
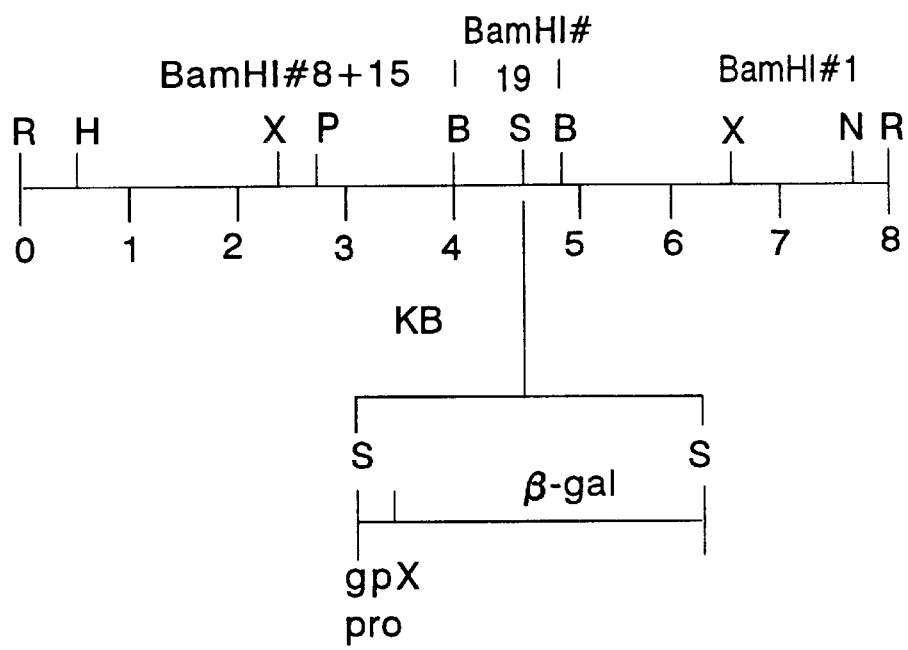

These experiments show that HVT is amenable to the procedures described within this application for the insertion and expression of foreign genes in herpesviruses. In particular, two sites for insertion of foreign DNA have been identified (FIGS. 1B and 1C).

Example 2

S-HVT-003

S-HVT-003 is a herpesvirus of turkeys (HVT) that contains the E. coli β-galactosidase (lacZ) gene and the infectious bursal disease virus (IBDV) strain S40747 large segment of RNA (as a cDNA copy) (SEQ ID NO: 1) inserted into the unique long region of the HVT genome. This IBDV DNA contains one open reading frame that encodes three proteins (5'VP2-VP4-VP3 3') (SEQ ID NO: 2), two of which are antigens to provide protection against IBDV infections of chickens. Expression of the genes for both β-galactosidase and the IBDV polyprotein are under the control of the pseudorabies virus (PRV) gpX gene promoter. S-HVT-003 was made by homologous recombination. S-HVT-003 was deposited on Jul. 21, 1987 pursuant to the Budapest Treaty on the International Deposit of Microorganism for Purposes of Patent Procedure with the Patent Culture Depository of the American Type Culture Collection, 123C1 Parklawn Drive, Rockville, Md. 20852 U.S.A. under ATCC Accession No. VR 2178.

The IBDV genes were cloned by the cDNA CLONING PROCEDURE. Clones representing the genome of IBDV were screened by SOUTHERN BLOTTING OF DNA procedure against blots containing authentic IBDV RNA. Positive clones were then characterized by restriction mapping to identify groups of clones. Two such clones were identified, that together were found to represent the entire coding region of the IBDV large segment of RNA (3.3 kb dsRNA). One cDNA clone (2-84) contained an approximately 2500 base pair fragment representing the first half of the IBDV gene. The second clone (2-40) contained an approximately 2000 base pair fragment representing the distal half of the IBDV gene. Plasmid 2-84/2-40, representing the entire IBDV gene, was constructed by joining clone 2-84 and 2-40 at a unique PvuII site present in the overlapping sequences.

The IBDV genome can be obtained from plasmid 2-84/2-40 as an approximately 3400 base pair SmaI to HpaI fragment. Confirmation of the nature of the proteins encoded by the IBDV gene was obtained by expressing the clone (2-84/2-40) in *E. coli* and detecting VP3 antigen using antiserum made against purified IBDV capsid proteins on Western blots. The cDNA of the IBDV large segment of RNA encoding the IBDV antigens show one open reading frame that will henceforth be referred to as the IBDV gene. The sequence of an Australian IBDV strain has been published which bears close homology to applicants' sequence (Hudson et al, 1986). Comparison of the amino acid differences between the two viruses revealed 29 amino acid changes within the 1012 amino acid coding region. There were only 3 amino acid differences deduced for VP4 and only 8 in VP3. In contrast, VP2 contained 18 amino acid changes, 14 of which were clustered between amino acids 139 to 332.

For insertion into the genome of HVT, the coding region for the IBDV gene was cloned between the PRV gpX promoter and the HSV TK poly-A signal sequence, creating plasmid 191-23. To aid in the identification of HVT recombinants made by homologous recombination containing the IBDV gene, the gpX promoted IBDV fragment from plasmid 191-23 was inserted behind (in tandem to) a lacZ gene controlled by a gpX promoter. The resultant plasmid, 191-47, contains the *E.coli* lacZ gene and the IBDV gene under the control of individual PRV gpX promoters. In constructing plasmid 191-47, various DNA fragments were joined by recombinant DNA techniques using either naturally occurring restriction sites or synthetic linker DNA. Details concerning the construction of these genes contained in plasmid 191-47 can be seen in FIGS. 2A, 2B, 2C and 2D.

The first segment of DNA (Segment 1, FIG. 2A) contains the gpX promoter region including the residues encoding the first seven amino acids of the gpX gene, and was derived from a subclone of the PRV BamHI #10 fragment as an approximately 800 base pair SalI to BamHI fragment. The second segment of DNA (Segment 2, FIG. 2A) contains the *E. coli* β-galactosidase coding region from amino acid 10 to amino acid 1024 and was derived from the plasmid pJF751 (obtained from Jim Hoch, Scripps Clinic and Research Foundation) as an approximately 3300 base pair BamHI to BalI fragment followed by an approximately 40 base pair AvaI to SmaI fragment. The third segment of DNA (Segment 3, FIG. 2A) contains the gpX poly A signal sequence and was derived from a subclone of the PRV BamHI #7 fragment as an approximately 700 base pair NdeI to StuI fragment. Segment three was joined to segment two by ligating the NdeI end which had been filled in according to the POLYMERASE FILL-IN REACTION, to the SmaI site. The fourth segment of DNA (Segment 4, FIG. 2A) contains the gpX promoter (TATA box and cap site) and was derived from a subclone of the PRV BamHI #10 fragment as an approximately 330 base pair NaeI to AluI fragment. Additionally, segment four contains approximately 36 base pairs of HSV TK 5'untranslated leader sequence as a PstI to BglII fragment in which the PstI site has been joined to the AluI site through the use of a synthetic DNA linker (McKnight and Kingbury, 1982). DNA segments four through six were inserted as a unit into the unique KpnI site of segment three which is located 3' of the gpX poly A signal sequence. The fifth segment of DNA (Segment 5, FIG. 2A) contains the entire coding region of the IBDV large segment of RNA (cDNA clone) as an approximately 3400 base pair SmaI to HpaI fragment. The SmaI site of segment five was fused to the BglII site of segment four which had been filled in according to the POLYMERASE FILL IN REACTION. Expression of the IBDV gene (5'VP2-VP4-VP3 3') is under the control of the gpX promoter (segment 4), but utilizes its own natural start and stop codons. The sixth segment of DNA (Segment 6, FIG. 2A) contains the HSV TK poly-A signal sequence as an approximately 800 base pair SmaI fragment (obtained from Bernard Roizman, Univ. of Chicago). The HpaI site of segment five was fused to the SmaI site of segment six through the use of a synthetic DNA linker.

In summary, the construct used to create S-HVT-003 (plasmid 191-47) contains (5' to 3') the PRV promoter, the gpX TATA box, the gpX cap site, the first seven amino acids of gpX, the *E. coli* β-galactosidase (lacZ) gene, the PRV poly-A signal sequence, the PRV gpX promoter, the gpX TATA box, the gpx cap site, a fusion within the gpX untranslated 5' leader to the IBDV gene, IBDV start codon, a fusion within the IBDV untranslated 3' end to HSV TK untranslated 3' end, and the TK poly-A signal sequence. The cassette containing these genes was engineered such that it was flanked by two EcoRI restriction endonuclease sites. As a result, an approximately 9100 base pair fragment containing both lacZ gene and the IBDV gene can be obtained by digestion with EcoRI. Henceforth, the 9161 base pair EcoRI fragment will be referred to as the IBDV/lacZ cassette. The following procedures were used to construct S-HVT-003 by homologous recombination. The IBDV/lacZ cassette was inserted into the unique XhoI site present within a subclone of the HVT BamHI #16 fragment. To achieve this, the XhoI site was first changed to an EcoRI site through the use of an EcoRI linker. This site had previously been shown to be nonessential in HVT by the insertion of lacZ (S-HVT-001). It was also shown that the flanking homology regions in BamHI #16 were efficient in homologous recombination. Shown in FIGS. 3A and 3B, the genomic location of the BamHI #16 fragment maps within the unique long region of HVT. The BamHI #16 fragment is approximately 3329 base pairs in length (SEQ ID NOs: 3, 4, 5, 6, and 7). HVT DNA was prepared by the PREPARATION OF HERPESVIRUS DNA procedure., Cotransfections of HVT DNA and plasmid DNA into primary chick embryo fibroblast (CEF) cells were done according to the DNA TRANSFECTION FOR GENERATING RECOMBINANT HERPESVIRUS. The recombinant virus resulting from the cotransfection stock was purified by three successive rounds of plaque purification using the BLUOGAL SCREEN FOR RECOMBINANT HERPESVIRUS procedure. When 100% of the plaques were blue, the DNA was analyzed for the presence of the IBDV gene by the SOUTHERN BLOTTING OF DNA procedure. Southern blots, probing EcoRI digested S-HVT-003 DNA with an IBDV specific nick translated probe (plasmid 2-84/2-40), confirmed the presence of the 9100 base pair EcoRI fragment. This result confirmed that S-HVT-003 contained both the lacZ gene and the IBDV gene incorporated into its genome. Additional Southern blots, using a probe specific for BamHI #16, confirmed that the homologous recombination occurred at the appropriate position in BamHI #16 and that no deletions were created. No differences in the growth of S-HVT-003 compared to wild type virus (S-HVT-000) were observed in vitro.

Expression of IBDV specific proteins from S-HVT-003 were assayed in vitro using the WESTERN BLOTTING PROCEDURE. Cellular lysates were prepared as described in PREPARATION OF HERPESVIRUS CELL LYSATES. Briefly, the proteins contained in the cellular lysates of S-HVT-003 were separated by polyacrylamide gel electrophoresis, transferred to nitrocellulose, and probed with either an antiserum made against denatured purified IBDV capsid proteins or antiserum made against a synthetic peptide corresponding to a predicted imuno dominant region of the IBDV 40 kd (VP2) capsid protein. The filters were washed and treated with [$^{125}$] protein A to detect the position of the bound antibodies. FIG. 4 shows the results obtained using the antiserum made against denatured purified IBDV capsid proteins, which have been shown by the applicants to react primarily with VP3 (32 kd protein). As seen, S-HVT-003 produces a protein which is immunologically indistinguishable from the authentic VP3 protein from intact IBDV virions. Moreover, the polyprotein appears to be processed correctly, producing a VP3 species that comigrates with the authentic VP3 protein. Recent evidence using an Australian IBDV stain indicates that VP4 is involved in the processing of the precursor polyprotein into mature VP2 and VP3 protein species (Jagadish, et al., 1988). FIG. 5 shows the results obtained using a rabbit antiserum raised against a synthetic peptide that is homologous to a 14 amino acid region of the IBDV VP2 (40 kd) capsid protein. As seen, S-HVT-003 produces a protein that is immunologically indistinguishable from the authentic viral VP2 protein. In addition, the VP2 protein produced from S-HVT-003 comigrates with the 40 kd species of VP2 isolated from intact IBDV virions. This species represents a major component of infectious (complete) viral particles.

In summary, analysis of the expression of IBDV specific proteins from S-HVT-003 has shown that the polyprotein is processed in CEF cell culture, producing proteins of the appropriate size that react to immunological reagents specific for either VP2 or VP3 proteins on Western blots.

The following set of experiments was carried out in chickens to analyze the in vivo expression of the IBDV genes contained within S-HVT-003 as determined by seroconversion data, serum neutralization results, and protection from IBDV challenge.

The first experiment was designed to show the seroconversion of chickens to IBDV upon being vaccinated with S-HVT-003. Eleven 11-week-old chickens, seronegative to HVT and IBDV were obtained from SPAFAS Inc. Six birds were vaccinated subcutaneously in the abdominal region with 0.5 ml of a cellular suspension of CEF cells containing S-HVT-003 (40,000 PFU/ml). Serum samples were obtained every seven days for eight weeks for all birds in this study. On day 28 (4th week), three of these birds received a boost of S-HVT-003, while the other three birds received 0.5 ml of an inactivated IBDV vaccine inoculated subcutaneously in the cervical region. Three additional birds were given only the inactivated vaccine on day 28. Two birds served as contact controls and received no vaccinations. On day 56, all birds were sacrificed and necropsied. Table 1 show the results of the serum neutralization assay against IBDV. No detectable SN activity was observed in the birds given only S-HVT-003. Additionally, only one of the three birds that were given only the inactivated vaccine demonstrated low but detectable SN activity. SN titers were also detected in one of the three birds that received the S-HVT-003 followed by the inactivated IBDV vaccine boost; these titers were at a much higher level than with the inactivated IBDV vaccine alone. These results suggest that S-HVT-003 is priming the chicken for a secondary response against IBDV. In vitro analysis of the serum samples by WESTERN BLOTTING confirmed the seroconversion of the chickens to IBDV upon vaccination with S-HVT-003 both prior to and after boosts administered on day 28.

TABLE 1

| Vaccine Group | Bird No. | DAY 28 | 31 | 35 | 38 | 42 | 49 |
|---|---|---|---|---|---|---|---|
| HVT-003 | 265 | <2 | <2 | <2 | <2 | <2 | <2 |
| HVT-003 | 266 | <2 | <2 | <2 | <2 | <2 | <2 |
|  | 267 | <2 | <2 | <2 | <2 | <2 | <2 |
| HVT-003 | 260 | <2 | <2 | <2 | <2 | <2 | <2 |
| IBDV[a] | 264 | <2 | <2 | <2 | 1:64 | 1:256 | 1:512 |
|  | 269 | <2 | <2 | <2 | <2 | <2 | <2 |
| C | 261 | <2 | <2 | <2 | <2 | <2 | <2 |
| IBDV[a] | 262 | <2 | <2 | <2 | <2 | 1:4 | 1:4 |
|  | 263 | <2 | <2 | <2 | <2 | <2 | <2 |
| C | 270 | <2 | <2 | <2 | <2 | <2 | <2 |
|  | 271 | <2 | <2 | <2 | <2 | <2 | <2 |

[a]Commercial

In the second experiment, twenty five 1-day old SPF chicks were vaccinated with S-HVT-003 (20 with 0.2 ml subcutaneously and 5 by bilateral eyedrop). Twenty chicks were kept as controls. On days four and seven postinfection, five vaccinates and two control birds were bled, sacrificed and their spleens removed for virus isolation. Spleen cell suspensions were made by standard method, and ~1×10$^6$ cells in 3 ml of chick embryo fibroblast (CEF) growth media were inoculated directly onto secondary cells. Cultures were incubated for 6–7 days and then scored for cytopathic effects (CPE) as determined by observing cell morphology. The cultures were passed a second time, and again scored for CPE. The results are shown in Table 2. All nonvaccinated control birds remained negative for HVT for both day 4 and 7 spleen cell isolations. Four out of the five birds vaccinated with S-HVT-003 were positive for HVT at day 4 for both the first and second passages. One bird did not produce virus, this may represent a vaccination failure. Five out of five birds were positive for HVT on day 7 at both passage one and two. Overall, the vector recovery experiment demonstrates that S-HVT-003 replicates as well as wild type HVT virus in vivo and that insertion of the IBDV/lacZ cassette into the XhoI site of BamHI #16 does not result in detectable attenuation of virus. Subsequent experiments examining the recovered virus by the BLUOGAL SCREEN FOR RECOMBINANT HERPESVIRUS procedure confirmed the in vivo stability of S-HVT-003, by demonstrating β-galactosidase expression in 100% of the viruses.

TABLE 2

| | Harvest Date | | | |
|---|---|---|---|---|
| | Day 4 | | Day 7 | |
| Sample | P1 | P2 | P1 | P2 |
| N 1 | — | — | | |
| N 2 | – | – | | |
| N 3 | | | – | – |
| N 4 | | | – | – |
| T 1 | – | – | | |
| T 2 | 2+ | 2+ | | |
| T 3 | 2+ | 2+ | | |
| T 4 | + | 4+ | | |
| T 5 | 3+ | 3+ | | |
| T 6 | | | 2+ | contaminated |
| T 7 | | | + | 5+ |
| T 8 | | | + | 5+ |
| T 8 | | | + | 5+ |

TABLE 2-continued

| | Harvest Date | | | |
| --- | --- | --- | --- | --- |
| | Day 4 | | Day 7 | |
| Sample | P1 | P2 | P1 | P2 |
| T 9 | | | + | 5+ |
| T10 | | | + | 5+ |

N = control, T = vaccinated
CPE ranged from negative (−) to 5+

At days 0, 4, 7, 14, 21, and 27 postinfection, blood samples were obtained from the rest of the chickens for determining serum ELISA titers against IBDV and HVT antigens as well as for virus neutralizing tests against IBDV. Additionally, at 21 days postinfection five control and fourteen vaccinated chicks were challenged with virulent IBDV by bi-lateral eyedrop ($10^{3.8}EID_{50}$). All birds were sacrificed 6-days post challenge and bursa to body weight ratios were calculated. A summary of the results is shown in tables 3 and 4, respectively. As presented in Table 3, no antibodies were detected against HVT antigens by ELISA prior to 21–27 days post vaccination. In chickens, the immune response during the first two weeks post hatch is both immature and parentally suppressed, and therefore these results are not totally unexpected. In contrast, IBDV ELISA's were negative up to day 21 post-vaccination, and were only detectable after challenge on day 27. The ELISA levels seen on day 27 post-vaccination indicate a primary response to IBDV. Table 4 comparing the Bursa-to-Body weight ratios for challenged controls and vaccinated/challenged groups show no significant differences. Vaccination with S-HVT-003 under these conditions did not prevent infection of the vaccinated birds by IBDV challenge, as indicated by the death of four vaccinated birds following challenge.

TABLE 3

| | ELISA | | VN |
| --- | --- | --- | --- |
| Sample Group | HVT | IBDV | IBDV |
| C-0 (n = 3) | 0 | 0 | <100 |
| C-4 (n = 2) | 0 | 0 | nd |
| T-4 (n = 5) | 0 | 0 | nd |
| C-7 (n = 2) | 0 | 0 | <100 |
| T-7 (n = 5) | 0 | 0 | <100 |
| C-14 (n = 5) | 0 | 0 | nd |
| T-14 (n = 14) | 0 | 0 | <100 |
| C-21 (n = 5) | 0 | 0 | nd |
| T-21 (n = 14) | 1 | 0 | <100 |
| C-27 (n = 5) | 0 | 0 | nd |
| CC-27 (n = 5) | 0 | 5 | nd |
| CT-27 (n − 10) | 3.2 | 2 | nd |

C = control
T = vaccinated
CC = challenged control
CT = Challenged & vaccinated.

ELISA titers are GMTs and they range from 0–9.

TABLE 4

| Sample Group | Body wt. | Bursa wt. | BBR |
| --- | --- | --- | --- |
| Control (n = 5) | 258.8 | 1.5088 | 0.0058 |
| Challenge Control (n = 5) | 209 | 0.6502 | 0.0031 |
| Challenge Treated (n = 10) | 215.5 | 0.5944 | 0.0027 |

Values are mean values. Body weights are different in control group because challenged birds did not feed well. Four challenged-treated birds died.

A third experiment was conducted repeating Experiment 2 but using immunologically responsive chicks (3 weeks of age). Six three week old SPF leghorn chickens were vaccinated intraperitoneally with 0.2 ml of S-HVT-003 (one drop in each eye). Serum samples were obtained every seven days for six-weeks and the birds were challenged with the virulent USDA standard challenge IBDV virus on day 43 post-vaccination. Six days post challenge, the control, vaccinated-challenged, and challenged groups were sacrificed and bursas were harvested for probing with anti-IBDV monoclonal antibodies (MAB) (provided by Dr. David Snyder, Virginia-Maryland Regional College of Veterinary Medicine). Bursal homogenates were prepared by mixing 1 ml of 0.5% NP40 with one bursa. Bursa were then ground and briefly sonicated. Supernatants from the homogenates were reacted with the R63 MAB which had been affixed to 96-well Elisa plates via a protein A linkage. After incubation, a biotin labeled preparation of the R63 MAB was added. After washing, an avidin-horse radish peroxidase conjugate was added and incubated. Tests were developed with Tris-malcate buffer (TMB)+$H_{22}$ substrate. The test results are presented in Table 5. The data show the presence of high levels of IBDV antigen in all bursa in the vaccinate-challenged group and in the challenged group. No IBDV antigen was detected in the controls. IBDV specific antigen could be detected at dilutions of over 1/1000, and there does not appear to be differences between vaccinated and non-vaccinated challenged groups. HVT titers as determined by ELISA were first detectable at day 7 in four out of the six birds vaccinated. By day 14, six out of six vaccinated birds showed titers to HVT. All six birds continued to show HVT titers throughout the experiment. No IBDV SN titers were seen prior to the challenge. In contrast, analysis of these same serum samples by the WESTERN BLOTTING procedure demonstrated the seroconversion of chickens vaccinated with S-HVT-003 to IBDV prior to administration of the virus challenge. The level of response, however, remains small unless boosted by challenge. Comparison between the vaccinated/challenged and challenged only groups clearly demonstrates that the level of reactivity by Western blots is much higher in the vaccinated/challenged group. These results show that S-HVT-003 is seroconverting vaccinated birds to IBDV, and suggest that the level of IBDV specific expression are not high enough to induce a neutralizing response in the birds.

S-HVT-003 shows the merit of the vaccine approach the applicants have invented. HVT has been engineered to simultaneously express the foreign antigens (β-galactosidase and IBDV antigens) that are recognized in the host by an

TABLE 5

| Serology: Herpes/IBDV ELISA titer | | | | | | | | |
|---|---|---|---|---|---|---|---|---|
| Bleed Date | | | | | | | | |
| Bird# | 11/3 | 11/10 | 11/14 | 11/24 | 12/1 | 12/8 | 12/15 | 12/22 |
| Vaccinated and Challenged | | | | | | | | |
| 221 | 0/0 | 7/0 | 5/0 | 6/0 | 5/0 | 5/0 | 5/0 | 3/3 |
| 41 | 0/0 | 4/0 | 4/0 | 1/0 | 1/0 | 1/0 | 1/0 | 1/3 |
| 42 | 0/0 | 3/0 | 2/0 | 1/0 | 5/0 | 5/0 | 5/0 | 3/2 |
| 43 | 0/0 | 0/0 | 5/0 | 5/0 | 5/0 | 5/0 | 3/0 | 3/2 |
| 44 | 0/0 | 1/0 | 5/0 | 1/0 | 2/0 | 1/0 | 1/0 | 2/4 |
| 45 | 0/0 | 0/0 | 1/0 | 1/0 | 1/0 | 1/0 | 1/0 | 1/3 |
| Control | | | | | | | | |
| 28 | 0/0 | | | | | | | 0/0 |
| 38 | 0/0 | | | | | | | 0/0 |
| 73 | 0/0 | | | | | | | 0/0 |
| 75 | 0/0 | | | | | | | 0/0 |
| Challenged Only | | | | | | | | |
| 40 | 0/0 | | | | | | | 0/3 |
| 74 | 0/0 | | | | | | | 0/5 |
| 39 | 0/0 | | | | | | | 0/3 |
| 72 | 0/0 | | | | | | | 0/3 |
| Maximum titer level is 9 | | | | | | | | |

Example 3

S-HVT-004

S-HVT-004 is a recombinant herpesvirus of turkeys that contains the Marek's disease virus (MDV) glycoprotein A (gA) gene inserted into the long unique region, and the β-galactosidase (lacZ) gene also inserted in the long unique region. The MDV antigen is more likely to elicit the proper antigentic response than the HVT equivalent antigen.

The MDV gA (SEQ ID NO: 8 and SEQ ID NO: 9) gene was cloned by standard DNA cloning gA procedures. An EcoRI restriction fragment had been reported to contain the MDV gA gene (Isfort et al., 1984) and this fragment was identified by size in the DNA clones. The region of the DNA reported to contain the gA gene was sequenced by applicants and found to contain a glycoprotein gene as expected. The DNA from this gene was used to find the corresponding gene in HVT by the SOUTHERN BLOTTING OF DNA procedure, and a gene in HVT was identified that contained a very similar sequence. This gene is the same gene previously called gA (Isfort et al., 1984).

For insertion into the genome of HVT, the MDV gA gene was used intact because it would have good herpesvirus signal sequences already. The lacZ gene was inserted into the XhoI fragment in BamHI fragment #16, and the MDV gA gene was inserted behind lacZ as shown in FIG. 6A and 6B. Flanking regions in BamHI #16 were used for the homologous recombination. HVT DNA and plasmid DNA were co-transfected according to the DNA TRANSFECTION FOR GENERATING RECOMBINANT HERPESVIRUS procedure into primary chick embryo fibroblast (CEF) cells. The virus from the transfection stock was purified by successive plaque purifications using the BLUOGAL SCREEN FOR RECOMBINANT HERPESVIRUS procedure. At the end of this procedure, when 100% of the plaques were blue, the DNA was analyzed for the presence of the MDV gA gene. S-HVT-004 is a recombinant virus that contains both the β-galactosidase gene and the MDV gA gene incorporated into the genome.

FIG. 6C shows the structure of S-HVT-004.

Example 4

NEWCASTLE DISEASE VIRUS

Newcastle disease virus (NDV) is closely related to PI-3 in overall structure. We have engineered the hemagglutinin (HN) and fusion (F) genes of PI-3 for expression in IBR (ref). Similarly we have cloned the hemagglutinin (HN) and fusion (F) genes from NDV for use in the herpesvirus delivery system (Herpesvirus of turkeys, HVT).

The procedures that we have utilized for construction of herpesvirus control sequences for expression have been applied to NDV.

INFECTIOUS BRONCHITIS VIRUS

Infectious bronchitis virus (IBV) is a virus of chickens closely related in overall structure to TGE. We have engineered the major neutralizing antigen of TGE for expression in PRV (ref). Similarly we have cloned the major neutralizing antigens from three strains of IBV: Massachusetts (SEQ ID NOs: 14 and 15), Connecticut (SEQ ID NOs: 18 and 19), and Arkansas-99 (SEQ ID NOs: 16 and 17) for use in a herpesvirus delivery system (HVT).

The procedures that we have utilized for the construction of herpesvirus control sequences for expression have been applied to IBV.

Example 5

S-HVT-045

S-HVT-045 is a recombinant herpesvirus of turkeys that contains the Marek's disease virus (MDV) glycoprotein B (gB) gene inserted into the short unique region. The MDV antigen is more likely to elicit the proper antigenic response than the HVT equivalent antigen. S-HVT-045 has been deposited on Oct. 15, 1992 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2383.

The MDV gB gene was cloned by standard DNA cloning procedures. The MDV gB gene was localized to a 3.9 kb EcoRI-SalI fragment using an oligonucleotide probe based on the HSV gB sequence in a region found to be conserved among known herpesvirus gB genes. The restriction map 3.9 kb EcoRI-SalI fragment is similar to the published map (Ross et al., 1989).

For insertion into the HVT genome, the MDV gB was used intact because it would have good herpesvirus signal sequences already. The MDV gB gene was inserted into a cloned 17.15 kb BamHI-EcoRI fragment derived from the HVT BamHI #1 fragment. The site used for insertion was the StuI site within HVT US2, previously utilized for the construction of S-HVT-012. The site was initially altered by insertion of a unique HindIII linker, and the MDV gB gene was inserted by standard DNA cloning procedures. Flanking regions in the 17.15 kb BamHI-EcoRI fragment were used, together with the remaining cloned HVT fragments using the PROCEDURE FOR GENERATING RECOMBINANT HERPESVIRUSES FROM OVERLAPPING SUBGENOMIC FRAGMENTS. The virus obtained from the transfection stock was plaque purified and the DNA was analyzed for the presence of the MDV gB gene. S-HVT-045 is a recombinant virus that contains the MDV gB gene incorporated into the genome at the StuI site in HVT US2 gene.

TESTING OF RECOMBLNANT S-HVT-045

Two studies were conducted to demonstrate the effectiveness of these recombinant HVT/MDV viruses in protecting against challenge with virulent Marek's disease virus. In Study A, one-day-old specific pathogen free (SPF) chicks were vaccinated with either S-HVT-045 or S-HVT-046.

Seven days post-vaccination, vaccinated chicks, and non-vaccinated, control chicks were challenged with the highly virulent MD-5 strain of Marek's disease virus. Following a 6-week post-challenge observation period for clinical signs typical of Marek's disease, all chicks were necropsied and examined for lesions diagnostic of Marek's disease. The results, in Table 6, show that both recombinant viruses gave complete protection against a challenge that caused Marek's disease in 90% of non-vaccinated control chicks.

In a second study, one-day-old chicks were vaccinated either with S-HVT-045 or S-HVT-047. A third group of chicks were vaccinated with a USDA-licensed, conventional vaccine comprised of HVT and SB-1 viruses. Five days post-vaccination, the vaccinated chicks and a group of non-vaccinated, control chicks were challenged with virulent Marek's virus, strain RB1B. The chicks were observed for 8 weeks for clinical signs of Marek's disease, then necropsied and observed for Marek's lesions. This study demonstrated the ability of HVT-045 and HVT-047 to provide 100% protection against challenge (Table 1). The commercial vaccine gave 96% protection, and 79% of the non-vaccinated chicks developed Marek's disease.

TABLE 6

EFFICACY OF RECOMBINANT HVT/MDV VIRUSES TO PROTECT SUSCEPTIBLE CHICKS AGAINST VIRULENT MAREK'S DISEASE VIRUS

| Vaccine Group | Marek's Protection | |
| --- | --- | --- |
|  | MD-5 Challenge | RB1B Challenge |
| S-HVT-045 | 20/20 | 24/24 |
| S-HVT-046 | 20/20 | Not Tested |
| S-HVT-047 | Not Tested | 24/24 |
| HVT[a] | Not Tested | 24/25 |
| Controls | 2/20 | 5/24 |

[a]commercial

Example 6
S-HVT-012

S-HVT-012 is a recombinant herpesvirus of turkeys that contains the *E. coli* β-galactosidase (lacZ) gene inserted into the short unique region. The lacZ gene was used to determine the viability of this insertion site in HVT [ATCC F-126 ("Calnek")]. S-HVT-012 has been deposited on Oct. 15, 1992 pursuant to the Budapest Treaty on the International Deposit of Microorganisms for the Purposes of Patent Procedure on with the Patent Culture Depository of the American Type Culture Collection, 12301 Parklawn Drive, Rockville, Md. 20852 U.S.A. under ATCC Accession No. VR 2382.

For insertion into the genome of HVT, the β-galactosidase gene was introduced into the unique StuI site of the cloned EcoRI fragment #7 of HVT, i.e., the fragment containing the StuI site within the US2 gene of HVT (as described in Methods and Materials). Flanking regions of EcoRI fragment #7 were used for homologous recombination. HVT DNA and plasmid DNA were co-transfected according to the DNA TRANSFECTION FOR GENERATING RECOMBINANT VIRUS procedure into primary chick embryo fibroblast (CEF) cells. A blue virus obtained from the transfection stock was purified by successive plaque purifications using the BLUOGAL SCREEN FOR RECOMBINANT HERPESVIRUS procedure. At the end of this procedure, when 100% of the plaques were blue, the DNA was analyzed for the presence of the lacZ gene. S-HVT-012 is a recombinant virus that contains the lacZ gene incorporated into the genome at the StuI site within the US2 gene of HVT.

S-HVT-012 may be formulated as a vaccine in the same manner as S-HVT-045. When administered to chickens, such a vaccine provides protection against Marek's disease virus.

Example 7
Sites for Insertion of Foreign DNA into HVT

In order to define appropriate insertion sites, a library of HVT BamHI and EcoRI restriction fragments was generated. Several of these restriction fragments (BamHI fragments #16 and #13, and EcoRI fragments #6, #7, and #9 (see FIG. 1)) were subjected to restriction mapping analysis. One unique restriction site was identified in each fragment as a potential insertion site. These sites included XhoI in BamHI fragments #13 and #16, and EcoRI fragment #9 and SalI in EcoRI fragment #6 and StuI in EcoRI fragment #7. A β-galactosidase (lacZ) marker gene was inserted in each of the potential sites. A plasmid containing such a foreign DNA insert may be used according to the DNA COTRANSFECTION FOR GENERATING RECOMBINANT HERPESVIRUSES to CONSTRUCT a HVT containing the foreign DNA. For this procedure to be successful it is important that the insertion site be in a region non-essential to the replication of the HVT and that the site be flanked with HVT DNA appropriate for mediating homologous recombination between virus and plasmid DNAS. The plasmids containing the lacZ marker gene were utilized in the DNA COTRANSFECTION FOR GENERATING RECOMBINANT HERPESVIRUSES. The generation of recombinant virus was determined by the BLUOGAL SCREEN FOR RECOMBINANT HERPESVIRUS. Three of the five sites were successfully used to generate a recombinant virus. In each case the resulting virus was easily purified to 100%, clearly defining an appropriate site for the insertion of foreign DNA. The three homology vectors used to define these sites are described below.

Example 7A
Homology Vector 172-29.31

The homology vector 172-29.31 contains the HVT BamHI #16 fragment and is useful for the insertion of foreign DNA into HVT. Plasmid 172-29.31 contains a unique XhoI restriction site into which foreign DNA may be cloned. We have demonstrated that the XhoI site in homology vector 172-29.31 may be used to insert foreign DNA into HVT by the construction of at least three recombinant HVT (see examples 1–3).

The homology vector 172-29.31 was further characterized by DNA sequence analysis. The complete sequences of the BamHI #16 fragment was determined. Approximately 2092 base pairs of the adjacent BamHI #13 fragment was also determined (see SEQ ID NO: 3). This sequence indicates that the open reading frame coding for HVT glycoprotein A (gA) spans the BamHI #16–BamHI #13 junction. The HVT gA gene is homologous to the HSV-1 glycoprotein C (gC). The XhoI site interrupts an ORF which lies directly upstream of the HVT gA gene. This ORF shows amino acid sequence homology to the PRV p43 and the VZV gene 15. The PRV and VZV genes are the homologues of HSV-1 UL43. Therefore we have designated this ORF as HVT UL43 (SEQ ID NO: 5). It should be noted that the HVT UL43 does not exhibit direct homology to HSV-1 UL43. Although HVT UL43 is located upstream of the HVT gC homologue it is encoded on the same DNA strand as HVT gA, where as the HSV-1 UL43 is on the opposite strand relative to HSV-1 gC. The XhoI site interrupts UL43 at approximately amino acid 6, suggesting that the UL43 gene is non-essential for HVT replication.

Example 7B
Homology Vector 435-47.R17

The homology vector 435-47.R17 contains the HVT EcoRI #7 fragment and is useful for the insertion of foreign DNA into HVT. Plasmid 435-47.R17 contains a unique HindIII restriction site into which foreign DNA may be cloned. The HindIII restriction site in plasmid results from the insertion of a HindIII linker into the naturally occurring StuI site of EcoRI fragment #7. We have demonstrated that the HindIII site in homology vector 435-47.R17 may be used to insert foreign DNA into HVT by the construction of at least 25 recombinant HVT.

DNA sequence analysis at the StuI indicated that this fragment contains open reading frames coding for US10, US2, and US3. The StuI site interrupts US2 at approximately amino acid 124, suggesting that the US2 gene is non-essential for HVT replication.

Example 7C
Homology Vector 172-63.1

The homology vector 172-63.1 contains the HVT EcoRI #9 fragment and is useful for the insertion of foreign DNA into HVT. Plasmid 172-63.1 contains a unique XhoI restriction site into which foreign DNA may be cloned. We have demonstrated that the XhoI site in homology vector 172-63.1 may be used to insert foreign DNA into HVT by the construction of S-HVT-014 (see example 8).

Example 8
S-HVT-014

S-HVT-014 is a recombinant herpesvirus of turkeys that contains the E. coli β-galactosidase (lacZ) gene inserted into the long unique region. The lacZ gene was used to determine the viability of this insertion site in HVT [ATCC F-126 ("Calnek")].

For insertion into the genome of HVT, the β-galactosidase gene was introduced into the unique XhoI site of the cloned EcoRI fragment #9 (as described in Methods and Materials). The XhoI site within the EcoRI #9 fragment of the HVT genome is the same site as the XhoI site within the BamHI #10 fragment used for constructing recombinant herpesviruses of turkeys described in Examples 16 through 19. Flanking regions of EcoRI fragment #9 were used for homologous recombination. HVT DNA and plasmid DNA were co-transfected according to the DNA TRANSFECTION FOR GENERATING RECOMBINANT VIRUS procedure into primary chick embryo fibroblast (CEF) cells. A blue virus obtained from the transfection stock was purified by successive plaque purifications using the BLUOGAL SCREEN FOR RECOMBINANT HERPESVIRUS procedure. At the end of this procedure when 100% of the plaques were blue. S-HVT-014 is a recombinant virus that contains the lacZ gene incorporated into the genome at the XhoI site within the EcoRI #9 fragment of HVT.

S-HVT-014 may be formulated as a vaccine in the same manner as S-HVT-045. When administered to chickens, such a vaccine provides protection against Marek's disease virus.

Example 9
S-HVT-005

S-HVT-005 is a recombinant herpesvirus of turkeys that contains the E. coli β-galactosidase (lacZ) gene inserted into the long unique region. The lacZ gene was used to determine the viability of this insertion site in HVT [ATCC F-126 ("Calnek")].

For insertion into the genome of HVT, the β-galactosidase gene was introduced into an approximately 1300 base pair deletion of the XhoI #9 fragment of HVT. The deletion which lies between the unique MluI and EcoRV sites removes the complete coding region of the HVT gA gene (see SEQ ID NO: 3). Flanking regions of XhoI fragment #9 were used for homologous recombination. HVT DNA and plasmid DNA were co-transfected according to the DNA TRANSFECTION FOR GENERATING RECOMBINANT VIRUS procedure into primary chick embryo fibroblast (CEF) cells. A blue virus obtained from the transfection stock was purified by successive plaque purifications using the BLUOGAL SCREEN FOR RECOMBINANT HERPESVIRUS procedure. At the end of this procedure, when 100% of the plaques were blue, the DNA was analyzed for the presence of the lacZ gene. S-HVT-005 is a recombinant virus that contains the lacZ gene incorporated into the genome in place of the deleted gA gene of HVT.

S-HVT-005 may be formulated as a vaccine in the same manner as S-HVT-045. When administered to chickens, such a vaccine provides protection against Marek's disease virus.

Example 10
Marek's Disease Vaccines

Recombinant HVT expressing glycoproteins from Marek's Disease Virus make superior vaccines for Marek's Disease. We have constructed several recombinant HVT expressing MDV glycoproteins: S-HVT-004 (Example 3), S-HVT-045 (Example 5), S-HVT-046 (Example 10A), S-HVT-047 (Example 10B), S-HVT-062 (Example 10C).

Example 10A
S-HVT-046

S-HVT-046 is a recombinant herpesvirus of turkeys that contains the Marek's disease virus (MDV) glycoprotein B (gB) and glycoprotein A (gA) genes inserted into the short unique region. The MDV genes are inserted in the same transcriptional orientation as the US2 gene. The MDV antigens are more likely to elicit the proper antigenic response than the HVT equivalent antigen.

S-HVT-046 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 437-26.26 with BamHI and HindIII, and 456-17.22 uncut. Insertion of the appropriate DNA was confirmed by southern blot analysis.

Example 10B
S-HVT-047

S-HVT-047 is a recombinant herpesvirus of turkeys that contains the MDV gB and gA genes inserted into the short unique region. The MDV genes are inserted in the opposite transcriptional orientation as the US2 gene. The MDV antigens are more likely to elicit the proper antigenic response than the HVT equivalent antigen.

S-HVT-047 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 437-26.26 with BamHI and HindIII, and 456-17.18 uncut. Insertion of the appropriate DNA was confirmed by southern blot analysis.

Example 10C
S-HVT-062

S-HVT-062 is a recombinant herpesvirus of turkeys that contains the MDV gB, glycoprotein D (gD) and gA genes inserted into the short unique region. The MDV genes are inserted in the same transcriptional orientation as the US2 gene. The MDV antigens are more likely to elicit the proper antigenic response than the HVT equivalent antigen. S-HVT-062 has been deposited on Feb. 23, 1993 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2401.

S-HVT-062 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 556-60.6 with BamHI and HindIII, and 456-17.22 uncut. Insertion of the appropriate DNA was confirmed by southern blot analysis.

TESTING OF RECOMBINANT HVT EXPRESSING MDV ANTIGENS

Two studies were conducted to demonstrate the effectiveness of these recombinant HVT/MDV viruses in protecting against challenge with virulent Marek's disease virus. In Study 1, one-day-old specific pathogen free (SPF) chicks were vaccinated with either S-HVT-045, S-HVT-046, or S-HVT-047. Five days post-vaccination, vaccinated chicks, and non-vaccinated, control chicks were challenged with MDV. Following a 6-week post-challenge observation period for clinical signs typical of Marek's disease, all chicks were necropsied and examined for lesions diagnostic of Marek's disease. The results, in Table 7, show these recombinant viruses gave complete protection against a challenge that caused Marek's disease in 84% of non-vaccinated control chicks.

In the second study, one-day-old chicks were vaccinated with S-HVT-062. Two more groups of chicks were vaccinated with a USDA-licensed, conventional vaccines comprised of HVT and a combination HVT and SB-1 viruses. Five days post-vaccination, the vaccinated chicks and a group of non-vaccinated, control chicks were challenged with MDV. The chicks were observed for 8 weeks for clinical signs of Marek's disease, then necropsied and observed for Marek's lesions. This study demonstrated the ability of S-HVT-062 to provide 100! protection against challenge (Table 7). The commercial vaccines gave 81% and 95% protection, respectively and 100% of the non-vaccinated chicks developed Marek's disease.

TABLE 7

EFFICACY OF RECOMBINANT HVT/MDV VIRUSES AGAINST VIRULENT MAREK'S VIRUS CHALLENGE

| Study | Vaccine Group | Dose[a] | Protection[b] |
|---|---|---|---|
| 1 | S-HVT-045 | $2.2 \times 10^3$ | 24/24 (100%) |
| 1 | S-HVT-046 | $2.2 \times 10^3$ | 20/20 (100%) |
| 1 | S-HVT-047 | $2.2 \times 10^3$ | 24/24 (100%) |
| 1 | Controls | | 7/44 (16%) |
| 1 | HVT/SB-1 | | 24/25 (96%) |
| 2 | S-HVT-062 | $7.5 \times 10^2$ | 32/32 (100%) |
| 2 | S-HVT-062 | $1.5 \times 10^3$ | 22/22 (100%) |
| 2 | Controls | | 0/20 (0%) |

TABLE 7-continued

EFFICACY OF RECOMBINANT HVT/MDV VIRUSES AGAINST VIRULENT MAREK'S VIRUS CHALLENGE

| Study | Vaccine Group | Dose[a] | Protection[b] |
|---|---|---|---|
| 2 | HVT[c] | $7.5 \times 10^2$ | 17/21 (81%) |
| 2 | HVT/SB-1[c] | $7.5 \times 10^2$ | 21/22 (95%) |

[a]PFU/0.1 ml.
[b]No. protected/Total; Challenge 5 days post-vaccination.
[c]Commercial vaccine.

Example 11
Bivalent Vaccines Against Newcastle Disease and Marek's Disease

Recombinant HVT expressing proteins from NDV make bivalent vaccines protecting against both Marek's Disease and Newcastle disease. We have constructed several recombinant HVT expressing NDV proteins S-HVT-007 (Example 11A), S-HVT-048 (Example 11B), S-HVT-049 (Example 11C), S-HVT-050 (Example 11D), and S-HVT-106 (Example 11E).

Example 11A
S-HVT-007

S-HVT-007 is a recombinant herpesvirus of turkeys that contains a E. coli lacZ NDV HN hybrid protein gene under the control of the PRV gX promoter and the NDV F gene under the control of the HSV-1 α4 promoter inserted into the long unique region. The NDV genes are inserted in the same transcriptional orientation as the UL43 gene.

To construct S-HVT-007, HVT DNA and the plasmid 255-18.B16 were co-transfected according to the DNA TRANSFECTION FOR GENERATING RECOMBINANT VIRUS procedure into primary chick embryo fibroblast (CEF) cells. A blue virus obtained from the transfection stock was purified by successive plaque purifications using the BLUOGAL SCREEN FOR RECOMBINANT HERPESVIRUS procedure. At the end of this procedure, when 100% of the plaques were blue.

Example 11B
S-HVT-048

S-HVT-048 is a recombinant herpesvirus of turkeys that contains the MDV gB and gA genes and the NDV F gene under the control of the HCMV immediate early promoter inserted into the short unique region. The MDV and NDV genes are inserted in the same transcriptional orientation as the US2 gene.

S-HVT-048 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 437-26.26 with BamHI and HindIII, and 535-70.3 uncut. Insertion of the appropriate DNA was confirmed by southern blot analysis.

Example 11C
S-HVT-049

S-HVT-049 is a recombinant herpesvirus of turkeys that contains the MDV gB and gA genes and the NDV HN gene under the control of the PRV gX promoter inserted into the short unique region. The MDV and NDV genes are inserted in the same transcriptional orientation as the US2 gene.

S-HVT-049 was constructed according to the PROCEDURE FOR GENERATING RECOMBINANT HERPES- VIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 437-26.26 with BamHI and HindIII, and 549-62.10 uncut. Insertion of the appropriate DNA was confirmed by southern blot analysis.

Example 11D

S-HVT-050

S-HVT-050 is a recombinant herpesvirus of turkeys that contains the MDV gB and gA genes and the NDV HN (SEQ ID NOs: 10 and 11) and F (SEQ ID NOs: 12 and 13) genes. The NDV genes are under the control of the PRV gX and HCMV immediately promoters respectively. All four genes are inserted into the short unique region in the same transcriptional orientation as the US2 gene.

S-HVT-050 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 437-26.26 with BamHI and HindIII, and 549-24.15 uncut. Insertion of the appropriate DNA was confirmed by southern blot analysis. S-HVT-050 has been deposited on Feb. 23, 1993 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2400.

Example 11E

S-HVT-106

S-HVT-106 is a recombinant herpesvirus of turkeys that contains the MDV gA, gB, gD genes and the NDV HN and F genes. The NDV genes are under the control of the PRV gX and HCMV immediately promoters respectively. All five genes are inserted into the short unique region in the same transcriptional orientation as the US2 gene.

S-HVT-106 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 437-26.26 with BamHI and HindIII, and 633-13.27 uncut.

TESTING OF RECOMBINANT HVT EXPRESSING NDV ANTIGENS

Two studies were conducted to demonstrate the effectiveness of these recombinant HVT/MDV/NDV viruses in protecting against challenge with virulent Newcastle and Marek's disease viruses. In Study 1, one-day-old specific pathogen free (SPF) chicks were vaccinated with either S-HVT-048, S-HVT-049, S-HVT-050, or a USDA-licensed, conventional vaccine comprised of NDV B1/B1 virus. Three weeks post-vaccination, vaccinated chicks, and non-vaccinated, control chicks were challenged with NDV. Birds were then observed for clinical signs of disease. The results, in Table 8, show these recombinant viruses (S-HVT-048 and S-HVT-050) gave complete protection against a is challenge that caused Newcastle disease in 100% of non-vaccinated control chicks. Recombinant virus S-HVT-049 gave partial protection against Newcastle disease.

In the second study, one-day-old chicks were vaccinated with S-HVT-050. Two more groups of chicks were vaccinated with a USDA-licensed, conventional vaccines comprised of HVT and a combination HVT and SB-1 viruses. Five days post-vaccination, the vaccinated chicks and a group of non-vaccinated, control chicks were challenged with MDV. The chicks were observed for 8 weeks for clinical signs of Marek's disease, then necropsied and observed for Marek's lesions. This study demonstrated the ability of S-HVT-050 to provide protection greater than the commercial Marek's disease vaccines.

TABLE 8

EFFICACY OF RECOMBINANT HVT/MDV/NDV VIRUSES AGAINST VIRULENT NEWCASTLE AND MAREK'S DISEASE VIRUS CHALLENGE

| Study | Vaccine Group | Dose[a] | Protection (%) | |
|---|---|---|---|---|
| | | | NDV[b] | MDV[c] |
| 1 | S-HVT-048 | $4.0 \times 10^4$ | 19/19 (100) | |
| 1 | S-HVT-049 | $3.0 \times 10^4$ | 4/20 (20) | |
| 1 | S-HVT-050 | $1.5 \times 10^4$ | 20/20 (100) | |
| 1 | Controls | | 0/20 (0) | |
| 1 | NDV B1/B1[d] | | 18/18 (100) | |
| 2 | S-HVT-050 | $7.5 \times 10^2$ | | 13/14 (93) |
| 2 | S-HVT-050 | $1.5 \times 10^3$ | | 16/17 (94) |
| 2 | Controls | | | 5/23 (22) |
| 2 | HVT[d] | | | 20/26 (77) |
| 2 | HVT/SB-1[d] | | | 10/12 (83) |

[a]PFU/0.2 ml.
[b]No. protected/Total; Challenge 3 weeks post-vaccination.
[c]No. protected/Total; Challenge 5 days post-vaccination.
[d]Commercial vaccine.

Example 12

Bivalent Vaccines Against Infectious Laryngotracheitis and Marek's Disease

Recombinant HVT expressing glycoproteins from ILT virus make bivalent vaccines protecting against both Marek's disease and infectious laryngotracheitis. We have constructed several recombinant HATT expressing ILT virus glycoproteins S-HVT-051 (Example 12A), S-HVT-052 (Example 12B), and S-HVT-104 (Example 11C).

Example 12A

S-HVT-051

S-HVT-051 is a recombinant herpesvirus of turkeys that contains the ILT virus gB gene inserted into the short unique region. The ILT gene is inserted in the same transcriptional orientation as the US2 gene.

S-HVT-051 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 437-26.26 with BamHI and HindIII, and 528-11.34 uncut. Insertion of the appropriate DNA was confirmed by southern blot analysis.

Example 12B

S-HVT-052

S-HVT-052 is a recombinant herpesvirus of turkeys that contains the ILT virus gD gene inserted into the short unique region. The ILT gene is inserted in the opposite transcriptional orientation as the US2 gene.

S-HVT-052 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 437-26.26 with BamHI and HindIII, and 528-03.37 uncut. Insertion of the appropriate DNA was confirmed by southern blot analysis.

Example 12C
S-HVT-104

S-HVT-104 is a recombinant herpesvirus of turkeys that contains six foreign genes. The MDV gA, gB, and gD genes are inserted in the unique short region in the same transcriptional orientation as the US2 gene. An $E.\ coli$ lacZ marker gene and the ILT gB and gD genes are inserted in BamHI #16 region in the same transcriptional orientation as the UL43 gene.

To construct S-HVT-104, DNA from S-HVT-062 and the plasmid 634-29.16 were co-transfected according to the DNA TRANSFECTION FOR GENERATING RECOMBINANT VIRUS procedure into primary chick embryo fibroblast (CEF) cells.

TESTING OF RECOMBINANT HVT EXPRESSING ILT ANTIGENS

The following study was conducted to demonstrate the effectiveness of these recombinant HVT/ILT viruses in protecting against challenge with virulent Infectious Laryngotracheitis virus. One-day-old specific pathogen free (SPF) chicks were vaccinated with either S-HVT-051, S-HVT-052, a combination of S-HVT-051 and S-HVT-052, or a USDA-licensed, conventional vaccine comprised of ILT virus. Two to three weeks post-vaccination, vaccinated chicks, and non-vaccinated, control chicks were challenged with ILT. Birds were then observed for clinical signs of disease. The results, in Table 9, show these recombinant viruses (S-HVT-051 and S-HVT-052) gave protection against challenge with ILT virus comparable to a commercial ILT vaccine.

Animals vaccinated with the vaccines described here may be easily differentiated from animals infected with virulent ILT. This is accomplished by testing the suspect birds for antibodies to any ILT antigens other than gB or gD. Examples of such antigens are ILT glycoproteins C, E, and G. Vaccinated, uninfected birds will be negative for these antigens whereas infected birds will be positive.

TABLE 9

EFFICACY OF RECOMBINANT HVT/ILT VIRUSES AGAINST VIRULENT INFECTIOUS LARYNGOTRACHEITIS VIRUS CHALLENGE

| Vaccine Group | Dose[a] | Protection[b] |
|---|---|---|
| S-HVT-051 | $2.1 \times 10^3$ | 28/30 (93%) |
| S-HVT-052 | $1.7 \times 10^3$ | 29/29 (100%) |
| S-HVT-051 + | $2.1 \times 10^3$ | 24/24 (100%) |
| S-HVT-052 | $1.7 \times 10^3$ | |
| Controls | | 2/30 (7%) |
| ILT[c] | | 29/30 (97%) |

[a]PFU/0.2 ml.
[b]No.protected/Total; Challenge 2–3 weeks post-vaccination.
[c]Commercial vaccine.

Example 13
Bivalent Vaccines Against Infectious Bursal Disease and Marek's Disease Recombinant HVT expressing proteins from IBDV make bivalent vaccines protecting against both Marek's Disease and infectious bursal disease. we have constructed several recombinant HVT expressing IBDV proteins. These viruses include S-HVT-003 (example 2) and S-HVT-096.

S-HVT-096 is a recombinant herpesvirus of turkeys that contains the IBDV VP2 gene, under the control of the HCMV immediate early promoter, inserted into the short unique region. The IBDV gene is inserted in the same transcriptional orientation as the US2 gene.

S-HVT-096 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 556-60.6 with BamHI, and 602-57.F1 uncut. Insertion of the appropriate DNA was confirmed by southern blot analysis.

S-HVT-096 was assayed for expression of VP2 by black plaque and western blot analysis. Both assays indicated that the virus was expressing high levels of protein which reacts specifically with an IBDV neutralizing monoclonal antibody. This virus will be useful as a vaccine against infectious bursal disease.

Example 14
Bivalent Vaccines Against Infectious Bronchitis and Marek's Disease

S-HVT-066 is a recombinant herpesvirus of turkeys that contains the MDV gB, gD and gA genes and the IBV spike and matrix genes. The IBV spike and matrix genes are under the control of the HCMV immediate early and PRV gX promoters respectively. All five genes are inserted into the short unique region. The MDV and IBV genes are inserted in the same transcriptional orientation as the US2 gene.

S-HVT-066 was constructed according to the PROCEDURE FOR GENERATING RECOMBINANT HERPESVIRUS FROM SUBGENOMIC DNA FRAGMENTS. The following combination of subgenomic clones and enzymes were used: 407-32.2C3 with NotI, 172-07.BA2 with BamHI, 407-32.5G6 with NotI, 407-32.1C1 with NotI, 437-26.24 with BamHI and HindIII, 556-60.6 with BamHI, and 567-72.1D uncut. Insertion of the appropriate DNA was confirmed by southern blot analysis.

S-HVT-066 was assayed for expression of the IBV spike protein by black plaque and western blot analysis. Both assays indicated that the virus was expressing high levels of protein which reacts specifically with an IBV neutralizing monoclonal antibody. This virus will be useful as a vaccine against infectious bronchitis.

Example 15
Vaccines utilizing HVT to express antigens from various pathogens.

We also anticipate that antigens from the following pathogens may also be utilized to develop poultry vaccines: Chick anemia agent, Avian encephalomyelitis virus, Avian reovirus, Avian paramyxoviruses, Avian influenza virus, Avian adenovirus, Fowl pox virus, Avian coronavirus, Avian rota virus, Salmonella spp $E.\ coli$, Pasteurella spp, Haemophilus spp, Chlamydia spp, Mycoplasma spp, Campylobacter spp, Bordetella spp, Poultry nematodes, cestodes, trematodes, Poultry mites/lice, Poultry protozoa (Eimeria spp, Histomonas spp, Trichomonas spp).

Example 16

Trivalent vaccines against Infectious Laryngotracheitis, Marek's Disease and Newcastle's Disease and bivalent vaccines against Infectious Laryngotracheitis and Marek's Disease are described. Superior protection against Infectious Laryngotracheitis is achieved with a vaccine combining S-HVT-123 (expressing ILTV gB and gD) with S-HVT-138, -139, or 140 (expressing ILTV gD and gI).

Example 16A

S-HVT-123

S-HVT-123 is a recombinant herpesvirus of turkeys that contains the ILT virus gB and gD genes inserted into a unique XhoI site converted to a NotI site in the BamHI #10 fragment of the HVT genome (FIGS. 13B and 15; SEQ ID NO. 48). S-HVT-123 further contains the MDV gA, gD, and gB genes inserted into a unique StuI site converted into a HindIII site in the HVT US2 gene. The ILTV genes and the MDV genes each use their own respective promoters. S-HVT-123 is useful as a vaccine in poultry against Infectious Laryngotracheitis and Marek's Disease. S-HVT-123 was constructed according to the PROCEDURE FOR GENERATING RECOMBINANT HERPESVIRUS FROM OVERLAPPING SUBGENOMIC FRAGMENTS. The following combination of subgenomic clones and enzymes were used: 407-32.2C3 wich NotI, 172-07.BA2 with BamHI, 407-32.5G6 with NotI, 672-07.C40 with NotI, 672-01.A40 with NotI, 721-38.1J uncut, 729-37.1 with AscI.

Example 16B

S-HVT-138

S-HVT-138 is a recombinant herpesvirus of turkeys that contains the ILT virus gD and gI genes inserted into a unique XhoI site converted to a PacI site in the BamHI #10 fragment of the HVT genome (FIGS. 13A and 15). The ILTV gD and gI genes are in the opposite transcriptional orientation to the open reading frame (ORF A) within the BamHI #10 fragment of the HVT genome (FIG. 14; SEQ ID NO. 48, 50). The ILTV gD and gI genes are expressed as overlapping transcripts from their own respective endogenous ILTV promoters, and share their own endogenous polyadenylation signal.

S-HVT-138 is useful as a vaccine in poultry against Infectious Laryngotracheitis and Marek's Disease. S-HVT-138 was constructed according to the PROCEDURE FOR GENERATING RECOMBINANT HERPESVIRUS FROM OVERLAPPING SUBGENOMIC FRAGMENTS. The following combination of subgenomic clones and enzymes were used: 407-32.2C3 with NotI, 172-07.BA2 with BamHI, 407-32.5G6 with NotI, 672-07.C40 with NotI, 672-01.A40 with NotI, 711-92.1A uncut, 415-09.BA1 with BamHI.

Example 16C

S-HVT-139

S-HVT-139 is a recombinant herpesvirus of turkeys that contains the ILT virus gD and gI genes inserted into a unique XhoI site converted to a PacI site in the BamHI #10 fragment of the HVT genome. The ILTV gD and gI genes are in the opposite transcriptional orientation to the open reading frame (ORF A) within the BamHI #10 fragment of the HVT genome (FIGS. 13A and 15; SEQ ID NO. 48, 50). S-HVT-139 further contains the MDV gA, gD, and gB genes inserted into a unique StuI site converted into a HindIII site in the HVT US2 gene. The ILTV gD and gI genes are expressed as overlapping transcripts from their own respective endogenous ILTV promoters, and the MDV genes are also expressed from their own endogenous promoters. S-HVT-139 is useful as a vaccine in poultry against Infectious Laryngotracheitis and Marek's Disease.

S-HVT-139 was constructed according to the PROCEDURE FOR GENERATING RECOMBINANT HERPESVIRUS FROM OVERLAPPING SUBGENOMIC FRAGMENTS. The following combination of subgenomic clones and enzymes were used: 407-32.2C3 with NotI, 172-07.BA2 with BamHI, 407-32.5G6 with NotI, 672-07.C40 with NotI, 672-01.A40 with NotI, 711-92.1A uncut, 721-38.1J uncut.

Example 16D

S-HVT-140

S-HVT-140 is a recombinant herpesvirus of turkeys that contains the ILT virus gD and gI genes inserted into a unique XhoI site converted to a PacI site in the BamHI #10 fragment of the HVT genome (FIGS. 13A and 15). The ILTV gD and gI genes are in the opposite transcriptional orientation to the open reading frame (ORF A) within the BamHI #10 fragment of the HVT genome (FIG. 14; SEQ ID NO. 48, 50). S-HVT-140 further contains the MDV gA, gD, and gB genes and the NDV F and HN genes inserted into a unique StuI site converted into a HindIII site in the HVT US2 gene. The ILTV gD and gI genes are expressed as overlapping transcripts from their own respective endogenous ILTV promoters, and the MDV genes are also expressed from their own respective endogenous MDV promoters. The NDV F gene is transcribed from the HCMV immediate early promoter, and the NDV HN gene is transcribed from the PRV gX promoter. S-HVT-140 is useful as a vaccine in poultry against Infectious Laryngotracheitis, Marek's Disease, and Newcastle's Disease.

S-HVT-140 was constructed according to the PROCEDURE FOR GENERATING RECOMBINANT HERPESVIRUS FROM OVERLAPPING SUBGENOMIC FRAGMENTS. The following combination of subgenomic clones and enzymes were used: 407-32.2C3 with Not5I, 172-07.BA2 with BamHI, 407-32.5G6 with NotI, 672-07.C40 with NotI, 672-01.A40 with NotI, 711-92.1A uncut, 722-60.E2 uncut.

Example 17

Trivalent vaccines against Infectious Bursal Disease, Marek's Disease and Newcastle's Disease and bivalent vaccines against Infectious Bursal Disease and Marek's Disease are described.

Example 17A

S-HVT-126

S-HVT-126 is a recombinant herpesvirus of turkeys that contains the IBDV VP2 gene inserted into a unique XhoI site converted to a PacI site in the BamHI #10 fragment in the HVT genome (FIGS. 13A and 15). The IBDV gene is in the same transcriptional orientation as the open reading frame (ORF A) within the BamHI #10 fragment of the HVT genome (FIG. 14; SEQ ID NO. 48, 50). The IBDV VP2 gene is expressed from an IBRV VP8 promoter. S-HVT-126 is useful as a vaccine in poultry against Infectious Bursal Disease and Marek's Disease.

S-HVT-126 was constructed according to the PROCEDURE FOR GENERATING RECOMBINANT HERPESVIRUS FROM OVERLAPPING SUBGENOMIC FRAGMENTS. The following combination of subgenomic clones and enzymes were used: 407-32.2C3 with NotI, 172-07.BA2 with BamHI, 407-32.5G6 with NotI, 672-07.C40 with NotI, 672-01.A40 with NotI, 706-57.A3 uncut, 415-09.BA1 with BamHI.

Example 17B

S-HVT-137

S-HVT-137 is a recombinant herpesvirus of turkeys that contains the IBDV VP2 gene inserted into a unique XhoI site converted to a PacI site in the BamHI #10 fragment in the HVT genome (FIGS. 13A and 15). The IBDV gene is in the same transcriptional orientation as the open reading frame (ORF A) within the BamHI #10 fragment of the HVT genome (FIG. 14; SEQ ID NO. 48, 50). S-HVT-137 further contains the MDV gA, gD, and gB genes inserted into a unique StuI site converted into a HindIII site in the HVT US2 gene. The IBDV VP2 gene is expressed from an IBRV VP8 promoter. The MDV genes are expressed from their own respective endogenous MDV promoters. S-HVT-137 is useful as a vaccine in poultry against Infectious Bursal Disease and Marek's Disease.

S-HVT-137 was constructed according to the PROCEDURE FOR GENERATING RECOMBINANT HERPESVIRUS FROM OVERLAPPING SUBGENOMIC FRAGMENTS. The following combination of subgenomic clones and enzymes were used: 407-32.2C3 with NotI, 172-07.BA2 with BamHI, 407-32.5G6 with NotI, 672-07.C40 with NotI, 672-01.A40 with NotI, 706-57.A3 uncut, 721-38.1J uncut.

Example 17C

S-HVT-143

S-HVT-143 is a recombinant herpesvirus of turkeys that contains the IBDV VP2 gene inserted into a unique XhoI site converted to a PacI site in the BamHI #10 fragment of the HVT genome (FIGS. 13A and 15). The IBDV gene is in the same transcriptional orientation as the open reading frame (ORF A) within the BamHI #10 fragment of the HVT genome (FIG. 14; SEQ ID NO. 48, 50). S-HVT-143 further contains the MDV gA, gD, and gB genes and the NDV F and HN genes inserted into a unique StuI site converted into a HindIII site in the HVT US2 gene. The IBDV VP2 gene is expressed from an IBRV VP8 promoter. The MDV genes are expressed from their own respective endogenous MDV promoters. The NDV F gene is transcribed from the HCMV immediate early promoter, and the NDV HN gene is transcribed from the PRV gX promoter. S-HVT-143 is useful as a vaccine in poultry against Infectious Bursal Disease, Marek's Disease, and Newcastle's Disease.

S-HVT-143 was constructed according to the PROCEDURE FOR GENERATING RECOMBINANT HERPESVIRUS FROM OVERLAPPING SUBGENOMIC FRAGMENTS. The following combination of subgenomic clones and enzymes were used: 407-32.2C3 with NotI, 172-07.BA2 with BamHI, 407-32.5G6 with NotI, 672-07.C40 with NotI, 672-01.A40 with NotI, 706-57.A3 uncut, 722-60.E2 uncut.

Example 18

S-HVT-128

S-HVT-128 is a recombinant herpesvirus of turkeys that contains the NDV HN and F genes inserted into a unique XhoI site converted to a PacI site in the BamHI #10 fragment of the HVT genome (FIGS. 13A and 15). S-HVT-128 further contains the MDV gA, gD, and gB genes inserted into a unique StuI site converted into a HindIII site in the HVT US2 gene. The NDV HN gene is expressed from the PRV gX promoter and the NDV F gene is expressed from the HCMV immediate early promoter. The MDV genes are expressed from their own respective endogenous MDV promoters. S-HVT-128 is useful as a vaccine in poultry against Newcastle's Disease and Marek's Disease.

S-HVT-128 was constructed according to the PROCEDURE FOR GENERATING RECOMBINANT HERPESVIRUS FROM OVERLAPPING SUBGENOMIC FRAGMENTS. The following combination of subgenomic clones and enzymes were used: 407-32.2C3 with NotI, 172-07.BA2 with BamHI, 407-32.5G6 with NotI, 672-07.C40 with NotI, 672-01.A40 with NotI, and 717-38.12 uncut. To a mixture of these six cosmids was added a limiting dilution of a recombinant HVT virus containing the MDV gA, gD, and gB genes inserted into the unique short region (see HVT-062) and the PRV gX promoter-lacZ gene inserted into an XhoI site converted to a NotI site in the BamHI #10 fragment within the unique long region of HVT. A recombinant virus S-HVT-128 was selected which was lac Z negative.

Example 19

HVT/MDV Recombinant Virus Vaccine

A recombinant virus vaccine containing MDV and HVT genomic sequences which protects against Marek's disease is produced by combining cosmids of MDV genomic DNA containing genes coding for the relevant protective antigens of virulent MDV serotype 2 and cosmids of HVT genomic DNA according to the PROCEDURE FOR GENERATING. RECOMBINANT HERPESVIRUS FROM OVERLAPPING SUBGENOMIC FRAGMENTS. The resulting virus is a vaccine that has the protective immune response to virulent MDV serotype 2 and the attenuated growth characteristics of the HVT. In one embodiment, a chimeric virus vaccine containing the MDV genes of the unique short and the HVT genes of the unique long is useful as a vaccine against Marek's disease in chickens. The MDV protective antigens within the unique short (gD, gE, and gI) elicit a protective immune response to MDV, while the virulence elements present in the unique long of MDV (55, 56, 57) are replaced by the attenuating unique long sequences of HVT. The result is an attenuated virus vaccine which protects against Marek's disease. Multivalent protection against Marek's disease, infectious laryngotracheitis, infectious bursal disease, Newcastle's disease, or another poultry pathogen is achieved by inserting the ILTV gB, gD, and gI genes, the IBDV VP2 gene, the NDV HN and F genes, or an antigen gene from a poultry pathogen into an XboI site converted to a PacI site or NotI site in the BamHI #10 fragment within the unique long region of HVT/MDV recombinant virus (FIGS. 13 and 15).

A cosmid was constructed containing the entire MDV unique short region. MDV genomic DNA contains several SmaI sites in the unique long and internal and terminal repeats of the virus, but no SmaI sites within the unique short of the virus. The entire unique short region of MDV was isolated by a partial restriction digestion of MDV genomic DNA with SmaI. A DNA fragment approximately 29,000 to 33,000 base pairs was isolated and cloned into a blunt ended site of the cosmid vector pWE15. To generate a recombinant HVT/MDV chimeric virus, the cosmid containing the MDV unique short region is combined with cosmids containing the HVT unique long region according to the PROCEDURE FOR GENERATING RECOMBINANT HERPESVIRUS FROM OVERLAPPING SUBGENOMIC FRAGMENTS. The following combination of subgenomic clones and enzymes are used: 407-32.2C3 with NotI, 172-07.BA2 with BamHI, 407-32.5G6 with NotI, 407-32.1C1 with NotI, and 739-27.16 with NotI.

The resulting virus vaccine provides superior protection against Marek's disease or as a multivalent vaccine against Marek's disease and infectious laryngotracheitis, infectious bursal disease, Newcastle's disease, or another poultry pathogen. This vaccine is superior because expression of MDV genes in the HVT/MDV chimera vaccine is safer and provides better protection against Marek's disease than vaccines presently available containing HVT and MDV type 1 (SB-1) or HVT alone. Secondly, one can demonstrate expression of the MDV glycoprotein genes in the absence of the homologous HVT genes for both diagnostic and regulatory purposes. This is useful since antibodies to an MDV glycoprotein will cross react with the homologous HVW glycoprotein. Finally, a recombinant HVT/MDV virus which contains a single copy of each glycoprotein gene is more stable that a recombinant virus containing two copies of a homologous glycoprotein gene from HVT and MDV which may delete by homologous recombination.

In an alternative embodiment, cosmids containing MDV protective antigen genes from the unique long (MDV gB and gC) are combined with cosmids containing HVT gene sequences from the unique short and the unique long, effectively avoiding the MDV virulence genes at the unique long/internal repeat junction and the unique long/terminal repeat junction (55, 56, and 57).

SB-1 strain is an MDV serotype 1 with attenuated pathogenicity. Vaccination with a combination of HVT and SB-1 live viruses protects against virulent MDV challenge better than vaccination with either virus alone. In an alternative embodiment of the present invention, a recombinant virus vaccine comprises the protective antigen genes of the virulent MDV serotype 2 combined with the attenuating genes of the non-virulent MDV serotypes 1 and 3, such as SB-1 and HVT. The genomic DNA corresponding to the unique long region of the recombinant virus is contributed by the SB-1 serotype. The genomic DNA corresponding to the unique short region is contributed by the HVT serotype. Three major glycoprotein antigens (gB, gA and gD) from the MDV serotype 2 are inserted into the unique short region of the virus.

The recombinant virus is constructed utilizing HVT subgenomic clones 672-01.A40, 672-07.C40 and 721-38.1J to reconstruct the unique short region. Subgenomic clone 721-38.1J contains an insertion of the MDV gB, gA, and gD genes. A large molar excess of these clones is cotransfected with a subfragment infectious dose of SB-1 genomic DNA. To determine the appropriate subfragment infectious dose, transfection of the SB-1 is titrated down to a dose which no longer yields virus plaques in cell culture. Such a dose contains subfragment genomic fragments spanning the unique long region of SB-1 which recombine with the HVT unique short subgenomic clones. Therefore, a virus resulting from recombination between overlapping homologous regions of the SB-1 and HVT subgenomic fragments is highly favored. Alternatively, SB-1 genomic fragments from the unique long region are subcloned into cosmid vectors. A recombinant virus containing the SB-1 unique long and the HVT unique short with the MDV, gB, gA, and gD genes is produced using the PROCEDURE FOR GENERATING RECOMBINANT HERPESVIRUS FROM OVERLAPPING SUBGENOMIC FRAGMENTS. This procedure is also used with an HVT subgenomic clone to insert antigen genes from other avian pathogens including but not limited to infectious laryngotracheitis virus, Newcastle's disease virus and infectious bursal disease virus.

References

1. Buckmaster et al., *J. Gen. Virol.* 69:2033, 1988.
2. F. A. Ferrari et al., *Journal of Bacteriology* 161, 556–562, 1985.
3. U. Gubler and B. J Hoffman, *Gene* 25, 263–269.
4. D. Hanahan, *Molecular Biology* 166, 557–580, 1983.
5. P. J. Hudson et al., *Nucleic Acid Research* 14, 5001–5012, 1986.
6. T. Igarashi et al., 10*th International Herpesvirus Workshop*, Abstract No. 17, Ann Arbor, Michigan, August 1985.
7. T. Ihara et al., *Virus Genes* 3, 127–140, 1989.
8. M. A. Innis et al., *PCR Protocols A Guide to Methods and Applications*, 84–91, Academic Press, Inc., San Diego, 1990.
9. R. J. Isfort et al., 9*th International Hexpesvirus Workshop*, Abstract No. 146, Seattle, Washington, August 1984.
10. M. N. Jagadish et al., *J. of Virol.* 62, 1084–1087, 1988.
11. Kawai and Nishizawa *Mol. and Cell Bio.* 4, 1172–1174, 1984.
12. B. Lomniczi et al., *Journal of Virology* 49, 970–979 1984.
13. Maniatis et al., *Molecular Cloning*, Cold Spring Harbor Laboratory, New York, 1982.
14. D. J. McGeoch et al., *Journal of Molecular Biology* 181, 1–13, 1985.
15. S. L. McKnight and R. Kingsbury, *Science* 217, 316–324, 1982.
16. L. J. N. Ross et al., *Journal of General Virology* 70, 1789–1804, 1989.
17. L. J. N. Ross et al., *Journal of General Virology* 72, 949–954, 1991.
18. J. Sambrook et al., *Molecular Cloning A Laboratory Manual Second Edition*, Cold Spring Harbor Press, 1989.
19. M. Zijil et al., *Journal of Virology* 62, 2191–2195, 1988.
20. Maniatis et al., *Intervirology* 16, 201–217, 1981.
21. S. L. Mansour et al., *Proc. Natl. Acad. Sci. USA* 82, 1359–1363, 1985.
22. C. Thummel et al., *Cell* 33, 455–464, 1983.
23. D. Scolnick, *Cell* 24, 135–143, 1981.
24. C. Thummel et al., *Cell* 23, 825–836, 1981.
25 Y. Haj-Ahmed and F. L. Graham, *J. of Virology* 57, 267–274, 1986.
26. M. Mackett et al., *Proc. Natl. Acad. Sci. USA* 79, 7415–7419, 1982.
27. D. Panicali and E. Paoletti, *Proc. Natl. Acad. Sci. USA* 79, 4927–4931, 1982.
28. E. Paoletti et al., *Proc. Natl. acad. Sci. USA* 81, 193–197, 1984.
29. G. L. Smith et al., *Nature* 302, 490–495, 1983.
30. J. H. Gillespie et al., *J. Clin. Microbiology* 23, 283–288, 1986.
31. D. Panicali et al., *Proc. Natl. Acad. Sci. USA* 80, 5364–5368, 1983.
32. G. L. Smith et al., *Proc. Natl. Acad. Sci. USA* 80, 7155–7159, 1983.
33. G. L. Smith et al., *Science* 224, 397–399, 1984.
34. M. Mackett et al., *Science* 227, 433–435, 1985.
35. E. S. Moccarski et al., *Cell* 22, 243–255, 1980.
40. L. E. Post and B. Roizman, *Cell* 25, 227–232, 1981.
41. K. L. Poffenberger et al., *Proc. Natl. Acad. Sci. USA* 80, 2690–2694, 1981.
42. M. G. Gibson and P. G. Spear, *Journal of Virology* 48, 396–404, 1983.
43. G. T.-Y,. Lee et al., *Proc. Natl. Acad. Sci. USA* 79, 6612–6616, 1982.
44. M.-F. Shih et al., *Proc. Natl. Acad. Sci. USA* 81, 5867–5870, 1984.
45. R. Desrosiers et al., *Ninth Annual Herpesvirus Meeting, Seattle*, Abstract #280, 1984.
46. M. Arsenakis and B. Roizman, in "The High Technology Route to Virus Vaccines", American Society for Microbiology, Washington D.C., 1985 (Proceedings of the First Annual Southwest Foundation for Biomedical Research International Symposium, Houston, Tex., Nov. 8–10 1984).
47. L. E. Post et al., *Tenth International Herpesvirus Workshop*, Ann Arbor, August 1985.
48. S. B. Mohanty and S. K. Dutta, *Veterinazy Virology*, Lea and Febiger, pubs., Philadelphia, 1981.
49. A. M. Griffin, *Journal of General Virology* 72, 393–398, 1991.

50. D. R. Thomsen et al., *Gene* 16, 207–217, 1981.
51. Carpenter, D. E. and Misra, V. Journal of General Virology 72 3077–3084, 1991.
52. Kibenge, F. S., Jackwood, D. J., Mercado, C. C., Journal of General Virology 71 569–577, 1990.
53. Fukuchi et al., Journal of Virology 51 102–109, 1984.
54. Fukuchi et al., Journal of Virology 53 994–997, 1985.
55. Ross, N., et al., Virus enes 7: 33–51, 1993.
56. Maotani, K. A., et al., Journal of Virology 58: 657–659, 1986.
57. Ross, L. J. N., et al., Journal of General Virology 64:2785–2790, 1983.

---

What is claimed is:

1. A recombinant herpesvirus of turkeys designated S-HVT-050 (ATCC Accession No. VR 2400).

2. A vaccine which comprises an effective immunizing amount of the recombinant herpesvirus of turkeys of claim 1 and a suitable carrier.

3. The vaccine of claim 2, wherein the suitable carrier is a physiologically balanced culture medium containing stabilizing agents.

4. The vaccine of claim 2, wherein the effective immunizing amount is from $10^2$ to $10^9$ PFU/dose.

5. A method of immunizing a fowl against Marek's disease virus which comprises administering to the fowl an effective immunizing dose of the vaccine of claim 2.

6. The method of immunizing a fowl in ovo against Marek's disease virus which comprises administering to the fowl in ovo an effective immunizing dose of the vaccine of claim 2.

7. The method of claim 5, wherein the vaccine is administered by intramuscular, subcutaneous, intraperitoneal or intravenous injection.

8. The method of claim 5, wherein the vaccine is administered intranasally, intraocularly, or orally.

9. A method of immunizing a fowl against disease caused by Newcastle disease virus which comprises administering to the fowl an effective immunizing dose of the vaccine of claim 2.

10. The method of immunizing a fowl in ovo against disease caused by Newcastle disease virus which comprises administering to the fowl in ovo an effective immunizing dose of the vaccine of claim 2.

11. The method of claim 9, wherein the vaccine is administered by intramuscular, subcutaneous, intraperitoneal or intravenous injection.

12. The method of claim 9, wherein the vaccine is administered intranasally or orally.

* * * * *

SEQUENCE LISTING (1) GENERAL INFORMATION:

(iii) NUMBER OF SEQUENCES: 56

(2) INFORMATION FOR SEQ ID NO:1:

(i) SEQUENCE CHARACTERISTICS:
      (A) LENGTH: 3350 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: CDS
      (B) LOCATION: 129..2522

(xi) SEQUENCE DESCRIPTION: SEQ ID NO:1:

```
GGATACGATC GGTCTGACCC GGGGGAGTCA CCCGGGGACA GCCGTCAAGG CCTTGTTCCA      60

GGATAGAACT CCTCCTTCTA CAACGCTATC ATTGATGGTC AGTAGAGATC AGACAAACGA     120

TCGCAGCG ATG ACA AAC CTG CAA GAT CAA ACC CAA CAG ATT GTT CCG TTC      170
         Met Thr Asn Leu Gln Asp Gln Thr Gln Gln Ile Val Pro Phe
           1               5                  10

ATA CGG AGC CTT CTG ATG CCA ACA ACC GGA CCG GCG TCC ATT CCG GAG       218
Ile Arg Ser Leu Leu Met Pro Thr Thr Gly Pro Ala Ser Ile Pro Glu
 15                  20                  25                  30

ACA CCC TGG AGA AGC ACA CTC TCA GGT CAG AGA CTG ACC TAC AAT TTG       266
Thr Pro Trp Arg Ser Thr Leu Ser Gly Gln Arg Leu Thr Tyr Asn Leu
                 35                  40                  45

ACT GTG GGG GAC ACA GGG TCA GGG CTA ATT GTC TTT TTC CCT GGA TTC       314
Thr Val Gly Asp Thr Gly Ser Gly Leu Ile Val Phe Phe Pro Gly Phe
                     50                  55                  60

CCT GGC TCA ATT GTG GGT GCT CAC TAC ACA CTG CAG AGC AAT GGG AAC       362
Pro Gly Ser Ile Val Gly Ala His Tyr Thr Leu Gln Ser Asn Gly Asn
         65                  70                  75

TAC AAG TTC GAT CGG ATG CTC CTG ACT GCC CAG AAC CTA CCG GCC AGT       410
Tyr Lys Phe Asp Arg Met Leu Leu Thr Ala Gln Asn Leu Pro Ala Ser
     80                  85                  90

TAC AAC TAC TGC AGG CTA GTG AGT CGG AGT CTC ACA GTG AGG TCA AGC       458
Tyr Asn Tyr Cys Arg Leu Val Ser Arg Ser Leu Thr Val Arg Ser Ser
 95                 100                 105                 110

ACA CTT CCT GGT GGC GTT TAT GCA CTA AAC GGC ACC ATA AAC GCC GTG       506
Thr Leu Pro Gly Gly Val Tyr Ala Leu Asn Gly Thr Ile Asn Ala Val
                115                 120                 125

ACC TTC CAA GGA AGC CTG AGT GAA CTG ACA GAT GTT AGC TAC AAT GGG       554
Thr Phe Gln Gly Ser Leu Ser Glu Leu Thr Asp Val Ser Tyr Asn Gly
            130                 135                 140

TTG ATG TCT GCA ACA GCC AAC ATC AAC GAC AAA ATT GGG AAC GTC CTA       602
Leu Met Ser Ala Thr Ala Asn Ile Asn Asp Lys Ile Gly Asn Val Leu
        145                 150                 155
```

-continued

| | | |
|---|---|---|
| GTA GGG GAA GGG GTC ACC GTC CTC AGC TTA CCC ACA TCA TAT GAT CTT<br>Val Gly Glu Gly Val Thr Val Leu Ser Leu Pro Thr Ser Tyr Asp Leu<br>160                                165                     170 | 650 |
| GGG TAT GTG AGG CTT GGT GAC CCC ATT CCC GCA ATA GGG CTT GAC CCA<br>Gly Tyr Val Arg Leu Gly Asp Pro Ile Pro Ala Ile Gly Leu Asp Pro<br>175                          180                        185                 190 | 698 |
| AAA ATG GTA GCC ACA TGT GAC AGC AGT GAC AGG CCC AGA GTC TAC ACC<br>Lys Met Val Ala Thr Cys Asp Ser Ser Asp Arg Pro Arg Val Tyr Thr<br>                        195                        200                     205 | 746 |
| ATA ACT GCA GCC GAT GAT TAC CAA TTC TCA TCA CAG TAC CAA CCA GGT<br>Ile Thr Ala Ala Asp Asp Tyr Gln Phe Ser Ser Gln Tyr Gln Pro Gly<br>          210                        215                     220 | 794 |
| GGG GTA ACA ATC ACA CTG TTC TCA GCC AAC ATT GAT GCC ATC ACA AGC<br>Gly Val Thr Ile Thr Leu Phe Ser Ala Asn Ile Asp Ala Ile Thr Ser<br>                 225                        230                     235 | 842 |
| CTC AGC GTT GGG GGA GAG CTC GTG TTT CGA ACA AGC GTC CAC GGC CTT<br>Leu Ser Val Gly Gly Glu Leu Val Phe Arg Thr Ser Val His Gly Leu<br>240                                245                     250 | 890 |
| GTA CTG GGC GCC ACC ATC TAC CTC ATA GGC TTT GAT GGG ACA ACG GTA<br>Val Leu Gly Ala Thr Ile Tyr Leu Ile Gly Phe Asp Gly Thr Thr Val<br>255                                260                     265                 270 | 938 |
| ATC ACC AGG GCT GTG GCC GCA AAC ACT GGG CTG ACG ACC GGC ACC GAC<br>Ile Thr Arg Ala Val Ala Ala Asn Thr Gly Leu Thr Thr Gly Thr Asp<br>                        275                        280                     285 | 986 |
| AAC CTT ATG CCA TTC AAT CTT GTG ATT CCA ACA AAC GAG ATA ACC CAG<br>Asn Leu Met Pro Phe Asn Leu Val Ile Pro Thr Asn Glu Ile Thr Gln<br>               290                        295                     300 | 1034 |
| CCA ATC ACA TCC ATC AAA CTG GAG ATA GTG ACC TCC AAA AGT GGT GGT<br>Pro Ile Thr Ser Ile Lys Leu Glu Ile Val Thr Ser Lys Ser Gly Gly<br>               305                        310                     315 | 1082 |
| CAG GCA GGG GAT CAG ATG TTA TGG TCG GCA AGA GGG AGC CTA GCA GTG<br>Gln Ala Gly Asp Gln Met Leu Trp Ser Ala Arg Gly Ser Leu Ala Val<br>320                                325                     330 | 1130 |
| ACG ATC CAT GGT GGC AAC TAT CCA GGG GCC CTC CGT CCC GTC ACG CTA<br>Thr Ile His Gly Gly Asn Tyr Pro Gly Ala Leu Arg Pro Val Thr Leu<br>335                                340                     345                 350 | 1178 |
| GTG GCC TAC GAA AGA GTG GCA ACA GGA TCC GTC GTT ACG GTC GCT GGG<br>Val Ala Tyr Glu Arg Val Ala Thr Gly Ser Val Val Thr Val Ala Gly<br>                        355                        360                     365 | 1226 |
| GTG AGC AAC TTC GAG CTG ATC CCA AAT CCT GAA CTA GCA AAG AAC CTG<br>Val Ser Asn Phe Glu Leu Ile Pro Asn Pro Glu Leu Ala Lys Asn Leu<br>               370                        375                     380 | 1274 |
| GTT ACA GAA TAC GGC CGA TTT GAC CCA GGA GCC ATG AAC TAC ACA AAA<br>Val Thr Glu Tyr Gly Arg Phe Asp Pro Gly Ala Met Asn Tyr Thr Lys<br>               385                        390                     395 | 1322 |
| TTG ATA CTG AGT GAG AGG GAC CGT CTT GGC ATC AAG ACC GTC TGG CCA<br>Leu Ile Leu Ser Glu Arg Asp Arg Leu Gly Ile Lys Thr Val Trp Pro<br>          400                        405                     410 | 1370 |
| ACA AGG GAG TAC ACT GAC TTT CGT GAA TAC TTC ATG GAG GTG GCC GAC<br>Thr Arg Glu Tyr Thr Asp Phe Arg Glu Tyr Phe Met Glu Val Ala Asp<br>415                                420                     425                 430 | 1418 |
| CTC AAC TCT CCC CTG AAG ATT GCA GGA GCA TTC GGC TTC AAA GAC ATA<br>Leu Asn Ser Pro Leu Lys Ile Ala Gly Ala Phe Gly Phe Lys Asp Ile<br>               435                        440                     445 | 1466 |
| ATC CGG GCC ATA AGG AGG ATA GCT GTG CCG GTG GTC TCC ACA TTG TTC<br>Ile Arg Ala Ile Arg Arg Ile Ala Val Pro Val Val Ser Thr Leu Phe<br>          450                        455                     460 | 1514 |
| CCA CCT GCC GCT CCC CTA GCC CAT GCA ATT GGG GAA GGT GTA GAC TAC<br>Pro Pro Ala Ala Pro Leu Ala His Ala Ile Gly Glu Gly Val Asp Tyr<br>465                                470                     475 | 1562 |

```
CTG CTG GGC GAT GAG GCA CAG GCT GCT TCA GGA ACT GCT CGA GCC GCG    1610
Leu Leu Gly Asp Glu Ala Gln Ala Ala Ser Gly Thr Ala Arg Ala Ala
    480                 485                 490

TCA GGA AAA GCA AGA GCT GCC TCA GGC CGC ATA AGG CAG CTG ACT CTC    1658
Ser Gly Lys Ala Arg Ala Ala Ser Gly Arg Ile Arg Gln Leu Thr Leu
495                 500                 505                 510

GCC GCC GAC AAG GGG TAC GAG GTA GTC GCG AAT CTA TTC CAG GTG CCC    1706
Ala Ala Asp Lys Gly Tyr Glu Val Val Ala Asn Leu Phe Gln Val Pro
                    515                 520                 525

CAG AAT CCC GTA GTC GAC GGG ATT CTT GCT TCA CCT GGG GTA CTC CGC    1754
Gln Asn Pro Val Val Asp Gly Ile Leu Ala Ser Pro Gly Val Leu Arg
                530                 535                 540

GGT GCA CAC AAC CTC GAC TGC GTG TTA AGA GAG GGT GCC ACG CTA TTC    1802
Gly Ala His Asn Leu Asp Cys Val Leu Arg Glu Gly Ala Thr Leu Phe
            545                 550                 555

CCT GTG GTT ATT ACG ACA GTG GAA GAC GCC ATG ACA CCC AAA GCA TTG    1850
Pro Val Val Ile Thr Thr Val Glu Asp Ala Met Thr Pro Lys Ala Leu
        560                 565                 570

AAC AGC AAA ATG TTT GCT GTC ATT GAA GGC GTG CGA GAA GAC CTC CAA    1898
Asn Ser Lys Met Phe Ala Val Ile Glu Gly Val Arg Glu Asp Leu Gln
575                 580                 585                 590

CCT CCA TCT CAA AGA GGA TCC TTC ATA CGA ACT CTC TCT GGA CAC AGA    1946
Pro Pro Ser Gln Arg Gly Ser Phe Ile Arg Thr Leu Ser Gly His Arg
                    595                 600                 605

GTC TAT GGA TAT GCT CCA GAT GGG GTA CTT CCA CTG GAG ACT GGG AGA    1994
Val Tyr Gly Tyr Ala Pro Asp Gly Val Leu Pro Leu Glu Thr Gly Arg
                610                 615                 620

GAC TAC ACC GTT GTC CCA ATA GAT GAT GTC TGG GAC GAC AGC ATT ATG    2042
Asp Tyr Thr Val Val Pro Ile Asp Asp Val Trp Asp Asp Ser Ile Met
            625                 630                 635

CTG TCC AAA GAT CCC ATA CCT CCT ATT GTG GGA AAC AGT GGA AAT CTA    2090
Leu Ser Lys Asp Pro Ile Pro Pro Ile Val Gly Asn Ser Gly Asn Leu
        640                 645                 650

GCC ATA GCT TAC ATG GAT GTG TTT CGA CCC AAA GTC CCA ATC CAT GTG    2138
Ala Ile Ala Tyr Met Asp Val Phe Arg Pro Lys Val Pro Ile His Val
655                 660                 665                 670

GCT ATG ACG GGA GCC CTC AAT GCT TGT GGC GAG ATT GAG AAA GTA AGC    2186
Ala Met Thr Gly Ala Leu Asn Ala Cys Gly Glu Ile Glu Lys Val Ser
                    675                 680                 685

TTT AGA AGC ACC AAG CTC GCC ACT GCA CAC CGA CTT GGC CTT AAG TTG    2234
Phe Arg Ser Thr Lys Leu Ala Thr Ala His Arg Leu Gly Leu Lys Leu
                690                 695                 700

GCT GGT CCC GGA GCA TTC GAT GTA AAC ACC GGG CCC AAC TGG GCA ACG    2282
Ala Gly Pro Gly Ala Phe Asp Val Asn Thr Gly Pro Asn Trp Ala Thr
            705                 710                 715

TTC ATC AAA CGT TTC CCT CAC AAT CCA CGC GAC TGG GAC AGG CTC CCC    2330
Phe Ile Lys Arg Phe Pro His Asn Pro Arg Asp Trp Asp Arg Leu Pro
        720                 725                 730

TAC CTC AAC CTA CCA TAC CTT CCA CCC AAT GCA GGA CGC CAG TAC CAC    2378
Tyr Leu Asn Leu Pro Tyr Leu Pro Pro Asn Ala Gly Arg Gln Tyr His
735                 740                 745                 750

CTT GCC ATG GCT GCA TCA GAG TTC AAG AGA CCC CGA ACT CGA GAG TGC    2426
Leu Ala Met Ala Ala Ser Glu Phe Lys Arg Pro Arg Thr Arg Glu Cys
                    755                 760                 765

CGT CAG AGC AAT GGA AGC AGC AGC CAA CGT GGA CCC ACT ATT CCA ATC    2474
Arg Gln Ser Asn Gly Ser Ser Ser Gln Arg Gly Pro Thr Ile Pro Ile
                770                 775                 780

TGC ACT CAG TGT GTT CAT GTG GCT GGA AGA GAA TGG GAT TGT GAC TGA   2522
Cys Thr Gln Cys Val His Val Ala Gly Arg Glu Trp Asp Cys Asp
            785                 790                 795
```

-continued

```
CATGGCCAAC TTCGCACTCA GCGACCCGAA CGCCCATCGG ATGCGAAATT TTTTTGCAAA      2582

CGACCACAAG CAGGCAGCAA GTCGCAAAGG GCCAAGTACG GGACAGCAGG CTACGGAGTG      2642

GAGGCTCGGG GCCCCCACAC CAGAGGAAGC ACAGAGGGAA AAAGCACAC GGATCTCAAA       2702

GAAGATGGAG ACCATGGGCA TCTACTTTGC AACACCAGAA TGGGTAGCAC TCAATGGGCA      2762

CCGAGGGCCA AGCCCCGGCC AGCTAAAGTA CGGGCAGAAC ACACGAGAAA TACGACCCA       2822

AACGAGGACT ATCTAGACTA CGTGCATGCA GAGAAGAGCC GGTTGGCATC AGAAGAACAA      2882

ATCCTAAGGG CAGCTACGTC AGATCTACGG GGCTCCAGGA CAGGCAGAGC ACCCCAAGCT      2942

TTCATAGACG AAGTTGCCAA AGTCTATGAA ATCAACCATG GACGTGGCCC AAACCAAGAA      3002

CAGATGAAAG ATCTGCTCTT GACTGCGATG GAGATGAAGC ATCGCAATCC CAGGCGGGCT      3062

CTACCAAAGC CCAAGCCAAA ACCCAATGCT CCAACACAGA GACCCCTGG  TCGGCTGGGG      3122

CTGGATCAGG ACCGTCTCTG ATGAGGACCT TGAGTGAGGC TCCTGGGAGT CTCCCGACAA      3182

CACCCGCGCA GGTGTGGACA CAATTCGGCC TTACAACATC CCAAATTGGA TCCGTTCGCG      3242

GGTCCCCAAA AAAAAAAAAA AAAAAAAAAA AAAAAAAAAA AAAAAAAAAA AAAAAAAAAA      3302

AAGTACCTTC TGAGGCGGAA AGAACCAGCC GGATCCCTCG AGGGATCC                   3350
```

(2) INFORMATION FOR SEQ ID NO:2:

(i) SEQUENCE CHARACTERISTICS:
        (A) LENGTH: 797 amino acids
        (B) TYPE: amino acid
        (D) TOPOLOGY: linear (ii) MOLECULE TYPE: protein (xi) SEQUENCE DESCRIPTION: SEQ ID NO:2:

```
Met Thr Asn Leu Gln Asp Gln Thr Gln Gln Ile Val Pro Phe Ile Arg
 1               5                  10                  15

Ser Leu Leu Met Pro Thr Thr Gly Pro Ala Ser Ile Pro Glu Thr Pro
                20                  25                  30

Trp Arg Ser Thr Leu Ser Gly Gln Arg Leu Thr Tyr Asn Leu Thr Val
            35                  40                  45

Gly Asp Thr Gly Ser Gly Leu Ile Val Phe Phe Pro Gly Phe Pro Gly
        50                  55                  60

Ser Ile Val Gly Ala His Tyr Thr Leu Gln Ser Asn Gly Asn Tyr Lys
 65                  70                  75                  80

Phe Asp Arg Met Leu Leu Thr Ala Gln Asn Leu Pro Ala Ser Tyr Asn
                85                  90                  95

Tyr Cys Arg Leu Val Ser Arg Ser Leu Thr Val Arg Ser Ser Thr Leu
            100                 105                 110

Pro Gly Gly Val Tyr Ala Leu Asn Gly Thr Ile Asn Ala Val Thr Phe
        115                 120                 125

Gln Gly Ser Leu Ser Glu Leu Thr Asp Val Ser Tyr Asn Gly Leu Met
    130                 135                 140

Ser Ala Thr Ala Asn Ile Asn Asp Lys Ile Gly Asn Val Leu Val Gly
145                 150                 155                 160

Glu Gly Val Thr Val Leu Ser Leu Pro Thr Ser Tyr Asp Leu Gly Tyr
                165                 170                 175

Val Arg Leu Gly Asp Pro Ile Pro Ala Ile Gly Leu Asp Pro Lys Met
            180                 185                 190

Val Ala Thr Cys Asp Ser Ser Asp Arg Pro Arg Val Tyr Thr Ile Thr
        195                 200                 205

Ala Ala Asp Asp Tyr Gln Phe Ser Ser Gln Tyr Gln Pro Gly Gly Val
```

```
             210                 215                 220
Thr Ile Thr Leu Phe Ser Ala Asn Ile Asp Ala Ile Thr Ser Leu Ser
225                 230                 235                 240

Val Gly Gly Glu Leu Val Phe Arg Thr Ser Val His Gly Leu Val Leu
                245                 250                 255

Gly Ala Thr Ile Tyr Leu Ile Gly Phe Asp Gly Thr Thr Val Ile Thr
                260                 265                 270

Arg Ala Val Ala Ala Asn Thr Gly Leu Thr Thr Gly Thr Asp Asn Leu
                275                 280                 285

Met Pro Phe Asn Leu Val Ile Pro Thr Asn Glu Ile Thr Gln Pro Ile
290                 295                 300

Thr Ser Ile Lys Leu Glu Ile Val Thr Ser Lys Ser Gly Gly Gln Ala
305                 310                 315                 320

Gly Asp Gln Met Leu Trp Ser Ala Arg Gly Ser Leu Ala Val Thr Ile
                325                 330                 335

His Gly Gly Asn Tyr Pro Gly Ala Leu Arg Pro Val Thr Leu Val Ala
                340                 345                 350

Tyr Glu Arg Val Ala Thr Gly Ser Val Val Thr Val Ala Gly Val Ser
                355                 360                 365

Asn Phe Glu Leu Ile Pro Asn Pro Glu Leu Ala Lys Asn Leu Val Thr
                370                 375                 380

Glu Tyr Gly Arg Phe Asp Pro Gly Ala Met Asn Tyr Thr Lys Leu Ile
385                 390                 395                 400

Leu Ser Glu Arg Asp Arg Leu Gly Ile Lys Thr Val Trp Pro Thr Arg
                405                 410                 415

Glu Tyr Thr Asp Phe Arg Glu Tyr Phe Met Glu Val Ala Asp Leu Asn
                420                 425                 430

Ser Pro Leu Lys Ile Ala Gly Ala Phe Gly Phe Lys Asp Ile Ile Arg
                435                 440                 445

Ala Ile Arg Arg Ile Ala Val Pro Val Val Ser Thr Leu Phe Pro Pro
                450                 455                 460

Ala Ala Pro Leu Ala His Ala Ile Gly Glu Gly Val Asp Tyr Leu Leu
465                 470                 475                 480

Gly Asp Glu Ala Gln Ala Ala Ser Gly Thr Ala Arg Ala Ala Ser Gly
                485                 490                 495

Lys Ala Arg Ala Ala Ser Gly Arg Ile Arg Gln Leu Thr Leu Ala Ala
                500                 505                 510

Asp Lys Gly Tyr Glu Val Val Ala Asn Leu Phe Gln Val Pro Gln Asn
                515                 520                 525

Pro Val Val Asp Gly Ile Leu Ala Ser Pro Gly Val Leu Arg Gly Ala
530                 535                 540

His Asn Leu Asp Cys Val Leu Arg Glu Gly Ala Thr Leu Phe Pro Val
545                 550                 555                 560

Val Ile Thr Thr Val Glu Asp Ala Met Thr Pro Lys Ala Leu Asn Ser
                565                 570                 575

Lys Met Phe Ala Val Ile Glu Gly Val Arg Glu Asp Leu Gln Pro Pro
                580                 585                 590

Ser Gln Arg Gly Ser Phe Ile Arg Thr Leu Ser Gly His Arg Val Tyr
                595                 600                 605

Gly Tyr Ala Pro Asp Gly Val Leu Pro Leu Glu Thr Gly Arg Asp Tyr
                610                 615                 620

Thr Val Val Pro Ile Asp Asp Val Trp Asp Ser Ile Met Leu Ser
625                 630                 635                 640
```

```
Lys Asp Pro Ile Pro Ile Val Gly Asn Ser Gly Asn Leu Ala Ile
                645                 650                 655

Ala Tyr Met Asp Val Phe Arg Pro Lys Val Pro Ile His Val Ala Met
            660                 665                 670

Thr Gly Ala Leu Asn Ala Cys Gly Glu Ile Glu Lys Val Ser Phe Arg
        675                 680                 685

Ser Thr Lys Leu Ala Thr Ala His Arg Leu Gly Leu Lys Leu Ala Gly
    690                 695                 700

Pro Gly Ala Phe Asp Val Asn Thr Gly Pro Asn Trp Ala Thr Phe Ile
705                 710                 715                 720

Lys Arg Phe Pro His Asn Pro Arg Asp Trp Asp Arg Leu Pro Tyr Leu
                725                 730                 735

Asn Leu Pro Tyr Leu Pro Pro Asn Ala Gly Arg Gln Tyr His Leu Ala
            740                 745                 750

Met Ala Ala Ser Glu Phe Lys Arg Pro Arg Thr Arg Glu Cys Arg Gln
        755                 760                 765

Ser Asn Gly Ser Ser Ser Gln Arg Gly Pro Thr Ile Pro Ile Cys Thr
    770                 775                 780

Gln Cys Val His Val Ala Gly Arg Glu Trp Asp Cys Asp
785                 790                 795
```

(2) INFORMATION FOR SEQ ID NO:3:

(i) SEQUENCE CHARACTERISTICS:
        (A) LENGTH: 5426 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 73..1182
        (D) OTHER INFORMATION: /product= "HVT UL42"

(ix) FEATURE:
        (A) NAME/KEY: CDS
        (B) LOCATION: 1306..2574
        (D) OTHER INFORMATION: /product= "HVT UL43"

(ix) FEATURE:
        (A) NAME/KEY: CDS
        (B) LOCATION: 2790..4259
        (D) OTHER INFORMATION: /product= "HVT gA"

(ix) FEATURE:
        (A) NAME/KEY: CDS
        (B) LOCATION: 4701..5339
        (D) OTHER INFORMATION: /product= "HVT UL45"

(xi) SEQUENCE DESCRIPTION: SEQ ID NO:3:

```
GGATCCGAGC TTCTACTATA CAACGCGGAC GATAATTTTG TCCACCCCAT CGGTGTTCGA      60

GAAAGGGTTT TT ATG ATG GCA GGA ATA ACT GTC GCA TGT GAC CAC ACT        108
              Met Met Ala Gly Ile Thr Val Ala Cys Asp His Thr
                1               5                   10

GCA GGA GAG GCT CAT ACA CCC GAG GAT ATG CAA AAG AAA TGG AGG ATT      156
Ala Gly Glu Ala His Thr Pro Glu Asp Met Gln Lys Lys Trp Arg Ile
        15                  20                  25

ATA TTG GCA GGG GAA AAA TTC ATG ACT ATA TCG GCA TCG TTG AAA TCG      204
Ile Leu Ala Gly Glu Lys Phe Met Thr Ile Ser Ala Ser Leu Lys Ser
    30                  35                  40
```

```
ATC GTC AGT TGT GTG AAA AAC CCC CTT CTC ACG TTT GGC GCA GAT GGG    252
Ile Val Ser Cys Val Lys Asn Pro Leu Leu Thr Phe Gly Ala Asp Gly
 45                  50                  55                  60

CTC ATT GTA CAA GGT ACT GTC TGC GGA CAG CGC ATT TTT GTT CCA ATC    300
Leu Ile Val Gln Gly Thr Val Cys Gly Gln Arg Ile Phe Val Pro Ile
                 65                  70                  75

GAC CGT GAT TCC TTC AGC GAA TAT GAA TGG CAT GGG CCA ACT GCG ATG    348
Asp Arg Asp Ser Phe Ser Glu Tyr Glu Trp His Gly Pro Thr Ala Met
             80                  85                  90

TTT CTA GCA TTA ACT GAT TCC AGA CGC ACT CTT TTA GAT GCA TTC AAA    396
Phe Leu Ala Leu Thr Asp Ser Arg Arg Thr Leu Leu Asp Ala Phe Lys
         95                 100                 105

TGT GAA AAG AGA AGG GCA ATT GAC GTC TCC TTT ACC TTC GCG GGA GAG    444
Cys Glu Lys Arg Arg Ala Ile Asp Val Ser Phe Thr Phe Ala Gly Glu
    110                 115                 120

CCT CCA TGT AGG CAT TTA ATC CAA GCC GTC ACA TAC ATG ACC GAC GGT    492
Pro Pro Cys Arg His Leu Ile Gln Ala Val Thr Tyr Met Thr Asp Gly
125                 130                 135                 140

GGT TCA GTA TCG AAT ACA ATC ATT AAA TAT GAG CTC TGG AAT GCG TCT    540
Gly Ser Val Ser Asn Thr Ile Ile Lys Tyr Glu Leu Trp Asn Ala Ser
                145                 150                 155

ACA ATT TTC CCC CAA AAA ACT CCC GAT GTT ACC TTT TCT CTA AAC AAA    588
Thr Ile Phe Pro Gln Lys Thr Pro Asp Val Thr Phe Ser Leu Asn Lys
            160                 165                 170

CAA CAA TTG AAC AAA ATA TTG GCC GTC GCT TCA AAA CTG CAA CAC GAA    636
Gln Gln Leu Asn Lys Ile Leu Ala Val Ala Ser Lys Leu Gln His Glu
        175                 180                 185

GAA CTT GTA TTC TCT TTA AAA CCT GAA GGA GGG TTC TAC GTA GGA ACG    684
Glu Leu Val Phe Ser Leu Lys Pro Glu Gly Gly Phe Tyr Val Gly Thr
    190                 195                 200

GTT TGT ACT GTT ATA AGT TTC GAA GTA GAT GGG ACT GCC ATG ACT CAG    732
Val Cys Thr Val Ile Ser Phe Glu Val Asp Gly Thr Ala Met Thr Gln
205                 210                 215                 220

TAT CCT TAC AAC CCT CCA ACC TCG GCT ACC CTA GCT CTC GTA GTA GCA    780
Tyr Pro Tyr Asn Pro Pro Thr Ser Ala Thr Leu Ala Leu Val Val Ala
                225                 230                 235

TGC AGA AAG AAG AAG GCG AAT AAA AAC ACT ATT TTA ACG GCC TAT GGA    828
Cys Arg Lys Lys Lys Ala Asn Lys Asn Thr Ile Leu Thr Ala Tyr Gly
            240                 245                 250

AGT GGT AAA CCC TTT TGT GTT GCA TTG GAA GAT ACT AGT GCA TTT AGA    876
Ser Gly Lys Pro Phe Cys Val Ala Leu Glu Asp Thr Ser Ala Phe Arg
        255                 260                 265

AAT ATC GTC AAT AAA ATC AAG GCG GGT ACG TCG GGA GTT GAT CTG GGG    924
Asn Ile Val Asn Lys Ile Lys Ala Gly Thr Ser Gly Val Asp Leu Gly
    270                 275                 280

TTT TAT ACA ACT TGC GAT CCG CCG ATG CTA TGT ATT CGC CCA CAC GCA    972
Phe Tyr Thr Thr Cys Asp Pro Pro Met Leu Cys Ile Arg Pro His Ala
285                 290                 295                 300

TTT GGA AGT CCT ACC GCA TTC CTG TTT TGT AAC ACA GAC TGT ATG ACA   1020
Phe Gly Ser Pro Thr Ala Phe Leu Phe Cys Asn Thr Asp Cys Met Thr
                305                 310                 315

ATA TAT GAA CTG GAA GAA GTA AGC GCC GTT GAT GGT GCA ATC CGA GCA   1068
Ile Tyr Glu Leu Glu Glu Val Ser Ala Val Asp Gly Ala Ile Arg Ala
            320                 325                 330

AAA CGC ATC AAC GAA TAT TTC CCA ACA GTA TCG CAG GCT ACT TCC AAG   1116
Lys Arg Ile Asn Glu Tyr Phe Pro Thr Val Ser Gln Ala Thr Ser Lys
        335                 340                 345

AAG AGA AAA CAG TCG CCG CCC CCT ATC GAA AGA GAA AGG AAA ACC ACC   1164
Lys Arg Lys Gln Ser Pro Pro Pro Ile Glu Arg Glu Arg Lys Thr Thr
    350                 355                 360
```

-continued

```
AGA GCG GAT ACC CAA TAAAATGCCA GACAAACCCG GCATCCTGGT TAGAGGGCAG      1219
Arg Ala Asp Thr Gln
365                 370

GTGGGCTGGG CCAACCTTCA CGGGCGTCCG ACAGATCGGT GACACTCATA CGTTAACTAA    1279

ACGCCGGCAG CTTTGCAGAA GAAAAT ATG CCT TCC GGA GCC AGC TCG AGT CCT    1332
                            Met Pro Ser Gly Ala Ser Ser Ser Pro
                             1               5

CCA CCA GCT TAT ACA TCT GCA GCT CCG CTT GAG ACT TAT AAC AGC TGG      1380
Pro Pro Ala Tyr Thr Ser Ala Ala Pro Leu Glu Thr Tyr Asn Ser Trp
 10              15                  20                  25

CTA AGT GCC TTT TCA TGC GCA TAT CCC CAA TGC ACT GCG GGA AGA GGA      1428
Leu Ser Ala Phe Ser Cys Ala Tyr Pro Gln Cys Thr Ala Gly Arg Gly
                 30                  35                  40

CAT CGA CAA AAT GGC AAG AAG TGT ATA CGG TGT ATA GTG ATC AGT GTA      1476
His Arg Gln Asn Gly Lys Lys Cys Ile Arg Cys Ile Val Ile Ser Val
             45                  50                  55

TGT TCC TTA GTG TGC ATC GCT GCA CAT TTA GCT GTT ACC GTG TCG GGA      1524
Cys Ser Leu Val Cys Ile Ala Ala His Leu Ala Val Thr Val Ser Gly
         60                  65                  70

GTG GCA TTA ATT CCG CTT ATC GAT CAA AAC AGA GCT TAC GGA AAC TGT      1572
Val Ala Leu Ile Pro Leu Ile Asp Gln Asn Arg Ala Tyr Gly Asn Cys
     75                  80                  85

ACG GTA TGT GTA ATT GCC GGA TTC ATC GCT ACG TTT GCT GCA CGA CTT      1620
Thr Val Cys Val Ile Ala Gly Phe Ile Ala Thr Phe Ala Ala Arg Leu
 90                  95                 100                 105

ACG ATA AGA CTT TCG GAA ACG CTT ATG CTA GTG GGC AAG CCG GCG CAG      1668
Thr Ile Arg Leu Ser Glu Thr Leu Met Leu Val Gly Lys Pro Ala Gln
             110                 115                 120

TTT ATA TTT GCT ATA ATC GCT TCC GTT GCG GAA ACA CTG ATC AAT AAC      1716
Phe Ile Phe Ala Ile Ile Ala Ser Val Ala Glu Thr Leu Ile Asn Asn
         125                 130                 135

GAG GCG CTT GCC ATC AGT AAT ACT ACT TAC AAA ACT GCA TTG CGA ATA      1764
Glu Ala Leu Ala Ile Ser Asn Thr Thr Tyr Lys Thr Ala Leu Arg Ile
     140                 145                 150

ATC GAA GTA ACA TCT TTG GCG TGT TTT GTT ATG CTC GGG GCA ATA ATT      1812
Ile Glu Val Thr Ser Leu Ala Cys Phe Val Met Leu Gly Ala Ile Ile
 155                 160                 165

ACA TCC CAC AAC TAT GTC TGC ATT TCA ACG GCA GGG GAC TTG ACT TGG      1860
Thr Ser His Asn Tyr Val Cys Ile Ser Thr Ala Gly Asp Leu Thr Trp
170                 175                 180                 185

AAG GGC GGG ATT TTT CAT GCT TAC CAC GGA ACA TTA CTC GGT ATA ACA      1908
Lys Gly Gly Ile Phe His Ala Tyr His Gly Thr Leu Leu Gly Ile Thr
             190                 195                 200

ATA CCA AAC ATA CAC CCA ATC CCT CTC GCG GGG TTT CTT GCA GTC TAT      1956
Ile Pro Asn Ile His Pro Ile Pro Leu Ala Gly Phe Leu Ala Val Tyr
         205                 210                 215

ACA ATA TTG GCT ATA AAT ATC GCT AGA GAT GCA AGC GCT ACA TTA TTA      2004
Thr Ile Leu Ala Ile Asn Ile Ala Arg Asp Ala Ser Ala Thr Leu Leu
     220                 225                 230

TCC ACT TGC TAT TAT CGC AAT TGC CGC GAG AGG ACT ATA CTT CGC CCT      2052
Ser Thr Cys Tyr Tyr Arg Asn Cys Arg Glu Arg Thr Ile Leu Arg Pro
 235                 240                 245

TCT CGT CTC GGA CAT GGT TAC ACA ATC CCT TCT CCC GGT GCC GAT ATG      2100
Ser Arg Leu Gly His Gly Tyr Thr Ile Pro Ser Pro Gly Ala Asp Met
250                 255                 260                 265

CTT TAT GAA GAA GAC GTA TAT AGT TTT GAC GCA GCT AAA GGC CAT TAT      2148
Leu Tyr Glu Glu Asp Val Tyr Ser Phe Asp Ala Ala Lys Gly His Tyr
             270                 275                 280

TCG TCA ATA TTT CTA TGT TAT GCC ATG GGG CTT ACA ACA CCG CTG ATT      2196
```

|     |     |     |     |     |     |     |     |     |     |     |     |     |
| --- | --- | --- | --- | --- | --- | --- | --- | --- | --- | --- | --- | --- |
| Ser | Ser | Ile | Phe | Leu | Cys | Tyr | Ala | Met | Gly | Leu | Thr | Thr | Pro | Leu | Ile |
|     |     | 285 |     |     |     |     | 290 |     |     |     |     | 295 |

```
ATT GCG CTC CAT AAA TAT ATG GCG GGC ATT AAA AAT TCG TCA GAT TGG          2244
Ile Ala Leu His Lys Tyr Met Ala Gly Ile Lys Asn Ser Ser Asp Trp
        300                 305                 310

ACT GCT ACA TTA CAA GGC ATG TAC GGG CTT GTC TTG GGA TCG CTA TCG          2292
Thr Ala Thr Leu Gln Gly Met Tyr Gly Leu Val Leu Gly Ser Leu Ser
        315                 320                 325

TCA CTA TGT ATT CCA TCC AGC AAC AAC GAT GCC CTA ATT CGT CCC ATT          2340
Ser Leu Cys Ile Pro Ser Ser Asn Asn Asp Ala Leu Ile Arg Pro Ile
330                 335                 340                 345

CAA ATT TTG ATA TTG ATA ATC GGT GCA CTG GCC ATT GCA TTG GCT GGA          2388
Gln Ile Leu Ile Leu Ile Ile Gly Ala Leu Ala Ile Ala Leu Ala Gly
                350                 355                 360

TGT GGT CAA ATT ATA GGG CCT ACA TTA TTT GCC GCG AGT TCG GCT GCG          2436
Cys Gly Gln Ile Ile Gly Pro Thr Leu Phe Ala Ala Ser Ser Ala Ala
                365                 370                 375

ATG TCA TGT TTT ACA TGT ATC AAT ATT CGC GCT ACT AAT AAG GGT GTC          2484
Met Ser Cys Phe Thr Cys Ile Asn Ile Arg Ala Thr Asn Lys Gly Val
                380                 385                 390

AAC AAA TTG GCA GCA GCC AGT GTC GTG AAA TCT GTA CTG GGC TTC ATT          2532
Asn Lys Leu Ala Ala Ala Ser Val Val Lys Ser Val Leu Gly Phe Ile
        395                 400                 405

ATT TCC GGG ATG CTT ACT TGC GTG CTA TTA CCA CTA TCG TGATAGATCG           2581
Ile Ser Gly Met Leu Thr Cys Val Leu Leu Pro Leu Ser
410                 415                 420

TCGGTCTGCG CATCGCCCAT GCTGGCGGAA CGCTCTTTCG AACCGTGAAT AAAACTTTGT        2641

ATCTACTAAA CAATAACTTT GTGTTTTATT GAGCGGTCGA AAACAATGAG GAGCTGCAAT        2701

TTAAAGCTAA CCGCATACGC CGGGCGGGTA AGACCATTT TATACCATAT TACGCATCTA        2761

TCGAAACTTG TTCGAGAACC GCAAGTAT ATG GTT TCC AAC ATG CGC GTT CTA           2813
                                Met Val Ser Asn Met Arg Val Leu
                                 1               5

CGC GTA CTG CGC CTG ACG GGA TGG GTG GGC ATA TTT CTA GTT CTG TCT          2861
Arg Val Leu Arg Leu Thr Gly Trp Val Gly Ile Phe Leu Val Leu Ser
        10                  15                  20

TTA CAG CAA ACC TCT TGT GCC GGA TTG CCC CAT AAC GTC GAT ACC CAT          2909
Leu Gln Gln Thr Ser Cys Ala Gly Leu Pro His Asn Val Asp Thr His
25                  30                  35                  40

CAT ATC CTA ACT TTC AAC CCT TCT CCC ATT TCG GCC GAT GGC GTT CCT          2957
His Ile Leu Thr Phe Asn Pro Ser Pro Ile Ser Ala Asp Gly Val Pro
                45                  50                  55

TTG TCA GAG GTG CCC AAT TCG CCT ACG ACC GAA TTA TCT ACA ACT GTC          3005
Leu Ser Glu Val Pro Asn Ser Pro Thr Thr Glu Leu Ser Thr Thr Val
                60                  65                  70

GCC ACC AAG ACA GCT GTA CCG ACG ACT GAA AGC ACT AGT TCC TCC GAA          3053
Ala Thr Lys Thr Ala Val Pro Thr Thr Glu Ser Thr Ser Ser Ser Glu
        75                  80                  85

GCG CAC CGC AAC TCT TCT CAC AAA ATA CCT GAT ATA ATC TGC GAC CGA          3101
Ala His Arg Asn Ser Ser His Lys Ile Pro Asp Ile Ile Cys Asp Arg
        90                  95                  100

GAA GAA GTA TTC GTA TTC CTT AAC AAT ACA GGA AGA ATT TTG TGT GAC          3149
Glu Glu Val Phe Val Phe Leu Asn Asn Thr Gly Arg Ile Leu Cys Asp
105                 110                 115                 120

CTT ATA GTC GAC CCC CCT TCA GAC GAT GAA TGG TCC AAC TTC GCT CTT          3197
Leu Ile Val Asp Pro Pro Ser Asp Asp Glu Trp Ser Asn Phe Ala Leu
                125                 130                 135

GAC GTC ACG TTC AAT CCA ATC GAA TAC CAC GCC AAC GAA AAG AAT GTA          3245
Asp Val Thr Phe Asn Pro Ile Glu Tyr His Ala Asn Glu Lys Asn Val
                140                 145                 150
```

```
GAG GTT GCC CGA GTG GCC GGT CTA TAC GGA GTA CCG GGG TCG GAT TAT      3293
Glu Val Ala Arg Val Ala Gly Leu Tyr Gly Val Pro Gly Ser Asp Tyr
        155                 160                 165

GCA TAC CCT AGG AAA TCG GAA TTA ATA TCC TCC ATT CGA CGG GAT CCC      3341
Ala Tyr Pro Arg Lys Ser Glu Leu Ile Ser Ser Ile Arg Arg Asp Pro
        170                 175                 180

CAG GGT TCT TTC TGG ACT AGT CCT ACA CCC CGT GGA AAT AAA TAT TTC      3389
Gln Gly Ser Phe Trp Thr Ser Pro Thr Pro Arg Gly Asn Lys Tyr Phe
185                 190                 195                 200

ATA TGG ATT AAT AAA ACA ATG CAC ACC ATG GGC GTG GAA GTT AGA AAT      3437
Ile Trp Ile Asn Lys Thr Met His Thr Met Gly Val Glu Val Arg Asn
                205                 210                 215

GTC GAC TAC AAA GAC AAC GGC TAC TTT CAA GTG ATA CTG CGT GAT AGA      3485
Val Asp Tyr Lys Asp Asn Gly Tyr Phe Gln Val Ile Leu Arg Asp Arg
        220                 225                 230

TTT AAT CGC CCA TTG GTA GAA AAA CAT ATT TAC ATG CGT GTG TGC CAA      3533
Phe Asn Arg Pro Leu Val Glu Lys His Ile Tyr Met Arg Val Cys Gln
        235                 240                 245

CGA CCC GCA TCC GTG GAT GTA TTG GCC CCT CCA GTT CTC AGC GGA GAA      3581
Arg Pro Ala Ser Val Asp Val Leu Ala Pro Pro Val Leu Ser Gly Glu
250                 255                 260

AAC TAC AAA GCA TCT TGC ATC GTT AGA CAT TTT TAT CCC CCG GGA TCT      3629
Asn Tyr Lys Ala Ser Cys Ile Val Arg His Phe Tyr Pro Pro Gly Ser
265                 270                 275                 280

GTC TAC GTA TCT TGG AGA CGT AAC GGA AAC ATT GCC ACA CCC CGC AAG      3677
Val Tyr Val Ser Trp Arg Arg Asn Gly Asn Ile Ala Thr Pro Arg Lys
                285                 290                 295

GAC CGT GAC GGG AGT TTT TGG TGG TTC GAA TCT GGC CGC GGG GCC ACA      3725
Asp Arg Asp Gly Ser Phe Trp Trp Phe Glu Ser Gly Arg Gly Ala Thr
                300                 305                 310

CTA GTA TCC ACA ATA ACC CTC GGA AAC TCT GGA CTC GAA TCT CCT CCA      3773
Leu Val Ser Thr Ile Thr Leu Gly Asn Ser Gly Leu Glu Ser Pro Pro
        315                 320                 325

AAG GTT TCC TGC TTG GTA GCG TGG AGG CAA GGC GAT ATG ATA AGC ACA      3821
Lys Val Ser Cys Leu Val Ala Trp Arg Gln Gly Asp Met Ile Ser Thr
        330                 335                 340

TCG AAT GCT ACA GCT GTA CCG ACG GTA TAT TAT CAC CCC CGT ATC TCT      3869
Ser Asn Ala Thr Ala Val Pro Thr Val Tyr Tyr His Pro Arg Ile Ser
345                 350                 355                 360

CTG GCA TTT AAA GAT GGG TAT GCA ATA TGT ACT ATA GAA TGT GTT CCC      3917
Leu Ala Phe Lys Asp Gly Tyr Ala Ile Cys Thr Ile Glu Cys Val Pro
                365                 370                 375

TCT GGG ATT ACT GTG AGG TGG TTA GTT CAT GAT GAA CCC CAG CCT AAC      3965
Ser Gly Ile Thr Val Arg Trp Leu Val His Asp Glu Pro Gln Pro Asn
                380                 385                 390

ACA ACT TAT GAT ACT GTG GTT ACA GGT CTC TGC AGG ACC ATC GAT CGT      4013
Thr Thr Tyr Asp Thr Val Val Thr Gly Leu Cys Arg Thr Ile Asp Arg
        395                 400                 405

TAT AGA AAT CTC GCC AGT CGG ATT CCA GTC CAG GAC AAC TGG GCG AAA      4061
Tyr Arg Asn Leu Ala Ser Arg Ile Pro Val Gln Asp Asn Trp Ala Lys
        410                 415                 420

ACG AAG TAT ACG TGC AGA CTA ATT GGA TAT CCG TTC GAC GTG GAT AGA      4109
Thr Lys Tyr Thr Cys Arg Leu Ile Gly Tyr Pro Phe Asp Val Asp Arg
425                 430                 435                 440

TTT CAA AAT TCC GAA TAT TAT GAT GCA ACG CCG TCG GCA AGA GGA ATG      4157
Phe Gln Asn Ser Glu Tyr Tyr Asp Ala Thr Pro Ser Ala Arg Gly Met
                445                 450                 455

CCG ATG ATT GTA ACA ATT ACG GCC GTT CTA GGA CTG GCC TTG TTT TTA      4205
Pro Met Ile Val Thr Ile Thr Ala Val Leu Gly Leu Ala Leu Phe Leu
                460                 465                 470
```

```
GGT ATT GGT ATC ATT ATC ACA GCC CTA TGC TTT TAC CTA CCG GGG CGG        4253
Gly Ile Gly Ile Ile Ile Thr Ala Leu Cys Phe Tyr Leu Pro Gly Arg
            475                 480                 485

AAT TAAGATTAAC CATCGTATGT GATATAAAAA TTATTAAGTG TTATAACCGA             4306
Asn
490

TCGCATTCTT CTGTTTCGAT TCACAATAAA TAAAATGGTA TTGTAATCAG CACCATCGCA      4366

TTGTTTCGTA GATGACTCAT GTTCAGTCCG CGTGATGTCA AAAATACGTA TTTTTGGTAT      4426

CACGCAGCGG CCAAAATGCC CATTATGTTA TTTTTACTCC AAACGCGGTA TTTAAAACAT      4486

CGGGACGTAC ATCATGTGGC GCACGTTAAT CGTATACGGT GCCGCTACAT TAAAAATCGC      4546

AAGTCTCCGA ATATCAAGCT CACGGCCAAA ACGTCGGTAA TAATCTTACG CATCGAATGT      4606

GATACGGATA CCGTACAATC GCTGAGTAGA TTTCCTATAT AGTTACTCAG TAGTGATACA      4666

CAATCACAAA ATCGCTGGGG TATATCATAT AAGA ATG ATG TCG CCC ACC CCT         4718
                                      Met Met Ser Pro Thr Pro
                                        1               5

GAA GAT GAT CGC GAT CTC GTT GTG GTT CGT GGA CGT CTC CGA ATG ATG        4766
Glu Asp Asp Arg Asp Leu Val Val Val Arg Gly Arg Leu Arg Met Met
             10                  15                  20

GAT AGC GGC ACG GAA ACA GAT AGA GAG CAA CGA CAT CCA CGT ACG ACT        4814
Asp Ser Gly Thr Glu Thr Asp Arg Glu Gln Arg His Pro Arg Thr Thr
         25                  30                  35

TGG CGA TCG ATC TGT TGT GGG TGT ACG ATA GGA ATG GTA TTT ACC ATA        4862
Trp Arg Ser Ile Cys Cys Gly Cys Thr Ile Gly Met Val Phe Thr Ile
 40                  45                  50

TTC GTT CTC GTA GCG GCA GTA TTG TTG GGA TCA CTA TTC ACT GTT TCA        4910
Phe Val Leu Val Ala Ala Val Leu Leu Gly Ser Leu Phe Thr Val Ser
 55                  60                  65                  70

TAC ATG GCC ATG GAA TCG GGA ACA TGT CCC GAT GAA TGG ATT GGT TTG        4958
Tyr Met Ala Met Glu Ser Gly Thr Cys Pro Asp Glu Trp Ile Gly Leu
             75                  80                  85

GGT TAT AGT TGC ATG CGC GTG GCC GGG AAA AAT GCA ACT GAT CTT GAG        5006
Gly Tyr Ser Cys Met Arg Val Ala Gly Lys Asn Ala Thr Asp Leu Glu
         90                  95                 100

GCG TTG GAT ACA TGT GCT CGG CAT AAC AGC AAA CTT ATT GAC TTC GCA        5054
Ala Leu Asp Thr Cys Ala Arg His Asn Ser Lys Leu Ile Asp Phe Ala
     105                 110                 115

AAC GCC AAA GTT CTG GTT GAA GCT ATC GCC CCA TTC GGT GTG CCA AAT        5102
Asn Ala Lys Val Leu Val Glu Ala Ile Ala Pro Phe Gly Val Pro Asn
120                 125                 130

GCA GCA TAT GGG GAA GTC TTC CGG TTA AGG GAC AGC AAA ACC ACG TGT        5150
Ala Ala Tyr Gly Glu Val Phe Arg Leu Arg Asp Ser Lys Thr Thr Cys
135                 140                 145                 150

ATA CGA CCT ACC ATG GGA GGA CCC GTG TCG GCA GAC TGT CCT GTA ACA        5198
Ile Arg Pro Thr Met Gly Gly Pro Val Ser Ala Asp Cys Pro Val Thr
             155                 160                 165

TGT ACC GTT ATA TGT CAG CGA CCC AGG CCT CTA AGT ACC ATG TCT TCC        5246
Cys Thr Val Ile Cys Gln Arg Pro Arg Pro Leu Ser Thr Met Ser Ser
         170                 175                 180

ATC ATT AGA GAT GCC CGC GTG TAT CTT CAT TTA GAA CGA CGC GAT TAT        5294
Ile Ile Arg Asp Ala Arg Val Tyr Leu His Leu Glu Arg Arg Asp Tyr
     185                 190                 195

TAT GAA GTC TAC GCC TCT GTC CTC TCT AAT GCG ATG AGT AAA TAAAAACGCA     5346
Tyr Glu Val Tyr Ala Ser Val Leu Ser Asn Ala Met Ser Lys
200                 205                 210

CCTCTAACGG TTACTGTGTT TATTATCCAA TCACACCATA GACATTATTA CAATAATATG      5406

GATCTTTATT TCATATAATG                                                  5426
```

(2) INFORMATION FOR SEQ ID NO:4:

(i) SEQUENCE CHARACTERISTICS:
        (A) LENGTH: 369 amino acids
        (B) TYPE: amino acid
        (D) TOPOLOGY: linear (ii) MOLECULE TYPE: protein (xi) SEQUENCE DESCRIPTION: SEQ ID NO:4:

```
Met Met Ala Gly Ile Thr Val Ala Cys Asp His Thr Ala Gly Glu Ala
  1               5                  10                  15

His Thr Pro Glu Asp Met Gln Lys Lys Trp Arg Ile Ile Leu Ala Gly
             20                  25                  30

Glu Lys Phe Met Thr Ile Ser Ala Ser Leu Lys Ser Ile Val Ser Cys
         35                  40                  45

Val Lys Asn Pro Leu Leu Thr Phe Gly Ala Asp Gly Leu Ile Val Gln
     50                  55                  60

Gly Thr Val Cys Gly Gln Arg Ile Phe Val Pro Ile Asp Arg Asp Ser
 65                  70                  75                  80

Phe Ser Glu Tyr Glu Trp His Gly Pro Thr Ala Met Phe Leu Ala Leu
                 85                  90                  95

Thr Asp Ser Arg Arg Thr Leu Leu Asp Ala Phe Lys Cys Glu Lys Arg
            100                 105                 110

Arg Ala Ile Asp Val Ser Phe Thr Phe Ala Gly Glu Pro Pro Cys Arg
        115                 120                 125

His Leu Ile Gln Ala Val Thr Tyr Met Thr Asp Gly Gly Ser Val Ser
    130                 135                 140

Asn Thr Ile Ile Lys Tyr Glu Leu Trp Asn Ala Ser Thr Ile Phe Pro
145                 150                 155                 160

Gln Lys Thr Pro Asp Val Thr Phe Ser Leu Asn Lys Gln Gln Leu Asn
                165                 170                 175

Lys Ile Leu Ala Val Ala Ser Lys Leu Gln His Glu Glu Leu Val Phe
            180                 185                 190

Ser Leu Lys Pro Glu Gly Gly Phe Tyr Val Gly Thr Val Cys Thr Val
        195                 200                 205

Ile Ser Phe Glu Val Asp Gly Thr Ala Met Thr Gln Tyr Pro Tyr Asn
    210                 215                 220

Pro Pro Thr Ser Ala Thr Leu Ala Leu Val Val Ala Cys Arg Lys Lys
225                 230                 235                 240

Lys Ala Asn Lys Asn Thr Ile Leu Thr Ala Tyr Gly Ser Gly Lys Pro
                245                 250                 255

Phe Cys Val Ala Leu Glu Asp Thr Ser Ala Phe Arg Asn Ile Val Asn
            260                 265                 270

Lys Ile Lys Ala Gly Thr Ser Gly Val Asp Leu Gly Phe Tyr Thr Thr
        275                 280                 285

Cys Asp Pro Pro Met Leu Cys Ile Arg Pro His Ala Phe Gly Ser Pro
    290                 295                 300

Thr Ala Phe Leu Phe Cys Asn Thr Asp Cys Met Thr Ile Tyr Glu Leu
305                 310                 315                 320

Glu Glu Val Ser Ala Val Asp Gly Ala Ile Arg Ala Lys Arg Ile Asn
                325                 330                 335

Glu Tyr Phe Pro Thr Val Ser Gln Ala Thr Ser Lys Lys Arg Lys Gln
            340                 345                 350

Ser Pro Pro Pro Ile Glu Arg Glu Arg Lys Thr Thr Arg Ala Asp Thr
```

|     |     |     |
| --- | --- | --- |
| 355 | 360 | 365 |

Gln (2) INFORMATION FOR SEQ ID NO:5:

(i) SEQUENCE CHARACTERISTICS:
        (A) LENGTH: 422 amino acids
        (B) TYPE: amino acid
        (D) TOPOLOGY: linear (ii) MOLECULE TYPE: protein (xi) SEQUENCE DESCRIPTION: SEQ ID NO:5:

```
Met Pro Ser Gly Ala Ser Ser Pro Pro Ala Tyr Thr Ser Ala
 1               5                  10                  15

Ala Pro Leu Glu Thr Tyr Asn Ser Trp Leu Ser Ala Phe Ser Cys Ala
                20                  25                  30

Tyr Pro Gln Cys Thr Ala Gly Arg Gly His Arg Gln Asn Gly Lys Lys
                35                  40                  45

Cys Ile Arg Cys Ile Val Ile Ser Val Cys Ser Leu Val Cys Ile Ala
            50                  55                  60

Ala His Leu Ala Val Thr Val Ser Gly Val Ala Leu Ile Pro Leu Ile
65                  70                  75                  80

Asp Gln Asn Arg Ala Tyr Gly Asn Cys Thr Val Cys Val Ile Ala Gly
                85                  90                  95

Phe Ile Ala Thr Phe Ala Ala Arg Leu Thr Ile Arg Leu Ser Glu Thr
                100                 105                 110

Leu Met Leu Val Gly Lys Pro Ala Gln Phe Ile Phe Ala Ile Ile Ala
                115                 120                 125

Ser Val Ala Glu Thr Leu Ile Asn Asn Glu Ala Leu Ala Ile Ser Asn
            130                 135                 140

Thr Thr Tyr Lys Thr Ala Leu Arg Ile Ile Glu Val Thr Ser Leu Ala
145                 150                 155                 160

Cys Phe Val Met Leu Gly Ala Ile Ile Thr Ser His Asn Tyr Val Cys
                165                 170                 175

Ile Ser Thr Ala Gly Asp Leu Thr Trp Lys Gly Gly Ile Phe His Ala
                180                 185                 190

Tyr His Gly Thr Leu Leu Gly Ile Thr Ile Pro Asn Ile His Pro Ile
                195                 200                 205

Pro Leu Ala Gly Phe Leu Ala Val Tyr Thr Ile Leu Ala Ile Asn Ile
            210                 215                 220

Ala Arg Asp Ala Ser Ala Thr Leu Leu Ser Thr Cys Tyr Tyr Arg Asn
225                 230                 235                 240

Cys Arg Glu Arg Thr Ile Leu Arg Pro Ser Arg Leu Gly His Gly Tyr
                245                 250                 255

Thr Ile Pro Ser Pro Gly Ala Asp Met Leu Tyr Glu Glu Asp Val Tyr
                260                 265                 270

Ser Phe Asp Ala Ala Lys Gly His Tyr Ser Ser Ile Phe Leu Cys Tyr
            275                 280                 285

Ala Met Gly Leu Thr Thr Pro Leu Ile Ile Ala Leu His Lys Tyr Met
            290                 295                 300

Ala Gly Ile Lys Asn Ser Ser Asp Trp Thr Ala Thr Leu Gln Gly Met
305                 310                 315                 320

Tyr Gly Leu Val Leu Gly Ser Leu Ser Ser Leu Cys Ile Pro Ser Ser
                325                 330                 335

Asn Asn Asp Ala Leu Ile Arg Pro Ile Gln Ile Leu Ile Leu Ile Ile
```

```
                    340                 345                 350
Gly Ala Leu Ala Ile Ala Leu Ala Gly Cys Gly Gln Ile Gly Pro
                355                 360                 365

Thr Leu Phe Ala Ala Ser Ser Ala Ala Met Ser Cys Phe Thr Cys Ile
370                 375                 380

Asn Ile Arg Ala Thr Asn Lys Gly Val Asn Lys Leu Ala Ala Ser
385                 390                 395                 400

Val Val Lys Ser Val Leu Gly Phe Ile Ile Ser Gly Met Leu Thr Cys
                405                 410                 415

Val Leu Leu Pro Leu Ser
                420
```

(2) INFORMATION FOR SEQ ID NO:6:

(i) SEQUENCE CHARACTERISTICS:
        (A) LENGTH: 489 amino acids
        (B) TYPE: amino acid
        (D) TOPOLOGY: linear (ii) MOLECULE TYPE: protein (xi) SEQUENCE DESCRIPTION: SEQ ID NO:6:

```
Met Val Ser Asn Met Arg Val Leu Arg Val Leu Arg Leu Thr Gly Trp
1               5                   10                  15

Val Gly Ile Phe Leu Val Leu Ser Leu Gln Gln Thr Ser Cys Ala Gly
                20                  25                  30

Leu Pro His Asn Val Asp Thr His His Ile Leu Thr Phe Asn Pro Ser
            35                  40                  45

Pro Ile Ser Ala Asp Gly Val Pro Leu Ser Glu Val Pro Asn Ser Pro
    50                  55                  60

Thr Thr Glu Leu Ser Thr Thr Val Ala Thr Lys Thr Ala Val Pro Thr
65                  70                  75                  80

Thr Glu Ser Thr Ser Ser Ser Glu Ala His Arg Asn Ser Ser His Lys
                85                  90                  95

Ile Pro Asp Ile Ile Cys Asp Arg Glu Glu Val Phe Val Phe Leu Asn
            100                 105                 110

Asn Thr Gly Arg Ile Leu Cys Asp Leu Ile Val Asp Pro Pro Ser Asp
        115                 120                 125

Asp Glu Trp Ser Asn Phe Ala Leu Asp Val Thr Phe Asn Pro Ile Glu
    130                 135                 140

Tyr His Ala Asn Glu Lys Asn Val Glu Val Ala Arg Val Ala Gly Leu
145                 150                 155                 160

Tyr Gly Val Pro Gly Ser Asp Tyr Ala Tyr Pro Arg Lys Ser Glu Leu
                165                 170                 175

Ile Ser Ser Ile Arg Arg Asp Pro Gln Gly Ser Phe Trp Thr Ser Pro
            180                 185                 190

Thr Pro Arg Gly Asn Lys Tyr Phe Ile Trp Ile Asn Lys Thr Met His
        195                 200                 205

Thr Met Gly Val Glu Val Arg Asn Val Asp Tyr Lys Asp Asn Gly Tyr
    210                 215                 220

Phe Gln Val Ile Leu Arg Asp Arg Phe Asn Arg Pro Leu Val Glu Lys
225                 230                 235                 240

His Ile Tyr Met Arg Val Cys Gln Arg Pro Ala Ser Val Asp Val Leu
                245                 250                 255

Ala Pro Pro Val Leu Ser Gly Glu Asn Tyr Lys Ala Ser Cys Ile Val
            260                 265                 270
```

```
Arg His Phe Tyr Pro Pro Gly Ser Val Tyr Val Ser Trp Arg Arg Asn
            275                 280                 285

Gly Asn Ile Ala Thr Pro Arg Lys Asp Arg Asp Gly Ser Phe Trp Trp
            290                 295                 300

Phe Glu Ser Gly Arg Gly Ala Thr Leu Val Ser Thr Ile Thr Leu Gly
305                 310                 315                 320

Asn Ser Gly Leu Glu Ser Pro Pro Lys Val Ser Cys Leu Val Ala Trp
                325                 330                 335

Arg Gln Gly Asp Met Ile Ser Thr Ser Asn Ala Thr Ala Val Pro Thr
            340                 345                 350

Val Tyr Tyr His Pro Arg Ile Ser Leu Ala Phe Lys Asp Gly Tyr Ala
            355                 360                 365

Ile Cys Thr Ile Glu Cys Val Pro Ser Gly Ile Thr Val Arg Trp Leu
            370                 375                 380

Val His Asp Glu Pro Gln Pro Asn Thr Thr Tyr Asp Thr Val Val Thr
385                 390                 395                 400

Gly Leu Cys Arg Thr Ile Asp Arg Tyr Arg Asn Leu Ala Ser Arg Ile
                405                 410                 415

Pro Val Gln Asp Asn Trp Ala Lys Thr Lys Tyr Thr Cys Arg Leu Ile
            420                 425                 430

Gly Tyr Pro Phe Asp Val Asp Arg Phe Gln Asn Ser Glu Tyr Tyr Asp
            435                 440                 445

Ala Thr Pro Ser Ala Arg Gly Met Pro Met Ile Val Thr Ile Thr Ala
450                 455                 460

Val Leu Gly Leu Ala Leu Phe Leu Gly Ile Gly Ile Ile Ile Thr Ala
465                 470                 475                 480

Leu Cys Phe Tyr Leu Pro Gly Arg Asn
                485

(2) INFORMATION FOR SEQ ID NO:7:

(i) SEQUENCE CHARACTERISTICS:
        (A) LENGTH: 212 amino acids
        (B) TYPE: amino acid
        (D) TOPOLOGY: linear (ii) MOLECULE TYPE: protein (xi) SEQUENCE DESCRIPTION: SEQ ID NO:7:

Met Met Ser Pro Thr Pro Glu Asp Arg Asp Leu Val Val Arg
1               5                   10                  15

Gly Arg Leu Arg Met Met Asp Ser Gly Thr Glu Thr Asp Arg Glu Gln
                20                  25                  30

Arg His Pro Arg Thr Thr Trp Arg Ser Ile Cys Cys Gly Cys Thr Ile
            35                  40                  45

Gly Met Val Phe Thr Ile Phe Val Leu Val Ala Ala Val Leu Leu Gly
            50                  55                  60

Ser Leu Phe Thr Val Ser Tyr Met Ala Met Glu Ser Gly Thr Cys Pro
65                  70                  75                  80

Asp Glu Trp Ile Gly Leu Gly Tyr Ser Cys Met Arg Val Ala Gly Lys
                85                  90                  95

Asn Ala Thr Asp Leu Glu Ala Leu Asp Thr Cys Ala Arg His Asn Ser
            100                 105                 110

Lys Leu Ile Asp Phe Ala Asn Ala Lys Val Leu Val Glu Ala Ile Ala
            115                 120                 125

Pro Phe Gly Val Pro Asn Ala Ala Tyr Gly Glu Val Phe Arg Leu Arg
            130                 135                 140
```

```
Asp Ser Lys Thr Thr Cys Ile Arg Pro Thr Met Gly Gly Pro Val Ser
145                 150                 155                 160

Ala Asp Cys Pro Val Thr Cys Thr Val Ile Cys Gln Arg Pro Arg Pro
                165                 170                 175

Leu Ser Thr Met Ser Ser Ile Ile Arg Asp Ala Arg Val Tyr Leu His
            180                 185                 190

Leu Glu Arg Arg Asp Tyr Tyr Glu Val Tyr Ala Ser Val Leu Ser Asn
        195                 200                 205

Ala Met Ser Lys
    210
```

(2) INFORMATION FOR SEQ ID NO:8:

(i) SEQUENCE CHARACTERISTICS:
      (A) LENGTH: 1506 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: CDS
      (B) LOCATION: 1..1506

(xi) SEQUENCE DESCRIPTION: SEQ ID NO:8:

```
ATG CTC ACG CCG CGT GTG TTA CGA GCT TTG GGG TGG ACT GGA CTC TTT      48
Met Leu Thr Pro Arg Val Leu Arg Ala Leu Gly Trp Thr Gly Leu Phe
1               5                   10                  15

TTT TTG CTT TTA TCT CCG AGC AAC GTC CTA GGA GCC AGC CTT AGC CGG      96
Phe Leu Leu Leu Ser Pro Ser Asn Val Leu Gly Ala Ser Leu Ser Arg
                20                  25                  30

GAT CTC GAA ACA CCC CCA TTT CTA TCC TTT GAT CCA TCC AAC ATT TCA     144
Asp Leu Glu Thr Pro Pro Phe Leu Ser Phe Asp Pro Ser Asn Ile Ser
            35                  40                  45

ATT AAC GGC GCG CCT TTA ACT GAG GTA CCT CAT GCA CCT TCC ACA GAA     192
Ile Asn Gly Ala Pro Leu Thr Glu Val Pro His Ala Pro Ser Thr Glu
        50                  55                  60

AGT GTG TCA ACA AAT TCG GAA AGT ACC AAT GAA CAT ACC ATA ACA GAA     240
Ser Val Ser Thr Asn Ser Glu Ser Thr Asn Glu His Thr Ile Thr Glu
65                  70                  75                  80

ACG ACG GGC AAG AAC GCA TAC ATC CAC AAC AAT GCG TCT ACG GAC AAG     288
Thr Thr Gly Lys Asn Ala Tyr Ile His Asn Asn Ala Ser Thr Asp Lys
                85                  90                  95

CAA AAT GCG AAC GAC ACT CAT AAA ACG CCC AAT ATA CTC TGC GAT ACG     336
Gln Asn Ala Asn Asp Thr His Lys Thr Pro Asn Ile Leu Cys Asp Thr
            100                 105                 110

GAA GAA GTT TTT GTT TTC CTT AAC GAA ACG GGA AGA TTT GTT TGT ACT     384
Glu Glu Val Phe Val Phe Leu Asn Glu Thr Gly Arg Phe Val Cys Thr
        115                 120                 125

CTC AAA GTC GAC CCC CCC TCG GAT AGT GAA TGG TCC AAC TTT GTT CTA     432
Leu Lys Val Asp Pro Pro Ser Asp Ser Glu Trp Ser Asn Phe Val Leu
130                 135                 140

GAT CTG ATC TTT AAC CCA ATT GAA TAC CAC GCC AAC GAA AAG AAT GTG     480
Asp Leu Ile Phe Asn Pro Ile Glu Tyr His Ala Asn Glu Lys Asn Val
145                 150                 155                 160

GAA GCG GCG CGT ATC GCT GGT CTC TAT GGA GTC CCC GGA TCA GAC TAT     528
Glu Ala Ala Arg Ile Ala Gly Leu Tyr Gly Val Pro Gly Ser Asp Tyr
                165                 170                 175
```

```
GCA TAC CCA CGT CAA TCT GAA TTA ATT TCT TCG ATT CGA CGA GAT CCC       576
Ala Tyr Pro Arg Gln Ser Glu Leu Ile Ser Ser Ile Arg Arg Asp Pro
            180                 185                 190

CAG GGC ACA TTT TGG ACG AGC CCA TCA CCT CAT GGA AAC AAG TAC TTC       624
Gln Gly Thr Phe Trp Thr Ser Pro Ser Pro His Gly Asn Lys Tyr Phe
        195                 200                 205

ATA TGG ATA AAC AAA ACA ACC AAT ACG ATG GGC GTG GAA ATT AGA AAT       672
Ile Trp Ile Asn Lys Thr Thr Asn Thr Met Gly Val Glu Ile Arg Asn
    210                 215                 220

GTA GAT TAT GCT GAT AAT GGC TAC ATG CAA GTC ATT ATG CGT GAC CAT       720
Val Asp Tyr Ala Asp Asn Gly Tyr Met Gln Val Ile Met Arg Asp His
225                 230                 235                 240

TTT AAT CGG CCT TTA ATA GAT AAA CAT ATT TAC ATA CGT GTG TGT CAA       768
Phe Asn Arg Pro Leu Ile Asp Lys His Ile Tyr Ile Arg Val Cys Gln
                245                 250                 255

CGA CCT GCA TCA GTG GAT GTA CTG GCC CCT CCA GTC CTC AGC GGA GAA       816
Arg Pro Ala Ser Val Asp Val Leu Ala Pro Pro Val Leu Ser Gly Glu
            260                 265                 270

AAT TAC AAG GCA TCT TGT ATC GTT AGA CAC TTT TAT CCC CCT GGA TCT       864
Asn Tyr Lys Ala Ser Cys Ile Val Arg His Phe Tyr Pro Pro Gly Ser
        275                 280                 285

GTC TAT GTA TCT TGG AGA CAG AAT GGA AAC ATT GCA ACT CCT CGG AAA       912
Val Tyr Val Ser Trp Arg Gln Asn Gly Asn Ile Ala Thr Pro Arg Lys
    290                 295                 300

GAT CGC GAT GGA AGT TTT TGG TGG TTC GAA TCT GGT AGA GGA GCT ACG       960
Asp Arg Asp Gly Ser Phe Trp Trp Phe Glu Ser Gly Arg Gly Ala Thr
305                 310                 315                 320

TTG GTT TCT ACA ATA ACA TTG GGA AAT TCA GGA ATT GAT TTC CCC CCC      1008
Leu Val Ser Thr Ile Thr Leu Gly Asn Ser Gly Ile Asp Phe Pro Pro
                325                 330                 335

AAA ATA TCT TGT CTG GTT GCC TGG AAG CAG GGT GAT ATG ATC AGC ACG      1056
Lys Ile Ser Cys Leu Val Ala Trp Lys Gln Gly Asp Met Ile Ser Thr
            340                 345                 350

ACG AAT GCC ACA GCT ATC CCG ACG GTA TAT CAT CAT CCC CGT TTA TCC      1104
Thr Asn Ala Thr Ala Ile Pro Thr Val Tyr His His Pro Arg Leu Ser
        355                 360                 365

CTG GCT TTT AAA GAT GGG TAT GCA ATA TGT ACT ATA GAA TGT GTC CCC      1152
Leu Ala Phe Lys Asp Gly Tyr Ala Ile Cys Thr Ile Glu Cys Val Pro
    370                 375                 380

TCT GAG ATT ACT GTA CGG TGG TTA GTA CAT GAT GAA GCG CAG CCT AAC      1200
 Ser Glu Ile Thr Val Arg Trp Leu Val His Asp Glu Ala Gln Pro Asn
385                 390                 395                 400

ACA ACT TAT AAT ACT GTG GTT ACA GGT CTC TGC CGG ACC ATC GAT CGC      1248
Thr Thr Tyr Asn Thr Val Val Thr Gly Leu Cys Arg Thr Ile Asp Arg
                405                 410                 415

CAT AGA AAT CTC CTC AGC CGC ATT CCA GTA TGG GAC AAT TGG ACG AAA      1296
His Arg Asn Leu Leu Ser Arg Ile Pro Val Trp Asp Asn Trp Thr Lys
            420                 425                 430

ACA AAA TAT ACG TGC AGA CTC ATA GGC TAC CCC TTC GAT GAA GAT AAA      1344
Thr Lys Tyr Thr Cys Arg Leu Ile Gly Tyr Pro Phe Asp Glu Asp Lys
        435                 440                 445

TTT CAA GAT TCG GAA TAT TAC GAT GCA ACT CCA TCT GCA AGA GGA ACA      1392
Phe Gln Asp Ser Glu Tyr Tyr Asp Ala Thr Pro Ser Ala Arg Gly Thr
    450                 455                 460

CCC ATG GTT ATT ACG GTT ACG GCA GTT TTG GGA TTG GCT GTA ATT TTA      1440
Pro Met Val Ile Thr Val Thr Ala Val Leu Gly Leu Ala Val Ile Leu
465                 470                 475                 480

GGG ATG GGG ATA ATC ATG ACT GCC CTA TGT TTA TAC AAC TCC ACA CGA      1488
Gly Met Gly Ile Ile Met Thr Ala Leu Cys Leu Tyr Asn Ser Thr Arg
                485                 490                 495
```

```
AAA AAT ATT CGA TTA TAA                                            1506
Lys Asn Ile Arg Leu
            500

(2) INFORMATION FOR SEQ ID NO:9:

(i) SEQUENCE CHARACTERISTICS:
        (A) LENGTH: 501 amino acids
        (B) TYPE: amino acid
        (D) TOPOLOGY: linear (ii) MOLECULE TYPE: protein (xi) SEQUENCE DESCRIPTION: SEQ ID NO:9:

Met Leu Thr Pro Arg Val Leu Arg Ala Leu Gly Trp Thr Gly Leu Phe
    1               5                   10                  15

Phe Leu Leu Leu Ser Pro Ser Asn Val Leu Gly Ala Ser Leu Ser Arg
                    20                  25                  30

Asp Leu Glu Thr Pro Pro Phe Leu Ser Phe Asp Pro Ser Asn Ile Ser
                35                  40                  45

Ile Asn Gly Ala Pro Leu Thr Glu Val Pro His Ala Pro Ser Thr Glu
    50                  55                  60

Ser Val Ser Thr Asn Ser Glu Ser Thr Asn Glu His Thr Ile Thr Glu
    65                  70                  75                  80

Thr Thr Gly Lys Asn Ala Tyr Ile His Asn Asn Ala Ser Thr Asp Lys
                    85                  90                  95

Gln Asn Ala Asn Asp Thr His Lys Thr Pro Asn Ile Leu Cys Asp Thr
                100                 105                 110

Glu Glu Val Phe Val Phe Leu Asn Glu Thr Gly Arg Phe Val Cys Thr
                115                 120                 125

Leu Lys Val Asp Pro Pro Ser Asp Ser Glu Trp Ser Asn Phe Val Leu
    130                 135                 140

Asp Leu Ile Phe Asn Pro Ile Glu Tyr His Ala Asn Glu Lys Asn Val
    145                 150                 155                 160

Glu Ala Ala Arg Ile Ala Gly Leu Tyr Gly Val Pro Gly Ser Asp Tyr
                    165                 170                 175

Ala Tyr Pro Arg Gln Ser Glu Leu Ile Ser Ser Ile Arg Arg Asp Pro
                180                 185                 190

Gln Gly Thr Phe Trp Thr Ser Pro Ser Pro His Gly Asn Lys Tyr Phe
                195                 200                 205

Ile Trp Ile Asn Lys Thr Thr Asn Thr Met Gly Val Glu Ile Arg Asn
    210                 215                 220

Val Asp Tyr Ala Asp Asn Gly Tyr Met Gln Val Ile Met Arg Asp His
    225                 230                 235                 240

Phe Asn Arg Pro Leu Ile Asp Lys His Ile Tyr Ile Arg Val Cys Gln
                    245                 250                 255

Arg Pro Ala Ser Val Asp Val Leu Ala Pro Pro Val Leu Ser Gly Glu
                260                 265                 270

Asn Tyr Lys Ala Ser Cys Ile Val Arg His Phe Tyr Pro Pro Gly Ser
                275                 280                 285

Val Tyr Val Ser Trp Arg Gln Asn Gly Asn Ile Ala Thr Pro Arg Lys
    290                 295                 300

Asp Arg Asp Gly Ser Phe Trp Trp Phe Glu Ser Gly Arg Gly Ala Thr
    305                 310                 315                 320

Leu Val Ser Thr Ile Thr Leu Gly Asn Ser Gly Ile Asp Phe Pro Pro
                    325                 330                 335
```

```
Lys Ile Ser Cys Leu Val Ala Trp Lys Gln Gly Asp Met Ile Ser Thr
            340                 345                 350

Thr Asn Ala Thr Ala Ile Pro Thr Val Tyr His His Pro Arg Leu Ser
            355                 360                 365

Leu Ala Phe Lys Asp Gly Tyr Ala Ile Cys Thr Ile Glu Cys Val Pro
    370                 375                 380

Ser Glu Ile Thr Val Arg Trp Leu Val His Asp Glu Ala Gln Pro Asn
385                 390                 395                 400

Thr Thr Tyr Asn Thr Val Val Thr Gly Leu Cys Arg Thr Ile Asp Arg
                405                 410                 415

His Arg Asn Leu Leu Ser Arg Ile Pro Val Trp Asp Asn Trp Thr Lys
            420                 425                 430

Thr Lys Tyr Thr Cys Arg Leu Ile Gly Tyr Pro Phe Asp Glu Asp Lys
            435                 440                 445

Phe Gln Asp Ser Glu Tyr Tyr Asp Ala Thr Pro Ser Ala Arg Gly Thr
    450                 455                 460

Pro Met Val Ile Thr Val Thr Ala Val Leu Gly Leu Ala Val Ile Leu
465                 470                 475                 480

Gly Met Gly Ile Ile Met Thr Ala Leu Cys Leu Tyr Asn Ser Thr Arg
                485                 490                 495

Lys Asn Ile Arg Leu
            500

(2) INFORMATION FOR SEQ ID NO:10:

(i) SEQUENCE CHARACTERISTICS:
        (A) LENGTH: 1734 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..1734

(xi) SEQUENCE DESCRIPTION: SEQ ID NO:10:

ATG GAC CGC GCC GTT AGC CAA GTT GCG TTA GAG AAT GAT GAA AGA GAG       48
Met Asp Arg Ala Val Ser Gln Val Ala Leu Glu Asn Asp Glu Arg Glu
  1               5                  10                  15

GCA AAA AAT ACA TGG CGC TTG ATA TTC CGG ATT GCA ATC TTA TTC TTA       96
Ala Lys Asn Thr Trp Arg Leu Ile Phe Arg Ile Ala Ile Leu Phe Leu
                 20                  25                  30

ACA GTA GTG ACC TTG GCT ATA TCT GTA GCC TCC CTT TTA TAT AGC ATG      144
Thr Val Val Thr Leu Ala Ile Ser Val Ala Ser Leu Leu Tyr Ser Met
             35                  40                  45

GGG GCT AGC ACA CCT AGC GAT CTT GTA GGC ATA CCG ACT AGG ATT TCC      192
Gly Ala Ser Thr Pro Ser Asp Leu Val Gly Ile Pro Thr Arg Ile Ser
         50                  55                  60

AGG GCA GAA GAA AAG ATT ACA TCT ACA CTT GGT TCC AAT CAA GAT GTA      240
Arg Ala Glu Glu Lys Ile Thr Ser Thr Leu Gly Ser Asn Gln Asp Val
 65                  70                  75                  80

GTA GAT AGG ATA TAT AAG CAA GTG GCC CTT GAG TCT CCA TTG GCA TTG      288
Val Asp Arg Ile Tyr Lys Gln Val Ala Leu Glu Ser Pro Leu Ala Leu
                 85                  90                  95

TTA AAT ACT GAG ACC ACA ATT ATG AAC GCA ATA ACA TCT CTC TCT TAT      336
Leu Asn Thr Glu Thr Thr Ile Met Asn Ala Ile Thr Ser Leu Ser Tyr
```

-continued

|   |   | 100 |   |   |   | 105 |   |   |   | 110 |   |   |   |   |
|---|---|---|---|---|---|---|---|---|---|---|---|---|---|---|

```
CAG ATT AAT GGA GCT GCA AAC AAC AGC GGG TGG GGG GCA CCT ATT CAT        384
Gln Ile Asn Gly Ala Ala Asn Asn Ser Gly Trp Gly Ala Pro Ile His
            115                 120                 125

GAC CCA GAT TAT ATA GGG GGG ATA GGC AAA GAA CTC ATT GTA GAT GAT        432
Asp Pro Asp Tyr Ile Gly Gly Ile Gly Lys Glu Leu Ile Val Asp Asp
            130                 135                 140

GCT AGT GAT GTC ACA TCA TTC TAT CCC TCT GCA TTT CAA GAA CAT CTG        480
Ala Ser Asp Val Thr Ser Phe Tyr Pro Ser Ala Phe Gln Glu His Leu
145                 150                 155                 160

AAT TTT ATC CCG GCG CCT ACT ACA GGA TCA GGT TGC ACT CGA ATA CCC        528
Asn Phe Ile Pro Ala Pro Thr Thr Gly Ser Gly Cys Thr Arg Ile Pro
                165                 170                 175

TCA TTT GAC ATG AGT GCT ACC CAT TAC TGC TAC ACC CAT AAT GTA ATA        576
Ser Phe Asp Met Ser Ala Thr His Tyr Cys Tyr Thr His Asn Val Ile
                180                 185                 190

TTG TCT GGA TGC AGA GAT CAC TCA CAC TCA CAT CAG TAT TTA GCA CTT        624
Leu Ser Gly Cys Arg Asp His Ser His Ser His Gln Tyr Leu Ala Leu
                195                 200                 205

GGT GTG CTC CGG ACA TCT GCA ACA GGG AGG GTA TTC TTT TCT ACT CTG        672
Gly Val Leu Arg Thr Ser Ala Thr Gly Arg Val Phe Phe Ser Thr Leu
210                 215                 220

CGT TCC ATC AAC CTG GAC GAC ACC CAA AAT CGG AAG TCT TGC AGT GTG        720
Arg Ser Ile Asn Leu Asp Asp Thr Gln Asn Arg Lys Ser Cys Ser Val
225                 230                 235                 240

AGT GCA ACT CCC CTG GGT TGT GAT ATG CTG TGC TCG AAA GCC ACG GAG        768
Ser Ala Thr Pro Leu Gly Cys Asp Met Leu Cys Ser Lys Ala Thr Glu
                245                 250                 255

ACA GAG GAA GAA GAT TAT AAC TCA GCT GTC CCT ACG CGG ATG GTA CAT        816
Thr Glu Glu Glu Asp Tyr Asn Ser Ala Val Pro Thr Arg Met Val His
                260                 265                 270

GGG AGG TTA GGG TTC GAC GGC CAA TAT CAC GAA AAG GAC CTA GAT GTC        864
Gly Arg Leu Gly Phe Asp Gly Gln Tyr His Glu Lys Asp Leu Asp Val
                275                 280                 285

ACA ACA TTA TTC GGG GAC TGG GTG GCC AAC TAC CCA GGA GTA GGG GGT        912
Thr Thr Leu Phe Gly Asp Trp Val Ala Asn Tyr Pro Gly Val Gly Gly
                290                 295                 300

GGA TCT TTT ATT GAC AGC CGC GTG TGG TTC TCA GTC TAC GGA GGG TTA        960
Gly Ser Phe Ile Asp Ser Arg Val Trp Phe Ser Val Tyr Gly Gly Leu
305                 310                 315                 320

AAA CCC AAT ACA CCC AGT GAC ACT GTA CAG GAA GGG AAA TAT GTG ATA       1008
Lys Pro Asn Thr Pro Ser Asp Thr Val Gln Glu Gly Lys Tyr Val Ile
                325                 330                 335

TAC AAG CGA TAC AAT GAC ACA TGC CCA GAT GAG CAA GAC TAC CAG ATT       1056
Tyr Lys Arg Tyr Asn Asp Thr Cys Pro Asp Glu Gln Asp Tyr Gln Ile
                340                 345                 350

CGA ATG GCC AAG TCT TCG TAT AAG CCT GGA CGG TTT GGT GGG AAA CGC       1104
Arg Met Ala Lys Ser Ser Tyr Lys Pro Gly Arg Phe Gly Gly Lys Arg
                355                 360                 365

ATA CAG CAG GCT ATC TTA TCT ATC AAA GTG TCA ACA TCC TTA GGC GAA       1152
Ile Gln Gln Ala Ile Leu Ser Ile Lys Val Ser Thr Ser Leu Gly Glu
                370                 375                 380

GAC CCG GTA CTG ACT GTA CCG CCC AAC ACA GTC ACA CTC ATG GGG GCC       1200
Asp Pro Val Leu Thr Val Pro Pro Asn Thr Val Thr Leu Met Gly Ala
385                 390                 395                 400

GAA GGC AGA ATT CTC ACA GTA GGG ACA TCC CAT TTC TTG TAT CAG CGA       1248
Glu Gly Arg Ile Leu Thr Val Gly Thr Ser His Phe Leu Tyr Gln Arg
                405                 410                 415

GGG TCA TCA TAC TTC TCT CCC GCG TTA TTA TAT CCT ATG ACA GTC AGC       1296
Gly Ser Ser Tyr Phe Ser Pro Ala Leu Leu Tyr Pro Met Thr Val Ser
```

```
            420                 425                 430
AAC AAA ACA GCC ACT CTT CAT AGT CCT TAT ACA TTC AAT GCC TTC ACT    1344
Asn Lys Thr Ala Thr Leu His Ser Pro Tyr Thr Phe Asn Ala Phe Thr
        435                 440                 445

CGG CCA GGT AGT ATC CCT TGC CAG GCT TCA GCA AGA TGC CCC AAC TCA    1392
Arg Pro Gly Ser Ile Pro Cys Gln Ala Ser Ala Arg Cys Pro Asn Ser
    450                 455                 460

TGT GTT ACT GGA GTC TAT ACA GAT CCA TAT CCC CTA ATC TTC TAT AGA    1440
Cys Val Thr Gly Val Tyr Thr Asp Pro Tyr Pro Leu Ile Phe Tyr Arg
465                 470                 475                 480

AAC CAC ACC TTG CGA GGG GTA TTC GGG ACA ATG CTT GAT GGT GAA CAA    1488
Asn His Thr Leu Arg Gly Val Phe Gly Thr Met Leu Asp Gly Glu Gln
                485                 490                 495

GCA AGA CTT AAC CCT GCG TCT GCA GTA TTC GAT AGC ACA TCC CGC AGT    1536
Ala Arg Leu Asn Pro Ala Ser Ala Val Phe Asp Ser Thr Ser Arg Ser
            500                 505                 510

CGC ATA ACT CGA GTG AGT TCA AGC AGC ATC AAA GCA GCA TAC ACA ACA    1584
Arg Ile Thr Arg Val Ser Ser Ser Ile Lys Ala Ala Tyr Thr Thr
        515                 520                 525

TCA ACT TGT TTT AAA GTG GTC AAG ACC AAT AAG ACC TAT TGT CTC AGC    1632
Ser Thr Cys Phe Lys Val Val Lys Thr Asn Lys Thr Tyr Cys Leu Ser
    530                 535                 540

ATT GCT GAA ATA TCT AAT ACT CTC TTC GGA GAA TTC AGA ATC GTC CCG    1680
Ile Ala Glu Ile Ser Asn Thr Leu Phe Gly Glu Phe Arg Ile Val Pro
545                 550                 555                 560

TTA CTA GTT GAG ATC CTC AAA GAT GAC GGG GTT AGA GAA GCC AGG TCT    1728
Leu Leu Val Glu Ile Leu Lys Asp Asp Gly Val Arg Glu Ala Arg Ser
                565                 570                 575

GGC TAG                                                            1734
Gly
```

(2) INFORMATION FOR SEQ ID NO:11:

(i) SEQUENCE CHARACTERISTICS:
        (A) LENGTH: 577 amino acids
        (B) TYPE: amino acid
        (D) TOPOLOGY: linear (ii) MOLECULE TYPE: protein (xi) SEQUENCE DESCRIPTION: SEQ ID NO:11:

```
Met Asp Arg Ala Val Ser Gln Val Ala Leu Glu Asn Asp Glu Arg Glu
1               5                   10                  15

Ala Lys Asn Thr Trp Arg Leu Ile Phe Arg Ile Ala Ile Leu Phe Leu
            20                  25                  30

Thr Val Val Thr Leu Ala Ile Ser Val Ala Ser Leu Leu Tyr Ser Met
        35                  40                  45

Gly Ala Ser Thr Pro Ser Asp Leu Val Gly Ile Pro Thr Arg Ile Ser
    50                  55                  60

Arg Ala Glu Glu Lys Ile Thr Ser Thr Leu Gly Ser Asn Gln Asp Val
65                  70                  75                  80

Val Asp Arg Ile Tyr Lys Gln Val Ala Leu Glu Ser Pro Leu Ala Leu
                85                  90                  95

Leu Asn Thr Glu Thr Thr Ile Met Asn Ala Ile Thr Ser Leu Ser Tyr
            100                 105                 110

Gln Ile Asn Gly Ala Ala Asn Asn Ser Gly Trp Gly Ala Pro Ile His
        115                 120                 125

Asp Pro Asp Tyr Ile Gly Gly Ile Gly Lys Glu Leu Ile Val Asp Asp
    130                 135                 140
```

```
Ala Ser Asp Val Thr Ser Phe Tyr Pro Ser Ala Phe Gln Glu His Leu
145                 150                 155                 160

Asn Phe Ile Pro Ala Pro Thr Thr Gly Ser Gly Cys Thr Arg Ile Pro
            165                 170                 175

Ser Phe Asp Met Ser Ala Thr His Tyr Cys Tyr Thr His Asn Val Ile
        180                 185                 190

Leu Ser Gly Cys Arg Asp His Ser His Ser His Gln Tyr Leu Ala Leu
    195                 200                 205

Gly Val Leu Arg Thr Ser Ala Thr Gly Arg Val Phe Phe Ser Thr Leu
210                 215                 220

Arg Ser Ile Asn Leu Asp Asp Thr Gln Asn Arg Lys Ser Cys Ser Val
225                 230                 235                 240

Ser Ala Thr Pro Leu Gly Cys Asp Met Leu Cys Ser Lys Ala Thr Glu
            245                 250                 255

Thr Glu Glu Glu Asp Tyr Asn Ser Ala Val Pro Thr Arg Met Val His
        260                 265                 270

Gly Arg Leu Gly Phe Asp Gly Gln Tyr His Glu Lys Asp Leu Asp Val
    275                 280                 285

Thr Thr Leu Phe Gly Asp Trp Val Ala Asn Tyr Pro Gly Val Gly Gly
290                 295                 300

Gly Ser Phe Ile Asp Ser Arg Val Trp Phe Ser Val Tyr Gly Gly Leu
305                 310                 315                 320

Lys Pro Asn Thr Pro Ser Asp Thr Val Gln Glu Gly Lys Tyr Val Ile
            325                 330                 335

Tyr Lys Arg Tyr Asn Asp Thr Cys Pro Asp Glu Gln Asp Tyr Gln Ile
        340                 345                 350

Arg Met Ala Lys Ser Ser Tyr Lys Pro Gly Arg Phe Gly Gly Lys Arg
    355                 360                 365

Ile Gln Gln Ala Ile Leu Ser Ile Lys Val Ser Thr Ser Leu Gly Glu
370                 375                 380

Asp Pro Val Leu Thr Val Pro Pro Asn Thr Val Thr Leu Met Gly Ala
385                 390                 395                 400

Glu Gly Arg Ile Leu Thr Val Gly Thr Ser His Phe Leu Tyr Gln Arg
            405                 410                 415

Gly Ser Ser Tyr Phe Ser Pro Ala Leu Leu Tyr Pro Met Thr Val Ser
        420                 425                 430

Asn Lys Thr Ala Thr Leu His Ser Pro Tyr Thr Phe Asn Ala Phe Thr
    435                 440                 445

Arg Pro Gly Ser Ile Pro Cys Gln Ala Ser Ala Arg Cys Pro Asn Ser
450                 455                 460

Cys Val Thr Gly Val Tyr Thr Asp Pro Tyr Pro Leu Ile Phe Tyr Arg
465                 470                 475                 480

Asn His Thr Leu Arg Gly Val Phe Gly Thr Met Leu Asp Gly Glu Gln
            485                 490                 495

Ala Arg Leu Asn Pro Ala Ser Ala Val Phe Asp Ser Thr Ser Arg Ser
        500                 505                 510

Arg Ile Thr Arg Val Ser Ser Ser Ile Lys Ala Ala Tyr Thr Thr
    515                 520                 525

Ser Thr Cys Phe Lys Val Val Lys Thr Asn Lys Thr Tyr Cys Leu Ser
    530                 535                 540

Ile Ala Glu Ile Ser Asn Thr Leu Phe Gly Glu Phe Arg Ile Val Pro
545                 550                 555                 560

Leu Leu Val Glu Ile Leu Lys Asp Asp Gly Val Arg Glu Ala Arg Ser
            565                 570                 575
```

Gly (2) INFORMATION FOR SEQ ID NO:12:

(i) SEQUENCE CHARACTERISTICS:
        (A) LENGTH: 1662 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..1662

(xi) SEQUENCE DESCRIPTION: SEQ ID NO:12:

```
ATG GGC TCC AGA CCT TCT ACC AAG AAC CCA GCA CCT ATG ATG CTG ACT        48
Met Gly Ser Arg Pro Ser Thr Lys Asn Pro Ala Pro Met Met Leu Thr
 1               5                  10                  15

ATC CGG GTC GCG CTG GTA CTG AGT TGC ATC TGT CCG GCA AAC TCC ATT        96
Ile Arg Val Ala Leu Val Leu Ser Cys Ile Cys Pro Ala Asn Ser Ile
             20                  25                  30

GAT GGC AGG CCT CTT GCA GCT GCA GGA ATT GTG GTT ACA GGA GAC AAA       144
Asp Gly Arg Pro Leu Ala Ala Ala Gly Ile Val Val Thr Gly Asp Lys
         35                  40                  45

GCA GTC AAC ATA TAC ACC TCA TCC CAG ACA GGA TCA ATC ATA GTT AAG       192
Ala Val Asn Ile Tyr Thr Ser Ser Gln Thr Gly Ser Ile Ile Val Lys
     50                  55                  60

CTC CTC CCG AAT CTG CCA AAG GAT AAG GAG GCA TGT GCG AAA GCC CCC       240
Leu Leu Pro Asn Leu Pro Lys Asp Lys Glu Ala Cys Ala Lys Ala Pro
 65                  70                  75                  80

TTG GAT GCA TAC AAC AGG ACA TTG ACC ACT TTG CTC ACC CCC CTT GGT       288
Leu Asp Ala Tyr Asn Arg Thr Leu Thr Thr Leu Leu Thr Pro Leu Gly
                 85                  90                  95

GAC TCT ATC CGT AGG ATA CAA GAG TCT GTG ACT ACA TCT GGA GGG GGG       336
Asp Ser Ile Arg Arg Ile Gln Glu Ser Val Thr Thr Ser Gly Gly Gly
            100                 105                 110

AGA CAG GGG CGC CTT ATA GGC GCC ATT ATT GGC GGT GTG GCT CTT GGG       384
Arg Gln Gly Arg Leu Ile Gly Ala Ile Ile Gly Gly Val Ala Leu Gly
        115                 120                 125

GTT GCA ACT GCC GCA CAA ATA ACA GCG GCC GCA GCT CTG ATA CAA GCC       432
Val Ala Thr Ala Ala Gln Ile Thr Ala Ala Ala Ala Leu Ile Gln Ala
    130                 135                 140

AAA CAA AAT GCT GCC AAC ATC CTC CGA CTT AAA GAG AGC ATT GCC GCA       480
Lys Gln Asn Ala Ala Asn Ile Leu Arg Leu Lys Glu Ser Ile Ala Ala
145                 150                 155                 160

ACC AAT GAG GCT GTG CAT GAG GTC ACT GAC GGA TTA TCG CAA CTA GCA       528
Thr Asn Glu Ala Val His Glu Val Thr Asp Gly Leu Ser Gln Leu Ala
                165                 170                 175

GTG GCA GTT GGG AAG ATG CAG CAG TTC GTT AAT GAC CAA TTT AAT AAA       576
Val Ala Val Gly Lys Met Gln Gln Phe Val Asn Asp Gln Phe Asn Lys
            180                 185                 190

ACA GCT CAG GAA TTA GAC TGC ATC AAA ATT GCA CAG CAA GTT GGT GTA       624
Thr Ala Gln Glu Leu Asp Cys Ile Lys Ile Ala Gln Gln Val Gly Val
        195                 200                 205

GAG CTC AAC CTG TAC CTA ACC GAA TCG ACT ACA GTA TTC GGA CCA CAA       672
Glu Leu Asn Leu Tyr Leu Thr Glu Ser Thr Thr Val Phe Gly Pro Gln
    210                 215                 220
```

| | | |
|---|---|---|
| ATC ACT TCA CCT GCC TTA AAC AAG CTG ACT ATT CAG GCA CTT TAC AAT<br>Ile Thr Ser Pro Ala Leu Asn Lys Leu Thr Ile Gln Ala Leu Tyr Asn<br>225      230      235      240 | | 720 |
| CTA GCT GGT GGG AAT ATG GAT TAC TTA TTG ACT AAG TTA GGT ATA GGG<br>Leu Ala Gly Gly Asn Met Asp Tyr Leu Leu Thr Lys Leu Gly Ile Gly<br>      245      250      255 | | 768 |
| AAC AAT CAA CTC AGC TCA TTA ATC GGT AGC GGC TTA ATC ACC GGT AAC<br>Asn Asn Gln Leu Ser Ser Leu Ile Gly Ser Gly Leu Ile Thr Gly Asn<br>    260      265      270 | | 816 |
| CCT ATT CTA TAC GAC TCA CAG ACT CAA CTC TTG GGT ATA CAG GTA ACT<br>Pro Ile Leu Tyr Asp Ser Gln Thr Gln Leu Leu Gly Ile Gln Val Thr<br>    275      280      285 | | 864 |
| CTA CCT TCA GTC GGG AAC CTA AAT AAT ATG CGT GCC ACC TAC TTG GAA<br>Leu Pro Ser Val Gly Asn Leu Asn Asn Met Arg Ala Thr Tyr Leu Glu<br>290      295      300 | | 912 |
| ACC TTA TCC GTA AGC ACA ACC AGG GGA TTT GCC TCG GCA CTT GTC CCA<br>Thr Leu Ser Val Ser Thr Thr Arg Gly Phe Ala Ser Ala Leu Val Pro<br>305      310      315      320 | | 960 |
| AAA GTG GTG ACA CGG GTC GGT TCT GTG ATA GAA GAA CTT GAC ACC TCA<br>Lys Val Val Thr Arg Val Gly Ser Val Ile Glu Glu Leu Asp Thr Ser<br>      325      330      335 | | 1008 |
| TAC TGT ATA GAA ACT GAC TTA GAT TTA TAT TGT ACA AGA ATA GTA ACG<br>Tyr Cys Ile Glu Thr Asp Leu Asp Leu Tyr Cys Thr Arg Ile Val Thr<br>    340      345      350 | | 1056 |
| TTC CCT ATG TCC CCT GGT ATT TAC TCC TGC TTG AGC GGC AAT ACA TCG<br>Phe Pro Met Ser Pro Gly Ile Tyr Ser Cys Leu Ser Gly Asn Thr Ser<br>    355      360      365 | | 1104 |
| GCC TGT ATG TAC TCA AAG ACC GAA GGC GCA CTT ACT ACA CCA TAT ATG<br>Ala Cys Met Tyr Ser Lys Thr Glu Gly Ala Leu Thr Thr Pro Tyr Met<br>370      375      380 | | 1152 |
| ACT ATC AAA GGC TCA GTC ATC GCT AAC TGC AAG ATG ACA ACA TGT AGA<br>Thr Ile Lys Gly Ser Val Ile Ala Asn Cys Lys Met Thr Thr Cys Arg<br>385      390      395      400 | | 1200 |
| TGT GTA AAC CCC CCG GGT ATC ATA TCG CAA AAC TAT GGA GAA GCC GTG<br>Cys Val Asn Pro Pro Gly Ile Ile Ser Gln Asn Tyr Gly Glu Ala Val<br>    405      410      415 | | 1248 |
| TCT CTA ATA GAT AAA CAA TCA TGC AAT GTT TTA TCC TTA GGC GGG ATA<br>Ser Leu Ile Asp Lys Gln Ser Cys Asn Val Leu Ser Leu Gly Gly Ile<br>    420      425      430 | | 1296 |
| ACT TTA AGG CTC AGT GGG GAA TTC GAT GTA ACT TAT CAG AAG AAT ATC<br>Thr Leu Arg Leu Ser Gly Glu Phe Asp Val Thr Tyr Gln Lys Asn Ile<br>      435      440      445 | | 1344 |
| TCA ATA CAA GAT TCT CAA GTA ATA ATA ACA GGC AAT CTT GAT ATC TCA<br>Ser Ile Gln Asp Ser Gln Val Ile Ile Thr Gly Asn Leu Asp Ile Ser<br>450      455      460 | | 1392 |
| ACT GAG CTT GGG AAT GTC AAC AAC TCG ATC AGT AAT GCC TTG AAT AAG<br>Thr Glu Leu Gly Asn Val Asn Asn Ser Ile Ser Asn Ala Leu Asn Lys<br>465      470      475      480 | | 1440 |
| TTA GAG GAA AGC AAC AGA AAA CTA GAC AAA GTC AAT GTC AAA CTG ACC<br>Leu Glu Glu Ser Asn Arg Lys Leu Asp Lys Val Asn Val Lys Leu Thr<br>      485      490      495 | | 1488 |
| AGC ACA TCT GCT CTC ATT ACC TAT ATC GTT TTG ACT ATC ATA TCT CTT<br>Ser Thr Ser Ala Leu Ile Thr Tyr Ile Val Leu Thr Ile Ile Ser Leu<br>    500      505      510 | | 1536 |
| GTT TTT GGT ATA CTT AGC CTG ATT CTA GCA TGC TAC CTA ATG TAC AAG<br>Val Phe Gly Ile Leu Ser Leu Ile Leu Ala Cys Tyr Leu Met Tyr Lys<br>    515      520      525 | | 1584 |
| CAA AAG GCG CAA CAA AAG ACC TTA TTA TGG CTT GGG AAT AAT ACC CTA<br>Gln Lys Ala Gln Gln Lys Thr Leu Leu Trp Leu Gly Asn Asn Thr Leu<br>530      535      540 | | 1632 |

```
GAT CAG ATG AGA GCC ACT ACA AAA ATG TGA                                    1662
Asp Gln Met Arg Ala Thr Thr Lys Met
545                 550
```

(2) INFORMATION FOR SEQ ID NO:13:

(i) SEQUENCE CHARACTERISTICS:
        (A) LENGTH: 553 amino acids
        (B) TYPE: amino acid
        (D) TOPOLOGY: linear (ii) MOLECULE TYPE: protein (xi) SEQUENCE DESCRIPTION: SEQ ID NO:13:

```
Met Gly Ser Arg Pro Ser Thr Lys Asn Pro Ala Pro Met Met Leu Thr
1               5                   10                  15

Ile Arg Val Ala Leu Val Leu Ser Cys Ile Cys Pro Ala Asn Ser Ile
                20                  25                  30

Asp Gly Arg Pro Leu Ala Ala Gly Ile Val Val Thr Gly Asp Lys
            35                  40                  45

Ala Val Asn Ile Tyr Thr Ser Ser Gln Thr Gly Ser Ile Ile Val Lys
        50                  55                  60

Leu Leu Pro Asn Leu Pro Lys Asp Lys Glu Ala Cys Ala Lys Ala Pro
65                  70                  75                  80

Leu Asp Ala Tyr Asn Arg Thr Leu Thr Thr Leu Leu Thr Pro Leu Gly
                85                  90                  95

Asp Ser Ile Arg Arg Ile Gln Glu Ser Val Thr Thr Ser Gly Gly Gly
            100                 105                 110

Arg Gln Gly Arg Leu Ile Gly Ala Ile Ile Gly Gly Val Ala Leu Gly
        115                 120                 125

Val Ala Thr Ala Ala Gln Ile Thr Ala Ala Ala Ala Leu Ile Gln Ala
130                 135                 140

Lys Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ala
                165                 170                 175

Val Ala Val Gly Lys Met Gln Gln Phe Val Asn Asp Gln Phe Asn Lys
            180                 185                 190

Thr Ala Gln Glu Leu Asp Cys Ile Lys Ile Ala Gln Gln Val Gly Val
        195                 200                 205

Glu Leu Asn Leu Tyr Leu Thr Glu Ser Thr Thr Val Phe Gly Pro Gln
210                 215                 220

Ile Thr Ser Pro Ala Leu Asn Lys Leu Thr Ile Gln Ala Leu Tyr Asn
225                 230                 235                 240

Leu Ala Gly Gly Asn Met Asp Tyr Leu Leu Thr Lys Leu Gly Ile Gly
                245                 250                 255

Asn Asn Gln Leu Ser Ser Leu Ile Gly Ser Gly Leu Ile Thr Gly Asn
            260                 265                 270

Pro Ile Leu Tyr Asp Ser Gln Thr Gln Leu Leu Gly Ile Gln Val Thr
        275                 280                 285

Leu Pro Ser Val Gly Asn Leu Asn Asn Met Arg Ala Thr Tyr Leu Glu
290                 295                 300

Thr Leu Ser Val Ser Thr Thr Arg Gly Phe Ala Ser Ala Leu Val Pro
305                 310                 315                 320

Lys Val Val Thr Arg Val Gly Ser Val Ile Glu Glu Leu Asp Thr Ser
                325                 330                 335

Tyr Cys Ile Glu Thr Asp Leu Asp Leu Tyr Cys Thr Arg Ile Val Thr
```

```
            340                 345                 350
Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
370                 375                 380

Thr Ile Lys Gly Ser Val Ile Ala Asn Cys Lys Met Thr Thr Cys Arg
385                 390                 395                 400

Cys Val Asn Pro Pro Gly Ile Ile Ser Gln Asn Tyr Gly Glu Ala Val
                405                 410                 415

Ser Leu Ile Asp Lys Gln Ser Cys Asn Val Leu Ser Leu Gly Gly Ile
            420                 425                 430

Thr Leu Arg Leu Ser Gly Glu Phe Asp Val Thr Tyr Gln Lys Asn Ile
        435                 440                 445

Ser Ile Gln Asp Ser Gln Val Ile Ile Thr Gly Asn Leu Asp Ile Ser
    450                 455                 460

Thr Glu Leu Gly Asn Val Asn Asn Ser Ile Ser Asn Ala Leu Asn Lys
465                 470                 475                 480

Leu Glu Glu Ser Asn Arg Lys Leu Asp Lys Val Asn Val Lys Leu Thr
                485                 490                 495

Ser Thr Ser Ala Leu Ile Thr Tyr Ile Val Leu Thr Ile Ile Ser Leu
            500                 505                 510

Val Phe Gly Ile Leu Ser Leu Ile Leu Ala Cys Tyr Leu Met Tyr Lys
        515                 520                 525

Gln Lys Ala Gln Gln Lys Thr Leu Leu Trp Leu Gly Asn Asn Thr Leu
    530                 535                 540

Asp Gln Met Arg Ala Thr Thr Lys Met
545                 550
```

(2) INFORMATION FOR SEQ ID NO:14:

(i) SEQUENCE CHARACTERISTICS:
        (A) LENGTH: 3489 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..3489

(xi) SEQUENCE DESCRIPTION: SEQ ID NO:14:

```
ATG TTG GTA ACA CCT CTT TTA CTA GTG ACT CTT TTG TGT GTA CTA TGT      48
Met Leu Val Thr Pro Leu Leu Leu Val Thr Leu Leu Cys Val Leu Cys
1               5                   10                  15

AGT GCT GCT TTG TAT GAC AGT AGT TCT TAC GTT TAC TAC CAA AGT          96
Ser Ala Ala Leu Tyr Asp Ser Ser Ser Tyr Val Tyr Tyr Gln Ser
            20                  25                  30

GCC TTT AGA CCA CCT AAT GGT TGG CAT TTA CAC GGG GGT GCT TAT GCG     144
Ala Phe Arg Pro Pro Asn Gly Trp His Leu His Gly Gly Ala Tyr Ala
        35                  40                  45

GTA GTT AAT ATT TCT AGC GAA TCT AAT AAT GCA GGC TCT TCA CCT GGG     192
Val Val Asn Ile Ser Ser Glu Ser Asn Asn Ala Gly Ser Ser Pro Gly
    50                  55                  60

TGT ATT GTT GGT ACT ATT CAT GGT GGT CGT GTT GTT AAT GCT TCT TCT    240
Cys Ile Val Gly Thr Ile His Gly Gly Arg Val Val Asn Ala Ser Ser
```

```
                65                    70                    75                    80
ATA GCT ATG ACG GCA CCG TCA TCA GGT ATG GCT TGG TCT AGC AGT CAG      288
Ile Ala Met Thr Ala Pro Ser Ser Gly Met Ala Trp Ser Ser Ser Gln
                        85                    90                    95

TTT TGT ACT GCA CAC TGT AAC TTT TCA GAT ACT ACA GTG TTT GTT ACA      336
Phe Cys Thr Ala His Cys Asn Phe Ser Asp Thr Thr Val Phe Val Thr
                        100                   105                   110

CAT TGT TAT AAA TAT GAT GGG TGT CCT ATA ACT GGC ATG CTT CAA AAG      384
His Cys Tyr Lys Tyr Asp Gly Cys Pro Ile Thr Gly Met Leu Gln Lys
                115                   120                   125

AAT TTT TTA CGT GTT TCT GCT ATG AAA AAT GGC CAG CTT TTC TAT AAT      432
Asn Phe Leu Arg Val Ser Ala Met Lys Asn Gly Gln Leu Phe Tyr Asn
        130                   135                   140

TTA ACA GTT AGT GTA GCT AAG TAC CCT ACT TTT AAA TCA TTT CAG TGT      480
Leu Thr Val Ser Val Ala Lys Tyr Pro Thr Phe Lys Ser Phe Gln Cys
145                   150                   155                   160

GTT AAT AAT TTA ACA TCC GTA TAT TTA AAT GGT GAT CTT GTT TAC ACC      528
Val Asn Asn Leu Thr Ser Val Tyr Leu Asn Gly Asp Leu Val Tyr Thr
                        165                   170                   175

TCT AAT GAG ACC ACA GAT GTT ACA TCT GCA GGT GTT TAT TTT AAA GCT      576
Ser Asn Glu Thr Thr Asp Val Thr Ser Ala Gly Val Tyr Phe Lys Ala
                        180                   185                   190

GGT GGA CCT ATA ACT TAT AAA GTT ATG AGA AAA GTT AAA GCC CTG GCT      624
Gly Gly Pro Ile Thr Tyr Lys Val Met Arg Lys Val Lys Ala Leu Ala
                195                   200                   205

TAT TTT GTT AAT GGT ACT GCA CAA GAT GTT ATT TTG TGT GAT GGA TCA      672
Tyr Phe Val Asn Gly Thr Ala Gln Asp Val Ile Leu Cys Asp Gly Ser
                210                   215                   220

CCT AGA GGC TTG TTA GCA TGC CAG TAT AAT ACT GGC AAT TTT TCA GAT      720
Pro Arg Gly Leu Leu Ala Cys Gln Tyr Asn Thr Gly Asn Phe Ser Asp
225                   230                   235                   240

GGC TTT TAT CCT TTT ATT AAT AGT AGT TTA GTT AAG CAG AAG TTT ATT      768
Gly Phe Tyr Pro Phe Ile Asn Ser Ser Leu Val Lys Gln Lys Phe Ile
                        245                   250                   255

GTC TAT CGT GAA AAT AGT GTT AAT ACT ACT TTT ACG TTA CAC AAT TTC      816
Val Tyr Arg Glu Asn Ser Val Asn Thr Thr Phe Thr Leu His Asn Phe
                        260                   265                   270

ACT TTT CAT AAT GAG ACT GGC GCC AAC CCT AAT CCT AGT GGT GTT CAG      864
Thr Phe His Asn Glu Thr Gly Ala Asn Pro Asn Pro Ser Gly Val Gln
                275                   280                   285

AAT ATT CTA ACT TAC CAA ACA CAA ACA GCT CAG AGT GGT TAT TAT AAT      912
Asn Ile Leu Thr Tyr Gln Thr Gln Thr Ala Gln Ser Gly Tyr Tyr Asn
        290                   295                   300

TTT AAT TTT TCC TTT CTG AGT AGT TTT GTT TAT AAG GAG TCT AAT TTT      960
Phe Asn Phe Ser Phe Leu Ser Ser Phe Val Tyr Lys Glu Ser Asn Phe
305                   310                   315                   320

ATG TAT GGA TCT TAT CAC CCA AGT TGT AAT TTT AGA CTA GAA ACT ATT     1008
Met Tyr Gly Ser Tyr His Pro Ser Cys Asn Phe Arg Leu Glu Thr Ile
                        325                   330                   335

AAT AAT GGC TTG TGG TTT AAT TCA CTT TCA GTT TCA ATT GCT TAC GGT     1056
Asn Asn Gly Leu Trp Phe Asn Ser Leu Ser Val Ser Ile Ala Tyr Gly
                        340                   345                   350

CCT CTT CAA GGT GGT TGC AAG CAA TCT GTC TTT AGT GGT AGA GCA ACT     1104
Pro Leu Gln Gly Gly Cys Lys Gln Ser Val Phe Ser Gly Arg Ala Thr
                355                   360                   365

TGT TGT TAT GCT TAT TCA TAT GGA GGT CCT TCG CTG TGT AAA GGT GTT     1152
Cys Cys Tyr Ala Tyr Ser Tyr Gly Gly Pro Ser Leu Cys Lys Gly Val
                370                   375                   380

TAT TCA GGT GAG TTA GAT CTT AAT TTT GAA TGT GGA CTG TTA GTT TAT     1200
Tyr Ser Gly Glu Leu Asp Leu Asn Phe Glu Cys Gly Leu Leu Val Tyr
```

```
385                 390                 395                 400
GTT ACT AAG AGC GGT GGC TCT CGT ATA CAA ACA GCC ACT GAA CCG CCA    1248
Val Thr Lys Ser Gly Gly Ser Arg Ile Gln Thr Ala Thr Glu Pro Pro
                    405                 410                 415

GTT ATA ACT CGA CAC AAT TAT AAT AAT ATT ACT TTA AAT ACT TGT GTT    1296
Val Ile Thr Arg His Asn Tyr Asn Asn Ile Thr Leu Asn Thr Cys Val
                    420                 425                 430

GAT TAT AAT ATA TAT GGC AGA ACT GGC CAA GGT TTT ATT ACT AAT GTA    1344
Asp Tyr Asn Ile Tyr Gly Arg Thr Gly Gln Gly Phe Ile Thr Asn Val
                435                 440                 445

ACC GAC TCA GCT GTT AGT TAT AAT TAT CTA GCA GAC GCA GGT TTG GCT    1392
Thr Asp Ser Ala Val Ser Tyr Asn Tyr Leu Ala Asp Ala Gly Leu Ala
            450                 455                 460

ATT TTA GAT ACA TCT GGT TCC ATA GAC ATC TTT GTT GTA CAA GGT GAA    1440
Ile Leu Asp Thr Ser Gly Ser Ile Asp Ile Phe Val Val Gln Gly Glu
465                 470                 475                 480

TAT GGT CTT ACT TAT TAT AAG GTT AAC CCT TGC GAA GAT GTC AAC CAG    1488
Tyr Gly Leu Thr Tyr Tyr Lys Val Asn Pro Cys Glu Asp Val Asn Gln
                    485                 490                 495

CAG TTT GTA GTT TCT GGT GGT AAA TTA GTA GGT ATT CTT ACT TCA CGT    1536
Gln Phe Val Val Ser Gly Gly Lys Leu Val Gly Ile Leu Thr Ser Arg
                500                 505                 510

AAT GAG ACT GGT TCT CAG CTT CTT GAG AAC CAG TTT TAC ATT AAA ATC    1584
Asn Glu Thr Gly Ser Gln Leu Leu Glu Asn Gln Phe Tyr Ile Lys Ile
            515                 520                 525

ACT AAT GGA ACA CGT CGT TTT AGA CGT TCT ATT ACT GAA AAT GTT GCA    1632
Thr Asn Gly Thr Arg Arg Phe Arg Arg Ser Ile Thr Glu Asn Val Ala
530                 535                 540

AAT TGC CCT TAT GTT AGT TAT GGT AAG TTT TGT ATA AAA CCT GAT GGT    1680
Asn Cys Pro Tyr Val Ser Tyr Gly Lys Phe Cys Ile Lys Pro Asp Gly
545                 550                 555                 560

TCA ATT GCC ACA ATA GTA CCA AAA CAA TTG GAA CAG TTT GTG GCA CCT    1728
Ser Ile Ala Thr Ile Val Pro Lys Gln Leu Glu Gln Phe Val Ala Pro
                    565                 570                 575

TTA CTT AAT GTT ACT GAA AAT GTG CTC ATA CCT AAC AGT TTT AAT TTA    1776
Leu Leu Asn Val Thr Glu Asn Val Leu Ile Pro Asn Ser Phe Asn Leu
                580                 585                 590

ACT GTT ACA GAT GAG TAC ATA CAA ACG CGT ATG GAT AAG GTC CAA ATT    1824
Thr Val Thr Asp Glu Tyr Ile Gln Thr Arg Met Asp Lys Val Gln Ile
            595                 600                 605

AAT TGT CTG CAG TAT GTT TGT GGC AAT TCT CTG GAT TGT AGA GAT TTG    1872
Asn Cys Leu Gln Tyr Val Cys Gly Asn Ser Leu Asp Cys Arg Asp Leu
610                 615                 620

TTT CAA CAA TAT GGG CCT GTT TGT GAC AAC ATA TTG TCT GTA GTA AAT    1920
Phe Gln Gln Tyr Gly Pro Val Cys Asp Asn Ile Leu Ser Val Val Asn
625                 630                 635                 640

AGT ATT GGT CAA AAA GAA GAT ATG GAA CTT TTG AAT TTC TAT TCT TCT    1968
Ser Ile Gly Gln Lys Glu Asp Met Glu Leu Leu Asn Phe Tyr Ser Ser
                    645                 650                 655

ACT AAA CCG GCT GGT TTT AAT ACA CCA TTT CTT AGT AAT GTT AGC ACT    2016
Thr Lys Pro Ala Gly Phe Asn Thr Pro Phe Leu Ser Asn Val Ser Thr
                660                 665                 670

GGT GAG TTT AAT ATT TCT CTT CTG TTA ACA ACT CCT AGT AGT CCT AGA    2064
Gly Glu Phe Asn Ile Ser Leu Leu Leu Thr Thr Pro Ser Ser Pro Arg
            675                 680                 685

AGG CGT TCT TTT ATT GAA GAC TTG CTA TTT ACA AGC GTT GAA TCT GTT    2112
Arg Arg Ser Phe Ile Glu Asp Leu Leu Phe Thr Ser Val Glu Ser Val
690                 695                 700

GGA TTA CCA ACA GAT GAC GCA TAC AAA AAT TGC ACT GCA GGA CCT TTA    2160
Gly Leu Pro Thr Asp Asp Ala Tyr Lys Asn Cys Thr Ala Gly Pro Leu
```

```
705                 710                 715                 720

GGT TTT CTT AAG GAC CTT GCG TGT GCT CGT GAA TAT AAT GGT TTG CTT    2208
Gly Phe Leu Lys Asp Leu Ala Cys Ala Arg Glu Tyr Asn Gly Leu Leu
            725                 730                 735

GTG TTG CCT CCC ATT ATA ACA GCA GAA ATG CAA ACT TTG TAT ACT AGT    2256
Val Leu Pro Pro Ile Ile Thr Ala Glu Met Gln Thr Leu Tyr Thr Ser
            740                 745                 750

TCT CTA GTA GCT TCT ATG GCT TTT GGT GGT ATT ACT GCA GCT GGT GCT    2304
Ser Leu Val Ala Ser Met Ala Phe Gly Gly Ile Thr Ala Ala Gly Ala
            755                 760                 765

ATA CCT TTT GCC ACA CAA CTG CAG GCT AGA ATT AAT CAC TTG GGT ATT    2352
Ile Pro Phe Ala Thr Gln Leu Gln Ala Arg Ile Asn His Leu Gly Ile
            770                 775                 780

ACC CAG TCA CTT TTG TTG AAG AAT CAA GAA AAA ATT GCT GCT TCC TTT    2400
Thr Gln Ser Leu Leu Leu Lys Asn Gln Glu Lys Ile Ala Ala Ser Phe
785             790                 795                 800

AAT AAG GCC ATT GGT CGT ATG CAG GAA GGT TTT AGA AGT ACA TCT CTA    2448
Asn Lys Ala Ile Gly Arg Met Gln Glu Gly Phe Arg Ser Thr Ser Leu
            805                 810                 815

GCA TTA CAA CAA ATT CAA GAT GTT GTT AAT AAG CAG AGT GCT ATT CTT    2496
Ala Leu Gln Gln Ile Gln Asp Val Val Asn Lys Gln Ser Ala Ile Leu
            820                 825                 830

ACT GAG ACT ATG GCA TCA CTT AAT AAA AAT TTT GGT GCT ATT TCT TCT    2544
Thr Glu Thr Met Ala Ser Leu Asn Lys Asn Phe Gly Ala Ile Ser Ser
            835                 840                 845

GTG ATT CAA GAA ATC TAC CAG CAA CTT GAC GCC ATA CAA GCA AAT GCT    2592
Val Ile Gln Glu Ile Tyr Gln Gln Leu Asp Ala Ile Gln Ala Asn Ala
            850                 855                 860

CAA GTG GAT CGT CTT ATA ACT GGT AGA TTG TCA TCA CTT TCT GTT TTA    2640
Gln Val Asp Arg Leu Ile Thr Gly Arg Leu Ser Ser Leu Ser Val Leu
865             870                 875                 880

GCA TCT GCT AAG CAG GCG GAG CAT ATT AGA GTG TCA CAA CAG CGT GAG    2688
Ala Ser Ala Lys Gln Ala Glu His Ile Arg Val Ser Gln Gln Arg Glu
            885                 890                 895

TTA GCT ACT CAG AAA ATT AAT GAG TGT GTT AAG TCA CAG TCT ATT AGG    2736
Leu Ala Thr Gln Lys Ile Asn Glu Cys Val Lys Ser Gln Ser Ile Arg
            900                 905                 910

TAC TCC TTT TGT GGT AAT GGA CGA CAT GTT CTA ACC ATA CCG CAA AAT    2784
Tyr Ser Phe Cys Gly Asn Gly Arg His Val Leu Thr Ile Pro Gln Asn
            915                 920                 925

GCA CCT AAT GGT ATA GTG TTT ATA CAC TTT TCT TAT ACT CCA GAT AGT    2832
Ala Pro Asn Gly Ile Val Phe Ile His Phe Ser Tyr Thr Pro Asp Ser
            930                 935                 940

TTT GTT AAT GTT ACT GCA ATA GTG GGT TTT TGT GTA AAG CCA GCT AAT    2880
Phe Val Asn Val Thr Ala Ile Val Gly Phe Cys Val Lys Pro Ala Asn
945             950                 955                 960

GCT AGT CAG TAT GCA ATA GTA CCC GCT AAT GGT AGG GGT ATT TTT ATA    2928
Ala Ser Gln Tyr Ala Ile Val Pro Ala Asn Gly Arg Gly Ile Phe Ile
            965                 970                 975

CAA GTT AAT GGT AGT TAC TAC ATC ACA GCA CGA GAT ATG TAT ATG CCA    2976
Gln Val Asn Gly Ser Tyr Tyr Ile Thr Ala Arg Asp Met Tyr Met Pro
            980                 985                 990

AGA GCT ATT ACT GCA GGA GAT ATA GTT ACG CTT ACT TCT TGT CAA GCA    3024
Arg Ala Ile Thr Ala Gly Asp Ile Val Thr Leu Thr Ser Cys Gln Ala
            995                 1000                1005

AAT TAT GTA AGT GTA AAT AAG ACC GTC ATT ACT ACA TTC GTA GAC AAT    3072
Asn Tyr Val Ser Val Asn Lys Thr Val Ile Thr Thr Phe Val Asp Asn
            1010                1015                1020

GAT GAT TTT GAT TTT AAT GAC GAA TTG TCA AAA TGG TGG AAT GAC ACT    3120
Asp Asp Phe Asp Phe Asn Asp Glu Leu Ser Lys Trp Trp Asn Asp Thr
```

-continued

```
        1025              1030              1035              1040

AAG CAT GAG CTA CCA GAC TTT GAC AAA TTC AAT TAC ACA GTA CCT ATA         3168
Lys His Glu Leu Pro Asp Phe Asp Lys Phe Asn Tyr Thr Val Pro Ile
             1045              1050              1055

CTT GAC ATT GAT AGT GAA ATT GAT CGT ATT CAA GGC GTT ATA CAG GGT         3216
Leu Asp Ile Asp Ser Glu Ile Asp Arg Ile Gln Gly Val Ile Gln Gly
             1060              1065              1070

CTT AAT GAC TCT TTA ATA GAC CTT GAA AAA CTT TCA ATA CTC AAA ACT         3264
Leu Asn Asp Ser Leu Ile Asp Leu Glu Lys Leu Ser Ile Leu Lys Thr
             1075              1080              1085

TAT ATT AAG TGG CCT TGG TAT GTG TGG TTA GCC ATA GCT TTT GCC ACT         3312
Tyr Ile Lys Trp Pro Trp Tyr Val Trp Leu Ala Ile Ala Phe Ala Thr
             1090              1095              1100

ATT ATC TTC ATC TTA ATA CTA GGA TGG GTT TTC TTC ATG ACT GGA TGT         3360
Ile Ile Phe Ile Leu Ile Leu Gly Trp Val Phe Phe Met Thr Gly Cys
1105              1110              1115              1120

TGT GGT TGT TGT TGT GGA TGC TTT GGC ATT ATG CCT CTA ATG AGT AAG         3408
Cys Gly Cys Cys Cys Gly Cys Phe Gly Ile Met Pro Leu Met Ser Lys
                  1125              1130              1135

TGT GGT AAG AAA TCT TCT TAT TAC ACG ACT TTT GAT AAC GAT GTG GTA         3456
Cys Gly Lys Lys Ser Ser Tyr Tyr Thr Thr Phe Asp Asn Asp Val Val
             1140              1145              1150

ACT GAA CAA AAC AGA CCT AAA AAG TCT GTT TAA                             3489
Thr Glu Gln Asn Arg Pro Lys Lys Ser Val
             1155              1160

(2) INFORMATION FOR SEQ ID NO:15:

(i) SEQUENCE CHARACTERISTICS:
        (A) LENGTH: 1162 amino acids
        (B) TYPE: amino acid
        (D) TOPOLOGY: linear (ii) MOLECULE TYPE: protein (xi) SEQUENCE DESCRIPTION: SEQ ID NO:15:

Met Leu Val Thr Pro Leu Leu Val Thr Leu Leu Cys Val Leu Cys
 1               5                  10                  15

Ser Ala Ala Leu Tyr Asp Ser Ser Ser Tyr Val Tyr Tyr Gln Ser
                20                  25                  30

Ala Phe Arg Pro Pro Asn Gly Trp His Leu His Gly Ala Tyr Ala
                35                  40                  45

Val Val Asn Ile Ser Ser Glu Ser Asn Asn Ala Gly Ser Ser Pro Gly
         50                  55                  60

Cys Ile Val Gly Thr Ile His Gly Gly Arg Val Val Asn Ala Ser Ser
 65                  70                  75                  80

Ile Ala Met Thr Ala Pro Ser Ser Gly Met Ala Trp Ser Ser Gln
                85                  90                  95

Phe Cys Thr Ala His Cys Asn Phe Ser Asp Thr Thr Val Phe Val Thr
                100                 105                 110

His Cys Tyr Lys Tyr Asp Gly Cys Pro Ile Thr Gly Met Leu Gln Lys
                115                 120                 125

Asn Phe Leu Arg Val Ser Ala Met Lys Asn Gly Gln Leu Phe Tyr Asn
                130                 135                 140

Leu Thr Val Ser Val Ala Lys Tyr Pro Thr Phe Lys Ser Phe Gln Cys
145                 150                 155                 160

Val Asn Asn Leu Thr Ser Val Tyr Leu Asn Gly Asp Leu Val Tyr Thr
                165                 170                 175

Ser Asn Glu Thr Thr Asp Val Thr Ser Ala Gly Val Tyr Phe Lys Ala
```

-continued

```
                180                 185                 190
Gly Gly Pro Ile Thr Tyr Lys Val Met Arg Lys Val Lys Ala Leu Ala
            195                 200                 205

Tyr Phe Val Asn Gly Thr Ala Gln Asp Val Ile Leu Cys Asp Gly Ser
210                 215                 220

Pro Arg Gly Leu Leu Ala Cys Gln Tyr Asn Thr Gly Asn Phe Ser Asp
225                 230                 235                 240

Gly Phe Tyr Pro Phe Ile Asn Ser Ser Leu Val Lys Gln Lys Phe Ile
                245                 250                 255

Val Tyr Arg Glu Asn Ser Val Asn Thr Thr Phe Thr Leu His Asn Phe
            260                 265                 270

Thr Phe His Asn Glu Thr Gly Ala Asn Pro Asn Pro Ser Gly Val Gln
        275                 280                 285

Asn Ile Leu Thr Tyr Gln Thr Gln Thr Ala Gln Ser Gly Tyr Tyr Asn
    290                 295                 300

Phe Asn Phe Ser Phe Leu Ser Ser Phe Val Tyr Lys Glu Ser Asn Phe
305                 310                 315                 320

Met Tyr Gly Ser Tyr His Pro Ser Cys Asn Phe Arg Leu Glu Thr Ile
                325                 330                 335

Asn Asn Gly Leu Trp Phe Asn Ser Leu Ser Val Ser Ile Ala Tyr Gly
            340                 345                 350

Pro Leu Gln Gly Gly Cys Lys Gln Ser Val Phe Ser Gly Arg Ala Thr
        355                 360                 365

Cys Cys Tyr Ala Tyr Ser Tyr Gly Gly Pro Ser Leu Cys Lys Gly Val
    370                 375                 380

Tyr Ser Gly Glu Leu Asp Leu Asn Phe Glu Cys Gly Leu Leu Val Tyr
385                 390                 395                 400

Val Thr Lys Ser Gly Gly Ser Arg Ile Gln Thr Ala Thr Glu Pro Pro
                405                 410                 415

Val Ile Thr Arg His Asn Tyr Asn Asn Ile Thr Leu Asn Thr Cys Val
            420                 425                 430

Asp Tyr Asn Ile Tyr Gly Arg Thr Gly Gln Gly Phe Ile Thr Asn Val
        435                 440                 445

Thr Asp Ser Ala Val Ser Tyr Asn Tyr Leu Ala Asp Ala Gly Leu Ala
    450                 455                 460

Ile Leu Asp Thr Ser Gly Ser Ile Asp Ile Phe Val Val Gln Gly Glu
465                 470                 475                 480

Tyr Gly Leu Thr Tyr Tyr Lys Val Asn Pro Cys Glu Asp Val Asn Gln
                485                 490                 495

Gln Phe Val Ser Gly Gly Lys Leu Val Gly Ile Leu Thr Ser Arg
            500                 505                 510

Asn Glu Thr Gly Ser Gln Leu Leu Glu Asn Gln Phe Tyr Ile Lys Ile
        515                 520                 525

Thr Asn Gly Thr Arg Arg Phe Arg Arg Ser Ile Thr Glu Asn Val Ala
    530                 535                 540

Asn Cys Pro Tyr Val Ser Tyr Gly Lys Phe Cys Ile Lys Pro Asp Gly
545                 550                 555                 560

Ser Ile Ala Thr Ile Val Pro Lys Gln Leu Glu Gln Phe Val Ala Pro
                565                 570                 575

Leu Leu Asn Val Thr Glu Asn Val Leu Ile Pro Asn Ser Phe Asn Leu
            580                 585                 590

Thr Val Thr Asp Glu Tyr Ile Gln Thr Arg Met Asp Lys Val Gln Ile
        595                 600                 605
```

```
Asn Cys Leu Gln Tyr Val Cys Gly Asn Ser Leu Asp Cys Arg Asp Leu
    610                 615                 620

Phe Gln Gln Tyr Gly Pro Val Cys Asp Asn Ile Leu Ser Val Val Asn
625                 630                 635                 640

Ser Ile Gly Gln Lys Glu Asp Met Glu Leu Leu Asn Phe Tyr Ser Ser
                645                 650                 655

Thr Lys Pro Ala Gly Phe Asn Thr Pro Phe Leu Ser Asn Val Ser Thr
                660                 665                 670

Gly Glu Phe Asn Ile Ser Leu Leu Leu Thr Thr Pro Ser Ser Pro Arg
            675                 680                 685

Arg Arg Ser Phe Ile Glu Asp Leu Leu Phe Thr Ser Val Glu Ser Val
        690                 695                 700

Gly Leu Pro Thr Asp Asp Ala Tyr Lys Asn Cys Thr Ala Gly Pro Leu
705                 710                 715                 720

Gly Phe Leu Lys Asp Leu Ala Cys Ala Arg Glu Tyr Asn Gly Leu Leu
                725                 730                 735

Val Leu Pro Pro Ile Ile Thr Ala Glu Met Gln Thr Leu Tyr Thr Ser
                740                 745                 750

Ser Leu Val Ala Ser Met Ala Phe Gly Gly Ile Thr Ala Ala Gly Ala
            755                 760                 765

Ile Pro Phe Ala Thr Gln Leu Gln Ala Arg Ile Asn His Leu Gly Ile
        770                 775                 780

Thr Gln Ser Leu Leu Leu Lys Asn Gln Glu Lys Ile Ala Ala Ser Phe
785                 790                 795                 800

Asn Lys Ala Ile Gly Arg Met Gln Glu Gly Phe Arg Ser Thr Ser Leu
                805                 810                 815

Ala Leu Gln Gln Ile Gln Asp Val Val Asn Lys Gln Ser Ala Ile Leu
            820                 825                 830

Thr Glu Thr Met Ala Ser Leu Asn Lys Asn Phe Gly Ala Ile Ser Ser
        835                 840                 845

Val Ile Gln Glu Ile Tyr Gln Gln Leu Asp Ala Ile Gln Ala Asn Ala
850                 855                 860

Gln Val Asp Arg Leu Ile Thr Gly Arg Leu Ser Ser Leu Ser Val Leu
865                 870                 875                 880

Ala Ser Ala Lys Gln Ala Glu His Ile Arg Val Ser Gln Gln Arg Glu
                885                 890                 895

Leu Ala Thr Gln Lys Ile Asn Glu Cys Val Lys Ser Gln Ser Ile Arg
            900                 905                 910

Tyr Ser Phe Cys Gly Asn Gly Arg His Val Leu Thr Ile Pro Gln Asn
        915                 920                 925

Ala Pro Asn Gly Ile Val Phe Ile His Phe Ser Tyr Thr Pro Asp Ser
    930                 935                 940

Phe Val Asn Val Thr Ala Ile Val Gly Phe Cys Val Lys Pro Ala Asn
945                 950                 955                 960

Ala Ser Gln Tyr Ala Ile Val Pro Ala Asn Gly Arg Gly Ile Phe Ile
                965                 970                 975

Gln Val Asn Gly Ser Tyr Tyr Ile Thr Ala Arg Asp Met Tyr Met Pro
            980                 985                 990

Arg Ala Ile Thr Ala Gly Asp Ile Val Thr Leu Thr Ser Cys Gln Ala
        995                 1000                1005

Asn Tyr Val Ser Val Asn Lys Thr Val Ile Thr Thr Phe Val Asp Asn
    1010                1015                1020

Asp Asp Phe Asp Phe Asn Asp Glu Leu Ser Lys Trp Trp Asn Asp Thr
1025                1030                1035                1040
```

```
Lys His Glu Leu Pro Asp Phe Asp Lys Phe Asn Tyr Thr Val Pro Ile
            1045                1050                1055

Leu Asp Ile Asp Ser Glu Ile Asp Arg Ile Gln Gly Val Ile Gln Gly
            1060                1065                1070

Leu Asn Asp Ser Leu Ile Asp Leu Glu Lys Leu Ser Ile Leu Lys Thr
            1075                1080                1085

Tyr Ile Lys Trp Pro Trp Tyr Val Trp Leu Ala Ile Ala Phe Ala Thr
            1090                1095                1100

Ile Ile Phe Ile Leu Ile Leu Gly Trp Val Phe Phe Met Thr Gly Cys
    1105                1110                1115                1120

Cys Gly Cys Cys Gly Cys Phe Gly Ile Met Pro Leu Met Ser Lys
            1125                1130                1135

Cys Gly Lys Lys Ser Ser Tyr Tyr Thr Thr Phe Asp Asn Asp Val Val
            1140                1145                1150

Thr Glu Gln Asn Arg Pro Lys Lys Ser Val
            1155                1160
```

(2) INFORMATION FOR SEQ ID NO:16:

(i) SEQUENCE CHARACTERISTICS:
  (A) LENGTH: 1846 base pairs
  (B) TYPE: nucleic acid
  (C) STRANDEDNESS: double
  (D) TOPOLOGY: linear (ii) MOLECULE TYPE: DNA (genomic)

(iii) HYPOTHETICAL: NO (iv) ANTI-SENSE: NO (ix) FEATURE:
  (A) NAME/KEY: CDS
  (B) LOCATION: 1..1846

(xi) SEQUENCE DESCRIPTION: SEQ ID NO:16:

```
ATG TTG GTG AAG TCA CTG TTT CTA GTG ACC ATT TTG TTT GCA CTA TGT    48
Met Leu Val Lys Ser Leu Phe Leu Val Thr Ile Leu Phe Ala Leu Cys
  1               5                  10                  15

AGT GCT AAT TTA TAT GAC AAC GAA TCT TTT GTG TAT TAC TAC CAG AGT    96
Ser Ala Asn Leu Tyr Asp Asn Glu Ser Phe Val Tyr Tyr Tyr Gln Ser
             20                  25                  30

GCT TTT AGG CCA GGA CAT GGT TGG CAT TTA CAT GGA GGT GCT TAT GCA   144
Ala Phe Arg Pro Gly His Gly Trp His Leu His Gly Gly Ala Tyr Ala
         35                  40                  45

GTA GTT AAT GTG TCT AGT GAA AAT AAT AAT GCA GGT ACT GCC CCA AGT   192
Val Val Asn Val Ser Ser Glu Asn Asn Asn Ala Gly Thr Ala Pro Ser
 50                  55                  60

TGC ACT GCT GGT GCT ATT GGC TAC AGT AAG AAT TTC AGT GCG GCC TCA   240
Cys Thr Ala Gly Ala Ile Gly Tyr Ser Lys Asn Phe Ser Ala Ala Ser
 65                  70                  75                  80

GTA GCC ATG ACT GCA CCA CTA AGT GGT ATG TCA TGG TCT GCC TCA TCT   288
Val Ala Met Thr Ala Pro Leu Ser Gly Met Ser Trp Ser Ala Ser Ser
                 85                  90                  95

TTT TGT ACA GCT CAC TGT AAT TTT ACT TCT TAT ATA GTG TTT GTT ACA   336
Phe Cys Thr Ala His Cys Asn Phe Thr Ser Tyr Ile Val Phe Val Thr
            100                 105                 110

CAT TGT TTT AAG AGC GGA TCT AAT AGT TGT CCT TTG ACA GGT CTT ATT   384
His Cys Phe Lys Ser Gly Ser Asn Ser Cys Pro Leu Thr Gly Leu Ile
        115                 120                 125

CCA AGC GGT TAT ATT CGT ATT GCT GCT ATG AAA CAT GGA AGT CGT ACG   432
Pro Ser Gly Tyr Ile Arg Ile Ala Ala Met Lys His Gly Ser Arg Thr
```

```
                130                     135                     140
CCT GGT CAC TTA TTT TAT AAC TTA ACA GTT TCT GTG ACT AAA TAT CCT        480
Pro Gly His Leu Phe Tyr Asn Leu Thr Val Ser Val Thr Lys Tyr Pro
145                     150                     155                 160

AAG TTT AGA TCG CTA CAA TGT GTT AAT AAT CAT ACT TCT GTA TAT TTA        528
Lys Phe Arg Ser Leu Gln Cys Val Asn Asn His Thr Ser Val Tyr Leu
                165                     170                     175

AAT GGT GAC CTT GTT TTC ACA TCT AAC TAT ACT GAA GAT GTT GTA GCT        576
Asn Gly Asp Leu Val Phe Thr Ser Asn Tyr Thr Glu Asp Val Val Ala
            180                     185                     190

GCA GGT GTC CAT TTT AAA AGT GGT GGA CCT ATA ACT TAT AAA GTT ATG        624
Ala Gly Val His Phe Lys Ser Gly Gly Pro Ile Thr Tyr Lys Val Met
        195                     200                     205

AGA GAG GTT AAA GCC TTG GCT TAT TTT GTC AAT GGT ACT GCA CAT GAT        672
Arg Glu Val Lys Ala Leu Ala Tyr Phe Val Asn Gly Thr Ala His Asp
    210                     215                     220

GTC ATT CTA TGT GAT GAC ACA CCT AGA GGT TTG TTA GCA TGC CAA TAT        720
Val Ile Leu Cys Asp Asp Thr Pro Arg Gly Leu Leu Ala Cys Gln Tyr
225                     230                     235                 240

AAT ACT GGC AAT TTT TCA GAT GGC TTC TAT CCT TTT ACT AAT ACT AGT        768
Asn Thr Gly Asn Phe Ser Asp Gly Phe Tyr Pro Phe Thr Asn Thr Ser
                245                     250                     255

ATT GTT AAG GAT AAG TTT ATT GTT TAT CGT GAA AGT AGT GTC AAT ACT        816
Ile Val Lys Asp Lys Phe Ile Val Tyr Arg Glu Ser Ser Val Asn Thr
            260                     265                     270

ACT TTG ACA TTA ACT AAT TTC ACG TTT AGT AAT GAA AGT GGT GCC CCT        864
Thr Leu Thr Leu Thr Asn Phe Thr Phe Ser Asn Glu Ser Gly Ala Pro
        275                     280                     285

CCT AAT ACA GGT GGT GTT GAC AGT TTT ATT TTA TAC CAG ACA CAA ACA        912
Pro Asn Thr Gly Gly Val Asp Ser Phe Ile Leu Tyr Gln Thr Gln Thr
    290                     295                     300

GCT CAG AGT GGT TAT TAT AAT TTT AAT TTT TCA TTT CTG AGT AGT TTT        960
Ala Gln Ser Gly Tyr Tyr Asn Phe Asn Phe Ser Phe Leu Ser Ser Phe
305                     310                     315                 320

GTT TAT AGG GAA AGT AAT TAT ATG TAT GGA TCT TAC CAT CCG GCT TGT       1008
Val Tyr Arg Glu Ser Asn Tyr Met Tyr Gly Ser Tyr His Pro Ala Cys
                325                     330                     335

AGT TTT AGA CCT GAA ACC CTT AAT GGT TTG TGG TCT AAT TCC CTT TCT       1056
Ser Phe Arg Pro Glu Thr Leu Asn Gly Leu Trp Ser Asn Ser Leu Ser
            340                     345                     350

GTT TCA TTA ATA TAC GGT CCC ATT CAA GGT GGT TGT AAG CAA TCT GTA       1104
Val Ser Leu Ile Tyr Gly Pro Ile Gln Gly Gly Cys Lys Gln Ser Val
        355                     360                     365

TTT AAT GGT AAA GCA ACT TGT TGT TAT GCT TAT TCA TAC GGA GGA CCT       1152
Phe Asn Gly Lys Ala Thr Cys Cys Tyr Ala Tyr Ser Tyr Gly Gly Pro
    370                     375                     380

CGT GCT TGT AAA GGT GTC TAT AGA GGT GAG CTA ACA CAG CAT TTT GAA       1200
Arg Ala Cys Lys Gly Val Tyr Arg Gly Glu Leu Thr Gln His Phe Glu
385                     390                     395                 400

TGT GGT TTG TTA GTT TAT GTT ACT AAG AGC GAT GGC TCC CGT ATA CAA       1248
Cys Gly Leu Leu Val Tyr Val Thr Lys Ser Asp Gly Ser Arg Ile Gln
                405                     410                     415

ACT GCA ACA CAA CCA CCT GTA TTA ACC CAA AAT TTT TAT AAT AAC ATC       1296
Thr Ala Thr Gln Pro Pro Val Leu Thr Gln Asn Phe Tyr Asn Asn Ile
            420                     425                     430

ACT TTA GGT AAG TGT GTT GAT TAT AAT GTT TAT GGT AGA ACT GGA CAA       1344
Thr Leu Gly Lys Cys Val Asp Tyr Asn Val Tyr Gly Arg Thr Gly Gln
        435                     440                     445

GGT TTT ATT ACT AAT GTA ACT GAT TTA GCT ACT TCC CAT AAT TAC TTA       1392
Gly Phe Ile Thr Asn Val Thr Asp Leu Ala Thr Ser His Asn Tyr Leu
```

```
      450                 455                 460
GCG GAG GGA GGA TTA GCT ATT TTA GAT ACA TCT GGT GCC ATA GAC ATC        1440
Ala Glu Gly Gly Leu Ala Ile Leu Asp Thr Ser Gly Ala Ile Asp Ile
465                 470                 475                 480

TTC GTT GTA CAA GGT GAA TAT GGC CCT AAC TAC TAT AAG GTT AAT CTA        1488
Phe Val Val Gln Gly Glu Tyr Gly Pro Asn Tyr Tyr Lys Val Asn Leu
                485                 490                 495

TGT GAA GAT GTT AAC CAA CAG TTT GTA GTT TCT GGT GGT AAA TTA GTA        1536
Cys Glu Asp Val Asn Gln Gln Phe Val Val Ser Gly Gly Lys Leu Val
            500                 505                 510

GGT ATT CTC ACT TCA CGT AAT GAA ACT GGT TCT CAG CCT CTT GAA AAC        1584
Gly Ile Leu Thr Ser Arg Asn Glu Thr Gly Ser Gln Pro Leu Glu Asn
        515                 520                 525

CAG TTT TAC ATT AAG ATC ACT AAT GGA ACA CAT CGT TCT AGA CGT TCT        1632
Gln Phe Tyr Ile Lys Ile Thr Asn Gly Thr His Arg Ser Arg Arg Ser
    530                 535                 540

GTT AAT GAA AAT GTT ACG AAT TGC CCT TAT GTT AGT TAT GGC AAG TTT        1680
Val Asn Glu Asn Val Thr Asn Cys Pro Tyr Val Ser Tyr Gly Lys Phe
545                 550                 555                 560

TGT ATA AAA CCT GAT GGT TCA GTT TCT CCT ATA GTA CCA AAA GAA CTT        1728
Cys Ile Lys Pro Asp Gly Ser Val Ser Pro Ile Val Pro Lys Glu Leu
                565                 570                 575

GAA CAG TTT GTG GCA CCT TTA CTT AAT GTT ACT GAA AAT GTG CTC ATA        1776
Glu Gln Phe Val Ala Pro Leu Leu Asn Val Thr Glu Asn Val Leu Ile
            580                 585                 590

CCT AAC AGT TTT AAC TTA ACT GTT ACA GAT GAG TAC ATA CAA ACG CGT        1824
Pro Asn Ser Phe Asn Leu Thr Val Thr Asp Glu Tyr Ile Gln Thr Arg
        595                 600                 605

ATG GAT AAG GTC CAA ATT AGG A                                          1846
Met Asp Lys Val Gln Ile Arg
    610                 615

(2) INFORMATION FOR SEQ ID NO:17:

(i) SEQUENCE CHARACTERISTICS:
        (A) LENGTH: 615 amino acids
        (B) TYPE: amino acid
        (D) TOPOLOGY: linear (ii) MOLECULE TYPE: protein (xi) SEQUENCE DESCRIPTION: SEQ ID NO:17:

Met Leu Val Lys Ser Leu Phe Leu Val Thr Ile Leu Phe Ala Leu Cys
1               5                   10                  15

Ser Ala Asn Leu Tyr Asp Asn Glu Ser Phe Val Tyr Tyr Gln Ser
            20                  25                  30

Ala Phe Arg Pro Gly His Gly Trp His Leu His Gly Gly Ala Tyr Ala
        35                  40                  45

Val Val Asn Val Ser Ser Glu Asn Asn Asn Ala Gly Thr Ala Pro Ser
    50                  55                  60

Cys Thr Ala Gly Ala Ile Gly Tyr Ser Lys Asn Phe Ser Ala Ala Ser
65                  70                  75                  80

Val Ala Met Thr Ala Pro Leu Ser Gly Met Ser Trp Ser Ala Ser Ser
                85                  90                  95

Phe Cys Thr Ala His Cys Asn Phe Thr Ser Tyr Ile Val Phe Val Thr
            100                 105                 110

His Cys Phe Lys Ser Gly Ser Asn Ser Cys Pro Leu Thr Gly Leu Ile
        115                 120                 125

Pro Ser Gly Tyr Ile Arg Ile Ala Ala Met Lys His Gly Ser Arg Thr
    130                 135                 140
```

```
Pro Gly His Leu Phe Tyr Asn Leu Thr Val Ser Val Thr Lys Tyr Pro
145                 150                 155                 160

Lys Phe Arg Ser Leu Gln Cys Val Asn Asn His Thr Ser Val Tyr Leu
                165                 170                 175

Asn Gly Asp Leu Val Phe Thr Ser Asn Tyr Thr Glu Asp Val Val Ala
            180                 185                 190

Ala Gly Val His Phe Lys Ser Gly Gly Pro Ile Thr Tyr Lys Val Met
        195                 200                 205

Arg Glu Val Lys Ala Leu Ala Tyr Phe Val Asn Gly Thr Ala His Asp
    210                 215                 220

Val Ile Leu Cys Asp Asp Thr Pro Arg Gly Leu Leu Ala Cys Gln Tyr
225                 230                 235                 240

Asn Thr Gly Asn Phe Ser Asp Gly Phe Tyr Pro Phe Thr Asn Thr Ser
                245                 250                 255

Ile Val Lys Asp Lys Phe Ile Val Tyr Arg Glu Ser Ser Val Asn Thr
            260                 265                 270

Thr Leu Thr Leu Thr Asn Phe Thr Phe Ser Asn Glu Ser Gly Ala Pro
        275                 280                 285

Pro Asn Thr Gly Gly Val Asp Ser Phe Ile Leu Tyr Gln Thr Gln Thr
    290                 295                 300

Ala Gln Ser Gly Tyr Tyr Asn Phe Asn Phe Ser Phe Leu Ser Ser Phe
305                 310                 315                 320

Val Tyr Arg Glu Ser Asn Tyr Met Tyr Gly Ser Tyr His Pro Ala Cys
                325                 330                 335

Ser Phe Arg Pro Glu Thr Leu Asn Gly Leu Trp Ser Asn Ser Leu Ser
            340                 345                 350

Val Ser Leu Ile Tyr Gly Pro Ile Gln Gly Gly Cys Lys Gln Ser Val
        355                 360                 365

Phe Asn Gly Lys Ala Thr Cys Cys Tyr Ala Tyr Ser Tyr Gly Gly Pro
    370                 375                 380

Arg Ala Cys Lys Gly Val Tyr Arg Gly Glu Leu Thr Gln His Phe Glu
385                 390                 395                 400

Cys Gly Leu Leu Val Tyr Val Thr Lys Ser Asp Gly Ser Arg Ile Gln
                405                 410                 415

Thr Ala Thr Gln Pro Pro Val Leu Thr Gln Asn Phe Tyr Asn Asn Ile
            420                 425                 430

Thr Leu Gly Lys Cys Val Asp Tyr Asn Val Tyr Gly Arg Thr Gly Gln
        435                 440                 445

Gly Phe Ile Thr Asn Val Thr Asp Leu Ala Thr Ser His Asn Tyr Leu
    450                 455                 460

Ala Glu Gly Gly Leu Ala Ile Leu Asp Thr Ser Gly Ala Ile Asp Ile
465                 470                 475                 480

Phe Val Val Gln Gly Glu Tyr Gly Pro Asn Tyr Tyr Lys Val Asn Leu
                485                 490                 495

Cys Glu Asp Val Asn Gln Gln Phe Val Val Ser Gly Gly Lys Leu Val
            500                 505                 510

Gly Ile Leu Thr Ser Arg Asn Glu Thr Gly Ser Gln Pro Leu Glu Asn
        515                 520                 525

Gln Phe Tyr Ile Lys Ile Thr Asn Gly Thr His Arg Ser Arg Arg Ser
    530                 535                 540

Val Asn Glu Asn Val Thr Asn Cys Pro Tyr Val Ser Tyr Gly Lys Phe
545                 550                 555                 560

Cys Ile Lys Pro Asp Gly Ser Val Ser Pro Ile Val Pro Lys Glu Leu
```

```
                    565                 570                 575
Glu Gln Phe Val Ala Pro Leu Leu Asn Val Thr Glu Asn Val Leu Ile
            580                 585                 590

Pro Asn Ser Phe Asn Leu Thr Val Thr Asp Glu Tyr Ile Gln Thr Arg
        595                 600                 605

Met Asp Lys Val Gln Ile Arg
    610                 615

(2) INFORMATION FOR SEQ ID NO:18:

(i) SEQUENCE CHARACTERISTICS:
        (A) LENGTH: 2116 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:18:
```

| | | | | | |
|---|---|---|---|---|---|
| TATAATTATC | TAGCAGACGC | AGGTATGGCT | ATTTTAGATA | CATCTGGTTC | CATAGACATC | 60 |
| TTTGTTGCAC | AAGGTGAATA | TGGCCTTACT | TATTATAAGG | CTAACCCTTG | CGAAGACGTC | 120 |
| AACCAGCAGT | TTGTAGTTTC | TGGTGGTAAA | TTAGTAGGTA | TTCTTACTTC | ACGTAATGAG | 180 |
| ACTGGTTCTC | AGCTTCTTGA | GAACCAGTTT | TACATTAAAA | TCACTAATGG | AACACGTCGT | 240 |
| TCTAGACGTT | CTATTACTGC | AAATGTHACA | AATYGCCCTT | ATGTTAGCTA | TGGCAAGTTT | 300 |
| TGTCTAAAAC | CTGATGGYTC | AGYTTCTGYT | ATAGCACCAC | NNNNNNNNNN | NNNNNNNNNN | 360 |
| NNNNNNNNNN | NNNNNNNNNN | NNNNNNNNNN | NNNNNNNNNN | NNNNNNNNNN | NNNNNNNNNN | 420 |
| NNNNNNNNNN | NNNNNNNNNN | NNNNNNNNNN | NNNNNNNNNN | NNNNNNNNNN | NNNNNNNNNT | 480 |
| GTTTGTGGCA | ATTCTCTGGA | TTGTAGAAAG | TTGYTTCAAC | AATATGGGCC | TGTTTGBGAC | 540 |
| AACATATTGT | CTGTGGTAAA | TAGTGTTGGT | CAAAAAGAAG | ATATGGAACT | TCUAAATCTC | 600 |
| TATTCTTCTA | CTAAACCATC | TGGCTTTAAT | ACACCAGTTT | TTAGTAATCT | YAGCACTGGC | 660 |
| GATTTYAATA | TTTCTCTTYT | GGTTGACACC | TCCAGTAGTA | CTACTGGGCG | CTCTTTTATT | 720 |
| GAAGATCTTT | TATTTACAAG | TGTTGAATCT | GTTGGATTAC | CAACAGATGA | AGCTTATAAA | 780 |
| AAGTGCACTG | CAGGACCTTT | AGGCTTCCTT | AAGGACCTBG | CGTGTGCTCG | TGAATATAAT | 840 |
| GGCTTGCTTG | YNNNNNNCCC | TATTATAACA | GCAGAAATGC | AAACCTTGTA | TACTAGTTCT | 900 |
| TTAGTAGCTT | CTATGGCTTT | TGGTGGGATT | ACTGCAGCTG | GTGCTATACC | TTTTGCCACA | 960 |
| CAACTGCAGG | CTAGAATTAA | TCACTTGGGT | ATTACCCAGT | CACTTTTGCA | GAAAAATCAA | 1020 |
| GAAAAAATTG | CTGCCTCCTT | TAATAAGGCC | ATTGGCCATA | TGCAGGAAGG | TTTTAGAAGT | 1080 |
| ACATCTCTAG | CATTACAACA | AGTYCAMGAT | GTTGTTAATA | AGCAGAGTGC | TATTCTTACT | 1140 |
| GAGACTATGG | CATCACTTAA | TAAAAATTTK | GGTGCTATTT | CTTCTGTGAT | TCAAGATATC | 1200 |
| TACCAGCAAC | TTGACGCCAT | ACAAGCAAAT | GCTCAAGTGG | ATCGTCTTAT | AACTGGTAGA | 1260 |
| TTGTCATCAC | TTTCTGTTTT | AGCATCTGCT | AAGCAGGCGG | AGTATATTAG | AGTGTCACAA | 1320 |
| CAGCGTGAGT | TAGCTACTCA | GAAAATTAAT | GAGTGTGTTA | AATCACAGTC | TATTAGGTAC | 1380 |
| TCCTTTTGTG | GTAATGGACG | ACACGTTCTA | ACTATACCGC | AAAATGCACC | TAATGGTATA | 1440 |
| GTGTTTATAC | ACTTTACTTA | TACTCCAGAG | AGTTTTGKTA | ATGTTACTGC | AATAGTGGGT | 1500 |
| TTTTGTAARG | CCGCTAATGC | TAGTCAGTAT | GCAATAGTGC | CTGCTAATGG | CAGAGGTATT | 1560 |

-continued

```
TCTATACAAG TTAATGGTAG TCACTACATC ACTGCACGAG ATATGTATAT GCCAAGAGAT     1620

ATTACTGCAG GAGATATAGT TACGCTTACT TCTTGTCAAG CAAATTATGT AAGTGTAMMT     1680

AAGACCGTCA TTACYACATT HGTAGACAAT GATGATTTTG ATTTTGATGA CGAATTGTCA     1740

AAATGGTGGA ATGATACTAA GCATGAGCTA CCAGACTTTG ACGAATTCAA TTACACAGTA     1800

CCTATACTTG ACATTGGTAG TGAAATTGAT CGTATTCAAG GCGTTATACA GGGCCTTAAT     1860

GACTCTCTAA TAGACCTTGA AACACTATCA ATACTCAAAA CTTATATTAA GTGGCCTTGG     1920

TATGTGTGGT TAGCCATAGC TTTTGSCACT ATTATCTTCA TCCTAATATT AGGGTGGGTG     1980

TTTTTCATGA CTGGTTGTTG TGGTTGTTGT TGTGGATGCT TTGGCATTAT TCCTCTAATG     2040

AGCAAGTGTG GTAAGAAATC TTCTTATTAC ACGACTTTGG ATAATGATGT GGTAACTGAA     2100

CAAWACAGAC CYAAAA                                                     2116
```

(2) INFORMATION FOR SEQ ID NO:19:

(i) SEQUENCE CHARACTERISTICS:
        (A) LENGTH: 705 amino acids
        (B) TYPE: amino acid
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:19:

```
Tyr Asn Tyr Leu Ala Asp Ala Gly Met Ala Ile Leu Asp Thr Ser Gly
  1               5                  10                  15

Ser Ile Asp Ile Phe Val Ala Gln Gly Glu Tyr Gly Leu Thr Tyr Tyr
             20                  25                  30

Lys Ala Asn Pro Cys Glu Asp Val Asn Gln Gln Phe Val Val Ser Gly
         35                  40                  45

Gly Lys Leu Val Gly Ile Leu Thr Ser Arg Asn Glu Thr Gly Ser Gln
 50                  55                  60

Leu Leu Glu Asn Gln Phe Tyr Ile Lys Ile Thr Asn Gly Thr Arg Arg
 65                  70                  75                  80

Ser Arg Arg Ser Ile Thr Ala Asn Val Thr Asn Xaa Pro Tyr Val Ser
                 85                  90                  95

Tyr Gly Lys Phe Cys Leu Lys Pro Asp Gly Ser Xaa Ser Xaa Ile Ala
            100                 105                 110

Pro Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa
        130                 135                 140

Xaa Xaa Xaa Xaa Xaa Xaa Xaa Xaa Xaa Xaa Xaa Xaa Xaa Xaa
145                 150                 155                 160

Val Cys Gly Asn Ser Leu Asp Cys Arg Lys Leu Xaa Gln Gln Tyr Gly
                165                 170                 175

Pro Val Xaa Asp Asn Ile Leu Ser Val Val Asn Ser Val Gly Gln Lys
            180                 185                 190

Glu Asp Met Glu Leu Leu Asn Leu Tyr Ser Ser Thr Lys Pro Ser Gly
        195                 200                 205

Phe Asn Thr Pro Val Phe Ser Asn Leu Ser Thr Gly Asp Phe Asn Ile
    210                 215                 220

Ser Leu Leu Val Asp Thr Ser Ser Ser Thr Thr Gly Arg Ser Phe Ile
225                 230                 235                 240
```

```
Glu Asp Leu Leu Phe Thr Ser Val Glu Ser Val Gly Leu Pro Thr Asp
            245                 250                 255

Glu Ala Tyr Lys Lys Cys Thr Ala Gly Pro Leu Gly Phe Leu Lys Asp
            260                 265                 270

Leu Ala Cys Ala Arg Glu Tyr Asn Gly Leu Leu Xaa Xaa Xaa Pro Ile
            275                 280                 285

Ile Thr Ala Glu Met Gln Thr Leu Tyr Thr Ser Ser Leu Val Ala Ser
        290                 295                 300

Met Ala Phe Gly Gly Ile Thr Ala Ala Gly Ala Ile Pro Phe Ala Thr
305                 310                 315                 320

Gln Leu Gln Ala Arg Ile Asn His Leu Gly Ile Thr Gln Ser Leu Leu
            325                 330                 335

Gln Lys Asn Gln Glu Lys Ile Ala Ala Ser Phe Asn Lys Ala Ile Gly
            340                 345                 350

His Met Gln Glu Gly Phe Arg Ser Thr Ser Leu Ala Leu Gln Gln Val
            355                 360                 365

Xaa Asp Val Val Asn Lys Gln Ser Ala Ile Leu Thr Glu Thr Met Ala
370                 375                 380

Ser Leu Asn Lys Asn Xaa Gly Ala Ile Ser Ser Val Ile Gln Asp Ile
385                 390                 395                 400

Tyr Gln Gln Leu Asp Ala Ile Gln Ala Asn Ala Gln Val Asp Arg Leu
            405                 410                 415

Ile Thr Gly Arg Leu Ser Ser Leu Ser Val Leu Ala Ser Ala Lys Gln
            420                 425                 430

Ala Glu Tyr Ile Arg Val Ser Gln Gln Arg Glu Leu Ala Thr Gln Lys
            435                 440                 445

Ile Asn Glu Cys Val Lys Ser Gln Ser Ile Arg Tyr Ser Phe Cys Gly
            450                 455                 460

Asn Gly Arg His Val Leu Thr Ile Pro Gln Asn Ala Pro Asn Gly Ile
465                 470                 475                 480

Val Phe Ile His Phe Thr Tyr Thr Pro Glu Ser Phe Xaa Asn Val Thr
            485                 490                 495

Ala Ile Val Gly Phe Cys Lys Ala Ala Asn Ala Ser Gln Tyr Ala Ile
            500                 505                 510

Val Pro Ala Asn Gly Arg Gly Ile Ser Ile Gln Val Asn Gly Ser His
            515                 520                 525

Tyr Ile Thr Ala Arg Asp Met Tyr Met Pro Arg Asp Ile Thr Ala Gly
            530                 535                 540

Asp Ile Val Thr Leu Thr Ser Cys Gln Ala Asn Tyr Val Ser Val Xaa
545                 550                 555                 560

Lys Thr Val Ile Thr Thr Xaa Val Asp Asn Asp Asp Phe Asp Phe Asp
            565                 570                 575

Asp Glu Leu Ser Lys Trp Trp Asn Asp Thr Lys His Glu Leu Pro Asp
            580                 585                 590

Phe Asp Glu Phe Asn Tyr Thr Val Pro Ile Leu Asp Ile Gly Ser Glu
            595                 600                 605

Ile Asp Arg Ile Gln Gly Val Ile Gln Gly Leu Asn Asp Ser Leu Ile
            610                 615                 620

Asp Leu Glu Thr Leu Ser Ile Leu Lys Thr Tyr Ile Lys Trp Pro Trp
625                 630                 635                 640

Tyr Val Trp Leu Ala Ile Ala Phe Xaa Thr Ile Ile Phe Ile Leu Ile
            645                 650                 655

Leu Gly Trp Val Phe Phe Met Thr Gly Cys Cys Gly Cys Cys Cys Gly
```

```
                  660                 665                 670
    Cys Phe Gly Ile Ile Pro Leu Met Ser Lys Cys Gly Lys Lys Ser Ser
                675                 680                 685

Tyr Tyr Thr Thr Leu Asp Asn Asp Val Val Thr Glu Gln Xaa Arg Pro
                690                 695                 700

Lys
    705

(2) INFORMATION FOR SEQ ID NO:20:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:20:

GAATTCGAGC TCGCCCGGGG ATCCTCTAGA GTCGAC                              36

(2) INFORMATION FOR SEQ ID NO:21:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 13..57

(xi) SEQUENCE DESCRIPTION: SEQ ID NO:21:

CACAGCTCAA CA ATG AAG TGG GCA ACG TGG ATC GAT CCC GTC GTT TTA       48
              Met Lys Trp Ala Thr Trp Ile Asp Pro Val Val Leu
                1               5                  10

CAA CGT CGT                                                          57
Gln Arg Arg
         15

(2) INFORMATION FOR SEQ ID NO:22:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:22:

Met Lys Trp Ala Thr Trp Ile Asp Pro Val Val Leu Gln Arg Arg
  1               5                  10                  15

(2) INFORMATION FOR SEQ ID NO:23:

(i) SEQUENCE CHARACTERISTICS:
        (A) LENGTH: 57 base pairs
        (B) TYPE: nucleic acid
```

(C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:23:

ACTCGGGCAG CGTTGGGTCC TGGGACTCTA GAGGATCGAT CCCCTATGGC GATCATC         57

(2) INFORMATION FOR SEQ ID NO:24:

(i) SEQUENCE CHARACTERISTICS:
            (A) LENGTH: 99 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:24:

GCGCCCACGT GGCCTGGTAC AATTCGAGCT CGCCCGGGGA TCCTCTAGAG TCGACTCTAG         60

AGGATCGATC CTCTAGAGTC GGCGGGACGA GCCCGCGAT         99

(2) INFORMATION FOR SEQ ID NO:25:

(i) SEQUENCE CHARACTERISTICS:
            (A) LENGTH: 57 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:25:

TCCACAGGAC CTGCAGCGAC CCGCTTAACA GCGTCAACAG CGTGCCGCAG ATCGGGG         57

(2) INFORMATION FOR SEQ ID NO:26:

(i) SEQUENCE CHARACTERISTICS:
            (A) LENGTH: 35 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:26:

GTTGATCCCG GGAGATGGGG GAGGCTAACT GAAAC         35

(2) INFORMATION FOR SEQ ID NO:27:

(i) SEQUENCE CHARACTERISTICS:
            (A) LENGTH: 103 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:27:

GCTCATGGTG GCCCCCGGGC GGTTCAACGA GGGCCAGTAC CGGCGCCTGG TGTCCGTCGA    60

CCTGCAGGTC GACTCTAGAG GATCCCCGGG CGAGCTCGAA TTC    103

(2) INFORMATION FOR SEQ ID NO:28:

(i) SEQUENCE CHARACTERISTICS:
        (A) LENGTH: 66 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:28:

GAATTCGAGC TCGCCCGGGG ATCCTCTAGA GTCGACGTCT GGGGCGCGGG GGTGGTGCTC    60

TTCGAG    66

(2) INFORMATION FOR SEQ ID NO:29:

(i) SEQUENCE CHARACTERISTICS:
        (A) LENGTH: 66 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 16..66

(xi) SEQUENCE DESCRIPTION: SEQ ID NO:29:

CTCCACAGCT CAACA ATG AAG TGG GCA ACG TGG ATC GAT CCC GTC GTT TTA    51
               Met Lys Trp Ala Thr Trp Ile Asp Pro Val Val Leu
               1           5                10

CAA CGT CGT GAC TGG    66
Gln Arg Arg Asp Trp
    15

(2) INFORMATION FOR SEQ ID NO:30:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO:30:

Met Lys Trp Ala Thr Trp Ile Asp Pro Val Val Leu Gln Arg Arg Asp
 1         5            10           15

Trp (2) INFORMATION FOR SEQ ID NO:31:

(i) SEQUENCE CHARACTERISTICS:
        (A) LENGTH: 132 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..93

(xi) SEQUENCE DESCRIPTION: SEQ ID NO:31:

```
GAC GAC TCC TGG AGC CCG TCA GTA TCG GCG GAA ATC CAG CTG AGC GCC      48
Asp Asp Ser Trp Ser Pro Ser Val Ser Ala Glu Ile Gln Leu Ser Ala
 1               5                  10                  15

GGT CGC TAC CAT TAC CAG TTG GTC TGG TGT CAA AAA GAT CTA GAA          93
Gly Arg Tyr His Tyr Gln Leu Val Trp Cys Gln Lys Asp Leu Glu
             20                  25                  30

TAAGCTAGAG GATCGATCCC CTATGGCGAT CATCAGGGC                          132
```

(2) INFORMATION FOR SEQ ID NO:32:

(i) SEQUENCE CHARACTERISTICS:
        (A) LENGTH: 31 amino acids
        (B) TYPE: amino acid
        (D) TOPOLOGY: linear (ii) MOLECULE TYPE: protein (xi) SEQUENCE DESCRIPTION: SEQ ID NO:32:

```
Asp Asp Ser Trp Ser Pro Ser Val Ser Ala Glu Ile Gln Leu Ser Ala
 1               5                  10                  15

Gly Arg Tyr His Tyr Gln Leu Val Trp Cys Gln Lys Asp Leu Glu
             20                  25                  30
```

(2) INFORMATION FOR SEQ ID NO:33:

(i) SEQUENCE CHARACTERISTICS:
        (A) LENGTH: 66 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:33:

```
AACGAGGGCC AGTACCGGCG CCTGGTGTCC GTCGACTCTA GAGGATCCCC GGGCGAGCTC    60

GAATTC                                                              66
```

(2) INFORMATION FOR SEQ ID NO:34:

(i) SEQUENCE CHARACTERISTICS:
        (A) LENGTH: 65 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:34:

CAGGTCGAAG CTTGGGCGCT GCCTATGTAG TGAAATCTAT ACTGGGATTT ATCATAACTA    60

GTTTA    65

(2) INFORMATION FOR SEQ ID NO:35:

(i) SEQUENCE CHARACTERISTICS:
        (A) LENGTH: 65 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:35:

AATAATCTAT CACTTTGTCA TGGAGATGCC CAAGCTTCGA CGACTCCCTT GGCCATGATG    60

AATGG    65

(2) INFORMATION FOR SEQ ID NO:36:

(i) SEQUENCE CHARACTERISTICS:
        (A) LENGTH: 65 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:36:

TATACCAGCT ACGGCGCTAG CATTCATGGT ATCCCGTGAT TGCTCGATGC TTTCCTTCTG    60

AATTC    65

(2) INFORMATION FOR SEQ ID NO:37:

(i) SEQUENCE CHARACTERISTICS:
        (A) LENGTH: 65 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:37:

AAGCTTGGCC TCGTCGTTAA TTAACCCAAT TCGAGCTCGC CCAGCTTGGG CTGCAGGTCG    60

GGAAC    65

(2) INFORMATION FOR SEQ ID NO:38:

(i) SEQUENCE CHARACTERISTICS:
        (A) LENGTH: 65 base pairs
        (B) TYPE: nucleic acid (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:38:

TGTTTCAGTT AGCCTCCCCC ATCTCCCGAC TCTAGAGGAT CTCGACATAG CGAATACATT    60

TATGG    65

(2) INFORMATION FOR SEQ ID NO:39:

(i) SEQUENCE CHARACTERISTICS:
        (A) LENGTH: 130 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:39:

AACGTATATA TTTTTCACGA CGTAGACCAC TATTGCCATG GACTCTAGAG GATCGGGTAC    60

CGAGCTCGAA TTGGGAAGCT TGTCGACTTA ATTAAGCGGC CGCGTTTAAA CGGCCCTCGA   120

GGCCAAGCTT   130

(2) INFORMATION FOR SEQ ID NO:40:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:40:

GTCGACGTCT GGGGCGCGGG GGTGGTGCTC TTCGAGACGC TGCCTACCCC AAGACGATCG    60

(2) INFORMATION FOR SEQ ID NO:41:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:41:

AGCTCAACAA TGAAGTGGGC AACGTGGATC GATCCCGTCG TTTTACAACG TCGTGACTGG    60

(2) INFORMATION FOR SEQ ID NO:42:

(i) SEQUENCE CHARACTERISTICS:

(A) LENGTH: 120 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:42:

GAGCCCGTCA GTATCGGCGG AAATCCAGCT GAGCGCCGGT CGCTACCATT ACCAGTTGGT    60

GTTGGTCTGG TGTCAAAAAG ATCCGGACCG CGCCGTTAGC CAAGTTGCGT TAGAGAATGA   120

(2) INFORMATION FOR SEQ ID NO:43:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:43:

ACACAGTCAC ACTCATGGGG GCCGAAGGCA GAATTCGTAA TCATGGTCAT AGCTGTTTCC    60

(2) INFORMATION FOR SEQ ID NO:44:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:44:

AAACCTGTCG TGCCAGCGAG CTCGGGATCC TCTAGAGGAT CCCCGGGCCC CGCCCCCTGC    60

(2) INFORMATION FOR SEQ ID NO:45:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:45:

TCGTCCACAC GGAGCGCGGC TGCCGACACG GATCCCGGTT GGCGCCCTCC AGGTGCAGGA    60

(2) INFORMATION FOR SEQ ID NO:46:

(i) SEQUENCE CHARACTERISTICS:
        (A) LENGTH: 60 base pairs
        (B) TYPE: nucleic acid (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:46:

AACCCCCCCC CCCCCCCCCC CCCCCCCCTG CAGGCATCGT GGTGTCACGC TCGTCGTTTG      60

(2) INFORMATION FOR SEQ ID NO:47:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:47:

TGTCATGCCA TCCGTAAGAT GCTTTTCTGT GACTGGTGAG TCGGATCCTC TAGAGTCGAC      60

(2) INFORMATION FOR SEQ ID NO:48:

(i) SEQUENCE CHARACTERISTICS:
        (A) LENGTH: 2681 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 146..481

(ix) FEATURE:
        (A) NAME/KEY: CDS
        (B) LOCATION: complement (602..1402)

(ix) FEATURE:
        (A) NAME/KEY: CDS
        (B) LOCATION: 1599..2135

(ix) FEATURE:
        (A) NAME/KEY: CDS
        (B) LOCATION: complement (2308..2634)

(xi) SEQUENCE DESCRIPTION: SEQ ID NO:48:

TTTATCGGAC CTTGGGTATT CAGGGGAACC CATCTGGTTG AAATGCATCC GACCCTGCAC      60

TTGATCCTGG TTACCCCGAC CCAANTTTTA AGCCGGCTGG CGCGGTCCCT AGATAACCCC     120

CCGCTTAAAA CTAGCCCCAA TATTGATGTG CAGATATAAC ACAGNNANCC GATCAATGGA     180

AGACATGCTA CGGCGGTCAT CTCCCGAAGA CATCACCGAT TCCCTAACAA TGTGCCTGAT     240

TATGTTATCG CGCATTCGTC GTACCATGCG CACCGCAGGA AATAAATATA GCTATATGAT     300

AGATCCAATG AATCGTATGT CTAATTACAC TCCAGGCGAA TGTATGACAG GTATATTGCG     360

ATATATTGAC GAACATGCTA GAAGGTGTCC TGATCACATA TGTAATTTGT ATATCACATG     420

TACACTTATG CCGATGTATG TGCACGGGCG ATATTTCTAT TGTAATTCAT TTTTTTGKTA     480

-continued

```
GTAAACTACC ACAGGCTGTC CGGAAATCTA AGTTAATGAA TAAAGTAGAT GGTTAATACT      540

CATTGCTTAG AATTGGACTA CTTTTAATYC TCTTTAATGT TCGTATTAAA TAAAAACATC      600

TTTAATAAAC TTCAGCCTCT TCGCTTATTG TAGAAATTGA GTATTCAMAA TCATGTTCAA      660

AGCCGTCTTC GGAGAGTGTA CTCGCCACGG TGGTTGGAAC ATCACTATGT CTACACGTCA      720

AATTTAAGCA CGTCAGGTCT GTCGAGGACA AGAAATGGTT AACTAGTGTT TCAATTATTC      780

TTATAAACGT TAAGCATTGT AAGCCCCCCG GCCGTCCGCA GCAACAATTT ACTAGTATGC      840

CGTGGGCTCC GGGACTATCA CGGATGTCCA ATTCGCACAT GCATATAATT TTTCTAGGGT      900

CTCTCATTTC GAGAAATCTT CGGGGATCCA TCAGCAATGC GGGCTGTAGT CCCGATTCCC      960

GTTTCAAATG AAGGTGCTCC AACACGGTCT TCAAAGCAAC CGGCATACCA GCAAACACAG     1020

ACTGCAACTC CCCGCTGCAA TGATTGGTTA TAAACAGTAA TCTGTCTTCT GGAAGTATAT     1080

TTCGCCCGAC AATCCACGGC GCCCCCAAAG TTAAAAACCA TCCATGTGTA TTTGCGTCTT     1140

CTCTGTTAAA AGAATATTGA CTGGCATTTT CCCGTTGACC GCCAGATATC CAAAGTACAG     1200

CACGATGTTG CACGGACGAC TTTGCAGTCA CCAGCCTTCC TTTCCACCCC CCACCAACA     1260

AAATGTTTAT CGTAGGACCC ATATCCGTAA TAAGGATGGG TCTGGCAGCA ACCCCATAGG     1320

CGCCTCGGCG TGGTAGTTCT CGAGGATACA TCCAAAGAGG TTGAGTATTC TCTCTACACT     1380

TCTTGTTAAA TGGAAAGTGC ATTTGCTTGT TCTTACAATC GGCCCGAGTC TCGTTCACAG     1440

CGCCTCGTTC ACACTTAAAC CACAAATAGT CTACAGGCTA TATGGGAGCC AGACTGAAAC     1500

TCACATATGA CTAATATTCG GGGGTGTTAG TCACGTGTAG CCCATTGTGT GCATATAACG     1560

ATGTTGGACG CGTCCTTATT CGCGGTGTAC TTGATACTAT GGCAGCGAGC ATGGGATATT     1620

CATCCTCGTC ATCGTTAACA TCTCTACGGG TTCAGAATGT TTGGCATGTC GTCGATCCTT     1680

TGCCCATCGT TGCAAATTAC AAGTCCGATC GCCATGACCG CGATAAGCCT GTACCATGTG     1740

GCATTAGGGT GACATCTCGA TCATACATTA TAAGACCAAC GTGCGAGTCT TCCAAAGACC     1800

TGCACGCCTT CTTCTTCGGA TTGTCAACGG GTTCTTCAGA ATCTATGCCC ATATCTGGCG     1860

TTGAGACCAT TGTGCGTTTA ATGAACAATA AAGCGGCATG CCATGGAAAG GAGGGCTGCA     1920

GATCTCCATT TTCTCACGCC ACTATCCTGG ACGCTGTAGA CGATAATTAT ACCATGAATA     1980

TAGAGGGGGT ATGTTTCCAC TGCCACTGTG ATGATAAGTT TTCTCCAGAT TGTTGGATAT     2040

CTGCATTTTC TGCTGCCGAA CAAACTTCAT CGCTATGCAA AGAGATGCGT GTGTACACGC     2100

GCCGGTGGAG TATACGGGAA ACTAAATGTT CATAGAGGTC TTTGGGCTAT ATGTTATTAA     2160

ATAAAATAAT TGACCAGTGA ACAATTTGTT TAATGTTAGT TTATTCAATG CATTGGTTGC     2220

AAATATTCAT TACTTCTCCA ATCCCAGGTC ATTCTTTAGC GAGATGATGT TATGACATTG     2280

CTGTGAAAAT TACTACAGGA TATATTTTTA AGATGCAGGA GTAACAATGT GCATAGTAGG     2340

CGTAGTTATC GCAGACGTGC AACGCTTCGC ATTTGAGTTA CCGAAGTGCC AACAGTGCT     2400

GCGGTTATGG TTTATGCGCA CAGAATCCAT GCATGTCCTA ATTGAACCAT CCGATTTTTC     2460

TTTTAATCGC GATCGATGTT TGGGCAACTG CGTTATTTCA GATCTAAAAA ATTTACCCTY     2520

TATGACCATC ACATCTCTCT GGYTCATACC CCGCTTGGGN TAAGATATCA TGTAGATTCC     2580

GCCCCTAAGA AATTGCAAAC TAACATNATT GNCGGGTTCC ATATACAATC CCATCTTGTC     2640

CNCTCGAAAT TACAAACTCG CGCAATAGAC CCCCGTACAT T                         2681
```

(2) INFORMATION FOR SEQ ID NO:49:

(i) SEQUENCE CHARACTERISTICS:
        (A) LENGTH: 111 amino acids

```
        (B) TYPE: amino acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:49:

Met Cys Arg Tyr Asn Thr Xaa Xaa Arg Ser Met Glu Asp Met Leu Arg
1               5                   10                  15

Arg Ser Ser Pro Glu Asp Ile Thr Asp Ser Leu Thr Met Cys Leu Ile
            20                  25                  30

Met Leu Ser Arg Ile Arg Arg Thr Met Arg Thr Ala Gly Asn Lys Tyr
        35                  40                  45

Ser Tyr Met Ile Asp Pro Met Asn Arg Met Ser Asn Tyr Thr Pro Gly
    50                  55                  60

Glu Cys Met Thr Gly Ile Leu Arg Tyr Ile Asp Glu His Ala Arg Arg
65                  70                  75                  80

Cys Pro Asp His Ile Cys Asn Leu Tyr Ile Thr Cys Thr Leu Met Pro
                85                  90                  95

Met Tyr Val His Gly Arg Tyr Phe Tyr Cys Asn Ser Phe Phe Xaa
            100                 105                 110

(2) INFORMATION FOR SEQ ID NO:50:

(i) SEQUENCE CHARACTERISTICS:
        (A) LENGTH: 266 amino acids
        (B) TYPE: amino acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:50:

Met His Phe Pro Phe Asn Lys Lys Cys Arg Glu Asn Thr Gln Pro Leu
1               5                   10                  15

Trp Met Tyr Pro Arg Glu Leu Pro Arg Arg Gly Ala Tyr Gly Val Ala
            20                  25                  30

Ala Arg Pro Ile Leu Ile Thr Asp Met Gly Pro Thr Ile Asn Ile Leu
        35                  40                  45

Leu Val Gly Gly Trp Lys Gly Arg Leu Val Thr Ala Lys Ser Ser Val
    50                  55                  60

Gln His Arg Ala Val Leu Trp Ile Ser Gly Gln Arg Glu Asn Ala
65                  70                  75                  80

Ser Gln Tyr Ser Phe Asn Arg Glu Asp Ala Asn Thr His Gly Trp Phe
                85                  90                  95

Leu Thr Leu Gly Ala Pro Trp Ile Val Gly Arg Asn Ile Leu Pro Glu
            100                 105                 110

Asp Arg Leu Leu Phe Ile Thr Asn His Cys Ser Gly Glu Leu Gln Ser
        115                 120                 125

Val Phe Ala Gly Met Pro Val Ala Leu Lys Thr Val Leu Glu His Leu
    130                 135                 140

His Leu Lys Arg Glu Ser Gly Leu Gln Pro Ala Leu Leu Met Asp Pro
145                 150                 155                 160
```

```
Arg Arg Phe Leu Glu Met Arg Asp Pro Arg Lys Ile Ile Cys Met Cys
                165                 170                 175

Glu Leu Asp Ile Arg Asp Ser Pro Gly Ala His Gly Ile Leu Val Asn
                180                 185                 190

Cys Cys Cys Gly Arg Pro Gly Gly Leu Gln Cys Leu Thr Phe Ile Arg
            195                 200                 205

Ile Ile Glu Thr Leu Val Asn His Phe Leu Ser Ser Thr Asp Leu Thr
        210                 215                 220

Cys Leu Asn Leu Thr Cys Arg His Ser Asp Val Pro Thr Thr Val Ala
225                 230                 235                 240

Ser Thr Leu Ser Glu Asp Gly Phe Glu His Asp Xaa Glu Tyr Ser Ile
                245                 250                 255

Ser Thr Ile Ser Glu Glu Ala Glu Val Tyr
                260                 265
```

(2) INFORMATION FOR SEQ ID NO:51:

(i) SEQUENCE CHARACTERISTICS:
        (A) LENGTH: 178 amino acids
        (B) TYPE: amino acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:51:

```
Met Ala Ala Ser Met Gly Tyr Ser Ser Ser Ser Leu Thr Ser Leu
1               5                   10                  15

Arg Val Gln Asn Val Trp His Val Val Asp Pro Leu Pro Ile Val Ala
                20                  25                  30

Asn Tyr Lys Ser Asp Arg His Asp Arg Asp Lys Pro Val Pro Cys Gly
                35                  40                  45

Ile Arg Val Thr Ser Arg Ser Tyr Ile Ile Arg Pro Thr Cys Glu Ser
        50                  55                  60

Ser Lys Asp Leu His Ala Phe Phe Gly Leu Ser Thr Gly Ser Ser
65                  70                  75                  80

Glu Ser Met Pro Ile Ser Gly Val Glu Thr Ile Val Arg Leu Met Asn
                85                  90                  95

Asn Lys Ala Ala Cys His Gly Lys Glu Gly Cys Arg Ser Pro Phe Ser
                100                 105                 110

His Ala Thr Ile Leu Asp Ala Val Asp Asp Asn Tyr Thr Met Asn Ile
                115                 120                 125

Glu Gly Val Cys Phe His Cys His Cys Asp Asp Lys Phe Ser Pro Asp
            130                 135                 140

Cys Trp Ile Ser Ala Phe Ser Ala Ala Glu Gln Thr Ser Ser Leu Cys
145                 150                 155                 160

Lys Glu Met Arg Val Tyr Thr Arg Arg Trp Ser Ile Arg Glu Thr Lys
                165                 170                 175

Cys Ser
```

(2) INFORMATION FOR SEQ ID NO:52:

(i) SEQUENCE CHARACTERISTICS:
        (A) LENGTH: 108 amino acids
        (B) TYPE: amino acid
        (C) STRANDEDNESS: double (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:52:

Met Gly Leu Tyr Met Glu Pro Xaa Asn Xaa Val Ser Leu Gln Phe Leu
1               5                  10                  15

Arg Gly Gly Ile Tyr Met Ile Ser Xaa Pro Lys Arg Gly Met Xaa Gln
            20                  25                  30

Arg Asp Val Met Val Ile Xaa Gly Lys Phe Phe Arg Ser Glu Ile Thr
        35                  40                  45

Gln Leu Pro Lys His Arg Ser Arg Leu Lys Glu Lys Ser Asp Gly Ser
    50                  55                  60

Ile Arg Thr Cys Met Asp Ser Val Arg Ile Asn His Asn Arg Ser Thr
65              70                  75                  80

Val Gly His Phe Gly Asn Ser Asn Ala Lys Arg Cys Thr Ser Ala Ile
            85                  90                  95

Thr Thr Pro Thr Met His Ile Val Thr Pro Ala Ser
            100                 105

(2) INFORMATION FOR SEQ ID NO:53:

(i) SEQUENCE CHARACTERISTICS:
             (A) LENGTH: 37 base pairs
             (B) TYPE: nucleic acid
             (C) STRANDEDNESS: single
             (D) TOPOLOGY: linear (ii) MOLECULE TYPE: DNA Oligonucleotide Primer (iii) HYPOTHETICAL: NO (iv) ANTI-SENSE: YES (xi) SEQUENCE DESCRIPTION: SEQ ID NO:53:

CTCGCTCGCC CATGATCATT AAGCAAGAAT TCCGTCG                                    37

(2) INFORMATION FOR SEQ ID NO:54:

(i) SEQUENCE CHARACTERISTICS:
             (A) LENGTH: 39 base pairs
             (B) TYPE: nucleic acid
             (C) STRANDEDNESS: single
             (D) TOPOLOGY: linear (ii) MOLECULE TYPE: DNA Oligonucleotide Primer (iii) HYPOTHETICAL: NO (iv) ANTI-SENSE: NO (xi) SEQUENCE DESCRIPTION: SEQ ID NO:54:

CTGGTTCGGC CCATGATCAG ATGACAAACC TGCAAGATC                                  39

(2) INFORMATION FOR SEQ ID NO:55:

(i) SEQUENCE CHARACTERISTICS:
             (A) LENGTH: 57 base pairs
             (B) TYPE: nucleic acid
             (C) STRANDEDNESS: double
             (D) TOPOLOGY: linear (ii) MOLECULE TYPE: DNA (genomic)

-continued (iii) HYPOTHETICAL: NO (iv) ANTI-SENSE: NO (xi) SEQUENCE DESCRIPTION: SEQ ID NO:55:

CTCGGCGTGG TAGTTCTCGA GGCCTTAATT AAGGCCCTCG AGGATACATC CAAAGAG        57

(2) INFORMATION FOR SEQ ID NO:56:

(i) SEQUENCE CHARACTERISTICS:
      (A) LENGTH: 63 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:56:

CGGCGTGGTA GTTCTCGAGG CCTTAAGCGG CCGCTTAAGG CCCTCGAGGA TACATCCAAA        60

GAG        63